(12) United States Patent
Jin et al.

(10) Patent No.: US 9,273,277 B2
(45) Date of Patent: Mar. 1, 2016

(54) COMPOSITIONS COMPRISING NANOSTRUCTURES FOR CELL, TISSUE AND ARTIFICIAL ORGAN GROWTH, AND METHODS FOR MAKING AND USING SAME

(71) Applicant: THE REGENTS OF THE UNIVERSITY OF CALIFORNIA, Oakland, CA (US)

(72) Inventors: Sungho Jin, San Diego, CA (US); Seunghan Oh, Jeonbuk (KR)

(73) Assignee: The Regents of the University of California, Oakland, CA (US)

( * ) Notice: Subject to any disclaimer, the term of this patent is extended or adjusted under 35 U.S.C. 154(b) by 164 days.

(21) Appl. No.: 13/858,042

(22) Filed: Apr. 6, 2013

(65) Prior Publication Data
US 2013/0344600 A1 Dec. 26, 2013

Related U.S. Application Data

(62) Division of application No. 11/913,062, filed as application No. PCT/US2006/016471 on Apr. 28, 2006, now Pat. No. 8,414,908.

(60) Provisional application No. 60/676,602, filed on Apr. 28, 2005, provisional application No. 60/710,051, filed on Aug. 22, 2005, provisional application No. 60/710,245, filed on Aug. 22, 2005, provisional application No. 60/773,868, filed on Feb. 15, 2006, provisional application No. 60/773,885, filed on Feb. 15, 2006.

(51) Int. Cl.
| | | |
|---|---|---|
| A61F 2/00 | (2006.01) | |
| C12M 1/00 | (2006.01) | |
| A61K 9/00 | (2006.01) | |
| A61L 27/06 | (2006.01) | |
| A61L 27/30 | (2006.01) | |
| A61L 27/54 | (2006.01) | |
| A61L 27/56 | (2006.01) | |
| C12M 1/12 | (2006.01) | |

(52) U.S. Cl.
CPC .............. *C12M 23/34* (2013.01); *A61K 9/0009* (2013.01); *A61K 9/0024* (2013.01); *A61K 9/0097* (2013.01); *A61L 27/06* (2013.01); *A61L 27/306* (2013.01); *A61L 27/54* (2013.01); *A61L 27/56* (2013.01); *C12M 25/00* (2013.01); *A61L 2300/254* (2013.01); *A61L 2300/256* (2013.01); *A61L 2300/406* (2013.01); *A61L 2300/414* (2013.01); *A61L 2300/416* (2013.01); *A61L 2300/43* (2013.01); *A61L 2300/624* (2013.01); *A61L 2400/12* (2013.01)

(58) Field of Classification Search
None
See application file for complete search history.

(56) References Cited

U.S. PATENT DOCUMENTS

| | | | |
|---|---|---|---|
| 5,726,524 | A | 3/1998 | Debe |
| 5,759,744 | A | 6/1998 | Brueck et al. |
| 6,030,266 | A | 2/2000 | Ida et al. |
| 6,303,932 | B1 | 10/2001 | Hamamura et al. |
| 6,414,307 | B1 | 7/2002 | Gerlach et al. |
| 6,593,034 | B1 | 7/2003 | Shirasaki |
| 6,842,229 | B2 | 1/2005 | Sreenivasan et al. |
| 6,924,493 | B1 | 8/2005 | Leung |
| 6,946,390 | B2 | 9/2005 | Schmidt |
| 6,949,756 | B2 | 9/2005 | Gerlach et al. |
| 6,956,333 | B2 | 10/2005 | Brune et al. |
| 6,989,546 | B2 | 1/2006 | Loschner et al. |
| 7,014,961 | B2 | 3/2006 | Ganguli et al. |
| 7,027,156 | B2 | 4/2006 | Watts et al. |
| 7,235,295 | B2 * | 6/2007 | Laurencin et al. ............ 428/364 |
| 2001/0023073 | A1 | 9/2001 | Bhatia et al. |
| 2002/0072116 | A1 | 6/2002 | Bhatia et al. |
| 2003/0153965 | A1 | 8/2003 | Supronowicz et al. |
| 2004/0137066 | A1 | 7/2004 | Jayaraman |
| 2004/0206448 | A1 * | 10/2004 | Dubrow ....................... 156/276 |
| 2006/0229715 | A1 * | 10/2006 | Istephanous et al. ........ 623/1.46 |

FOREIGN PATENT DOCUMENTS

| | | | |
|---|---|---|---|
| WO | WO2006/116752 | * | 11/2006 |

OTHER PUBLICATIONS

Acosta, "Metabolic activation and cytotoxicity of cyclophosphamide in primary cultures of postnatal rat hepatocytes", Biochemical Pharmacology (1981) 30: 3225-3230.

Agius, "Metabolic interactions of parenchymal hepatocytes and dividing epithelial cells in co-culture", J. Biochem. (1988) 252:23-28.

Allen, "In Vitro Zonation and Toxicity in a Hepatocyte Bioreactor", Toxicological Sciences (2005) 84:110-119.

(Continued)

*Primary Examiner* — Snigdha Maewall
(74) *Attorney, Agent, or Firm* — Gregory P. Einhorn; Greer Burns & Crain, Ltd.

(57) ABSTRACT

The invention provides articles of manufacture comprising biocompatible nanostructures comprising nanotubes and nanopores for, e.g., organ, tissue and/or cell growth, e.g., for bone, kidney or liver growth, and uses thereof, e.g., for in vitro testing, in vivo implants, including their use in making and using artificial organs, and related therapeutics. The invention provides lock-in nanostructures comprising a plurality of nanopores or nanotubes, wherein the nanopore or nanotube entrance has a smaller diameter or size than the rest (the interior) of the nanopore or nanotube. The invention also provides dual structured biomaterial comprising micro- or macro-pores and nanopores. The invention provides biomaterials having a surface comprising a plurality of enlarged diameter nanopores and/or nanotubes.

25 Claims, 58 Drawing Sheets

(56) References Cited

OTHER PUBLICATIONS

Begue, "Cultured human adult hepatocytes: a new model for drug metabolism studies", Biochemical Pharmacology (1983) 32:1643-1646.

Bhatia, "Microfabrication of Hepatocyte/Fibroblast Co-cultures: Role of Homotypic Cell Interactions", Biotechnology Progress (1998) 14:378-387.

Bissell, "Support of cultured rat hepatocytes by a laminin-rich gel", J. Clinical Investigation (1987) 79:801-812.

Chapman, "Parenchymal Cells From Adult Rat Liver in Nonproliferating Monolayer Culture: II. Ultrastructural Studies", J. Cell Biology (1973) 59:735-747.

Clayton, "Changes in liver-specific compared to common gene transcription during primary culture of mouse hepatocytes", Molecular and Cellular Biology (1983) 3:1552-1561.

Cotell, "Pulsed laser deposition of hydroxylapatite thin films on Ti-6Al-4V", J. of Applied Biomaterials (1992) 8:87-92.

De Groot, "Plasma sprayed coatings of hydroxylapatite", J. Biomedical Materials Res. (1987) 21:1375-1381.

Deschenes, "Hepatocytes from newborn and weanling rats in monolayer culture", In Vitro (1980) 16:722-730.

Dunn, "Hepatocyte function and extracellular matrix geometry: long-term culture in a sandwich configuration", FASEB J. (1989) 3:174-177.

Ebisawa et al., "Crystallization of (FeO, Fe2O3)—CaO—SiO2 Glasses and Magnetic Properties of Their Crystallized Products", J. of Ceramic Society of Japan, Int'l Edition (1991) 99:8-13.

Gong et al., "Titanium oxide nanotube arrays prepared by anodic oxidation", J. of Materials Research (2001) 16 (12):3331-3334.

Grisham, "Differentiation and Carcinogenesis in Liver Cell Cultures", Annals of the NY Acad. Sci (1980) 349:128-137.

Grisham, "Use of hepatic cell cultures to detect and evaluate the mechanisms of action of toxic chemicals", International Review of Experimental Pathology (1979) 20:123-210.

Guguen-Guilluozo, "Maintenance and reversibility of active albumin secretion by adult rat hepatocytes co-cultured with another liver epithelial cell type", Experimental Cell Res. (1983) 143-47-54.

Hafeli et al., "In vitro and in vivo toxicity of magnetic microspheres", J. of Magnetism and Magnetic Materials (1999) 194:76-82.

Hoet et al., "Nanoparticles—known and unknown health risks", J. of Nanobiotechnology (2004) 2:12-27.

Ikenaga et al., "Localized hyperthermic treatment of experimental bone tumors with ferromagnetic ceramics", J. of Orthopaedic Research (1993) 11:849-955.

Jordan et al., "Endocytosis of dextran and silan-coated magnetite nanoparticles and the eшect ect of intracellular hyperthermia on human mammary carcinoma cells in vitro", J. of Magnetism and Magnetic Materials (1999) 194:185-196.

Konaka et al., "Preparation and Magnetic Properties of Glass-Ceramics Containing α-Fe for Hyperthermia", J. of Ceramic Society of Japan, Int'l Edition (1997) 105:894-898.

Kuri-Harcuch and Mendoza-Figueroa, "Cultivation of adult rat hepatocytes on 3T3 cells: expression of various liver differentiated functions", Differentiation (1989) 41:148-157.

Lakshmi et al., "Sol-Gel Template Synthesis of Semiconductor Oxide Micro- and Nanostructures", Chemistry of Materials (1997) 9:2544-2550.

Macak, "Smooth Anodic TiO2 Nanotubes", Chem. Int. Ed. (2005) 44:7463-7465.

Meng et al., "7.Investigations of titanium oxide films deposited by d.c. reactive magnetron sputtering in different sputtering pressures", Thin Solid Films (1993) 226:22.

Miao et al., "Electrochemically induced sol-gel preparation of single-crystalline TiO2 nanowires", Nano Letters (2002) 2(7):717-720.

Michalopoulos, "Primary Culture of Parenchymal Liver Cell of Collagen Membranes", Experimental Cell Res. (1975) 94:70-78.

Oh, "Growth of nano-scale hydroxyapatite using chemically treated titanium oxide nanotubes", Biomaterials (2005) 26:4938-4943.

Reid, "Long-term cultures of normal rat hepatocytes on liver biomatrix", Ann. N.Y. Acad. Sci. (1980) 349:70-76.

Robbie et al., "Fabrication of thin films with highly porous microstructures", J. Vacuum Science & Technology (1995) 13(3):1032.

Rodriguez et al., "Reactively Sputter-Deposited Titanium Oxide Coatings with Parallel Penniform Microstructure", Adv. Mater. (2000) 12(5):341.

Salata, "Applications of nanoparticles in biology and medicine", J. of Nanobiotechnology (2004) 2:3.

Shirkhanzadeh, "Bioactive calcium phosphate coatings prepared by electrodeposition", J. Materials Science Letters (1991) 10:1415-1417.

Sirica, "Drug metabolism and effects of carcinogens in cultured hepatic cells", Pharmacology Review (1980) 31:205-228.

Thornton, "The microstructure of sputter-deposited coatings", J. Vac. Sci. Technol. (1986) A4(6):3059.

Uchida, "Structural dependence of apatite formation on titania gels in a simulated body fluid", J. Biomedical Materials Res. (2003) 64:164-170.

Yang, "Intramedullary Implant of Plasma-Sprayed Hydroxyapatite Coating: An interface Study", J. Biomedical Materials Res. (1997) 36:39-48.

Sul, Y.T., et al., "Oxidized implants and their influence on the bone response", J. Materials Science (2001) Materials in Medicine, vol. 12, 1025-1031.

International Search Report and Written Opinion for PCT/US06/16471, mailed Jun. 27, 2008, 5 pages.

Oh, Seung-Han et al., Growth of nano-scale hydroxyapatite using chemically treated titanium oxide nanotubes, Biomaterials, epub Feb. 24, 2005, vol. 26, pp. 4938-4943.

\* cited by examiner

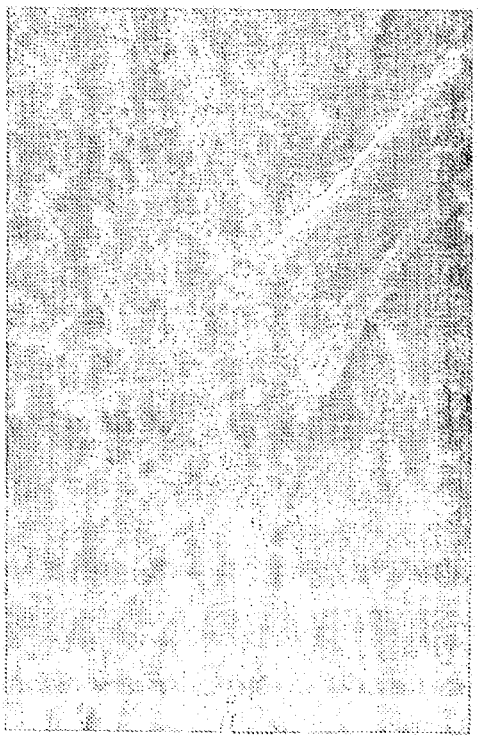
On Pure Ti
(12hr growth)
(a)
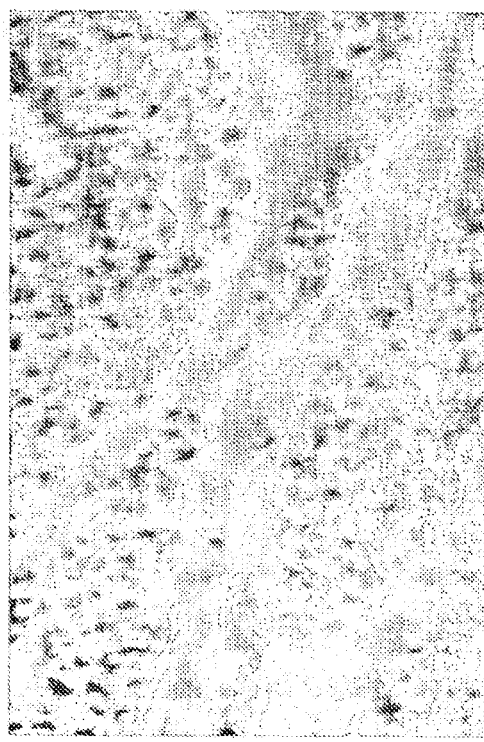
On anatase TiO$_2$ nanotubes (2hrs)
500 nm
(b)
Fig. 6

(a) Cells on Ti (b) Cells on as-deposited $TiO_2$ (amorphous)

(c) Cells on annealed $TiO_2$ (anatase)

200 μm

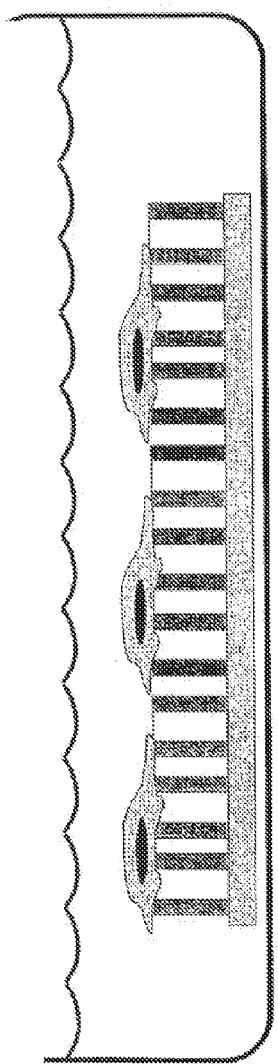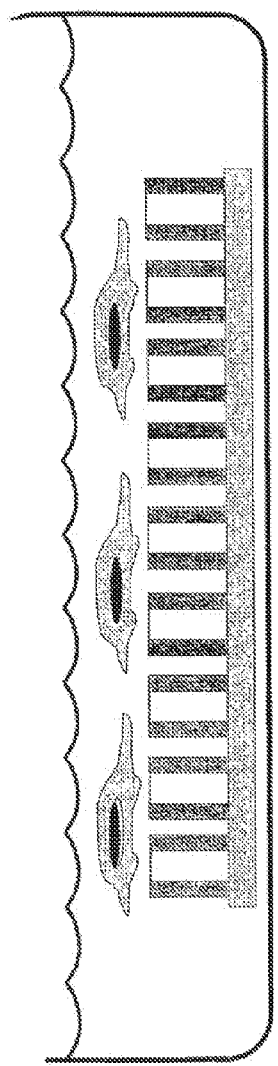
Fig. 16

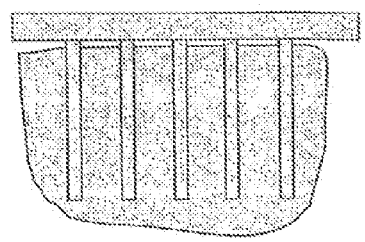
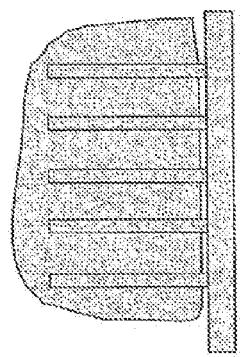
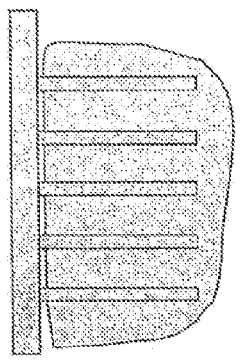
Fig. 26

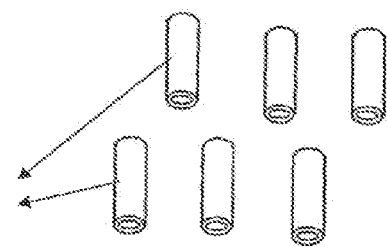
FIG 27(b)
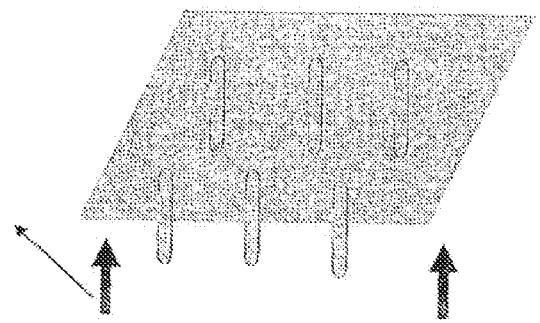
FIG 27(a)
Fig. 27

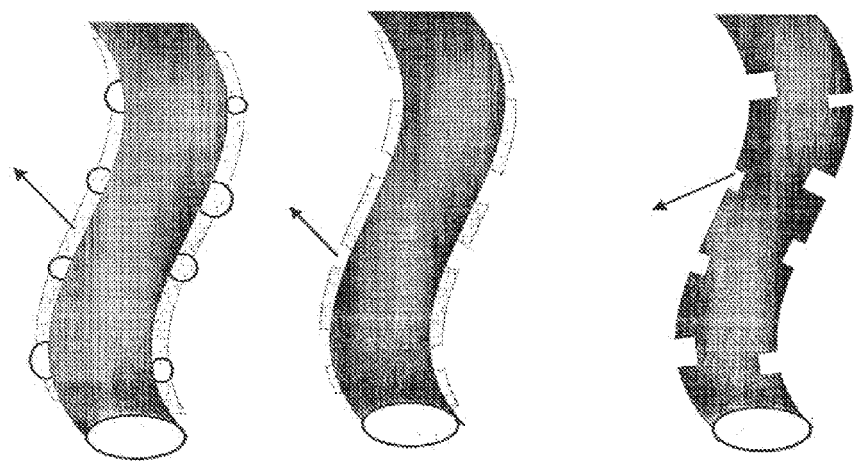
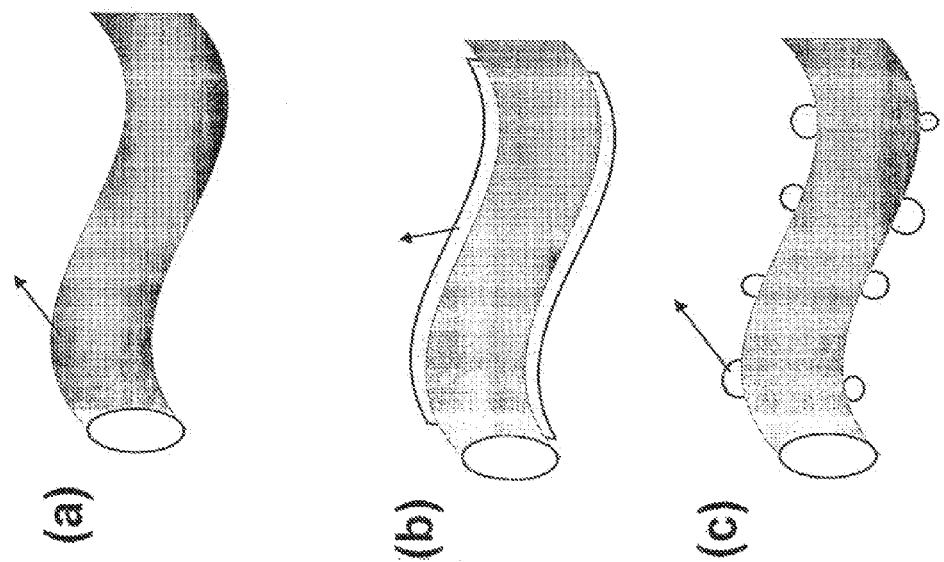
Fig. 47

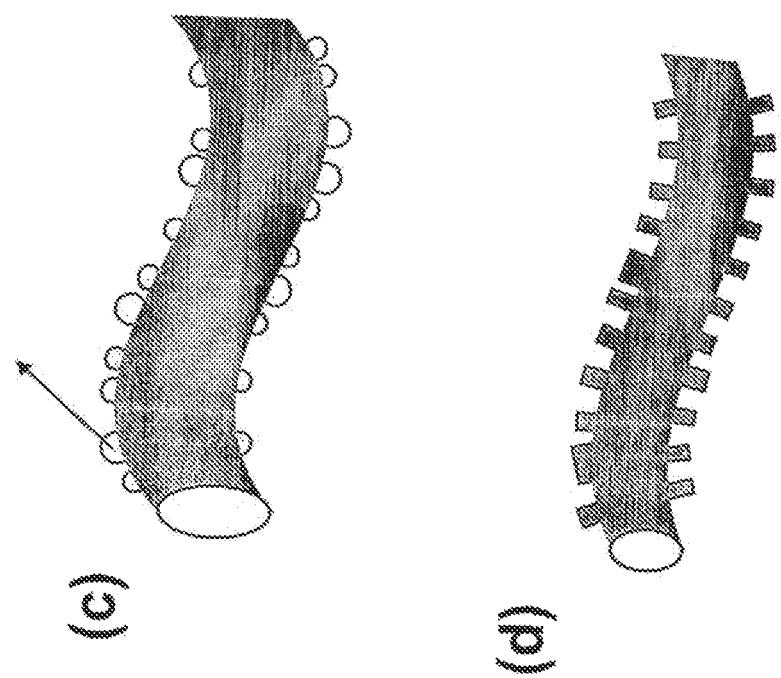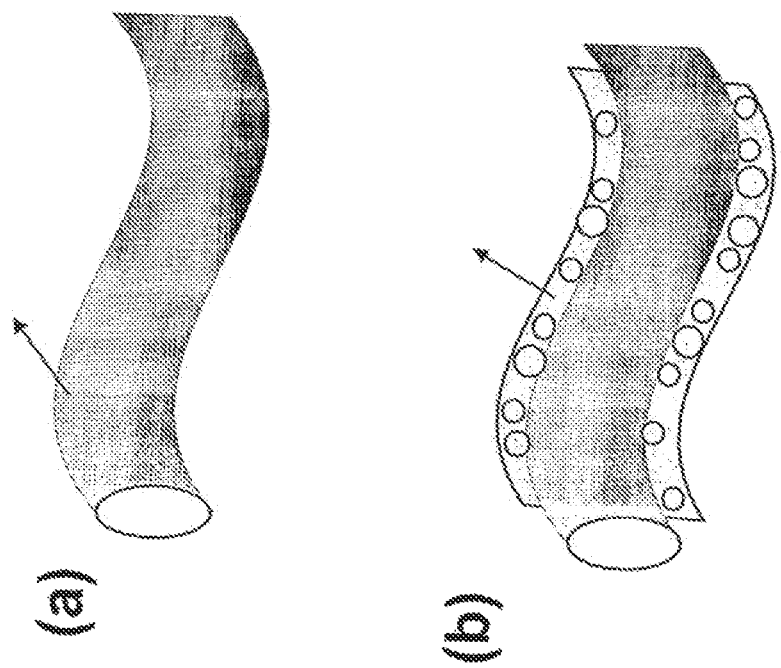
Fig. 49

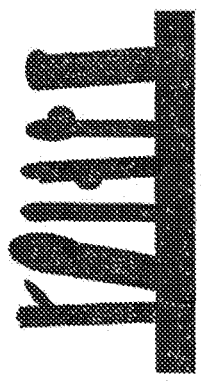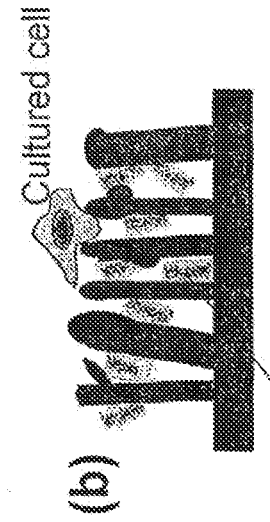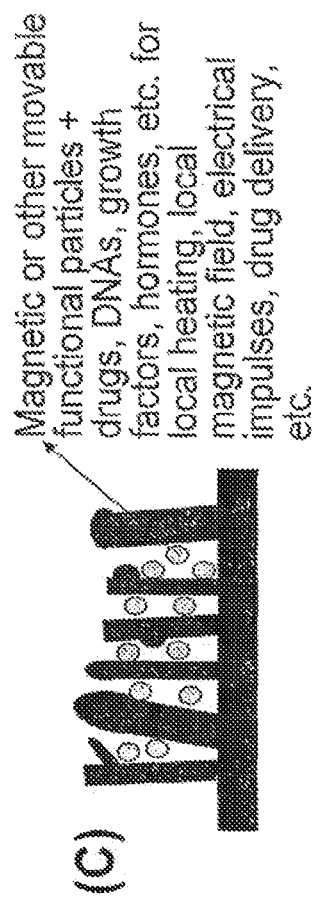
Fig. 52

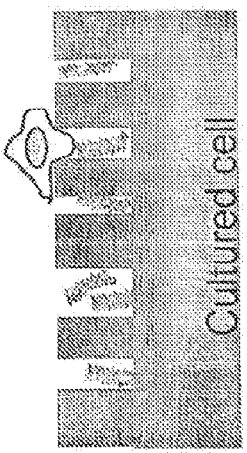
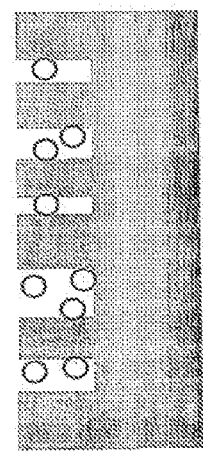
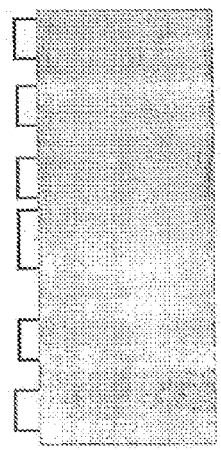
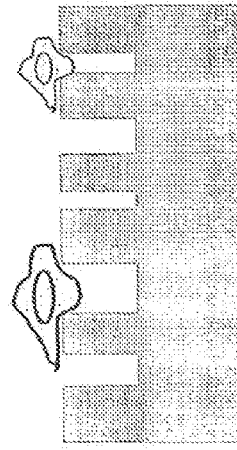
Fig. 53

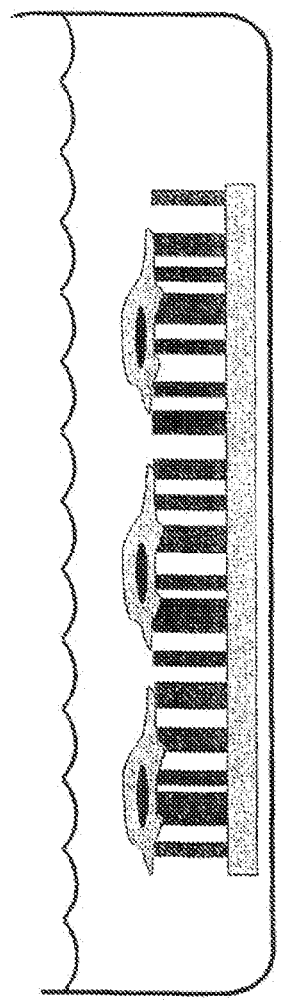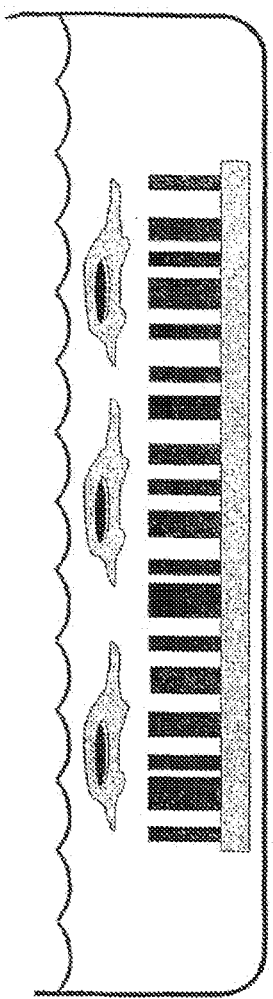
(a) Cell Proliferation using Randomized Nanopores or nanotubes
(b) Cell Harvesting by Tripsinization & Centrifugation
Fig. 57

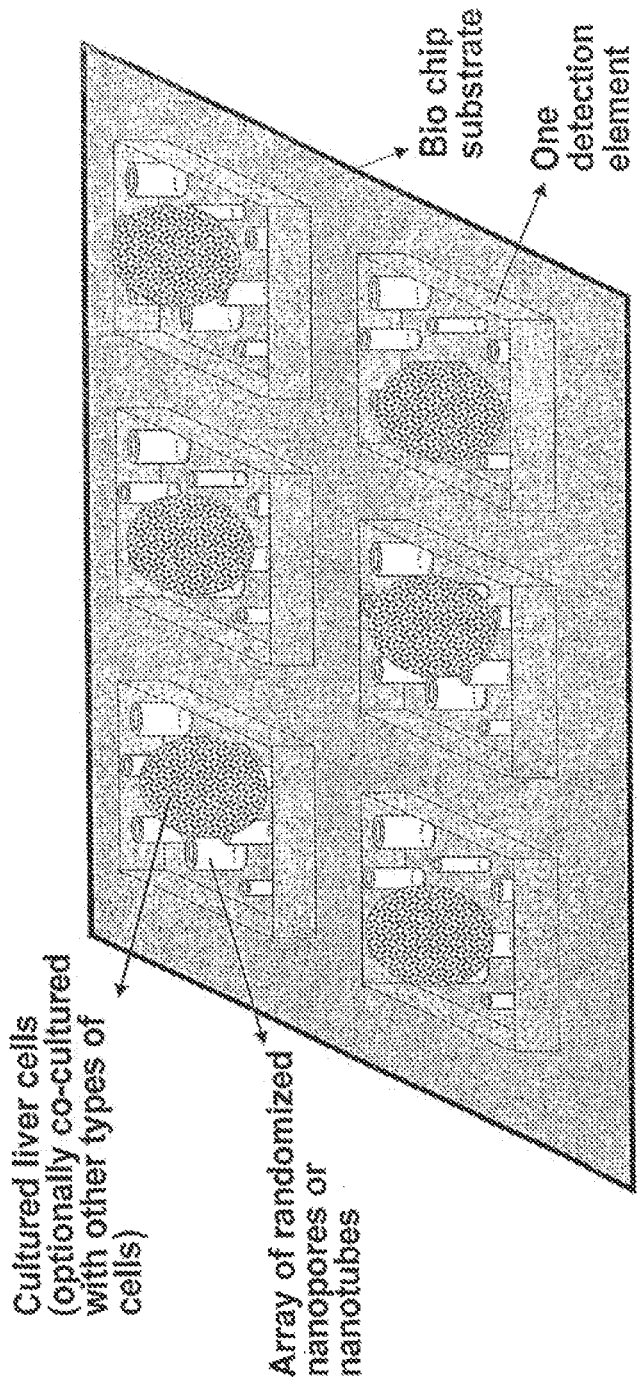

COMPOSITIONS COMPRISING NANOSTRUCTURES FOR CELL, TISSUE AND ARTIFICIAL ORGAN GROWTH, AND METHODS FOR MAKING AND USING SAME

CROSS-REFERENCE TO RELATED APPLICATIONS

This United States utility patent application is a divisional of U.S. patent application Ser. No. 11/913,062, filed Jun. 10, 2008, now pending, which is a §371 national phase of PCT international patent application no. PCT/US2006/016471 having an international filing date of Apr. 28, 2006, which claims benefit of priority to U.S. Provisional Patent Application Ser. No. 60/676,602, filed Apr. 28, 2005; U.S. Ser. No. 60/710,051, filed Aug. 22, 2005; U.S. Ser. No. 60/710,245, filed Aug. 22, 2005; U.S. Ser. No. 60/773,868, filed Feb. 15, 2006; and U.S. Ser. No. 60/773,885, filed Feb. 15, 2006. The aforementioned applications are expressly incorporated herein by reference in their entirety and for all purposes.

FIELD OF THE INVENTION

The present invention provides articles of manufacture comprising biocompatible nanostructures comprising nanotubes and nanopores for, e.g., organ, tissue and/or cell growth, e.g., for bone, tooth, kidney or liver growth, and uses thereof, e.g., for in vitro testing of drugs, chemicals or toxins, or as in vivo implants, including their use in making and using artificial tissues and organs, and related diagnostic, screening, research and development and therapeutic uses.

BACKGROUND OF THE INVENTION

It is known that the nano-scaled materials exhibit extraordinary electrical, optical, magnetic, chemical and biological properties, which cannot be achieved by micro-scaled or bulk counterparts. The development of nano-scaled materials has been intensively pursued in order to utilize such properties for various technical applications including biomedical and nano-bio applications.

Ti and Ti alloys are corrosion resistant, light, yet sufficiently strong for load-bearing, and are machinable. They are one of the few biocompatible metals which osseo-integrate (direct chemical or physical bonding with adjacent bone surface without forming a fibrous tissue interface layer). For these reasons, they have been used successfully as orthopaedic (orthopedic) and dental implants. See Handbook of biomaterial properties, ed. J. Black and G. Hasting, London; Chapman & Hall, 1998; Ratner et al., Biomaterials Science, San Diego, Calif., Academic press, 1996.

The bioactivity of Ti, such as the relatively easy formation of hydroxyapatite type bone mineral on Ti is primarily caused by the occurrence of Ti oxide on the surface of Ti and its alloys. Among the various crystal structures of Ti oxide, the anatase phase is known to be better than the rutile and other phases. See, e.g., Uchida (2003) J. Biomedical Materials Res. 64:164-170. Surface treatments such as roughening by sand blasting, formation of anatase phase $TiO_2$, hydroxyapatite coating, or other chemical treatment have been utilized to further improve the bioactivity of Ti surface and enhance bone growth.

While the fabrication of vertically aligned $TiO_2$ nanotubes on Ti substrate was demonstrated by anodization process, an investigation of such titanium oxide nanotubes for bone growth or other bio application has not been attempted. An investigation of such titanium oxide nanotubes for bone growth type bio application has only recently been reported, showing a significantly enhanced bone growth on $TiO_2$ nanotube array structure. See, e.g., Oh (2005) "Growth of Nanoscale Hydroxyapatite Using Chemically Treated Titanium Oxide Nanotubes", Biomaterials 26:4938-4943. Patients who go through Ti implant operations for repair of hip joints, broken bones, or dental implants often have to wait for many months of slow bone growth recovery before they are cured enough to get off the confinement on a bed or crutches and have a normal life. Accelerated bone growth would thus be very beneficial for such patients.

The structure of the anodized $TiO_2$ nanotube array, such as the diameter, spacing and height of nanotubes, is not always easy to control during the electrochemical anodization process of pore formation. For example, the largest reported diameter of $TiO_2$ nanotubes is less than approximately (about) 100 to 150 nm. While a portion of filopodia, the thin branches of growing cells, can get into such a small pores and enhance cell adhesion/growth, the approximately 100 nm regime of dimension is too small to accommodate the main part of typical osteoblast and many other cells as these have a much larger dimension of micrometers. In addition, the desired insertion of biological agents such as biomolecular growth factors, cytokines, collagens, antibiotics, antibodies, drug molecules, small molecules, inorganic nanoparticles, etc. within the pores for further accelerated cell/bone growth or for medical therapeutics can be facilitated if the inner diameter of the pores are made somewhat larger. Therefore, an ability to artificially design and construct a biocompatible nanostructure, e.g., with a specific desired nanotube diameter, nanopore dimension and spacing, is desirable for further controlled and accelerated growth of bones and cells. For orthopaedic and dental applications, a dual structure of larger dimension pores, which in one aspect can be of re-entrant shape, in combination of nanostructured surface would be desirable to have both accelerated cell/bone growth and physically locked-in bone configuration in the re-entrant large pores for improved mechanical durability on tensile or shear strain. Furthermore, if such a biocompatible nanostructure can be made to easily accommodate biological agent storage in the nano/micro pores to enhance multifunctional roles to additionally accelerate bone and cell growth, its practical usefulness can be much enhanced for various biomedical applications.

Coating of bioactive materials such as hydroxyapatite and calcium phosphate on Ti surface is a commonly used technique to make the Ti surface more bioactive for bone growth purposes. See, e.g., Shirkhanzadeh (1991) J. Materials Science Letters volume 10; de Groot (1987) J. Biomedical Materials Res. 21:1375-1381; Cotell (1992) J. of Applied Biomaterials 8:87-92. However, the fatal drawback of these currently available coating techniques is that such a flat and continuous coatings tend to fail by fracture or de-lamination at the interface between the implant and the coating as an adhesion failure, or at the interface between the coating and the bone, or at both boundary interfaces. Thick film coatings tends to introduce more interface stresses at the substrate-coating interface, especially in view of the lack of strong chemical bonding or the absence of common elements shared by the substrate (e.g., Ti implant) and the coating material. See, e.g., Yang (1997) J. Biomedical Materials Res. 36:39-48. It would thus be desirable if the interface is bonded with an improved and integrated structure, for example, with a locked-in configuration with a much increased adhesion area, and as a discrete, less continuous layer to minimize interface stress and de-lamination.

An additional, worthy consideration of bone growth/repair implants is the ability of the implants to withstand a tensile or shear stress, which tends to break off the interface bonding between the implant and the bone that is allowed to grow on the implant surface. It would thus be desirable if the surface geometry of the implant is improved so that not only nanoscale interfacial adhesions occur, but microscale and macroscale lock-in structure is provided to guard against slippage of the implant on tensile stress or breakage of the bond on shear stress.

Accelerated cell growth is also desirable not only for bones but also for a variety of cells including liver cells, kidney cells, blood vessel cells, skin cells, periodontal cells, stem cells, and so forth. Liver in human body is the largest gland and a dynamic organ which serves several important functions, working closely with many fundamental biological systems and bio-processes in the body. The liver is like the main chemical factory and food storehouse in human body, as it helps the body digest food and help purify the blood of the poisons and wastes. The complex functions associated with the liver include; (a) The regulation of blood glucose level, lipids and amino acids, (b) The production and secretion of bile, red blood cells, blood proteins (such as albumin, globulin, fibrinogen), cholesterol, and glucose, (c) The purification of blood by removing toxins, wastes, unnecessary hormones, and hemoglobin molecules, (d) The storage of blood, vitamins and minerals.

The parenchymal cells known as hepatocytes are the major cells populated in the liver. In additions, several other cells such as endothelial cells, adipocytes, fibroblastic cells and Kupffer cells are also included in the liver.

A significant portion of the human population (e.g., about one in ten people) has been afflicted with liver diseases such as hepatitis, liver cancer, and acute or chronic liver failure. Although liver transplantation is an optional treatment method, there is a very limited supply of donor organs, and the medical and associated costs for the transplant procedure and post-operation immunosuppressive drug therapy are considerable.

Many research investigations related to liver cell culture in vitro have been conducted to figure out the problem often caused by long-term culture of liver cells. Cultured liver cells can be useful for hepatocytes transplantation, implantable constructs and bioreactor production. The primary cultures of rat hepatocytes have been extensively used to research the effects of potential toxins on enzyme leakage, metabolism, and cellular membranes. See, e.g., Grisham (1979) International Review of Experimental Pathology 20:123-210; Acosta (1981) Biochemical Pharmacology 30:3225-3230. However, there are a number of known drawbacks about long-term liver cell culture as some loss of liver function is frequently observed. So far, there has been no successful means of proliferating healthy liver parenchymal cells.

In vitro culture of adult hepatocytes does not show prolonged ability to produce albumin and display cytochrome P-450 enzyme activity. In suspension culture, the viability of hepatocytes and their cytochrome P-450 enzyme activity declines gradually as a function of incubation time. In addition, cell division usually is limited to the first 24-48 hr of culture after which the cell division is no longer significant. See, e.g., Sirica (1980) Pharmacology Review 31:205-228; Clayton (1983) Molecular and Cellular Biology 3:1552-1561; Chapman (1973) J. Cell Biology 59:735-747. In a two-dimensional culture system, the viability of adult hepatocytes adhered to the culture plate show somewhat longer activity periods than other culture systems, but the functionality of hepatocytes decreased rapidly. See, e.g., Deschenes (1980) In Vitro 16:722-730.

To improve hepatocyte growth and prolong liver-specific functions in vitro, various kinds of matrices have been studied, such as type I and IV collagen substrates, homogenized liver biomatrix (see, e.g., Reid (1980) Ann. N.Y. Acad. Sci. 349:70-76), sandwich-shaped collagen substrate composed of two layers of type I collagen, and fibronectin coated plates. See, e.g., Michalopoulos (1975) Experimental Cell Res. 94:70-78, Bissell (1987) J. Clinical Investigation 79:801-812; Dunn (1989) FASEB J. 3:174-177; Deschenes (1980) In Vitro 16:722-730. Even though many of these experimental approaches have demonstrated an extended viability of hepatocyte and the stability of liver specific function under in vivo environment, they are still not satisfactory enough for practical applications.

An alternative way, which allows liver cells to possess some long-term viability and liver-specific functionality, utilized co-culturing liver parenchymal cells with a diversity of structurally supportive, non-parenchymal stromal cells or non-hepatic stromal cells. See, e.g., Allen (2005) Toxicological Sciences 84:110-119; Bhatia (1998) Biotechnology Progress 14:378-387. Adult hepatocytes co-cultured with endothelial cells of the same species showed good maintenance of liver-specific functions for several weeks in vitro, even though they did not show significant expansion in cell population. See articles by Guguen-Guilluozo (1983) Experimental Cell Res. 143:47-54; Begue (1983) Biochemical Pharmacology 32:1643-1646. In addition, rat hepatocytes which were co-cultured with human fibroblasts and endothelial cells were reported to exhibit stable cytochrome P-450 activity for more than 10 days. See, e.g., Kuri-Harcuch and Mendoza-Figueroa (1989) Differentiation 41:148-157; Begue (1983) Biochemical Pharmacology 32:1643-1646. Therefore, mixed hepatocyte co-culture systems with non-liver derived cells may provide microbiological environments similar to those in vivo by optimizing cell-cell interactions. However, there are still problems about the nature of non-liver derived cells. The viability and functional activities of co-cultured hepatic primary cell can be prolonged in vitro, but primary cell proliferation is limited or absent in these system, which is a critical flaw. Even though several reports indicate that non-parenchymal liver cells may express functions similar to hepatocytes, the nature of non-liver derived cells co-cultured with liver primary cells has not been established unequivocally. See, e.g., Grisham (1980) Annals of the NY Acad. Sci. 349:128-137. It is therefore highly desirable to develop culture methods and culture devices that can allow artificial in vitro (or in vivo) growth of healthy, fully functional and long-lasting liver cells that can be transplanted to the patients in need of liver cells.

There is also a critical need for an artificial liver device that can remove toxins and improve immediate and long-term survival of patients suffering from liver disease. An artificial liver device can be useful as a temporary artificial liver for patients awaiting a liver transplant, and also provide support for post-transplantation patients until the grafted liver functions adequately to sustain the patient. One of the major roadblocks to the development of an effective artificial liver device is the lack of a satisfactory liver cell line that can provide the functions of a liver.

Yet another benefit of being able to culture healthy liver cells is to meet the demands for supply of the cells for toxicity testing of enormous numbers of new or experimental drugs, chemicals, and therapeutics being developed in the pharmaceutical and chemical industry. With the unique toxin-filtering capability of liver cells, any toxicity of a new drug can be manifested first by the reaction of the liver cells. An array of liver cells can thus be utilized as a fast testing/screening vehicle to basically simultaneously evaluate the potential toxicity of many new drugs and compounds.

Two-dimensional and three-dimensionally cultured cells are useful not only for liver cell related applications, but for producing a number of other cells in a healthy and accelerated manner. There are needs to supply or implant various types of cells including bone cells, liver cells, kidney cells, blood vessel cells, skin cells, periodontal cells, stem cells, and other human or animal organ cells.

A fast growth and supply of cells especially rare cells, such as stem cell enrichment, can be crucial for many potential therapeutic applications as well as for enhancing the speed of advances in stem cell science and technology. In addition, fast detection and diagnosis of disease cells or possible bio-terror cells (such as epidemic diseases, anthrax or SARS) from a very small or trace quantity of available cells can be accomplished if the cell growth speed can be accelerated.

I. MULTIFUNCTIONAL BIOCOMPATIBLE IMPLANT AND ACCELERATED CELL GROWTH DEVICES

The invention provides medical devices comprising nano-scaled biocompatible implantable devices; including compositions (e.g., articles of manufacture) comprising nano-scaled biocompatible implantable devices such as implants (e.g., hip implants, knee implants, elbow implants, Ti rods for broken legs or arms, and the like), and methods of making and using them. Also provided are compositions and methods for accelerated cell growth.

SUMMARY

The invention provides compositions and methods for biocompatible nanostructure materials, devices and fabrication methods. Also provided are compositions and methods which enable maintained, organized and/or accelerated cell growth, including "mixed cell" growth and/or differentiation. There compositions and methods can be useful for a variety of therapeutic, disease diagnosis-prognosis, screening, injury reconstruction, orthopedic and dental, and cell-tissue supply applications.

In one embodiment, compositions and methods are provided for self-organized $TiO_2$ nanotube arrays grown on titanium metal or alloy substrate to accelerate cell proliferation. In one aspect, the base material can be pure Ti or can be an alloy based on Ti such as Ti—V—Al alloys. Other solid solution-hardened or precipitation-hardened alloys with increased mechanical strength and durability are also provided.

In another embodiment, compositions and methods are provided for a vertically aligned $TiO_2$ nanotube array adherent on Ti surface which induces strong cell adhesion and significantly enhances the formation kinetics of cells and associated bone growth. In one aspect, the $TiO_2$ nanotubes other biocompatible nanotubes are about from between about 10 to 1000 nm in diameter, about from between about 30 to 300 nm in diameter, or between about 60 to 200 nm in diameter.

In another aspect, the heights of the tubules are determined in part by a desired aspect ratio as relatively short height with an aspect ratio of about less than about 10, or about less than about 5 for ease of storing and eventual dispensing of drugs or biological agents intentionally placed within the tubule cavity. The height is determined as to reduce a possibility of long tubules breaking off and floating around in the human body. In one aspect, the height is from about 40 to 800 nm, or about from 100 to 400 nm.

In another aspect, the vertical alignment consists of an open top pore that is necessary for biocompatible implants and other related applications as described herein, as the open top of the nanowire allows the penetration of the cells into the nanopore cavity for good adhesion. In one aspect, the configuration of nano-gaps between aligned $TiO_2$ nanotubes is such that nutrients can pass through the bottom and top surfaces to feed the proliferating cells.

Also provided herein are compositions comprising multifunctional devices consisting of vertically aligned nanotubule structures capable of storing drugs or other biological agents, including drugs, growth factors, proteins, enzymes, hormones, antibiotics, antibodies, DNA, and nanoparticles, and methods for making and using them. Other biologically active materials are also provided, such as for example, vitamins and minerals.

The invention provides biocompatible vertically aligned nanotube array structures on a biocompatible substrate comprising a laterally separated nanotube arrangement wherein (i) the outer diameter of the nanotube is from between about 10 to 1000 nm, from about 30-300 nm, or from about 60-200 nm; and, (ii) the inside diameter of the nanotube is at least about 20% to 50% of the outer diameter; and (iii) the height of the nanotube is from between about 40 to 800 nm, and from between about 100 to 400 nm; and (iv) the aspect ratio is less than about 10, or less than about 5; and (v) the vertical alignment angle is within from between about 0 to 45 degrees, and from about 0 to 30 degrees off the vertical direction; and (vi) the lateral spacing between adjacent nanotubes is from between about 2 to 100 nm, and from about 5 to 30 nm; or, any combination thereof.

In one aspect, the array has a cell-growth accelerating effect, and it further comprises cells, e.g., functional cells, such as liver cells, kidney cells, nerve cells, myocytes, stem cells, supportive soft tissues such as muscles, skin cells, tendons, fibrous tissues, periodontal tissues, odontoblasts, dentinoblasts, cementoblasts, enameloblasts, odontogenic ectomesenchymal tissue, osteoblasts, osteoclasts, fibroblasts, and other cells and tissues involved in odontogenesis or bone formation, fat, blood vessels, and hard tissues such as bone and teeth, either as a single cell type culture or as a co-culture of at least two types of cells together, either in vitro or in vivo. In one aspect, the cell-growth accelerating effect induced by the biomaterial is at least by 25%; 50%; 100%; 200%; 300% or more.

In one aspect, the biocompatible vertically aligned nanotube array structure comprises a vertically aligned titanium oxide nanotube array structure on a titanium or titanium oxide substrate with a laterally separated nanotube arrangement. In one aspect, the sodium titanate nanostructures are superimposed onto the titanium oxide nanotube array structure; and in one aspect, hydroxyapatite formation is enhanced upon exposure of the nanotube array structure to simulated or living body fluid.

In one aspect, a composition (device) of the invention comprises a matrix material comprising a vertically aligned nanotube array structure comprising a biocompatible coating materials, e.g., Ti and Ti oxide, or comprising Zr, Hf, Nb, Ta, Mo, W and/or their alloys and/or oxides of these metals or alloys; and in one aspect, comprising a thickness of at least 1, 2, 3, 4 or 5 or more nm; and in one aspect the coating coverage of at least about 20%, 30%, 40%, 50%, 60%, 70%, 80% or more of the nanotube or nanopore surfaces; and in one aspect the matrix material comprises Ti, Zr, Hf, Nb, Ta, Mo, W, and/or their oxides, and/or alloys of these metals and oxides, and/or Si, Si oxide, Al, Al oxide, carbon, diamond, noble metals (such as Au, Ag, Pt and their alloys), polymer or plastic materials, or composite metals, ceramics and/or polymers.

In one aspect, the inside pore of the nanotubes comprise at least one biologically active agent selected from the group consisting of pharmaceutical compositions, therapeutic drugs, growth factors, proteins, enzymes, hormones, DNA, genes, antibiotics and antibodies. In one aspect, the inside pore of the nanotubes comprises magnetic nanoparticles.

The invention provides accelerated cell growth structures comprising the biocompatible vertically aligned nanotube array structure of the invention, and cells, wherein the cells are adherent to the nanotube structure; and cell growth is accelerated from at least about 25%, 50%, 75%, 100%, 125%, 150%, 175%, 200%, 250%, 300%, 400% or 500% or more. In one aspect, a nutrient fluid is supplied under the growing cells through a gap spacing between the nanotube; and, in one aspect, the nutrient fluid is also supplied from the top of the structure.

The invention provides orthopedic implants comprising the biocompatible vertically aligned nanotube array structure of the invention, wherein the surface is modified such that it comprises an adherent titanium oxide nanotube array; and, in one aspect, upon implantation into an animal, results in accelerated bone formation.

The invention provides dental implants comprising the biocompatible vertically aligned nanotube array structure of the invention, wherein the surface is modified such that it comprises an adherent titanium oxide nanotube array; and, in one aspect, upon implantation into an animal, results in accelerated bone formation.

The invention provides multi-functional implant devices comprising the biocompatible vertically aligned nanotube array structure of the invention, wherein the vertical pores of the nanotubes contain a reservoir of biologically active agents selected from the group consisting of pharmaceutical compositions, therapeutic drugs, cancer drugs, growth factors, proteins, enzymes, hormones, DNA, genes, antibiotics, antibodies, nanoparticles, and, in one aspect, other biologically active materials.

The invention provides multi-functional implant devices of the invention, wherein the device is designed for externally controlled release of a colloidal liquid upon application of ultrasonic or magnetic stimulation; and, in one aspect, the colloidal liquid comprises a biologically active agent and magnetic nanoparticles; and, in one aspect, the magnetic nanoparticles are selected from the group consisting of biocompatible iron-oxide particles of magnetite ($Fe_3O_4$) and maghemite ($Fe_2O_3$, or, $\gamma$-$Fe_2O_3$); and the size of the magnetic nanoparticles is from about 5-50 nm in diameter.

The invention provides multi-functional implant devices, wherein a cap is deposited at the upper end of the nanotube by oblique incident sputter deposition on a stationary or a rotating substrate; and, in one aspect, the cap is narrowed such that the colloidal liquid is retained in the nanotube before external stimulation for controlled release.

The invention provides methods of externally controlled release of a colloidal liquid into a subject comprising applying external stimulation by alternating current magnetic field to the multi-functional implant device of the invention, wherein the magnetic field causes agitation, movement and heat production from the magnetic nanoparticles comprised in the colloidal liquid resulting in its release from the implant device.

The invention provides methods for treating cancer, wherein the multi-functional implant device of the invention is implanted into a subject at the site of cancer; and, in one aspect, external stimulation is applied resulting in the local delivery of anti-cancer drugs and magnetic hyperthermia treatment.

The invention provides methods of cell proliferation comprising the biocompatible vertically aligned nanotube array structure of the invention and adherent cells, wherein upon adhesion the cells are induced to proliferate; and optionally the cells are grown in vivo, ex vivo or in vitro, and after proliferation, the cells are harvested.

The invention provides analytical diagnostic biochips comprising the biocompatible vertically aligned nanotube array structure of the invention; wherein the biochip can be used for the rapid diagnosis and detection of disease cells, cells involved in epidemic diseases or bioterrorism attacks, and cells related to forensic investigations. In one aspect, of the biocompatible vertically aligned nanotube array structures of the invention the nanotube array structure is subdivided along the X-Y matrix for the rapid detection of disease cells, cells involved in epidemic diseases or bioterrorism attacks, and cells related to forensic investigations; and the detection elements comprise the multiplicity of the nanotubes wherein the cells are placed and proliferated; and, in one aspect, the diagnosis and detection techniques utilized comprise optical detection, chemical detection, biological detection, and magnetic sensor detection.

The invention provides methods for producing biocompatible vertically aligned nanotube array structure of the invention, comprising: i) vertically aligned, biocompatible titanium oxide nanotubes with dimensions from about 100 nm outer diameter, about 90 nm inner diameter, 15 nm wall thickness, and about 250 nm height; and ii) the titanium oxide nanotube array structure is fabricated by anodization technique using a titanium sheet (optionally 25 nm thick, 99.5% purity) that is electrochemically processed, for example, in a 0.5% HF solution at 20 V for 30 min at room temperature; and iii) to crystallize the deposited amorphous-structure titanium nanotubes into the desired anatase phase, the nanotubes are heat-treated, for example, at about 500° C. for about 2 hrs. In alternative aspects, the methods for producing biocompatible vertically aligned nanotube array structure of the invention comprise: (i) providing a structure comprising vertically aligned, biocompatible titanium oxide nanotubes having dimensions of at least about 20, 30, 40, 50, 60, 70, 80, 90 or 100 or more outer diameter, or in a range from between about 10 to 100 nm outer diameter; and at least about 20, 30, 40, 50, 60, 70, 80, 90 or 100 nm or more inner diameter, or between about 10 to about 90 nm inner diameter; and at least about 10, 15, 20, 30, 40, 50, 60, 70, 80, 90 or 100 nm wall thickness; or between about 10 to 100 nm wall thickness; and/or at least about 20, 30, 40, 50, 60, 70, 80, 90, 100, 125, 150, 175, 200, 225 or 250 or more nm in height, or in a range from between about 20 to 300 nm in height; (ii) fabricating a titanium oxide nanotube array structure by anodization technique using a titanium sheet, optionally about at least 15, 20, 25, 30, 40, 50, 60, 70, 80, 90, 100, 125, 150, 175, 200, 225 or more nm thick, and optionally at least about 98%, 98.5%, 99%, or 99.5% purity, that optionally is electrochemically processed, and optionally is electrochemically processed in a 0.5% HF solution at an applied voltage of between about 10-30 V for between about 5-200 min, or 20 V for 30 min, optionally at room temperature; and (iii) crystallizing the deposited amorphous-structure titanium nanotubes into an anatase phase, wherein optionally the nanotubes are heat-treated at between about 450° C. to 550° C. for between about 0.1-24 hrs, or 500° C. for 2 hrs.

Also provided are various methods and uses of the biocompatible nanotube array devices as described herein, including for example, accelerating bone growth for orthopedic and dental implant applications; proliferation and harvesting of cells, especially rare cells; therapeutic applications via sustained release of pharmaceutical compositions; and rapid diagnosis of diseased cells, or those cells involved in epidemic diseases or bioterrorism attacks.

BRIEF DESCRIPTION OF THE DRAWINGS

The advantages, nature and additional features of the invention will appear more fully upon consideration of the illustrative embodiments described in the accompanying drawings. In the drawings:

FIG. 1(a)-(b) schematically illustrate exemplary devices comprising self-organized $TiO_2$ nanotube arrays grown on titanium substrate to accelerate cell proliferation: FIG. 1(a) illustrating a vertically aligned $TiO_2$ nanotube array; FIG. 1(b) illustrating the array with cell.

FIG. 2(a)-(b) illustrate SEM micrographs showing the microstructure of the vertically aligned $TiO_2$ nanotubes on titanium substrate; FIG. 3(a) low magnification, FIG. 3(b) high magnification.

FIG. 3(a)-(c) illustrate micrographs showing structures of the vertically aligned $TiO_2$ nanotubes on titanium substrate; FIG. 3(a) scanning electron microscope (SEM) micrograph, FIG. 3(b) longitudinal view transmission electron microscope (TEM) micrograph, FIG. 3(c) cross-sectional TEM.

FIG. 5(a)-(c) illustrate exemplary $TiO_2$ nanotube array structures with FIG. 5(a) an illustration of a micrograph of exemplary nano-inspired sodium titanate nanofiber structure on the ends of $TiO_2$ nanotubes; FIG. 5(b) a schematic illustration of an exemplary sodium titanate nanofiber structure; and FIG. 5(c) an illustration of a micrograph of an exemplary nanoscale hydroxyapatite phase rapidly formed on the NaOH treated $TiO_2$ nanotubes at a speed of about seven times faster than without the NaOH treatment.

FIG. 6: FIG. 6(a)-(b) illustrate comparative SEM micrographs showing the accelerated growth of osteoblast cells on the vertically aligned $TiO_2$ nanotubes of the invention (on anatase $TiO_2$ nanotubes at 2 hours), FIG. 6(b), as compared to the flat Ti surface (pure Ti, 12 hour growth), FIG. 6(a).

FIG. 7(a)-(b) illustrate micrographs showing the growth and adhesion of osteoblast cell on and into vertically nanoporous $TiO_2$ nanotubes of the invention; FIG. 7(a) low magnification, FIG. 7(b) higher magnification.

FIG. 8(a)-(c) illustrate back scattered electron SEM images of osteoblast cells on: FIG. 8(a) only Ti, FIG. 8(b) as-deposited (amorphous) aligned $TiO_2$ nanotubes, and FIG. 8(c) annealed, anatase $TiO_2$ nanotubes of the invention.

FIG. 10(a)-(b) illustrate comparative pictures of stem cell adhesion and growth shown as back scattered electron SEM images; FIG. 10(a) on flat Ti surface, FIG. 10(b) on an exemplary anatase-phase vertically aligned $TiO_2$ nanotube array of the invention.

FIG. 11(a)-(c) illustrate various exemplary orthopedic body implants of the invention comprising $TiO_2$ nanotubes or associated variations of the invention; FIG. 11(a), illustrating implants as orthopaedic and dental implants, including dental and periodontal implants, elbow implants, hip implants, knee implants, leg implants; FIG. 11(b) illustrating implants as implanted cells or organs, e.g., an artificial liver device; FIG. 11(c) illustrating implants as drug delivery devices for, e.g., stents, therapeutic devices, e.g., with insulin, or for cancer.

FIG. 12(a)-(d) illustrate examples of $TiO_2$ nanotube-based implants of the invention containing slow-releasing biological agents stored in the vertically aligned nanotube pores, and the process of cell growth: FIG. 12(a), with $TiO_2$ nanotubes (on a Ti substrate); FIG. 12(b), with biological additives; FIG. 12(c), with cells; FIG. 12(c), with growing cells adherent to the $TiO_2$ nanotubes.

FIG. 13(a)-(b) illustrate examples of $TiO_2$ nanotube-based implants of the invention comprising: FIG. 13(a) nanotubes with therapeutic agents plus magnetic nanoparticles stored in the vertically aligned nanotube pores; and FIG. 13(b) the process of drug release via magnetic particle movement or heating by the onset of applied magnetic field.

FIG. 14(a)-(b) illustrate an exemplary implant device of the invention in which the top open ends of the vertically aligned $TiO_2$ nanotubes which are intentionally made to be narrower in passage diameter after the magnetic nanoparticles are incorporated, FIG. 14(a); and an exemplary implant device with therapeutic medicine, FIG. 14(b).

FIG. 16: FIG. 16(a)-(b) are schematic illustrations of an exemplary cell-proliferation device of the invention based on $TiO_2$ nanotubes; showing cells proliferating on the $TiO_2$ nanotubes, FIG. 16(a); and a schematic of cell harvesting by trypsinization (followed by centrifugation), FIG. 16(b).

FIG. 18(a)-(c) is a schematic illustration of an exemplary cell analysis device which comprises $TiO_2$ nanotube arrays capable of accelerating cell proliferation to enhance cell-based assays; FIG. 18(a), illustrates optical detection by, e.g., microscope, fluorescent microscope, or CCD camera sensing of fluorescent or quantum dot tagged cells; FIG. 18(b), illustrates chemical or biological detection, e.g., based on signature reactions; FIG. 18(c), illustrates magnetic sensor detection, e.g., by using magnetically targeted antibody.

DETAILED DESCRIPTION

The invention provides compositions comprising multifunctional biocompatible implants and devices that accelerate cell growth comprising (or consisting of) biocompatible aligned nanotubule structures and methods for fabricating such devices, and methods for making and using them.

Figure 1:
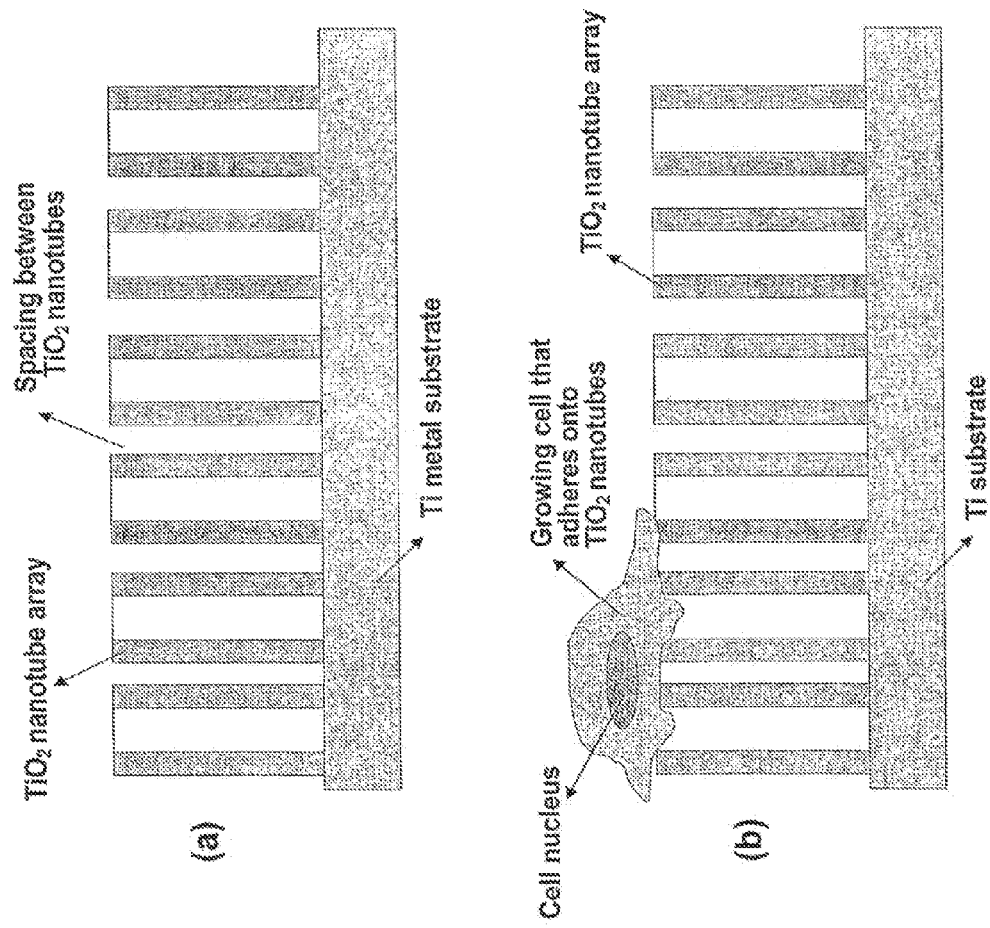
FIG. 1.
Figure 2:
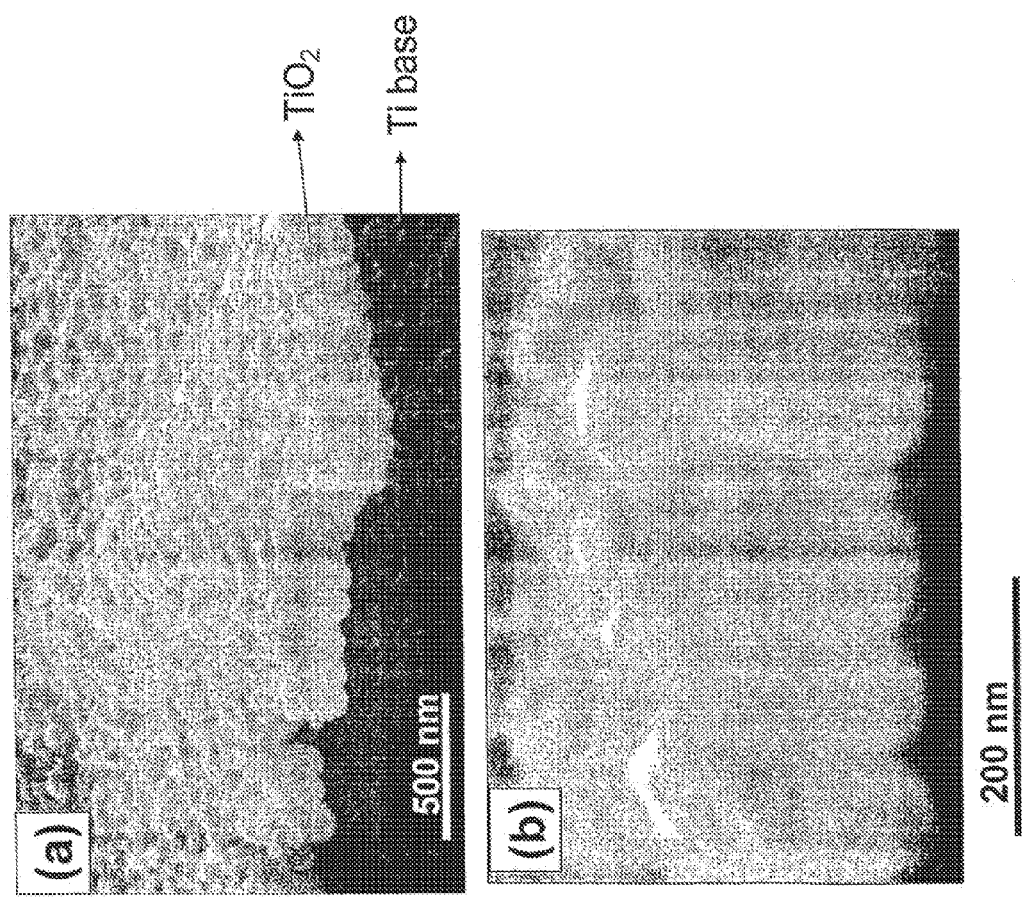
FIG. 2.
Figure 3:
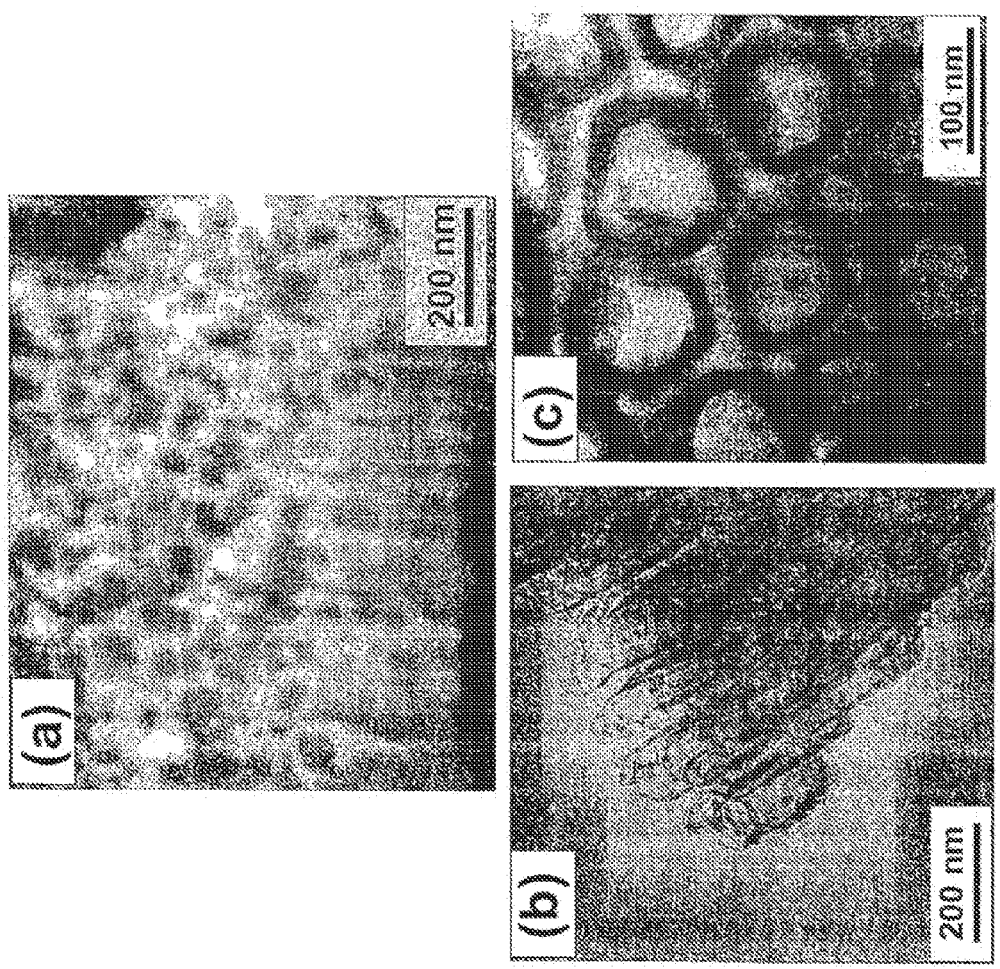
FIG. 3.

The invention provides compositions comprising vertically aligned $TiO_2$ nanotube arrays adherent on titanium surfaces, see, e.g., FIGS. 1, 2 and 3. Such nanotube arrays are capable of inducing strong cell adhesion and inducing rapid proliferation of cells, such as those involved in bone formation. The configuration of nano-gaps between the aligned TiO$_2$ nanotubes is such that nutrients can pass between the bottom as well as the top surface in order to feed the proliferating adherent cells. Adherent cells are generally healthy and fast growing, while the non-adherent cells often exhibit reduced or minimal growth.

Biocompatible implants consisting of TiO$_2$ nanotubes are provided that have use in osteogenic and dental applications. Also provided are multifunctional TiO$_2$ nanotubes devices capable of storing pharmaceutical compositions and biological agents. Examples include drugs, growth factors, hormones, proteins, enzymes, antibiotics, antibodies, DNA, nanoparticles, vitamins and minerals. The biocompatible TiO$_2$ nanotubes as described herein, are useful in a variety of applications including accelerating bone growth for orthopedic and dental repair; in vivo and in vitro accelerated growth of cells including functional cells (such as liver cells, kidney cells, nerve cells, myocytes, stem cells) or supportive tissues (soft tissues such as muscles, tendons, fibrous tissues, periodontal tissues, fat, blood vessels, or hard tissues such as bone and teeth), proliferation and/or harvesting of cells to be supplied for therapeutics and laboratory experiments, particularly rare cell types such as stem cells or disease cells; therapeutic applications for local sustained drug release; and rapid diagnosis of cell-based conditions, toxicities and/or diseases involved in, for example, infections, epidemics and/or biological warfare agent or toxin exposures.

EXAMPLES

The following examples are included for illustrative purposes only and are not intended to limit the scope of the invention.

Example 1

Bone- and Cell-Growth Promoting Nanostructures

An example of an exemplary bone- and cell-growth promoting nanostructure of the invention is shown in FIGS. 2 and 3. These exemplary structures of the invention are vertically aligned, biocompatible TiO$_2$ with a typical dimension of the hollow nanotubes as shown as being approximately (about) 100 nm outer diameter and approximately 70 nm inner diameter, with approximately 15 nm in wall thickness, and approximately 250 nm in height.

The exemplary TiO$_2$ nanotube array structure shown in FIG. 1-3 was fabricated by an exemplary anodization technique using a Ti sheet (0.25 mm thick, 99.5% purity) which is electrochemically processed in a 0.5% HF solution at 20 V for 30 min at room temperature. A platinum electrode (thickness: 0.1 mm, purity: 99.99%) was used as the cathode. To crystallize the deposited amorphous-structured TiO$_2$ nanotubes into the desired anatase phase, the specimens were heat-treated at 500° C. for 2 hrs. In one aspect, the amorphous TiO$_2$ nanotubes are crystallized to anatase phase by heat treatment, because an amorphous TiO$_2$ phase tends to be more susceptible to breakage by external stresses as compared to a crystalline phase.

For evaluation of bone growth on bioactive surface in terms of hydroxyapatite (HAp) formation, the TiO$_2$ nanotube specimens of FIG. 2 were soaked for 1, 2, 3 and 5 days, in 20 mL of a simulated body fluid (SBF) solution at 36.5° C., which contained ion concentrations nearly equal to those of human blood plasma with respect to Na$^+$, K$^+$, Ca$^{2+}$, Mg$^{2+}$, Cl$^-$, HCO$_3^-$, HPO$_4^{2-}$, and SO$_4^{2-}$ concentrations. After a pre-determined soaking time, the specimens were removed from the SBF solution, gently rinsed with distilled water, and then dried at 60° C. for 24 hrs.

Figure 4:
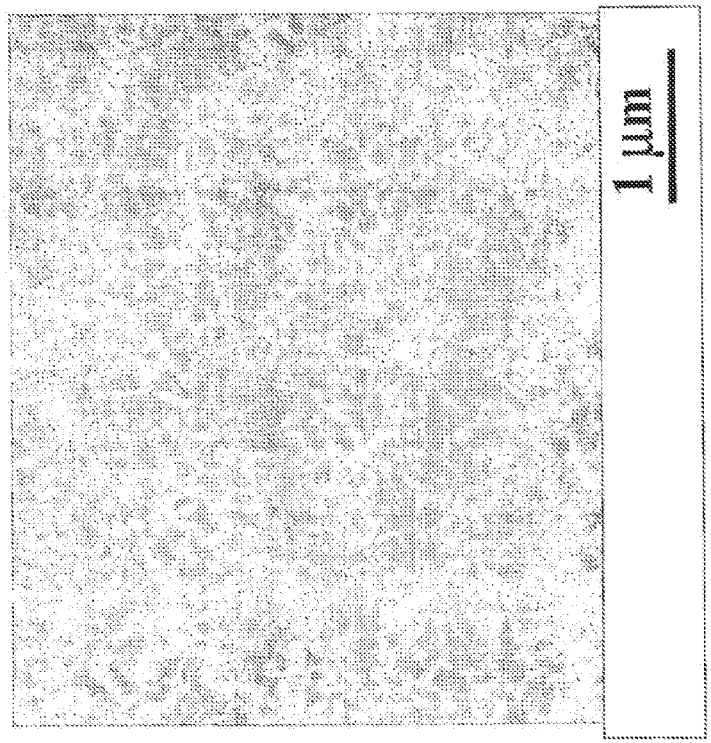
FIG. 4 illustrates a SEM micrograph showing the accelerated growth of hydroxyapatite on the aligned $TiO_2$ nanotubes about 2-4 times faster than flat Ti surface.

Another important factor for healthy cell growth is a continuous supply of nutrients (e.g. proteins, mineral ions, fluid, etc.) to the cell through the flow of body fluid. The gap (i.e. spacing) between adjacent TiO$_2$ nanotubules in FIG. 1-3 serves such a function by allowing the body fluid to continuously pass through and thereby supply nutrients to the bottom side of the growing cells. The desired gap between the nanotubules is in the range of about 2-100 nm, or about 5-30 nm. Too small a gap reduces the effectiveness of nutrient body fluid flow while too large a gap can pose a danger of reduced mechanical stability in the event of vertical or lateral stress or pressure. A transmission electron microscope (TEM) photograph shown for an exemplary TiO$_2$ nanotubule array structure, FIGS. 3(b) and (c), gives an average of approximately 15 nm spacing between the nanotubes. The SEM micrograph in FIG. 4 shows the accelerated growth of hydroxyapatite on the aligned TiO$_2$ nanotubes which occurred, at least about 2-4 times faster than on flat Ti surface.

Example 2

Nanofiber-Like or Nanoribbon-Like Structures

On exposure of the TiO$_2$ nanotubes to a 5 mole NaOH solution at approximately 60° C. for 60 minutes, it has been found that an additional, extremely fine, and predominantly nanofiber-like or nanoribbon-like structure of sodium titanate compound is introduced on the very top of the TiO$_2$ nanotubes as shown in FIG. 5(a). In this example, preferential occurrence of nanofibers at the top of nanotubes is presumably because of the nanotube contact with NaOH solution above and also possibly due to the surface-tension-related difficulty of NaOH solution getting into nanopores within and in-between TiO$_2$ nanotubes, as illustrated in FIG. 5(b). Compositional analysis by EDXA (energy dispersive x-ray analysis) in SEM confirms the presence of Na, Ti and O after the exposure of TiO$_2$ nanotubes to NaOH. The sodium titanate so introduced exhibits an extremely fine-scale nanofiber configuration with a dimension of approximately 8 nm in average diameter and approximately 50-100 nm long.

Figure 5:
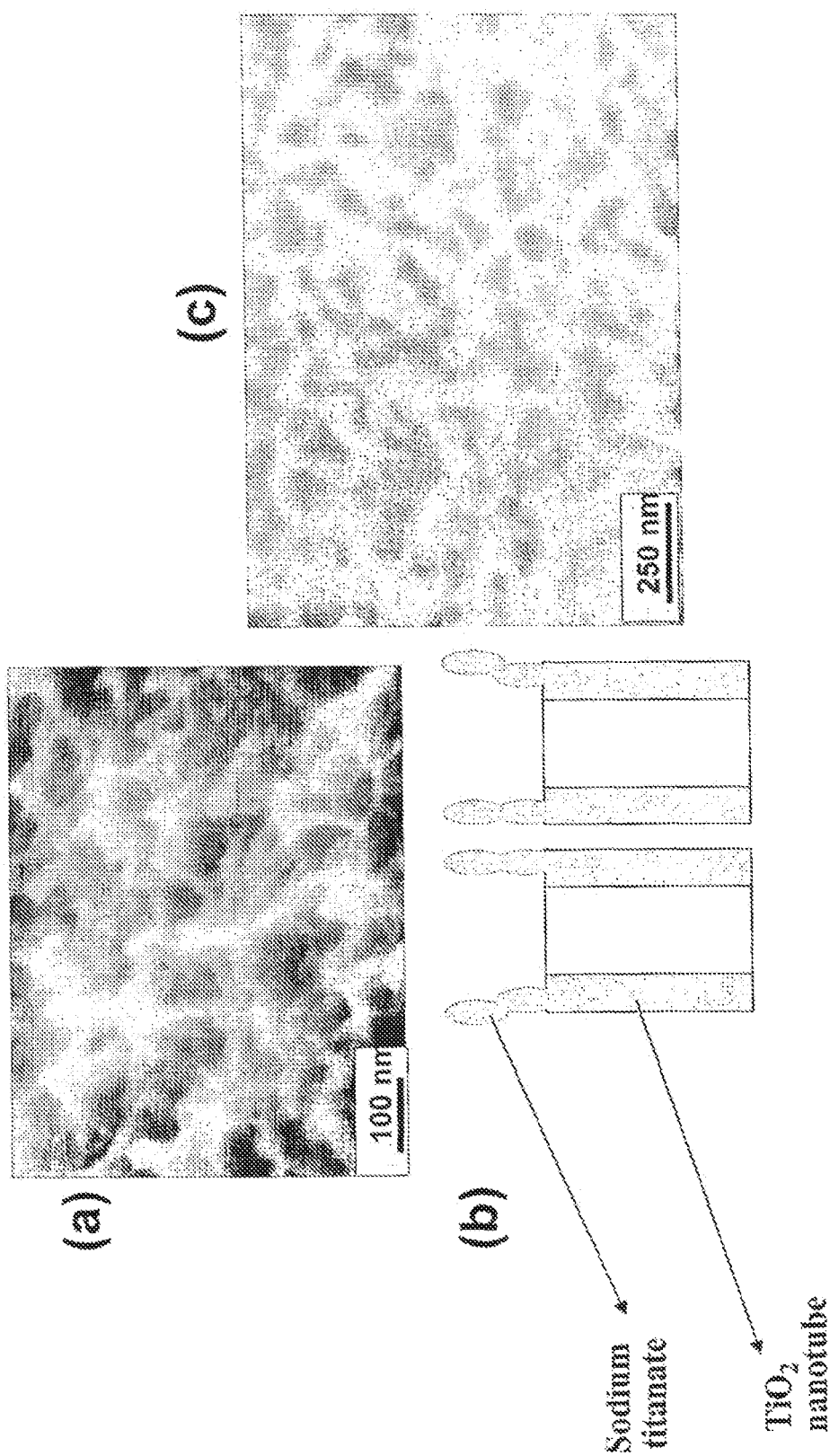
FIG. 5.

The growth of even finer scale structure from a given nanostructure as demonstrated in FIG. 5 can be of significant interest for basic materials development for nanotechnology, since such a concept can be utilized as one of the novel and efficient ways of creating extremely fine nanostructures in many different materials. It is believed that the nanofiber-shaped sodium titanate phase is formed in such a fine scale because of the physically confined geometry of the host structure, TiO$_2$ nanotubes. Since the nucleation and growth of the sodium titanate phase occurs on TiO$_2$ which has the ring-shaped end material facing outward with the tube wall thickness of only approximately 15 nm, the sodium titanate phase growing from the host surface is likely to be on the order of or less than this dimension, as is actually observed. The process of forming a "Nano-inspired Nanostructure" can also be viewed as a hierarchical construction of nanostructure, which can be important for nanostructural engineering, for example, for creation of catalyst structures with ultra-large surface area.

The formation of bone-growth related material such as the calcium phosphate mineral, hydroxyapatite (Ca$_{10}$(PO$_4$)$_6$(OH)$_2$), is an important issue for orthopedic and dental implants. Bone is a calcium phosphate based mineral which contains approximately 70% hydroxyapatite-like material with the remainder consisting mostly of collagen.

The "Nano-inspired Nanostructure" formation as shown in FIG. 5 has been found to have a profound effect on hydroxyapatite formation. When the $TiO_2$ nanotube surface covered with "Nano-inspired Nanostructure" of sodium titanate is subjected to the SBF (simulated body fluid) solution for formation of hydroxyapatite, it is seen that it takes less than one day soaking in SBF to have a complete coverage of the sample surface with hydroxyapatite. The formation of hydroxyapatite in the $TiO_2$ nanotube surface containing sodium titanate nanofibers is significantly accelerated as compared with the same $TiO_2$ nanotube surface but without the sodium titanate nanofibers. In the latter case, it took approximately 7 days for formation of detectable amount of hydroxyapatite, as compared with just one day for the sample covered with sodium titanate nanofibers.

As is evident from FIG. 5(c), the hydroxyapatite formed is by itself nanostructured with a nanofiber morphology resembling that of the sodium titanate. The nanofiber feature size of the hydroxyapatite phase formed is approximately 25 nm average diameter. It appears that the nanofiber hydroxyapatite nucleated and grew from the nanofiber sodium titanate precursor. The approximately 25 nm average diameter of the nanofiber hydroxyapatite is somewhat coarser than its precursor sodium titanate (approximately 8 nm) as might be anticipated for the extended (1 day) exposure to SBF. The nanofiber hydroxyapatite of such a dimension is, to the best of our knowledge, the smallest feature hydroxyapatite reported so far.

Example 3

Osteoblast Cell Growth on Nanotubes of the Invention

In order to estimate the effect of having an extremely fine nanostructure such as the vertically aligned $TiO_2$ nanotubes on cell growth behavior, an osteoblast cell growth on $TiO_2$ nanotubes was performed. The results demonstrate (indicate) that the introduction of nanostructure significantly improves bioactivity of implant and enhances osteoblast adhesion and growth. An adhesion of anchorage-dependent cells such as osteoblasts is a necessary prerequisite to subsequent cell functions such as synthesis of extracellular matrix proteins, and formation of mineral deposits. In general, many types of cells beside the osteoblast cells remain healthy and grow fast if they are well-adhered onto a substrate surface, particularly a nanostructure surface of this invention, while the cells not adhering to the surface tend to stop growing.

All the experimental specimens (0.5×0.5 $cm^2$) used for cell adhesion assays were sterilized by autoclaving. A pure Ti sheet polished by emery paper (#600 grit size) and chemically cleaned was used as a control group sample. For cell adhesion studies, MC3T3-E1 osteoblast cells (rat cells of the type CRL-2593, sub-clone 4, ATCC, Rockville, Md.) were used. Each 1 mL of cells was mixed with 10 ml of alpha minimum essential medium (α-MEM) in the presence of 10% fetal bovine serum (FBS) and 1% penicillin-streptomycin. The cell suspension was plated in a cell culture dish and incubated under 37° C., 5% $CO_2$ environment. When the concentration of the MC3T3-E1 osteoblastic cells reached approximately $3×10^5$ cells/ml, they were seeded onto the experimental substrate of interest (Ti $O_2$ or Ti) which were then placed on a 12-well polystyrene plate, and stored in a $CO_2$ incubator for 2, 12, 24 or 48 hrs to observe cell morphology and count viable attached cells as a function of incubation time. The concentration of the cells seeded onto the specimen substrate was approximately $5×10^4$ cells/ml.

After the selected incubation period, the samples were washed with 0.1 M phosphate buffer solution (PBS) and distilled water, respectively, and fixed with 2.5% glutaraldehyde in 0.1 M PBS for 1 hr. After fixing, they were rinsed three times with 0.1 M PBS for 10 min. For microscopic examination of cell structures and morphologies, the samples were dehydrated in a graded series of alcohol (50%, 75%, 90% and 100%) for 10 min and subsequently dried by supercritical point $CO_2$. The dehydrated samples were sputter-coated with approximately 2 nm thick gold for SEM examination. The morphology of $TiO_2$ nanotubes as well as that of the adhered cells was observed using SEM and TEM. In the quantitative assay, the adhered cells on sample surface were counted from back-scattered SEM images.

Shown in FIG. 6 are comparative SEM micrographs of the MC3T3-E1 cells cultured on pure Ti vs $TiO_2$ nanotubes. After approximately 2 hours of incubation, the osteoblast cells cultured on Ti surface, still remained in their original round shape, whereas the cells cultured on $TiO_2$ nanotubes attached onto the surface and started to spread by filopodia. It is well known that pure Ti has a few nm thick, native $TiO_2$ passivation layer which eventually causes the adhesion of osteoblastic cells, albeit at a much slower speed than the nanotube surface investigated in this work. It took approximately 12 hrs for a noticeable adhesion and propagation of the osteoblast cells to take place on Ti as shown in FIG. 6(a). The growths of cells and propagation of filopodia are compared for the Ti sample (FIG. 6(a)) versus the $TiO_2$ nanotubes (FIG. 6(b)) after 12 hrs and 2 hrs of incubation, respectively.

As discussed earlier, micrometer-sized bioactive materials (such as a hydroxyapatite layer coated on Ti implant surface) tend to exhibit interfacial failures, due to the much higher interfacial stress build-up between the dissimilar materials and also due too the lack of strong chemical bonding or the absence of sharing of common element species between the implant and the coating. The vertically aligned $TiO_2$ nanotube coating as described herein has the following structural advantages for reduced interfacial failure.

i. The exemplary vertically aligned $TiO_2$ nanotube coating is fabricated to be thin, e.g., less than about 800 nm, or less than about 400 nm.
 ii. The coating has a strong chemical bonding on the Ti substrate as the $TiO_2$ nanotube coating was prepared via chemical process, and since a common element of Ti is shared by the substrate and the coating.
 iii. The $TiO_2$ nanotube structure of FIG. 1-3 is made to be not continuous but is discrete, with a gap between adjacent nanotubes of approximately 15 nm. The desired lateral gap dimension is in the range of about 2-100 nm, or about 5-30 nm. Such a lateral sub-division of a nanotube array structure is important for minimizing the interfacial stresses between two dissimilar materials joined together, with the two materials involved often having substantially different crystal structure, lattice parameter, and coefficient of thermal expansion.

It has experimentally been confirmed that the vertically aligned $TiO_2$ nanotubes are strongly adherent to the Ti metal base, as it was very difficult to remove the nanotubes from the Ti surface by attempting to delaminate or scrape off or by bending of the Ti substrate. Such a strongly bonded and stable bone-promoting coating is important, especially in consideration of possible interference by fibroblast cells during bone growth near the Ti implants. It is well known that fibroblast cells are prone to attach on smooth surface layer in contrast to the osteoblastic cells which can attach well on rough surface.

(see e.g. Salata, Jour. of Nanobiotechnology (2): 3 (2004)). Once an opportunity and time is given for the fibrous tissues to form at the boundary interface between the implant and the growing bone, these tissues keep osteoblasts from adhering onto the surface of Ti implant, causing the undesirable loosening of the Ti implant. A rapid and strong adhesion of osteoblasts on implant surface is therefore an essential factor for successful bone growth.

In addition to the advantages in mechanical properties, the gaps present between adjacent $TiO_2$ nanotubes may also be useful as a pathway for continuous supply of the body fluid with ions, nutrients, proteins, etc. This is likely to contribute positively to the health of the growing cells. In the absence of such pathways, the proliferating cells will eventually completely cover the bioactive implant material surface, and the bottom surface of the growing osteoblast cells would then have very limited access to body fluid.

Presented in FIG. 7(a)-(b) are SEM micrographs showing the growth and adhesion of the osteoblast cells (after 2 hrs) on vertically nanoporous $TiO_2$ nanotubes. The micrographs clearly indicate that the filopodia of propagating osteoblast cells actually go into the vertical nanopores of the $TiO_2$ nanotubes. The observed rapid adherence and spread of osteoblastic cells cultured on $TiO_2$ nanotubes could be caused by three reasons. First, vertically aligned $TiO_2$ nanotubes exhibit enormously larger surface areas than the flat Ti surface. Second, the pronounced vertical topology contributes to the locked-in cell configuration. Thirdly, the pathway in-between $TiO_2$ nanotube arrays can allow the passage of body fluid and act as the supply/storage route of nutrient, which is an essential biological element for cell growth.

Figure 8:
FIG. 8.
Figure 9:
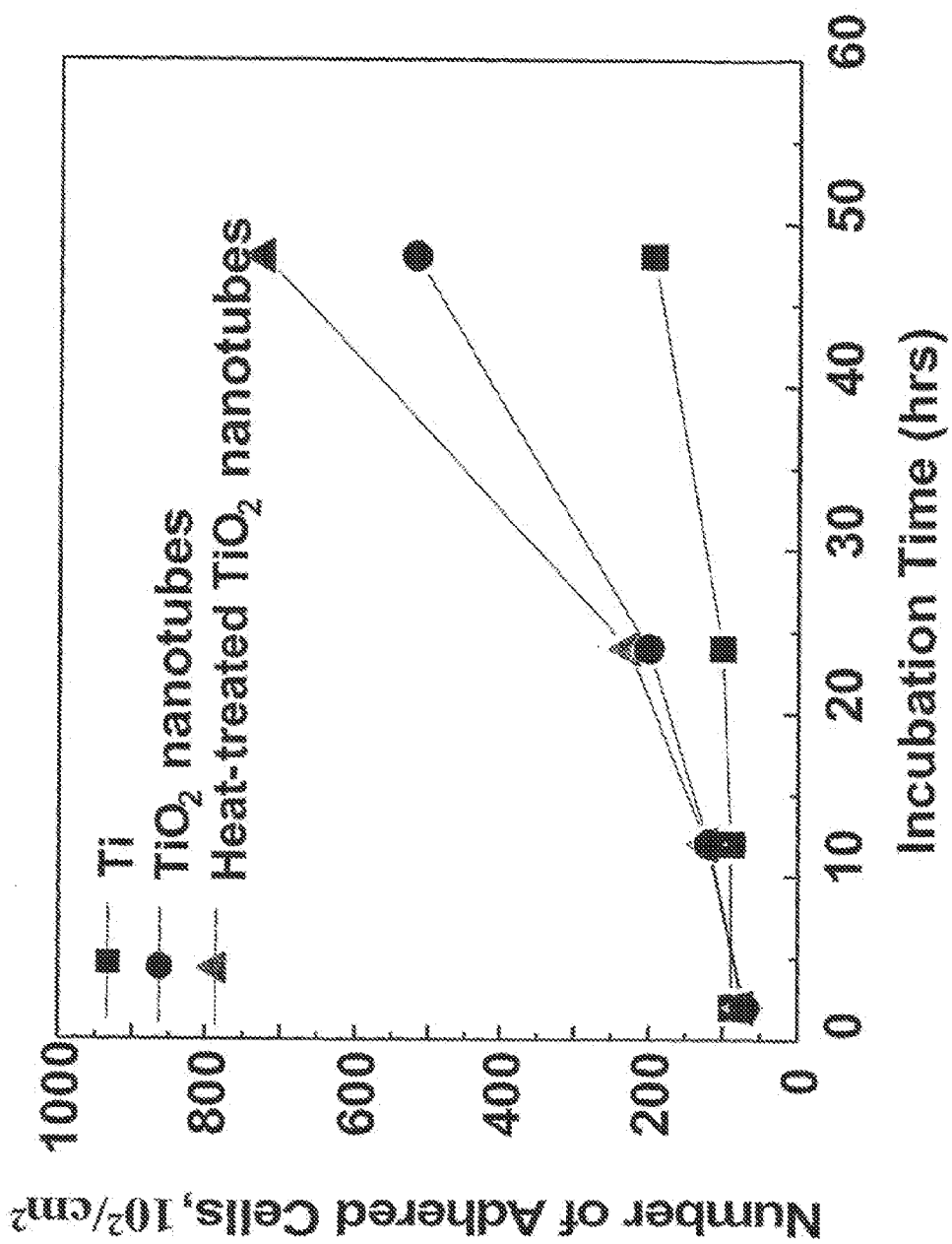
FIG. 9 illustrates a plot of the counted number of adhered cells (per square centimeter) as a function of incubation period in hours on the surface of Ti only, amorphous $TiO_2$ nanotubes, and anatase $TiO_2$ nanotubes of the invention.

FIG. 8 represents the comparative back-scattered SEM micrographs of the cells cultured on (a) pure Ti, (b) amorphous $TiO_2$ nanotubes, and (c) anatase $TiO_2$ nanotubes after 48 hrs of incubation. It is evident that adhesion and growth of the MC3T3-E1 osteoblast cells is significantly accelerated on $TiO_2$ nanotubes, and more so on anatase $TiO_2$ nanotubes, as compared to the amorphous $TiO_2$ nanotubes. The plot of the number of adhered cells as a function of culture period, FIG. 9, clearly confirms this trend, with the speed of cell adhesion and growth on anatase $TiO_2$ nanotubes being significantly higher after 48 hr culture, by as much as approximately 400% as compared to the Ti surface. It is noted that at the early stage, (e.g., after 2 hrs. incubation) there was no significant statistical difference in the data among the three surfaces investigated. However, the number of attached cells on the $TiO_2$ nanotubes dramatically increases as the culture time is extended to 12, 24 and 48 hrs.

Figure 10:
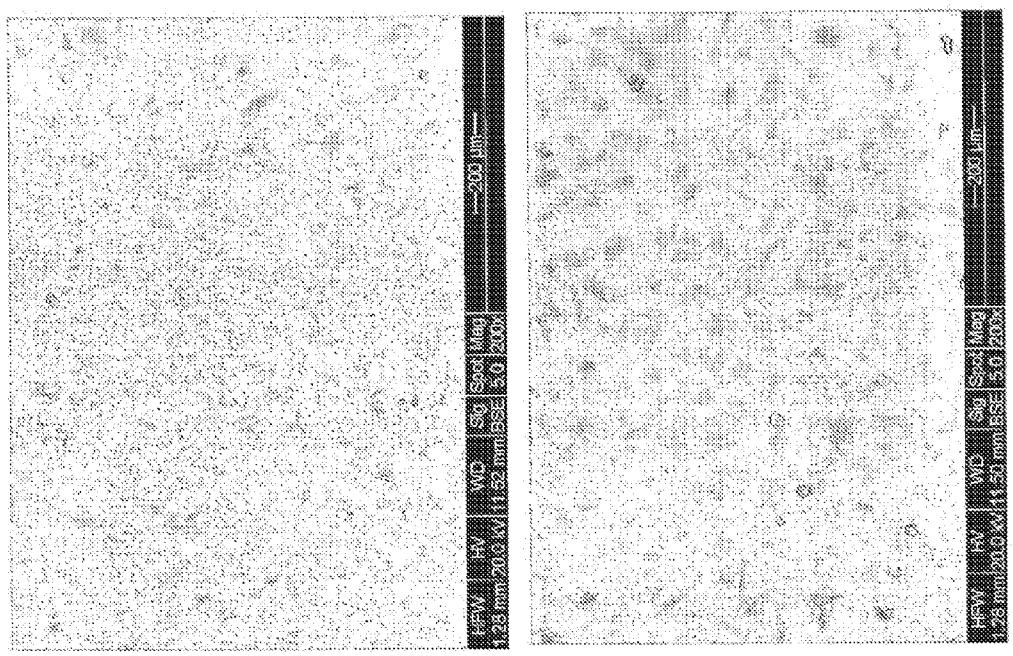
FIG. 10.

The accelerated cell growth on vertical $TiO_2$ nanotube array is not restricted to the osteoblast cells. A similar behavior is seen with other cells, for example, it has been found that stem cell growth is substantially accelerated on identical $TiO_2$ nanotube array. This is shown in FIG. 10 as comparative back scattered electron SEM images. The cells used were bone marrow-derived, adult rat mesenchymal stem cells grown on plain flat Ti for 12 hr incubation, FIG. 10(a), and on anatase $TiO_2$ nanotubes for identical incubation period. As is evident from FIG. 10, the stem cells adhere and grow much faster on the vertically aligned and laterally separated $TiO_2$ nanotubes than on the plain flat Ti.

In stem cell research and applications for curing of diseases, the enrichment of stem cells is a very critical issue. The stem cells are often rare and the available quantity is not always sufficient for many research and therapeutic uses. The discovery that the $TiO_2$ nanotubes can significantly accelerate the kinetics of stem cell proliferation is therefore important from a practical point of view. This exemplary vertically aligned $TiO_2$ nanotube array can also be utilized for such accelerated proliferation of many other types of cells.

The vertically aligned and laterally separated $TiO_2$ nanotube arrays as described herein have many useful applications some of which are listed below.

1. Orthopedic and Dental Implants with Accelerated Bone Formation

Figure 11:
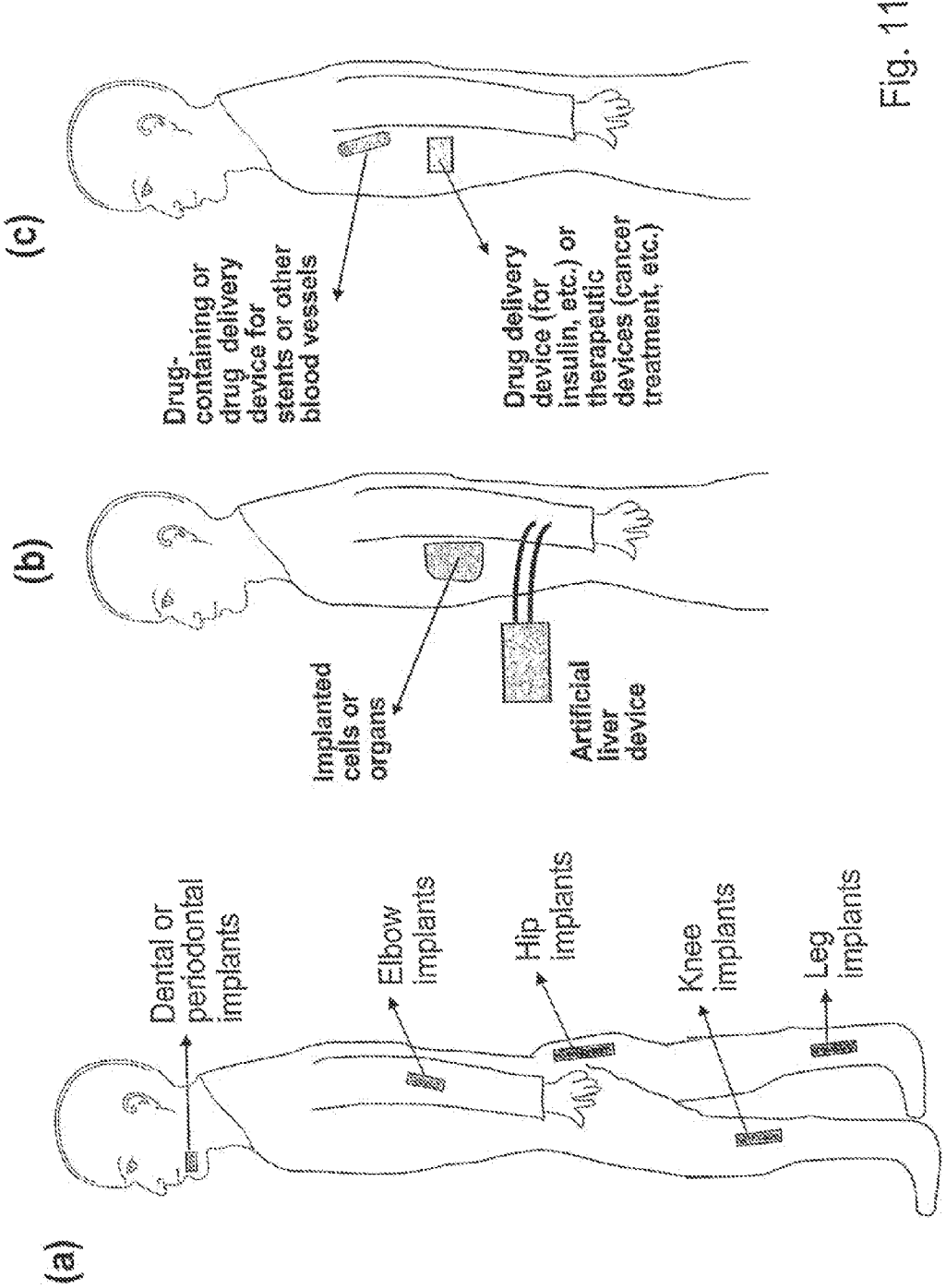
FIG. 11.

The invention provides orthopaedic (orthopedic) and dental implants capable of accelerated bone formation. In one aspect, fast recovery of Ti implant patients is an important benefit of using a $TiO_2$ nanotube array of the invention. Ti or Ti alloy implants (for example, hip implants, knee implants, elbow implants, Ti rods for broken legs or arms, etc., of the invention) with the surface modified to have a layer of the exemplary adherent $TiO_2$ nanotube array can be placed in human or animal body as illustrated in FIG. 11.

2. Multi-Functional Implants

The invention provides multi-functional implants comprising vertical pores of $TiO_2$ nanotubes. The vertical pores of the $TiO_2$ nanotubes of the invention can be utilized as a reservoir of various biologically active agents such as therapeutic drugs, growth factors, proteins, enzymes, hormones, DNA, genes, antibiotics, antibodies, magnetic nanoparticles, and so forth. The nanosize pores of $TiO_2$ nanotubes of the invention, as compared to microsized pores, have an advantage of being able to keep the stored biological agents much longer and allow slower release over a longer period of time. Multifunctional orthopedic or dental Ti implants of the invention can also continuously supply biological agents like a growth factor or bone morphogenic protein (BMP) that can be slowly released from the $TiO_2$ nanotube surface layer can be much more efficient than a simple implant material. In one aspect, slow release of antibiotics (such as penicillin, streptomycin, vancomycin) can prevent infections near the implant. Since both Ti and $TiO_2$ are biocompatible, the implant (not necessarily bone-related implants, but including other implants of the invention) can be pre-filled with one or more types of drugs can be used as a source of slow drug release within a human body, for example for treatment of cancer.

3. Externally Controllable Drug Release Devices

Figure 13:
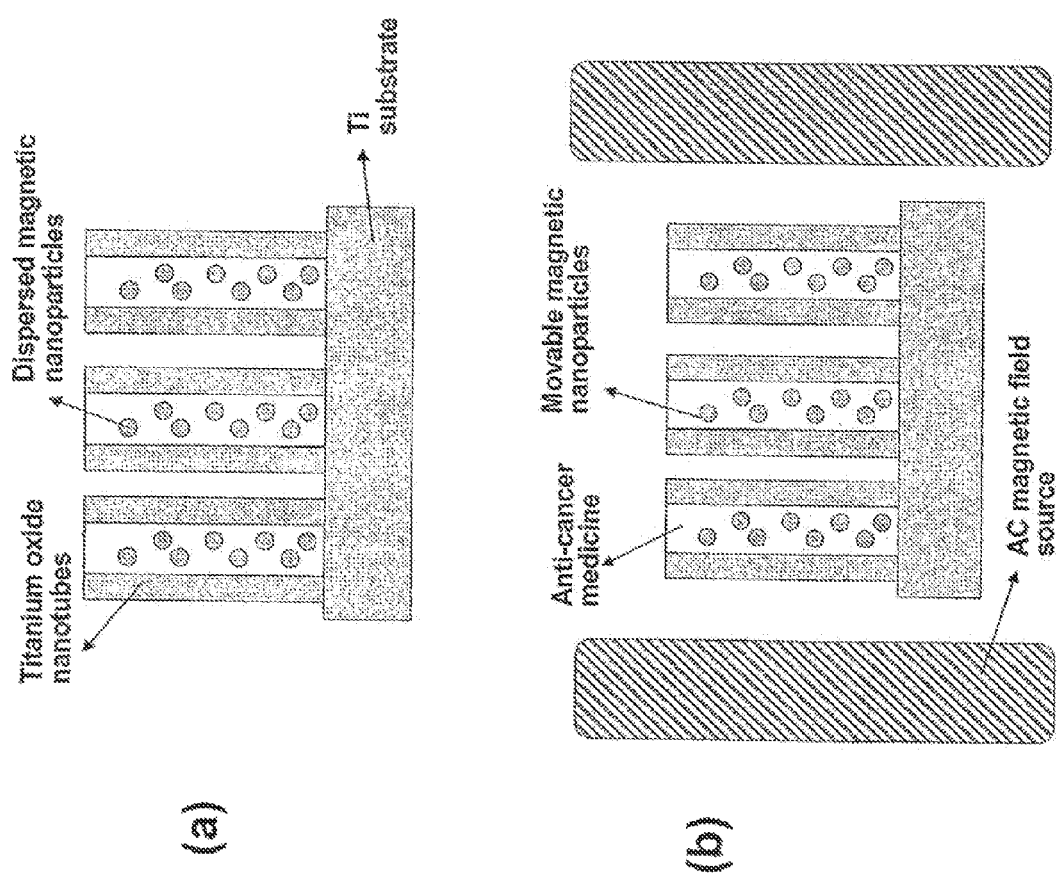
FIG. 13.
Figure 14:
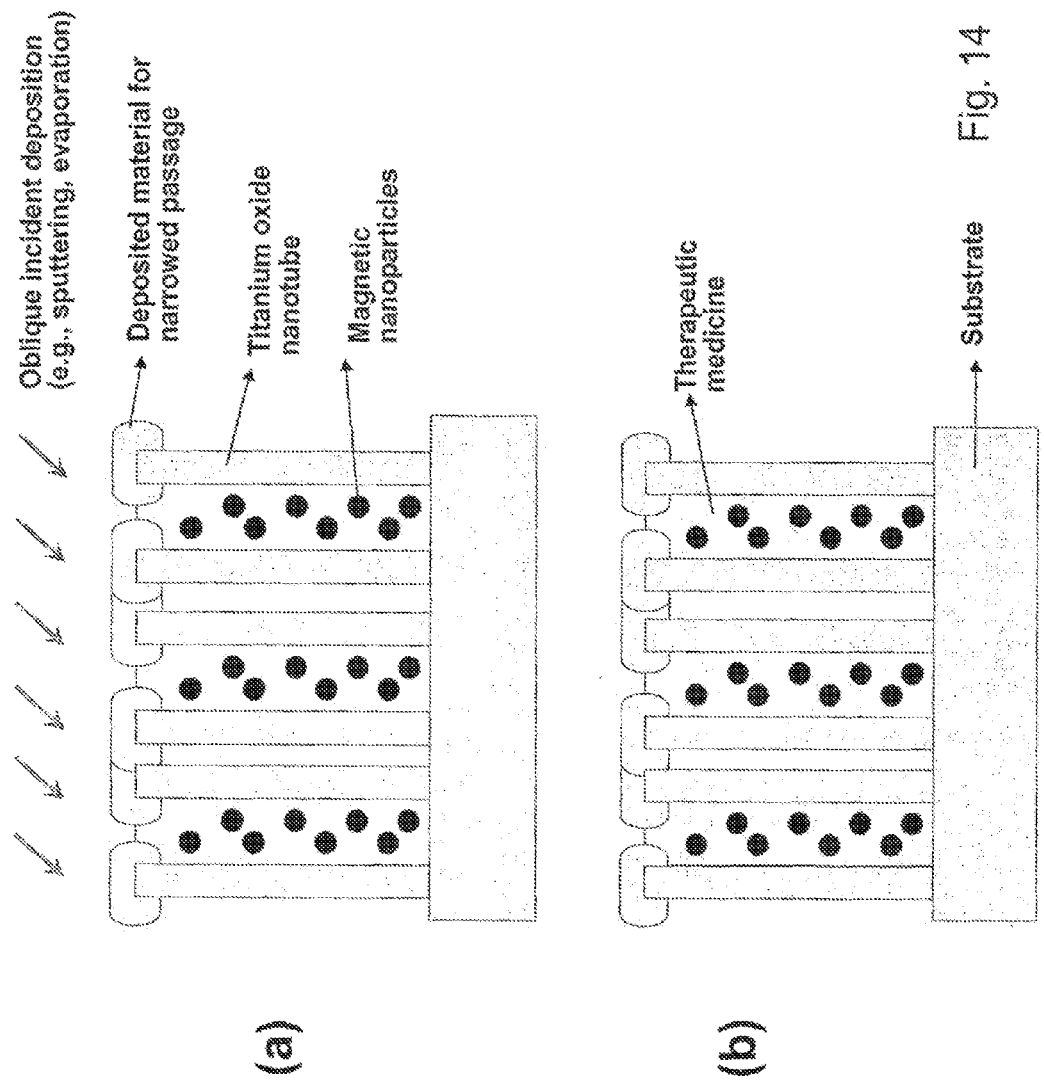
FIG. 14.

The invention provides externally controllable drug release devices. In one aspect, the invention provides externally controllable drug release devices in the form of, or in conjunction with, the multi-functional implants. The externally controllable drug release devices and/or the multi-functional implants can comprise magnetic nanoparticles, as illustrated in FIGS. 13 and 14. The externally controllable drug release devices and/or the multi-functional implants can be used in the magnetic hyperthermia treatment of cancer, e.g., using high frequency alternating current (AC) magnetic fields.

In one aspect of the externally controllable drug release devices, the drug comprises a biological agent, such as a cancer drug, which can be placed together with magnetic nanoparticles, in the nanopores of the $TiO_2$ nanotubes, which can be made to be released, for example, by ultrasonic or magnetic agitation of the colloidal liquid containing the mixture of the drug solution and the particles. Suitable magnetic nanoparticles for such use include biocompatible iron-oxide particles of magnetite ($Fe_3O_4$) or maghemite ($\gamma$-$Fe_2O_3$) in the particle size regime of 5-50 nm in average diameter.

Figure 15:
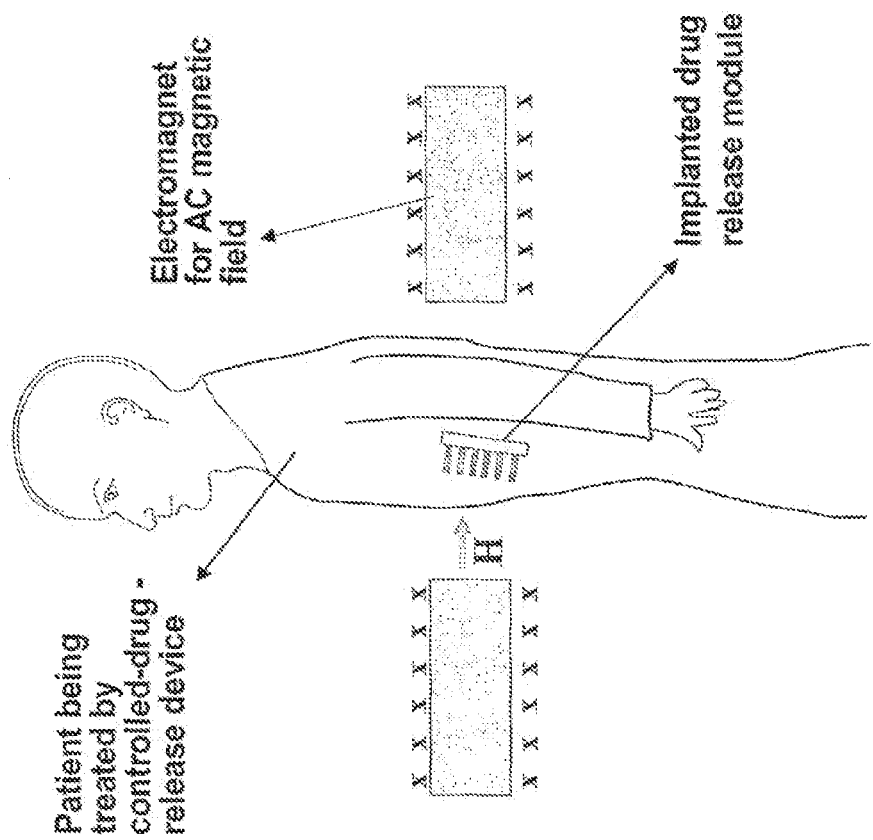
FIG. 15 is a schematic illustration of a patient treated by a controlled drug release implant device of the invention actuated by external stimuli—in this example an electromagnet for generating an AC magnetic field.

External stimulation of the magnetic nanoparticles by alternating current (AC) magnetic field can help release the cancer drug by mechanical agitation/movement of the magnetic particles or by heating of the drug-particle mixture due to the AC magnetic field. In FIG. 14, the diagram depicts a configuration of the $TiO_2$ nanotubes, which have caps at the upper end with a narrower passage diameter so that the drug, growth factor, protein or other biological agents are kept in the nanopore for a longer period of time with a slower release rate. The cap is deposited by oblique incident sputter deposition on a rotating substrate as illustrated in FIG. 14. Shown in FIG. 15 is a schematic illustration of a patient treated by a controlled drug release implant device actuated by external stimuli.

Magnetic-nanoparticle-containing $TiO_2$ nanotube structure such as illustrated in FIGS. 13 and 14 can also be useful for treatment of cancer via a combination of externally controllable drug release and magnetic hyperthermia treatment, for example, as an implant in bone cancer area or other cancer regions in general. There has been much progress in the magnetic hyperthermia treatment of cancer using high frequency alternating current (AC) magnetic field (see e.g. Jordan et al., Journal of Magnetism and Magnetic Materials 194:185-196 (1999)). However, the removal of the nanoparticles after the cancer treatment is an issue. The residue nanoparticles in the human body can be harmful for health and may possibly be a cause for side effects (Hafeli et al., Journal of Magnetism and Magnetic Materials 194:76-82 (1999) and Hoet et al., Journal of Nanobiotechnology, 2:12-27 (2004)).

For treatment of bone cancer, a physical confinement of magnetic nanoparticles within $Fe_2O_3$—CaO—$SiO_2$ glass-ceramics was employed to minimize such nanoparticle side effect (Ebisawa et al., Journal of the Ceramic Society of Japan, Int'l Edition, 99: 8-13 (1991), Ikenaga et al., Journal of Orthopaedic Research 11:849-955 (1993), and Konaka et al., Journal of the Ceramic Society of Japan, Intl. Edition, 105: 894-898 (1997)). They reported that temperature increased up to 50° C. in low AC magnetic field hyperthermia treatment, and cancer cells grown in the tibia of rabbit were annihilated within 5 weeks by nano-magnetite particles included in the glass-ceramics. However, there are some significant drawbacks in such a glass ceramic approach. First, glass-ceramics generally do not have good mechanical properties, and hence they are very vulnerable to shear stress and static fatigue. Another problem is the possible release of harmful ions constituting the glass-ceramic material such as iron, calcium and silicon ions into human body from the amorphous phase of the glass-ceramics. The implants as described herein, $TiO_2$ nanotubes on Ti, are mechanically sturdy and biocompatible, and magnetic nanoparticles can be confined within the nanopores of $TiO_2$ nanotubes during the magnetic hyperthermia treatment to minimize/prevent possibly harmful release and circulation of the particles inside human body. They can be implanted within cancerous bones or other cancer regions for safer magnetic hyperthermia treatment.

4. Cell Proliferation Devices

The invention provides cell proliferation devices comprising the $TiO_2$ nanotubes of the invention; and in one aspect these devices are used to accelerate cell growth. The increased number of cells generated by a cell proliferation device of the invention can be useful for accelerated supply of cells, such as stem cells for various research and development (R&D), industrial or medical uses, e.g., for therapeutic uses. An exemplary device is schematically illustrated in FIG. 16(a). The cells are cultured in a biocompatible environment with needed nutrient media. The cells that proliferate in the vertically aligned $TiO_2$ nanotube arrays are then harvested and supplied for other uses.

One exemplary method of harvesting the grown cells off the $TiO_2$ nanotube substrate is to use a process known as "trypsinization". Once cells are grown completely on whole surface of cell culture flask, the media fluid is removed by suction. After rinsing of the cells twice with PBS (phosphate buffer solution), trypsin is added to detach the cell from the surface. In general, 2-3 ml of trypsin is used for detaching cells grown on 10 cm² cell culture dish. After 2 minutes, most of the cells are detached from the $TiO_2$ nanotube surface, as illustrated in FIG. 16(b). After adding 10 ml of new medium, this fluid containing the detached stem cells is poured into a centrifuge tube. After centrifugation at appropriate rotation speed and time, all of the cells are separated. The medium is removed by suction, and 1 ml of new media is added for storage of the harvested cells or for additional culture. To estimate the number of proliferated cells, trypan blue assay are employed in conjunction with hematocytometry. The cells can also be in situ proliferated on the implant surfaces as the $TiO_2$ nanotubes as well as Ti substrate are biocompatible.

5. Analytical Diagnostic Biochip

Figure 17:
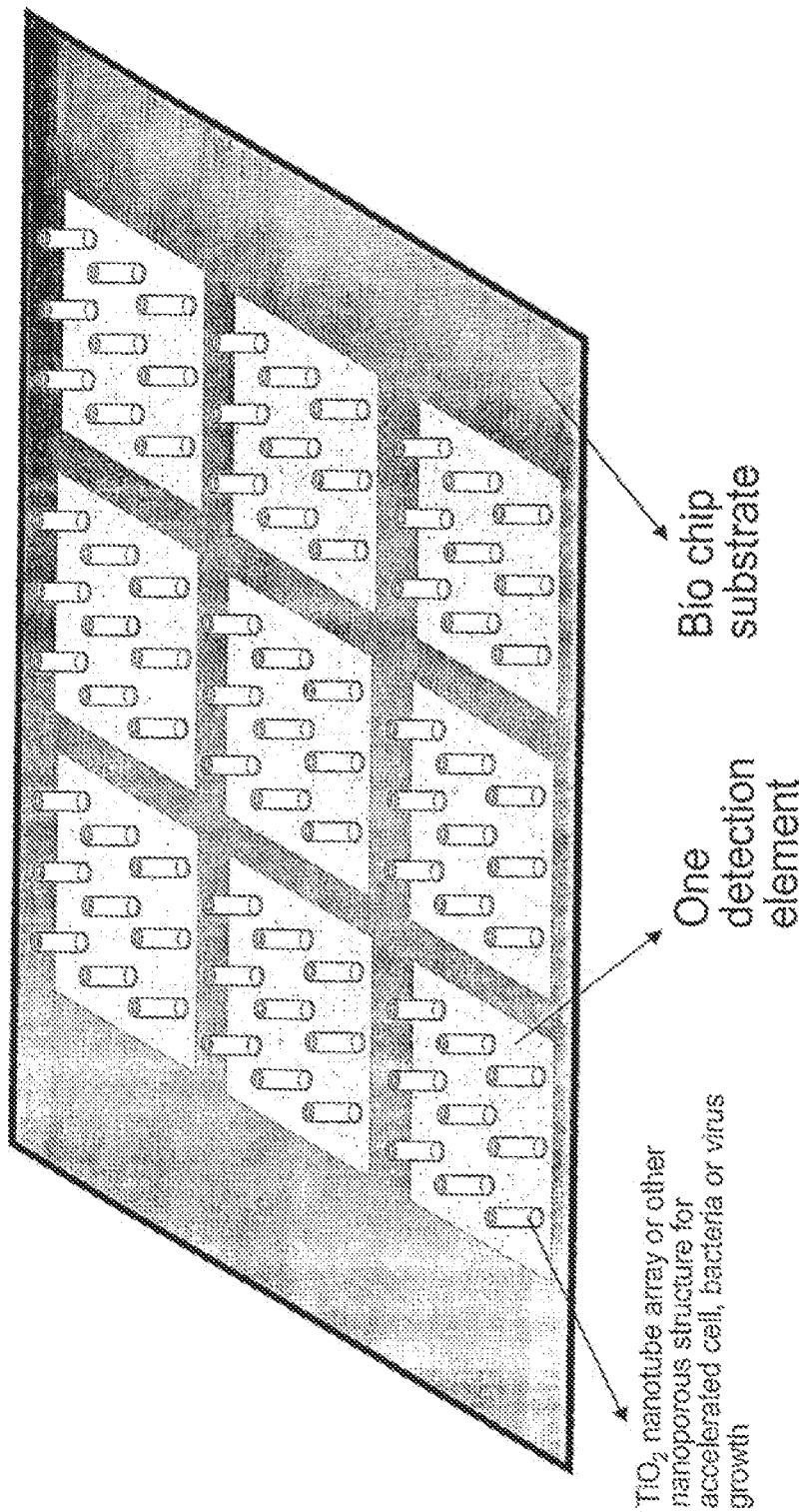
FIG. 17 is a schematic illustration of an exemplary X-Y matrix subdivided array of $TiO_2$ nanotube array structure of the invention for accelerated cell, bacterial or virus growth on a diagnostic biochip; detection elements comprising $TiO_2$ nanotube array structures upon a biochip substrate are illustrated.

The invention provides chips or arrays comprising the nanostructures of the invention, e.g., biochips, such as analytical diagnostic biochips. In one aspect, to carry out rapid diagnosis and detection of certain types of cells, such as diseased cells, or cells exposed to agents or chemicals, e.g., cells exposed to toxins, biological warfare agents, bacteria, spores (e.g., anthrax) viruses (e.g., SARS or influenza, such as the so-called "bird flu") and the like, these chips or arrays comprise an X-Y matrix subdivided array of $TiO_2$ nanotube array structures, e.g., produced as illustrated in FIG. 17. For diagnosis of diseases (especially epidemic diseases) or bacteria or viruses, rapid detection is essential when the available quantity of the cells is relatively small. Each of the detection elements in FIG. 17, which contains a multiplicity of $TiO_2$ nanotubes on which various types of cells to be analyzed, are placed and allowed to rapidly proliferate to a sufficient number for easy detection.

Figure 18:
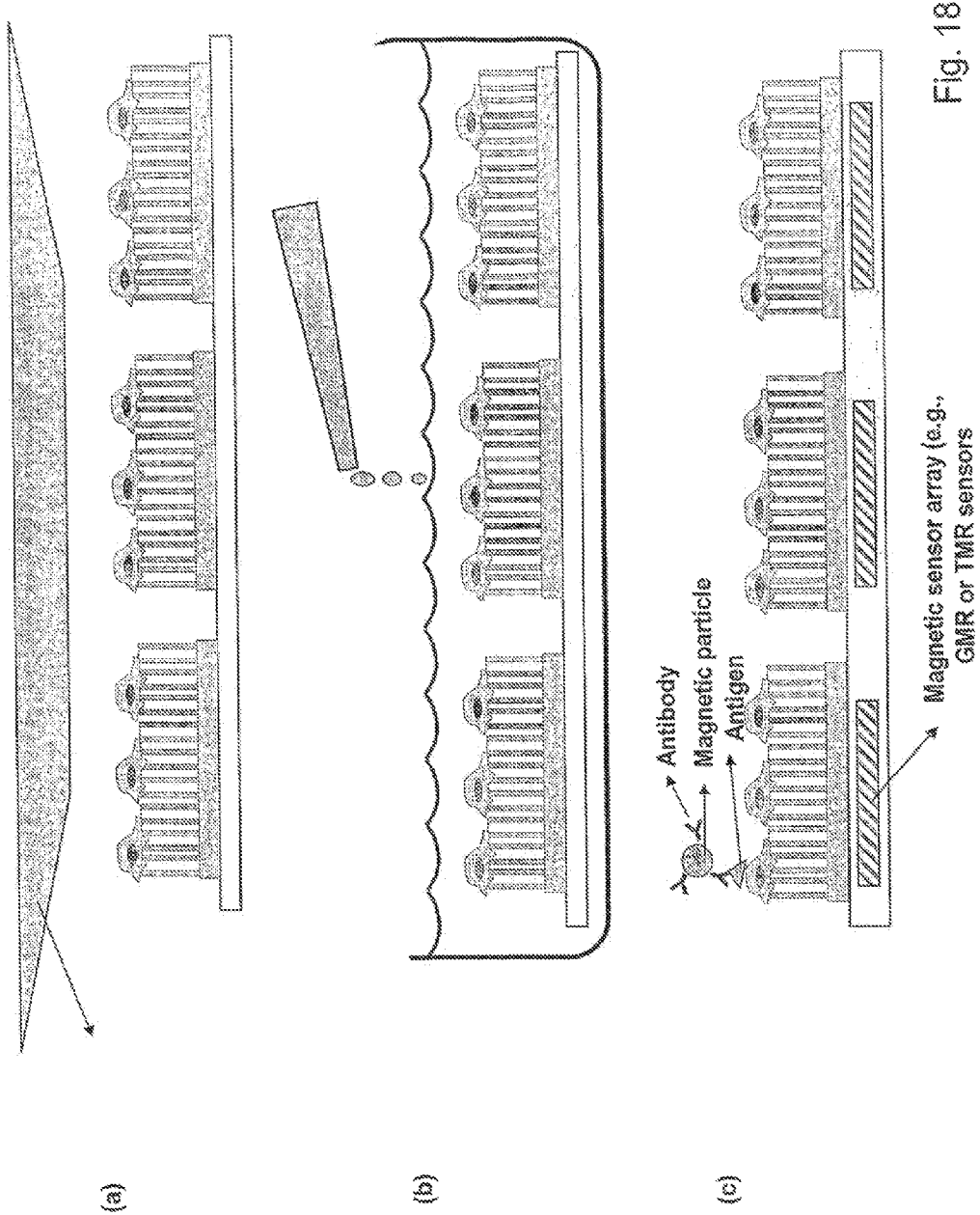
FIG. 18.

For analysis of cell types, various exemplary techniques, FIG. 18, can be used including (a) optical detection of morphology and size (using a microscope, fluorescent microscope, or CCD camera sensing of fluorescent or quantum dot tagged cells), (b) chemical or biological detection (e.g., based on signature reactions), (c) magnetic sensor detection (e.g., by using magnetically targeted antibody and its conjugation with certain types of antigens).

A number of embodiments of the invention have been described. Nevertheless, it will be understood that various modifications may be made without departing from the spirit and scope of the invention. For example, the materials involved do not have to be Ti oxide nanotubes on Ti-based metals, as the nanotubes and the substrate that the nanotubes are adhered to can be other biocompatible materials or non-biocompatible materials coated with biocompatible and bioactive surface layer such as Ti, or coated with biocompatible but bio-inert surface layer such as novel metal or polymer layer.

II. ARTIFICIALLY ENGINEERED BIOCOMPATIBLE NANOTUBE AND NANOPORE ARRAY FOR CELL AND BONE GROWTH AND METHOD FOR FABRICATING THEREOF

This aspect of the invention provides template devices comprising artificially engineered nanotube and nanopore structure covered with biocompatible material such as $TiO_2$. Also provided are artificial tissues and organs comprising theses template devices with sufficient and appropriate cells to provide a functional organ or tissue, e.g., including connective tissue cells, liver cells, bone cells, kidney cells, blood vessel cells, skin cells, periodontal cells, odontoblasts, dentinoblasts, cementoblasts, enameloblasts, odontogenic ectomesenchymal tissue, osteoblasts, osteoclasts, fibroblasts, and other cells and tissues involved in odontogenesis or bone formation, and/or stem cells.

Also provided are methods for enhanced culturing of two-dimensionally and three-dimensionally configured cells/organs using these template devices of the invention. These structures of the invention induce strong cell adhesion and significantly enhance the formation kinetics of cells.

The three-dimensionally placed nano-gaps between aligned nanotubes and nanopores allow a continuous supply of various nutrients to the growing cells. The nanotube and nanopore structure can be either retractable from or permanently kept in the grown cells. This 3-dimensional cell and tissue culture device of the invention, which can comprise stored biological agents within the nanotube reservoirs, can improve growth of configured and healthy cells including liver cells, bone cells, kidney cells, blood vessel cells, skin cells, periodontal cells, odontoblasts, dentinoblasts, cementoblasts, enameloblasts, odontogenic ectomesenchymal tissue, osteoblasts, osteoclasts, fibroblasts, and other cells and tissues involved in odontogenesis or bone formation and/or stem cells, to name just a few examples. The 3-dimensional cell and tissue culture device of the invention, and cultured cells derived from these devices, can be useful for rapid supply of needed cells for research and development, e.g., for drug development or testing or for therapeutics, or for preparation of partial or full implant organs, for externally controllable drug release and therapeutic treatments, for efficient toxicity testing of drugs and chemicals, and/or for diagnosis/detection of disease or forensic cells.

SUMMARY

The invention provides arrays comprising a solid substrate and a plurality of vertically aligned, laterally spaced, nanotubes associated with the substrate, wherein each nanotube comprises a nanopore. In one aspect, the outer diameter of each nanotube is between about 10 to 1000 nm, or, the outer diameter of each nanotube is between about 30 to 300 nm, or the outer diameter of each nanotube is between about 60 to 200 nm.

In one aspect, a nanopore of each nanotube comprises a diameter of (at least) about 5%, 6%, 7%, 8%, 9%, 10%, 11%, 12%, 13%, 14%, 15%, 20%, 25%, 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75% or more, of the outer diameter of the nanotube.

In one aspect, the height of at least one, several or all (each) nanotube is about 40 to 1000 nm, or, about 100 to 400 nm, or 200 to 800 nm, and the like.

In one aspect, the aspect ratio of each nanotube is less than about 15, less than about 14, less than about 13, less than about 12, less than about 11, less than about 10, or less than about 9, less than about 8, less than about 7, less than about 6, or less than about 5.

In one aspect, the alignment angle of the vertically aligned nanotubes is between about 0 to 50, 45, 40, 35, 30, 25, 20, 15 or 10 degrees off the vertical direction, or, the alignment angle of the vertically aligned nanotubes is about 0 to 60 degrees off the vertical direction.

In one aspect, adjacent, vertically aligned nanotubes are laterally spaced from between about 2 to 100 nm, or between about 5 to 30 nm, or between about 10 to 90 nm and the like.

In one aspect, adjacent, the arrays comprise a biocompatible surface. The biocompatible surface can comprise a compound selected from the group consisting of Ti, Ti oxide, ceramic, noble metals, and polymer materials.

The arrays of the invention can further comprise two-dimensionally and/or three-dimensionally cultured cells selected from the group consisting bone cells, liver cells, kidney cells, blood vessel cells, skin cells, periodontal cells, odontoblasts, dentinoblasts, cementoblasts, enameloblasts, odontogenic ectomesenchymal tissue, osteoblasts, osteoclasts, fibroblasts, and other cells and tissues involved in odontogenesis or bone formation and/or stem cells, to name just a few examples, and other human or animal organ cells. The arrays of the invention can further comprise two-dimensionally and/or three-dimensionally cultured organs, wherein the organ comprises one or more cells selected from the group consisting of bone cells, liver cells, kidney cells, blood vessel cells, skin cells, periodontal cells, stem cells, and other human or animal organ cells.

The arrays of the invention can further comprise a means for retracting or withdrawing or removing (and the like) the nanotubes from the three-dimensionally cultured cells such that only the cells and/or organs are left. In one aspect, the three-dimensionally cultured cells or organs are permanently or semi-permanently associated with the nanotubes of the array.

The invention provides methods for accelerating the growth of cells, the method comprising contacting the cells with an array of the invention in the presence of a nutrient fluid suitable for sustaining growth of the cells. In one aspect of the method, cell growth is accelerated by about 25%, 50%, 75%, 100%, 150%, 200%, 250% or 300% or more. In one aspect, the nutrient fluid is supplied under the growing cells through the spacing between the parallel nanotubes.

The invention provides arrays comprising a solid substrate and a plurality of vertically aligned, laterally spaced, nanotubes associated with the substrate, wherein each nanotube comprises at least one nanopore and the array comprises "dental" cells (e.g., odontoblasts, dentinoblasts, cementoblasts, enameloblasts, odontogenic ectomesenchymal tissue, osteoblasts, fibroblasts, and other cells and tissues involved in odontogenesis) suitable for odontogenesis, and implantation and regeneration of dental tissue, e.g., teeth, dentin, cementum, enamel or supporting structures, in a subject, e.g., a human.

The invention provides arrays comprising a solid substrate and a plurality of vertically aligned, laterally spaced, nanotubes associated with the substrate, wherein each nanotube comprises at least one nanopore and wherein the array comprises orthopaedic cells suitable for implantation and regeneration of bone and/or joint tissue in a subject.

The invention provides arrays comprising a solid substrate and a plurality of vertically aligned, laterally spaced, nanotubes associated with the substrate, wherein each nanotube comprises at least one nanopore and wherein the array comprises one or more biologically active agents selected from the group consisting of therapeutic drugs, growth factors, proteins, collagens, stem cells, enzymes, hormones, DNA's, genes, antibiotics, antibodies, and magnetic nanoparticles.

The invention provides arrays comprising a solid substrate and a plurality of vertically aligned, laterally spaced, nanotubes associated with the substrate, wherein each nanotube comprises at least one nanopore and wherein the array comprises a colloidal composition comprising magnetic nanoparticles interspersed with a biological agent selected from the group consisting of therapeutic drugs, cancer drugs, growth factors, proteins, collagens, stem cells, enzymes, hormones, DNA's, genes, antibiotics, and antibodies.

The invention provides methods for selectively releasing a biological agent in a subject, the method comprising implanting an array of the invention in a subject and contacting the array with ultrasonic or magnetic agitation of the colloidal composition, wherein the biological agent is released from the array. In one aspect, the magnetic nanoparticle is selected from the group consisting of iron-oxide particles of magnetite ($Fe_3O_4$) or maghemite ($\gamma$-$Fe_2O_3$). In one aspect, the nanoparticles are about 5 to 50 nm in average diameter, or about 5, 10, 15, 20, 25, 30, 35, 40, 45, 50, 75, 100 or more nm in average diameter.

In one aspect, the magnetic agitation comprises external stimulation of the magnetic nanoparticles by alternating current (AC) magnetic field. The biological agent can be released from the array by mechanical agitation/movement of the magnetic particles or by heating of the composition resulting from the AC magnetic field.

In one aspect, the array or chip of the invention further comprises nanotubes configured with narrow passage caps at the upper end of the nanotube, wherein the narrow passage inhibits the release of the biological agent from the nanopore. In one aspect, the "cap", or narrowed passage, is deposited by oblique incident sputter deposition on a stationary or a rotating substrate.

The invention provides methods for treating a cell proliferation disorder, the method comprising: a) implanting an array of the invention into a subject (e.g., a human in need thereof), wherein the array is implanted at or near the site of a cell proliferation disorder; and b) contacting the array with magnetic agitation, wherein the agitation accelerates biological agent release and provides magnetic hyperthermia treatment at the site of implantation.

The invention provides systems for growing and harvesting selected cells, the system comprising: a) an array of the invention operably associated with a device for removing the cells or tissue from the array; and b) a computer operably associated with a), wherein the computer comprises instructions for automatically contacting the cells with a suitable growth media and for harvesting the mature cells. In one aspect, the cells comprise connective tissue cells (e.g., fibroblasts), bone cells, liver cells, pancreatic cells (e.g., beta cells), kidney cells, blood vessel cells, odontoblasts, dentinoblasts, cementoblasts, enameloblasts, odontogenic ectomesenchymal tissue, osteoblasts, osteoclasts and/or skin cells. In one aspect, the cells are embryonic or adult stem cells. In one aspect, the cells are removed by trypsinization. In one aspect, the cells are harvested using mechanical means such as suction and centrifugal process, or optionally in combination with trypsinization.

The invention provides methods for the diagnosis, prognosis or detection of a disease or condition (e.g., allergies, toxicities, genetic condition) comprising implanting an array or chip, e.g., a biochip, comprising an array of the invention in a subject in need thereof (e.g., a human), or, using the array or chip in situ or in vitro. In one aspect, the array comprises a cell or tissue relevant for the diagnosis, prognosis or detection.

The invention provides a method for detecting a biological agent, e.g., a toxin, a poison or a biological warfare agent, e.g., anthrax, the method comprising use of an array or chip, e.g., a biochip of the invention, e.g., providing an array comprising an X-Y matrix subdivided array of nanotubes (e.g., comprising a plurality of nanotubes), each nanotube (or set of nanotubes, e.g., each row, or a cluster of tubes) comprising a specific type of cell for analysis.

The invention provides a biomimetic array, or artificially constructed cell culture, comprising liver cells for performing drug/chemical toxicity testing, the array comprising an array of the invention comprising liver cells (e.g., parenchymal cells, or hepatocytes, endothelial cells, adipocytes, fibroblastic cells and/or Kupffer cells) for evaluation of new drugs for testing of safety and toxicity issues. The invention provides methods for evaluating the toxicity of a compound, e.g., a drug, small molecule, food additive or food coloring, cosmetic, pesticide, natural product, biological warfare agent, and the like, using a biomimetic array of the invention. In one aspect, the array is contacted with a test material such as a chemical (e.g., a drug, small molecule, food additive or food coloring, cosmetic, pesticide), a polymer, an injection fluid, a biological agent (e.g., a toxin, biological warfare agent, e.g., a gas, such as Mustard gas, Sarin).

The invention provides methods for manufacturing an array of the invention, e.g., using the exemplary methods described herein.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

FIG. 19: FIG. 19(*a*) to (*c*): schematically illustrate exemplary processing steps for guided anodization of Ti using pre-fabricated nano spot array of the invention for controlled $TiO_2$ nanotube geometry; 19(*a*), illustrates preparing Ti metal sheet, foil or film; 19(*b*), illustrates use of lithography or self-assembly process to make nano spot array at desired periodicity; 19(*c*), illustrates guided anodization to fabricate a $TiO_2$ nanotube array with predetermined size and periodicity.

FIG. 20: FIG. 20(*a*) to (*c*): schematically illustrate an exemplary lithographical fabrication of gapped nanotube array of the invention followed by coating with a biocompatible layer such as Ti or $TiO_2$; FIG. 20(*a*), illustrates preparing Si or any other directionally-etchable material; FIG. 20(*b*), illustrates an exemplary lithographically patterned nanotube array; FIG. 20(*c*), illustrates the deposit of Ti or $TiO_2$ coating to cover the nanotube surface.

FIG. 21: FIG. 21(*a*) to (*e*): schematically illustrate an alternative exemplary method of creating biocompatible nanotube array of the invention comprising steps of lithographical fabrication of nanocavity, inside wall deposition, matrix etching for nanotube array, followed by coating with a biocompatible layer such as Ti or $TiO_2$; FIG. 21(*a*), illustrates preparing an Al or Si layer (bulk or deposited film); FIG. 21(*b*), illustrates the step of lithographically patterning a hole array (round or square cavities); FIG. 21(*c*), illustrates the step of depositing biocompatible metal or ceramic cylinder (e.g., Au, Pd, carbon); FIG. 21(*d*), illustrates the step of etching off the matrix to produce open-pore cylinder array; FIG. 21(*e*), illustrates the step of depositing Ti or $TiO_2$ coating to cover the surface.

FIG. 22: FIG. 22(*a*) to (*c*): schematically illustrate an exemplary process of preparing channeled array of the invention, comprising parallel-aligned nanocavities comprising a surface coating of biocompatible layer such as Ti or $TiO_2$; FIG. 22(*a*) illustrates an exemplary patterned nano-cavity array, made e.g., by lithography or self-assembly process, on Si, any metallic, ceramic or plastic substrate; FIG. 22(*b*) illustrates the step of coating the surface with biocompatible Ti or $TiO_2$ film; FIG. 22(*c*) illustrates the step of providing sideway linear or x-y crossing groove paths to allow fluid flow.

FIG. 23: FIG. 23(*a*) to (*d*): schematically illustrate an accelerated 3-dimensional cell growth using exemplary structures of the invention comprising retractable or permanently retained sheets with parallel-aligned and gapped nanotube array on their surfaces; FIG. 23(a) illustrates an exemplary device of the invention comprising parallel-configured, retractable Ti wires or ribbons with a $TiO_2$ nanotube surface; FIG. 23(b) illustrates the step of accelerated cell growth on the parallel Ti wires or ribbons (e.g., for liver, blood vessel, bone cells, etc.); FIG. 23(c) illustrates the step of optionally pulling out titanium oxide nanotubes; FIG. 23(d) illustrates the final result of practicing this exemplary device and method of the invention—a cultured 3-dimensional cell system.

Figure 24:
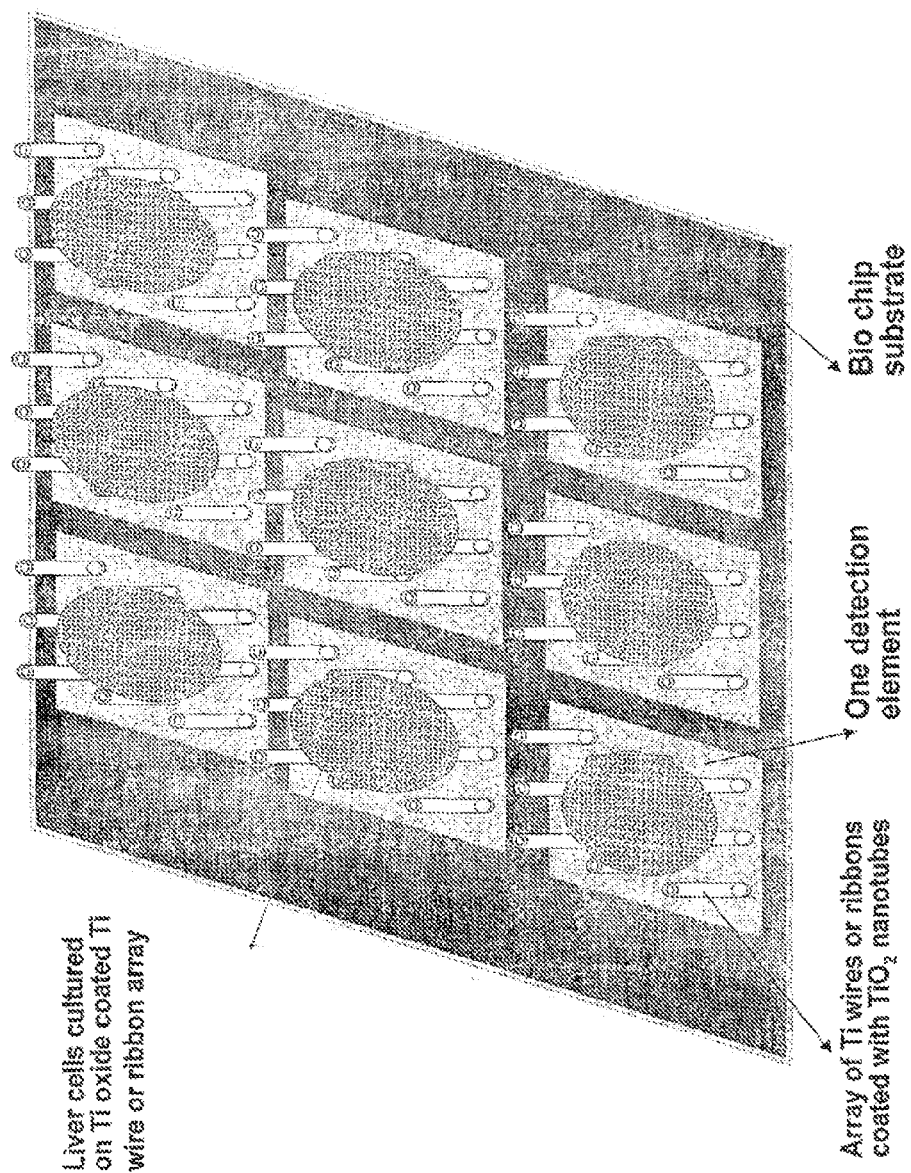

FIG. 24 schematically illustrates an exemplary bio-chip device for toxicity testing of drugs or chemicals, with the device comprising an array of cultured liver cells grown in a rapidly and healthy manner on an parallel-aligned and laterally spaced nanotubes coated device of the invention, with biocompatible surface layer.

It is to be understood that the drawings are for purposes of illustrating the concepts of the invention and are not to scale. Like reference symbols in the various drawings indicate like elements.

DETAILED DESCRIPTION

The invention provides artificially engineered biocompatible nanotube- and/or nanopore-comprising arrays comprising alternative materials or alternative fabrication techniques for biocompatible nanotube and nanopore array for rapid growth of cells/tissues/bones.

The invention provides enhanced culturing of two-dimensionally and three-dimensionally configured cells/organs/bones using template devices comprising artificially engineered nanotube and nanopore structure covered with biocompatible material such as $TiO_2$. This exemplary structure induces a strong cell adhesion and significantly enhances the formation kinetics of cells. In these exemplary designed, fabricated and aligned nanotubes of the invention, the practical limit of anodization-based processing (which produce a rather limited $TiO_2$ nanotube diameter, about 100 nm regime) can be overcome. In these exemplary designed nanotubes of the invention, a desired diameter can be greater than about 100 nm, and in one aspect the cell growth can be accelerated and optimized. In one aspect, the three-dimensionally placed nano-gaps between the nanotubes can allow a continuous supply of various nutrients to the growing cells. The nanotube and nanopore structure of the invention can be either retractable from the cultured cells or can be permanently kept in the grown cells. One exemplary cell and tissue culture device of the invention comprises stored biological agents within the nanotube reservoirs, can improve growth of configured and healthy cells, including for example, liver cells, bone cells, kidney cells, nerve cells, blood vessel cells, skin cells, periodontal cells, stem cells. Such cultured cells can be useful for rapid supply of needed cells for R&D or therapeutics, for preparation of partial or full implant organs, for externally controllable drug release and therapeutic treatments, for efficient toxicity testing of drugs and chemicals, and for diagnosis/detection of disease or forensic cells.

In one aspect, nanotubes of the invention are fabricated in such a way that they have a controlled, pre-determined diameter, and/or an inter-nanotube gap spacing, and/or a predetermined height (as compared with the typical anodized $TiO_2$). In one aspect, the surface of the nanotube array, or in one aspect—at least the top surface, or all the surfaces, are coated with a biocompatible layer, such as Ti or $TiO_2$, or other biocompatible metallic, ceramic, polymer, or biomolecule coating.

In one aspect, the nanotube alignment comprises a vertical alignment with a open top pore, which in some applications may be crucial for bio implant and related applications, as disclosed herein. In one aspect, the open top of the nanotubes allows the penetration of the cells into the nanopore cavity for good adhesion. In one aspect, the open top of the nanotubes also allows easy supply of the biological agents stored in the nanopores. In one aspect, the cells that adhere well to a surface generally stay healthy and grow fast, while the cells that do not adhere exhibit reduced or minimal growth. In one aspect, the desired angle of vertical alignment is within than about 10, 20 or 30 degrees off the perpendicular axis.

In one aspect, the nanoscale Ti oxide structures of the invention comprise Ti and Ti alloys that are corrosion resistant, light, yet sufficiently strong for load-bearing, and are machinable. They are one of the few biocompatible metals which osseo-integrate (direct chemical or physical bonding with adjacent bone surface without forming a fibrous tissue interface layer); thus, the nanoscale Ti oxide structures of the invention can directly bond, by e.g., chemical and/or physical bonding, with adjacent bone surface without forming a fibrous tissue interface layer. Thus, the nanoscale Ti oxide structures of the invention can be used as orthopaedic (orthopedic) and dental implants, e.g., with the devices described in the Handbook of Biomaterial Properties, edited by J. Black and G. Hasting, London; Chapman & Hall, 1998; or, Ratner et al., Biomaterials Science, San Diego, Calif.: Academic press; 1996.

While the invention is not limited by any particular mechanism of action, the bioactivity of Ti, such as the relatively easy formation of hydroxyapatite type bone mineral on Ti, is primarily caused by the occurrence of Ti oxide on the surface of Ti and its alloys. Various crystal structures of Ti oxide can be used in making the compositions of the invention, e.g., the anatase phase, which is known to be better than the rutile and other phases (however, the rutile and other phases can also be used), as described, e.g., by Uchida et al, Journal of Biomedical Materials Research (2003) 64:164-170.

Surface treatments such as roughening by sand blasting, formation of anatase phase $TiO_2$, hydroxyapatite coating, or other chemical treatment can also be utilized to further improve the bioactivity of Ti surfaces of the invention, and, in various aspects, to enhance cell, tissue and/or bone growth.

$TiO_2$ phase can be prepared by various techniques such as sol-gel method, electrophoretic deposition and anodization. See, e.g., Lakshmi, et al., Chemistry of Materials, Vol. 9, page 2544-2550 (1997), Miao, et al., Nano Letters, Vol. 2, No. 7, page 717-720 (2002); Gong, et al., Journal of Materials Research, Vol 16, No 12, page 3331-3334 (2001). In one aspect, a $TiO_2$ phase can be prepared by various techniques such as sol-gel method (see, e.g., U.S. Pat. No. 7,014,961); photolithographic patterning of a photoresist layer by patternwise exposure to short-wavelength ultraviolet light through a pattern-bearing photomass, as described in U.S. Pat. No. 6,593,034; electrophoretic deposition and anodization. See, e.g., Lakshmi, et al. (1997) Chemistry of Materials, 9:2544-2550; Miao, et al. (2002) Nano Letters 2:717-720; Gong, et al. (2001) J. Materials Res. 16:3331-3334; Macak (2005) Chem. Int. Ed., 44:7463-7465.

In one aspect, fabrication of vertically aligned $TiO_2$ nanotubes on Ti substrate can be done by anodization process, and the invention includes use of titanium oxide nanotubes for cell, tissue and/or bone growth or other bio application. Patients who go through Ti implant operations for repair of hip joints, broken bones, or dental implants often have to wait for many months of slow bone growth recovery before they are cured enough to get off the confinement on a bed or crutches and have a normal life. Accelerated bone growth would thus be very beneficial for such patients. Therefore, the biocompatible nanostructures in desirable configuration for enhanced bone growth and other cell growth is useful for a variety of bio applications. Furthermore, biocompatible nanostructures of the invention can be made to serve multi-functional roles to additionally accelerate tissue and/or cell growth (e.g., bone). In one aspect, they are used in orthopaedic and/or dental applications.

In one aspect, coating of bioactive materials such as hydroxyapatite and calcium phosphate on Ti surface is used to make the Ti surface more bioactive. See, e.g., Shirkhanzadeh et al, Journal of Materials Science Letters, Vol. 10, page (1991), de Groot et al., Journal of Biomedical Materials Research, Vol. 21, page 1375-1381 (1987), and Cotell et al., Journal of Applied Biomaterials, Vol. 8, page 87-92 (1992). The coating techniques of the invention, and the resultant structures of the invention, in contrast to flat and continuous coatings, fail less by fracture or delamination at the interface between the implant and the coating as an adhesion failure, or at the interface between the coating and the bone, or at both boundary interfaces. The coating techniques of the invention, and the resultant structures of the invention, in contrast to thick film coatings, introduce fewer interface stresses at the substrate-coating interface; see, e.g., Yang, et al., Journal of Biomedical Materials Research, Vol. 36, page 39-48 (1997). In one aspect, the interface is bonded with an improved and integrated structure, for example, with a locked-in configuration having a much increased adhesion area, and as a discrete, less continuous layer to minimize interface stress and de-lamination. In one aspect, accelerated hydroxyapatite and bone growth is accomplished on a mechanically adherent $TiO_2$ nanotube surface of the invention on a Ti substrate; see, e.g., Oh (2005) Biomaterials 26:4938-4943.

The invention provides compositions and methods for the fast growth and supply of cells and tissues, such as liver cells, kidney cells, blood vessel cells, and stem cells; and this can be crucial for many potential therapeutic and diagnostic applications. Liver cells can be cultured for partial or full liver implantation or for hepatic support of patients prior to liver transplant operation, as described, e.g., in US Patent Application Pub. No. US 2002/0072116 A1 by Bhatia et al.

The invention provides compositions and methods for the fast detection and diagnosis of diseased or abnormal cells, or cells exposed to or modified by a biological warfare agent, for example, compositions and methods of the invention can be used in fast detection and diagnosis biological or chemical warfare agents (e.g., gases, such as Sarin, mustard gas, etc., toxins), epidemic diseases, anthrax, influenza (e.g., the so-called "bird flu), or SARS.

In one aspect, the compositions and methods use a very small or trace quantity of available cells; this can be accomplished if the cell growth speed can be accelerated. In one aspect, an accelerated bone and cell growth using vertically aligned and laterally separated $TiO_2$ nanotube arrays are used, with the emphasis on two-dimensional cell growth.

Because desired cell growths for implant and other applications may require three-dimensionally configured cells, the invention provides methods and devices for producing such three-dimensionally cultured cells. In one aspect, the invention provides methods and devices for fast growth and supply of functional cells, such as liver or kidney cells, without a deterioration of their function(s), which can be critical for many organ (e.g., kidney or liver) therapeutic applications. In one aspect, the invention provides a bio-artificial liver or bio-artificial kidney support device. In one aspect, nanotubule structures of the invention are useful as substrates for efficient organ cell (e.g., kidney or liver cell) culture devices if the cells (e.g., liver cells) can be grown quickly in vitro without a major loss of their capability for complex functions.

In one aspect, the invention provides structures that are self-assembled in a simple anodization process, which in one aspect provides a viable, three dimensionally configured surface for enhanced cell growth and/or culture in vitro, in situ, ex vivo and in vivo. In controlling the specifics of nanotube diameter, spacing and height (the invention provides compositions having alternative nanotube diameters, spacing and heights), the compositions of the invention also can be used in various processing steps, different organ systems, varying combination of cells, and the like, as described herein.

This invention provides 2-dimensional and 3-dimensional cell culture devices comprising artificially patterned and shaped nanotube array(s) with a biocompatible coating, such as Ti or $TiO_2$. These structures of the invention enable accelerated growth of functional organ cells such as liver or kidney cells as well as other structural cells such as blood vessel cells, enzyme secretion vessels, periodontal, bone, teeth, or other hard tissue cells growth. The availability of such cultured cells can be useful for a variety of applications including i) organ-related therapeutic medical treatment including liver or kidney disease treatment, ii) orthopaedic, dental or periodontal processes, iii) supply of cells for various research or therapeutic purposes, and iv) disease diagnostic or toxicity testing of new drugs or chemicals.

Referring to the drawings, FIG. 1(a) schematically illustrates exemplary devices comprising exemplary artificially configured nanotube array. The nanotubes are fabricated in such a way that they have controlled, pre-determined diameter, inter-nanotube gap spacing, and height. The surface of the nanotube array, at least the top surface, or in one aspect on several or all the surfaces, are coated with a biocompatible layer such as Ti or $TiO_2$, or other metallic, ceramic, polymer, or biomolecule coating.

The nanotubes for the invention's devices can have any desired dimension, e.g., between about 10 to 1000 nm in diameter, or between about 30 to 300 nm, or anywhere in the nanoscale dimension of between about 60 to 200 nm in diameter. The desired heights of the tubules can be determined in part by the desired aspect ratio, as relatively short height with an aspect ratio of less than 10, or less than 5, in this aspect is preferred for ease of storing and eventual dispensing of drugs or biological agents intentionally placed within the tubule cavity. This nanotubule arrangement and size can maintain the function of the cells being cultured, e.g., kidney, liver or other cells, thus help the proliferation of these cells.

Exemplary heights of nanotubes can be between about 40 to 1000 nm, or between about 100 to 400 nm. In one aspect, a vertical alignment with open top pore is crucial for bioimplant or related applications, e.g., as in one aspect an open top a the nanowire allows the penetration of the cells into a nanopore cavity for good adhesion, as illustrated in the exemplary FIG. 1(b); this also allows easy supply of the biological agents stored in the nanopores.

Because it is well known that the cells that adhere well to a surface generally stay healthy and grow fast, while the cells that do not adhere exhibit reduced or minimal growth, in one aspect the desired angle of vertical alignment is within about 10, 20, 30 or 40 or more degrees off the perpendicular axis.

Exemplary micro-structural features and advantages of nanotube array structure are described in FIGS. 2 to 4, for the exemplary anodized, self-assembled $TiO_2$ structures of the invention. These scanning electron microscopy (SEM) and transmission electron microscopy (TEM) images show exemplary micro-structural features comprising vertically aligned, biocompatible $TiO_2$ with a typical dimension of the hollow nanotubes in FIGS. 2 and 3 being approximately 100 nm outer diameter and approximately 70 nm inner diameter with approximately 15 nm in wall thickness, and approximately 250 nm in height.

Exemplary nanotube array structures of the invention provide for healthy cell growth by providing a continuous supply of nutrients, including proteins, mineral ions, fluid, etc. to the cell through the flow of body fluid. The gap (spacing) between adjacent exemplary nanotubules in FIGS. 1-3 serves such a function of allowing the body fluid to continuously pass through and supply nutrients to the bottom side of the growing cells. The desired gap between the nanotubules in the exemplary structure of FIG. 1 is in the range of between about 2 to 100 nm, or between about 5-30 nm. In some aspects, too small a gap reduces the effectiveness of nutrient body fluid flow while too large a gap can pose a danger of reduced mechanical stability in the event of vertical or lateral stress or pressure.

Accelerated Cell Growth on $TiO_2$ Nanotube Array

Figure 7:
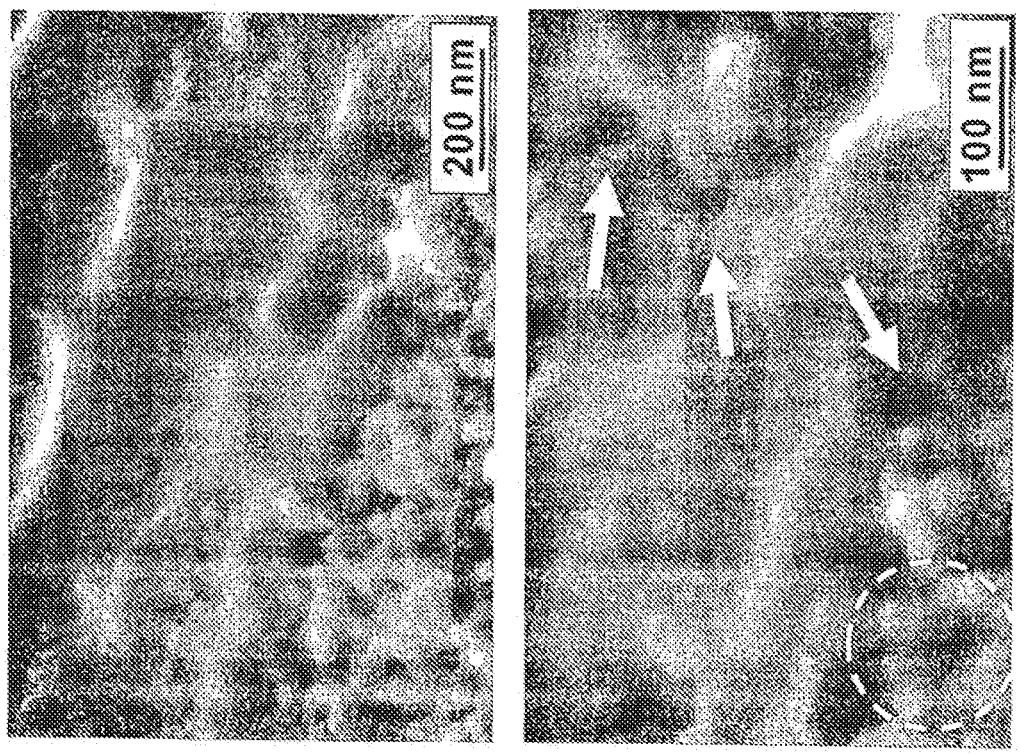
FIG. 7.

The invention provides nanotube structures that substantially improve cell adhesion and growth kinetics, an example of such an adhesion depicted in the exemplary structure of FIG. 7. An adhesion of anchorage-dependent cells such as osteoblasts is a crucial prerequisite to subsequent cell functions such as synthesis of extracellular matrix proteins, and formation of mineral deposits. In general, many types of cells beside the osteoblast cells remain healthy and grow fast if they are well-adhered onto a substrate surface, while the cells not adhering to the surface tends to stop growing.

In one aspect, nanotube structures (e.g., on orthopaedic or dental prostheses) can also comprise use of bone growth enhancing coatings comprising micrometer-sized bioactive materials, such as a hydroxyapatite layer coated on Ti implant surface; noting that the micrometer-sized materials alone may exhibit interfacial failures due to the much higher interfacial stress build-up between the dissimilar materials. Micrometer-sized materials alone also may fail due too the lack of strong chemical bonding or the absence of sharing of common element species between the implant and the coating. However, these disadvantages are mitigated by incorporation of the nanotube structures of the invention.

Exemplary vertically or parallel-aligned nanotube arrays can have the following structural advantages for reduced interfacial failure: (i) vertically or parallel-aligned nanotube arrays fabricated to be thin, e.g., less than 1000 nm, or less than 400 nm; (ii) nanotube arrays made as the same material as the base substrate material to ensure for strong bonding and mechanical stability of the nanotube array; and/or (iii) nanotube structures of FIG. 1 made to be not continuous but as discrete structures, e.g., with a gap between adjacent nanotubes of approximately 15 nm.

In one aspect, lateral gap dimensions are in the range of between about 2 to 100 nm, or between about 5 to 30 nm. In one aspect, this exemplary lateral sub-division of a nanotube array structures is important for minimizing the interfacial stresses between two dissimilar materials joined together, with the two materials involved often having substantially different crystal structure, lattice parameter, and coefficient of thermal expansion.

In one aspect, in addition to the advantages in mechanical properties, the gaps present between adjacent nanotubes may also be useful as a pathway for continuous supply of the body fluid with ions, nutrients, proteins, etc. This may contribute positively to the health of the growing cells. In one aspect, in the absence of such pathways, the proliferating cells may completely cover the bioactive implant material surface and the bottom surface of the growing osteoblast cells would then have very limited access to body fluid.

Presented in FIG. 7 are SEM micrographs showing the growth and adhesion of the osteoblast cells (after 2 hrs) on exemplary vertically or parallel-configured nanotube arrays, as an example of $TiO_2$ nanotubes. The micrographs clearly indicate that the filopodia of propagating osteoblast cells actually go into the vertical nanopores of the exemplary $TiO_2$ nanotubes.

Noting the invention is not limited by any particular mechanism of action, the observed rapid adherence and spread of osteoblastic cells cultured on $TiO_2$ nanotubes could be caused by three reasons. First, vertically aligned nanotubes exhibit enormously larger surface areas than the flat Ti surface. Second, the pronounced vertical topology contributes to the locked-in cell configuration. Thirdly, the pathway in-between nanotube arrays can allow the passage of body fluid and act as the supply/storage route of nutrient, which is an essential biological element for cell growth.

Figure 19:
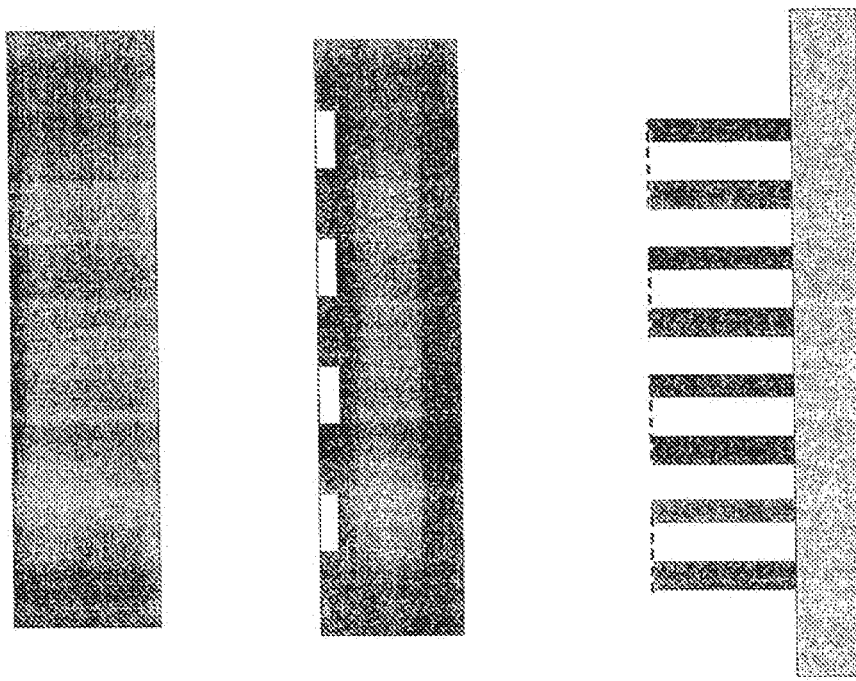

Schematically illustrated in FIG. 19 are exemplary processing steps for guided anodization of Ti using pre-fabricated nano spot array for controlled $TiO_2$ nanotube geometry. Various lithography techniques such as optical lithography (including laser lithography), electron beam lithography, ion beam lithography, self-assemble nanoparticle lithography, nano-imprint lithography, can be utilized to introduce an array of small etched cavity or indented cavity on the surface of Ti or Ti alloys. In one aspect, these pre-patterned spot locations serve as a nucleation spots during the subsequent anodization process. Such a guided anodization process creates more uniformly spaced, pre-controlled diameter and location of $TiO_2$ nanotube array.

In one aspect, a patterned $TiO_2$ nanotubule array is fabricated by an anodization process, for example, using the electrochemical processing in a 0.5% HF solution at 20 V for 30 min at room temperature (RT). An inert electrode such as a platinum electrode can be used as the cathode. To crystallize the as-deposited, amorphous-structured $TiO_2$ nanotubes into the desired anatase phase, the as-made nanotubes can be heat-treated at approximately 400° C. to 600° C. for anywhere between about 0.1 to 10 hrs. In one aspect, the amorphous $TiO_2$ nanotubes is crystallized to anatase phase by heat treatment, because an amorphous $TiO_2$ phase tends to be more susceptible to breakage by external stresses as compared to a crystalline phase. The use of the amorphous $TiO_2$ phase nanotube array for special applications is not excluded, however.

Figure 20:
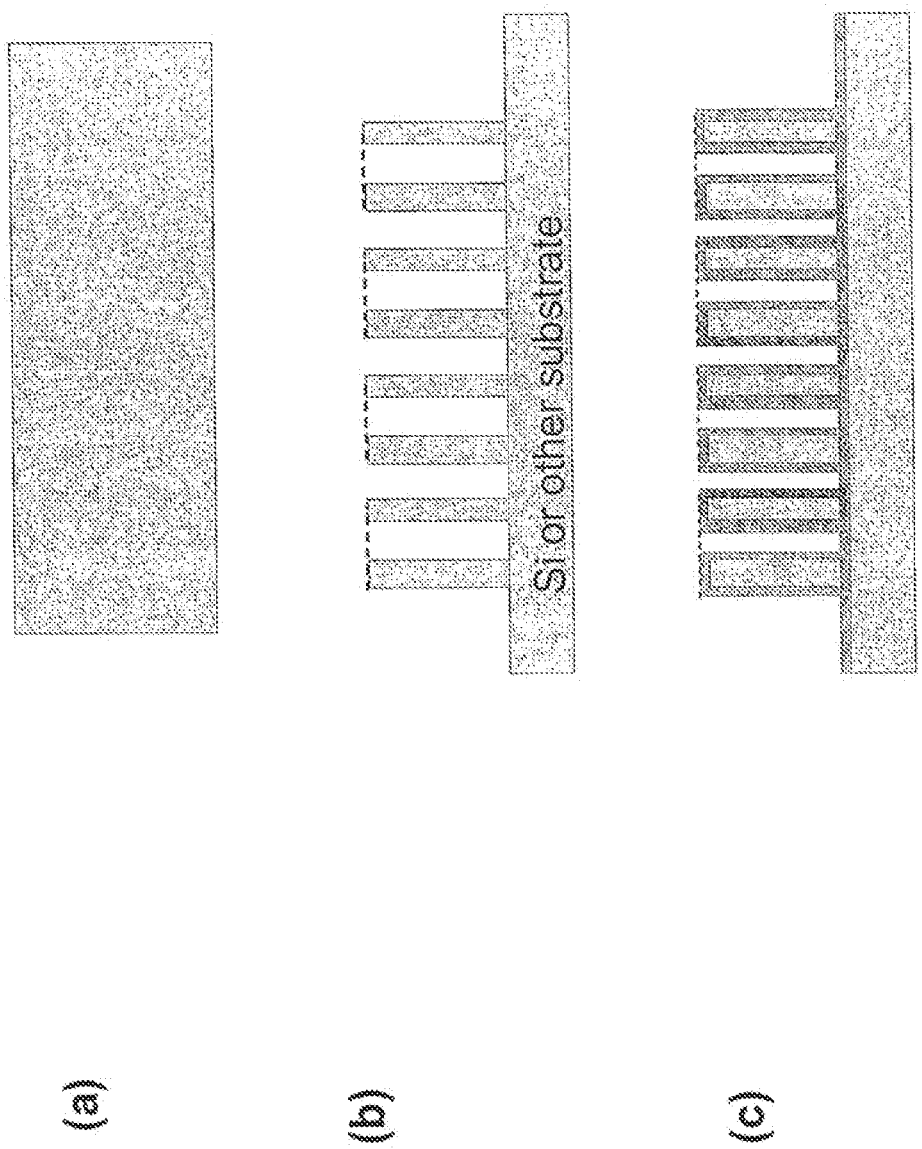
Figure 21:
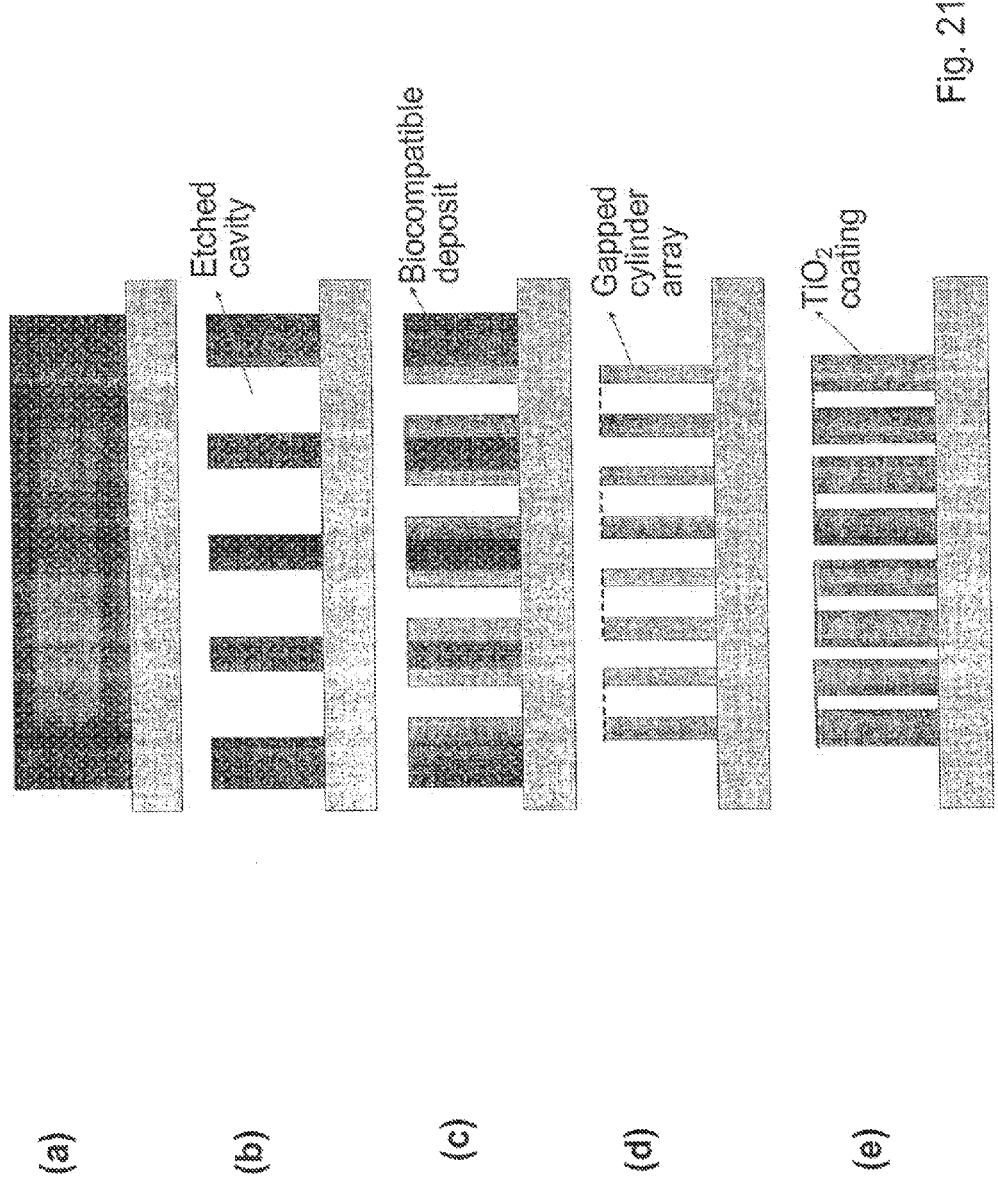

Shown in FIG. 20 is an exemplary lithographical fabrication of gapped nanotube array followed by coating with a biocompatible layer such as Ti or $TiO_2$, or various noble metal, ceramic, polymer or biomolecule layer. Well known lithography materials and processes, such as the use of photoresist materials like PMMA, lithography beam exposure, selective etching (chemical or reactive-ion-etching), washing and drying can be utilized for fabrication of such a gapped nanotube array structure. For deposition of the biocompatible layer, physical vapor deposition techniques such as evaporation, sputtering, laser ablation, chemical vapor deposition, or chemical processes can be used. A slightly oblique incident sputter or evaporation deposition can optionally be utilized to make the coating of the nanotube inside wall easier. If desired, the side and the back surfaces of the nanotube-containing substrate can also be coated with the similar biocompatible layer.

FIG. 7 describes an alternative exemplary method of the invention for creating biocompatible nanotube array comprising steps of lithographical fabrication of nanocavity, inside wall deposition of nanotube material such as Au, Pd, Pt, carbon, Ti or $TiO_2$, for example, by oblique incident sputtering. The matrix material can be then selectively etched away to leave only the nanotube array. For Al or Al-oxide matrix, NaOH solution can be used for etching. For Si matrix, known Si etching solution including KOH can be used. In one aspect, the nanotube array so fabricated is then coated with a biocompatible layer such as Ti or $TiO_2$, or various noble metal, ceramic, polymer or biomolecule layer, for example, using DC or RF sputtering, or chemical processes. If the nanotube array material itself is Ti or $TiO_2$, the last coating step can of course be omitted.

Figure 22:
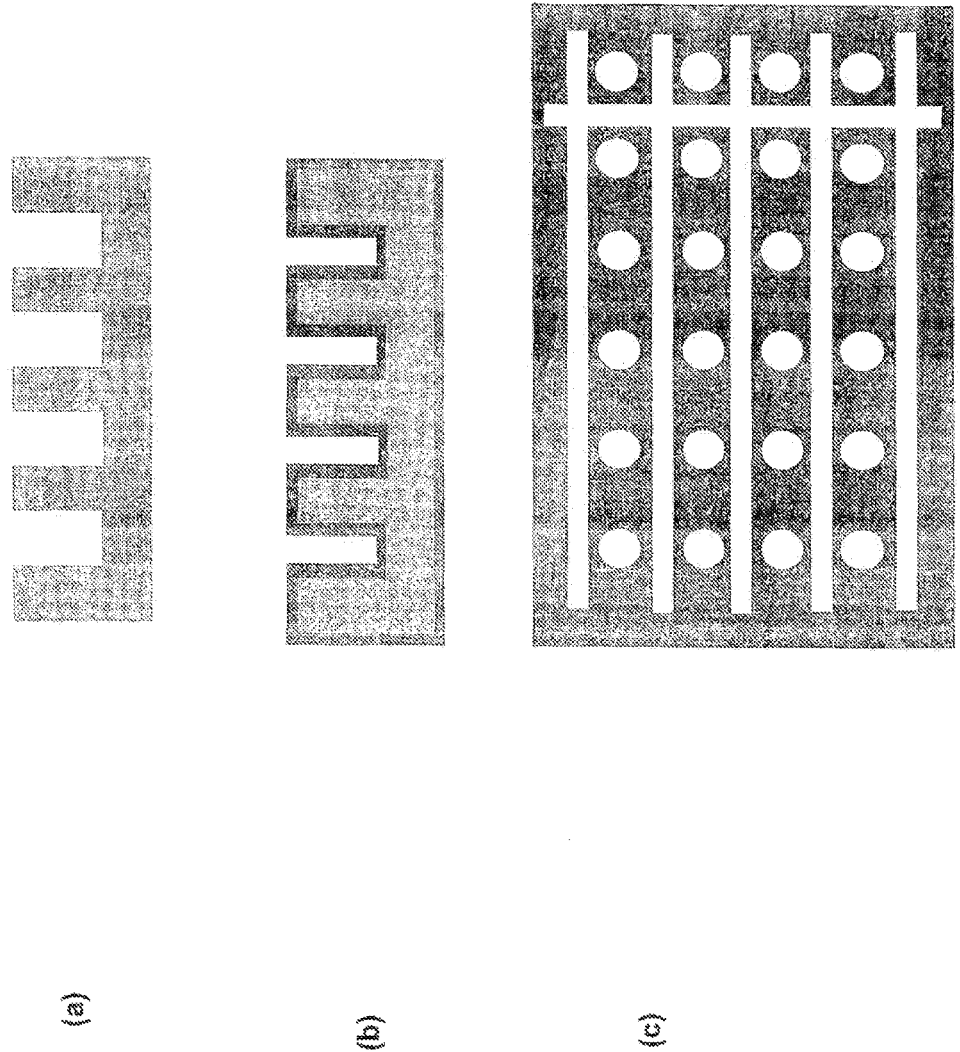

FIG. 22 schematically illustrates an exemplary process of preparing a channeled array of parallel-aligned nano-cavities comprising a surface coating of biocompatible layers such as Ti or $TiO_2$. Here the structure is less complicated than the nanotube array structure in that only patterned and diameter-controlled nano-cavity array is present. In one aspect, a channel structure is provided between the nano-cavities so that the biological fluid and nutrients are continuously supplied to the growing cells for healthy and accelerated cell culture. This structure also can be coated with a biocompatible layer such as Ti or $TiO_2$, or various noble metal, ceramic, polymer or biomolecule layer, for example, using DC or RF sputtering or chemical processes.

For these embodiments, the matrix material can be selected from Ti, Zr, Hf, Nb, Ta, Mo, W, and their oxides, or alloys of these metals and oxides. Other materials such as Si, Si oxide, Al, Al oxide, carbon, diamond, noble metals (such as Au, Ag, Pt and their alloys), polymer or plastic materials, or composite metals, ceramics or polymers can also be utilized to produce and use similar desired artificially generated nanotube or nanopore patterns. In one aspect, the surface of the nanotubes or nanopores are coated with biocompatible materials comprising Ti and/or Ti oxide, or Zr, Hf, Nb, Ta, Mo, W and/or their alloys or oxides of these metals and/or alloys, with a thickness of at least 1, 2, 3, 4 or 5 or more nm; and in one aspect the coating coverage of at least about at least 20%, 30%, 40%, 50%, 60%, 70%, 80% or more of the nanotube or nanopore surfaces.

Three-Dimensional Cell Growth

Figure 23:
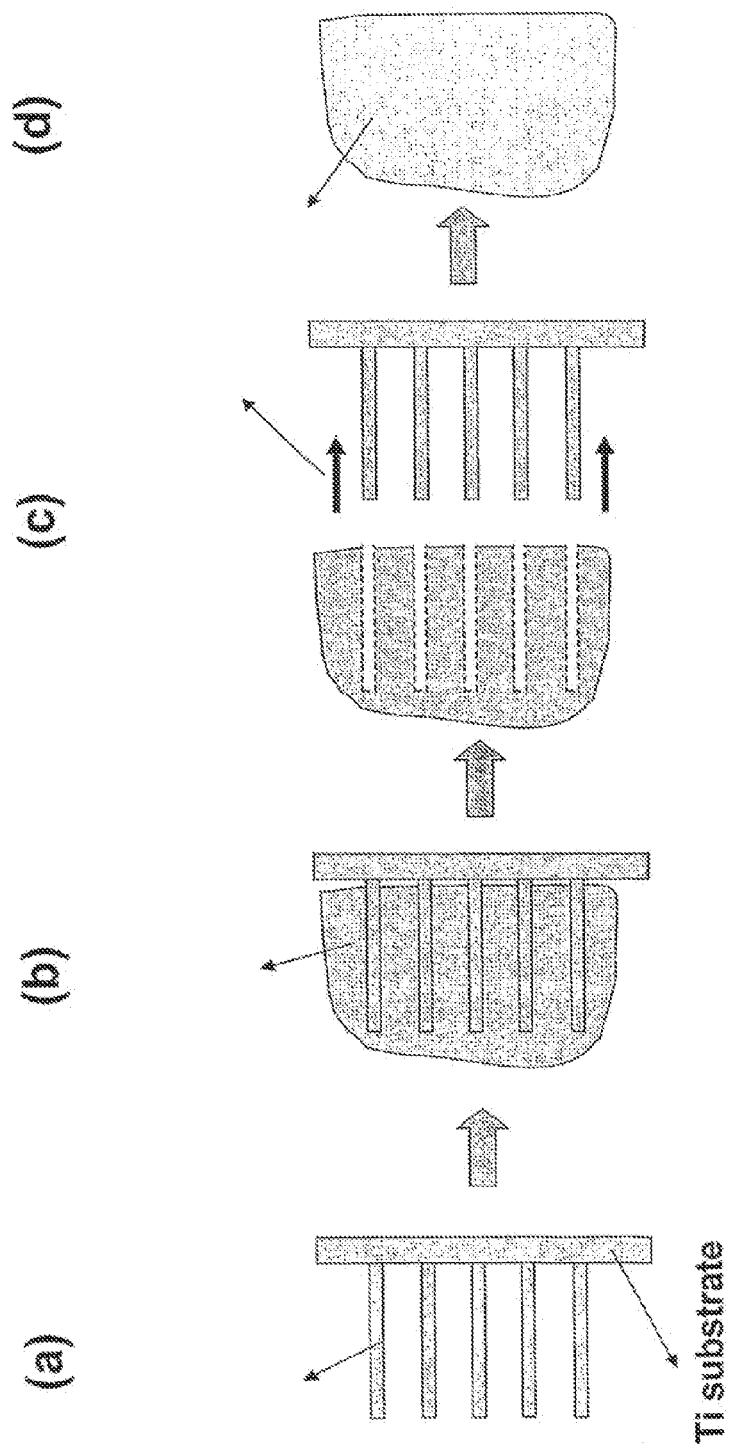

The invention also provides compositions and methods for 3-dimensional cell, tissue and organ growth and maintenance, e.g., for organ or hard tissue replacements. In one aspect, a three-dimensional (3-D) growth of cells with a substantial volume, rather than a thin, two-dimensional (2-D) surface coverage of cells, is desirable. The invention provides a 3-D cell culture technique using the nanotube arrays with a biocompatible surface in a 3-D configuration. Referring to the drawings, FIG. 23 schematically illustrates an exemplary novel approach of the invention. In one aspect, the growth base is made of subdivided and three-dimensionally positioned Ti ribbons, plates, wires, rods as illustrated in FIG. 23(a), which is in this example is made to be retractable so that the final cultured 3-D cells or organs do not contain the Ti metal any more as might be desired for some applications, although Ti and $TiO_2$ are well known to be biocompatible.

In one aspect, to obtain relatively large surface area for cell growth, the desired titanium metal ribbon thickness in FIG. 23(a) is in the range of between about 10 μm to 50,000 μm, or between about 25 to 2,500 μm. In one aspect, the desired volume fraction of the metal for the given targeted cell volume at the end of the planned cell culture period is at least 5%, 10%, 20% or 30% in volume. Each of the ribbon surface can be made to contain an aligned nanotube array with a desired dimension of nanotubes, as described above, e.g., a desired diameter of between about 10-1000 nm, between about 30-300 nm, or between about 60 to 200 nm in diameter; and the desired height can be in the range of between about 40 to 1000 nm, or between about 100 to 400 nm; and the desired angle can be vertical with an allowance of 10, 20, 30, 40 or more degree variation off the perpendicular axis; and the desired gap dimension between adjacent nanotubes can be in the range of between about 2 to 100 nm, or 5 to 30 nm.

In one aspect, the shape of these nanotubed ribbons is straight so that the metal arrays can be pulled out after desired volume of the cells are cultured, as illustrated in the exemplary FIGS. 23(b) and (c). The cultured growth can continue after the metal wire or ribbon array template structure is pulled out, and any minor surface damage or the thin empty gap created by the vacated template can be repaired/filled as illustrated in FIG. 23(d). This exemplary three-dimensionally cultured cell volume in an accelerated and nutrient-supplied manner can be useful for a variety of applications, including making a partially artificial or a fully artificial tissue or organ, e.g., liver, kidney, bone, periodontal tissue, blood vessel cells, skin cells, stem cells, and other human or animal organ cells etc.

The 3-D cultured cells can be in any orientation, i.e., horizontal, vertical or upside down depending on specific needs, especially in ex vivo or in vivo culture environment(s), for example, in the case of organ implants in human, animal, or xenotransplantation of human organs which are temporarily cultured in animals prior to human implantation.

Growth of Tube-Shaped Cells/Organs

An alternative embodiment of the invention comprises culturing 3-dimensional, tube-shaped cells, such as blood vessel cells or fluid, enzyme and/or hormone secretion tubes, intestine tubes, nerve "tubes" (e.g., Schwann cells), and the like, using nanotube-comprising compositions and methods of the invention. For example, in one aspect, using artificially engineered nanotube array surfaces of this invention, the cells are cultured into a tube configuration; and in one aspect, the after the cells are cultured into a tube configuration the rods are pulled out, leaving a ready made tubular cell structure (e.g., multi-cellular structure) or a tubular cell shape. Such a tube-shaped cells or cell structure can be used for repairing tissues or organs, e.g., repairing damaged blood vessels, nerves, fluid, enzyme and/or hormone secretion tubes, fluid, intestine tubes, to name just a few exemplary structures that can be built de novo, or used for the repair or reconstruction of tissues or organs, using the compositions and methods of the invention.

Co-Culturing

Another embodiment of the invention comprises a 3-dimensional cell growth process of culturing at least two types of cells together. Human or animal organs often contain more than one type of cells. Because it has been recognized that a co-culture during growth of cells, such as bone, kidney or liver cells, is beneficial in obtaining a higher quality cells (see, e.g., Begue (1983) Experimental Cell Res. 143:47-54; Angius (1988) J. Biochem. 252:23-28); US Patent application pub. No. US 2001/0023073, Bhatia et al.), or a better functional organization of cells—leading to a functional tissue or organ system, the invention provides compositions and methods comprising use of at least two types of cells together. The invention also provides methods for co-culture of different cells using the compositions of the invention, e.g., for making artificial organs or tissues, or for repairing or reconstructing organs or tissues in vivo, ex vivo or in situ.

For example, in one aspect cells are co-cultured using artificially engineered nanotube array surfaces of the invention, and in one aspect at least two different types of cells are co-cultured. For example, in the case of liver cell cultures (e.g., for making artificial liver organs or tissues, or for repairing or reconstructing damaged or diseased liver), parenchymal liver cells (hepatocytes) are cultured together with at least one of the following cells: fibroblast cells, blood vessel cells, Kupffer cells, epithelial cells, endothelial cells, skin cells (keratinocytes), hematopoietic cells, bone marrow cells, etc. Similarly, a culture of other organ cells (e.g., eyes, kidneys, bone, blood vessels, heart) using this exemplary approach can be carried out using an appropriate combination of cells.

Permanent or Semi-Permanent 3-D Cell/Organ Implants

The invention provides permanent or semi-permanent 2-D and/or 3-D cell/tissue/organ implants, e.g., for cell, tissue and/or organ growth or reconstruction, or for a medical treatment, e.g., to supplement or replace a diseased or injured organ or tissue, e.g., a kidney, liver, pancreas, nerve cell(s) (e.g., spinal cord) and the like. An exemplary artificially engineered nanotube array of the invention comprises a base structure of wire/rod/ribbon/sheet, as illustrated in FIGS. 9(a) and (b), which can be removed, or alternatively, the base structure can be optionally left in to be a component of inorganic-organic composite structure. The base structure can be made of Ti wires, ribbons, networks or sponges or any other biocompatible or bio-inert material such as a noble metal, silicon, polymer, etc., optionally coated with biocompatible or bioinert layer.

In some aspects, for such permanently retained metal structures, a locally bent or curved configuration of the base structure is preferred so as to provide a mechanical locking and more stable structure.

Nanopore-Reservoired Template for Multifunctional 3-D Cell/Organ Growth

The invention provides a nano-reservoir-comprising (e.g., a nanopore-reservoired) template for multifunctional 2-D or 3-D cell, tissue and/or organ growth or reconstruction. In one aspect, a benefit of this exemplary artificially engineered nanotube array structure is that the vertical pores within nanotubes are utilized as a reservoir (e.g., depository) of various biologically active agents to provide multi-functional capability, as illustrated schematically in FIG. 12, or to aid in the growth of, or guide a directional growth of cells, and/or in the maintenance of the cell, tissue and/or organ. In alternative aspects, therapeutic or test drugs, growth factors, proteins, collagens, enzymes, hormones, nucleic acids (e.g., siRNAs, antisense agents), DNA's, genes, antibiotics, antibodies, magnetic nanoparticles, small molecules, lipids, carbohydrates and so forth are used.

The filling of the nanotubes pores (and, in one aspect, also in-between the nanotubes) can be effected by a number of different methods. For example, in one aspect, ultrasonic agitation of the nanotube structure in a solution containing one or more of the biologically active agents is used. In one aspect, nano-sized pores of $TiO_2$ nanotubes are used. As compared to micro-sized pores, artificially engineered nanotube array structure of the invention have an advantage of being able to keep the stored biological agents much longer and allow slower release over a longer period of time; however, arrays and structures of the invention can comprise a mixture of micro-sized pores and/or tubes and nano-sized pores and tubes, depending on the desired reagent release effect.

In one aspect, 2-D and/or 3-D orthopaedic (artificial joint), eye, organ (e.g., liver, kidney), nerve (spinal cord), dental (e.g., odontogenic structures), skin and/or periodontal (e.g., tooth supporting structures) or any other cell implants of the invention comprise artificially engineered nanotube array structures comprising these nano-reservoir-comprising (e.g., a nanopore-reservoired) templates. In one aspect, an advantage of building in these nano-reservoirs is that a continuous supply, a defined duration supply, or an intermittent supply of biological or chemical agents can be designed in to the composition of the invention to effect a desired growth, differentiation, cell interaction or direction cell growth, and the like.

For example, a growth factor can be slowly released from the nanotubes, e.g., a bone morphogenic protein (BMP) type or collagen type growth factor can be placed into a nano-reservoir (or a micro-reservoir, which is an alternative option in some aspects). Another example is insertion of infection-preventing antibiotics (such as penicillin, streptomycin, vancomycin, and the like), which can be slowly released from the nanotubes; can be slowly released from the nano-reservoirs. Thus, compositions of the invention can be designed such that much more efficient and healthier cell or bone growth can be accomplished.

Other examples include 3-D bone growth, 3-D culturing liver or kidney or other organs, 3-D spinal cord, tooth or periodontal tissue re-growth, or re-growth or repair of other cells cells/tissues/organs, which can be further enhanced by using slowly released biological agents from the nanotube reservoirs. Another example is incorporation of therapeutic agents, e.g., drugs, biological agents or natural products, such as anti-cancer drugs, in the nanotube pores, e.g., where the cultured 3-D cells/organs are to be implanted into a body of a patient whose cancerous organs have been partially or fully removed.

In addition to the in vitro type cell culture aspects of the invention, the 3-D base structure of the invention can comprise use of artificially engineered nanotube array structures pre-filled with one or more types of drugs and biological agents, where the structures are left permanently or semi-permanently in vivo implanted as a source of slow drug release within an individual, e.g., a human body.

Externally Controllable Drug Release in 3-D Growing Cells/Organs

The invention provides devices, arrays, templates and other structures of the invention comprising nanotubes and/or nanopores or nano-reservoirs and controlled release compositions, e.g., an externally controllable drug release composition, e.g., in a 2-D or 3-D growing cells/tissue/organ of the invention. In one aspect, a device, array, template of the invention comprises multi-functional implants to implant or store remote-controllable media, such as magnetic nanoparticles, biodegradable agents, a colloidal liquid and the like. A biological or chemical agent, such as a cancer drug, can be placed together with (or within) a magnetic nanoparticle in the nanopore or nano-reservoir (or micro-reservoir, which is an alternative option in some aspects); for example, as in the exemplary nanotubes of FIG. 12.

The nanopore- or nano-reservoir-implanted composition can be designed for release, for example, by ultrasonic or magnetic agitation of a colloidal liquid containing a mixture of the drug solution and the particles. Exemplary magnetic nanoparticles for such use include biocompatible iron-oxide particles of magnetite ($Fe_3O_4$) or maghemite ($\gamma$-$Fe_2O_3$), e.g., in the particle size regime of between about 5 to 50 nm in average diameter. External stimulation of the magnetic nanoparticles by orientation-changing magnetic field or alternating current (AC) magnetic field can help release a biological reagent, a dye, an isotope (e.g., a radioactive agent), a drug or chemical, e.g., a cancer drug, by mechanical agitation/movement of the magnetic particles or by heating of the drug-particle mixture due to the AC magnetic field.

Magnetic-nanoparticle-containing nanotube structures of the invention can also be useful for treatment of a disease, injury or condition (e.g., a cancer) via a combination of externally controllable drug release and magnetic hyperthermia treatments, for example, as an implant in bone cancer area or other cancer regions in general. Because there has been much progress in the general magnetic hyperthermia treatment of cancer using high frequency alternating current (AC) magnetic field, these treatments can be incorporated when practicing this invention, see, e.g., Jordan (1999) J. of Magnetism and Magnetic Materials 194:185-196. The magnetic particles can be confined within the nanotubes, nanopores and/or nano-reservoirs, thus minimizing any complications that may arise from the nanoparticles in human body, yet induce local temperature rise for the magnetic hyperthermia treatment of cancer.

3-D Cell Proliferation and Supply Device

The invention provides artificially engineered nanotube array structures that can accelerate cell growth, e.g., in a 2-D or a 3-D cell growth pattern. For example, the increased number of cells generated by this exemplary device in a 3-D configuration can be useful for accelerated supply of various types of cells, such as bone cells, liver cells, kidney cells, nerve or blood vessel cells, skin cells, periodontal cells, stem cells, and other human or animal organ cells, and other human or animal cells for various R&D or therapeutic uses.

In one aspect, the cells are cultured in a biocompatible environment with needed nutrient media. In one aspect, the cells are proliferated on vertically or parallel-aligned nanotube arrays of the invention, and then can be harvested and supplied for various uses. One exemplary method of harvesting the grown 3-D cells off a nanotube arrayed substrate comprises use of linearly retractable, base structures; and then in one aspect, physically or mechanically removing the cells, e.g., as illustrated in FIG. 16(b). Vacuum suction is one of the possible processes for the mechanical removal of the cells from the retractable substrate.

Another exemplary method is to use a process known as "trypsinization". Once cells are grown completely on whole surface of cell culture flask, the media fluid is removed by suction. After rinsing of the cells twice with PBS (phosphate buffer solution), trypsin is added to detach the cell from the surface. A combination of the template retracting (mechanical removal) and trypsinization can also be utilized. The retrieved cells are then washed, stored and supplied to the people who want to purchase them. For trypsinization, generally approximately 2-3 ml of trypsin can be used for detaching cells grown on 10 $cm^2$ cell culture dish. After approximately 2 minutes, most of the cells are detached from the nanotube surface. After adding approximately 10 ml of new medium, this fluid containing the detached stem cells can be poured into a centrifuge tube. After centrifugation at appropriate rotation speed and time, all of the cells can be separated. The medium can be removed by suction, and 1 ml of new media can be added for storage of the harvested cells or for additional culture. To estimate the number of proliferated cells, trypan blue assay can be employed in conjunction with hematocytometry.

The 2-D or 3-D cultured cells prepared using the artificially engineered nanotube array structures of the invention can be useful for a variety of applications, e.g., in vivo implanting of cells or organs. For example, a patient can be supplied with cultured and implanted, three-dimensional functional cells such as liver, kidney, or blood vessel cells or organs, as illustrated in FIG. 11(b). Three-dimensionally cultured bones or tissues can also be utilized as dental, periodontal or orthopaedic body implants as illustrated in FIG. 11(a).

Analytical Diagnostic Biochip

In one aspect, the invention provides analytical diagnostic arrays, or biochips, comprising structures of the invention. For example, rapid growth of cells—such as growth facilitated by a large surface area—can be effected by use of a composition of the invention. For example, 2-D or 3-D cell culturing can be useful for carrying out fast diagnosis and detection of certain types of cells, such as diseases, toxins, poisons or biological or chemical warfare agents (e.g., *bacillus* spores, e.g., anthrax). In one aspect, the invention provides an X-Y matrix subdivided array, e.g., an artificially engineered nanotube array structure produced as illustrated in FIG. 17.

For diagnosis of diseases (especially epidemic diseases, e.g., SARS or influenza, e.g., the so-called "bird flu") or biological warfare agents (e.g., bio-terror germs, spores, e.g., anthrax, bacteria or viruses), as well as identifying cells to produce forensic evidence, the invention provides a rapid detection device, even when the available quantity of cells is relatively small. For example, FIG. 17 illustrates the detection elements comprising a multiplicity of parallel-configured and laterally gapped nanotubes of the invention upon which various types of cells are placed and allowed to rapidly proliferate. In this aspect, as a sufficient number of cells are rapidly grown in a shorter period of time, an easier and faster detection device and method is generated.

For analysis of cell types, various exemplary techniques, e.g., as illustrated in FIG. 18, can be used, including, e.g., FIG. 18(a) optical detection of morphology and size (using a microscope, fluorescent microscope, or CCD camera sensing of fluorescent or quantum dot tagged cells), FIG. 18(b) chemical or biological detection (e.g., based on signature reactions), FIG. 18(c) magnetic sensor detection (e.g., by using magnetically targeted antibody and its conjugation with certain types of antigens).

Liver Cell Array Device for Drug/Chemical Toxicity Testing

Another important application of the compositions of the invention, e.g., the exemplary bio-chip apparatus illustrated in FIG. 17, comprises their use as a base structure to culture liver cells for testing of new drugs, as illustrated in FIG. 24.

A variation of this embodiments includes having a rod or plate shape base structure in a vertically (or near vertically) arranged configuration; with in one aspect, each rod or plate base comprises a parallel—yet a laterally spaced-apart, nanotube array; this can make the 2-D or 3-D culture more effective. Because the 2-D or 3-D structured, nanotube array of the invention enables a rapid and healthy culture of liver cells in a desirable 2-D or 3-D configuration, the apparatus can be utilized for the important task of testing drug toxicity or chemical toxicity.

In one aspect, for toxicity testing, the 2-D or 3-D structured $TiO_2$-nanotubes are important for creating a stable "culture", e.g., an artificial organ, comprising an array of two- or three-dimensionally configured liver cells. These devices of the invention are important because when a drug is toxic to human or animal body under an in vivo situation, the liver is one of the first organs to sense it and try to isolate the toxic materials. Thus, these devices, e.g., bio-chips, of the invention can comprise an array of healthy, 2-D or three-dimensionally cultured liver cells, e.g., 10×10 ($10^2$), $10^3$, 100×100, $10^5$, or 1000×1000 cells as sensing elements, thus allowing simultaneous evaluation of many drugs for a much accelerated screening and development of biologically acceptable drugs.

Likewise, many chemicals, biological agents, gases, polymers, injection fluids, and composites and the like that may be useful for in vivo applications, or may be encountered in in vivo conditions (e.g., toxins, poisons) can be rapidly tested for toxicity, e.g., using the exemplary device of FIG. 18 and FIG. 24.

In one aspect, for analysis of the response of liver cells, various exemplary detection/analysis mechanisms, such as illustrated in FIG. 18 can be utilized, for example: (a) optical or microscopic sensing, (b) chemical or biological detection, and (c) magnetic sensor detection.

III. ARTICLES COMPRISING CONFIGURED NANOTUBULE STRUCTURE, THREE-DIMENSIONALLY CULTURED CELLS, METHOD FOR MAKING SUCH STRUCTURE AND CULTURING SUCH CELLS AND METHOD OF USING SUCH CELLS

The invention provides three-dimensionally cultured cells and tissues grown by using three-dimensionally configured templates comprising aligned nanotubule structure. The invention provides three-dimensionally cultured cells/organs, template devices composed of $TiO_2$ nanotubule structure which allows a growth of 3-dimensionally configured cells such as bone cells, liver cells, kidney cells, blood vessel cells, skin cells, periodontal cells, stem cells, and methods for applying such cell growth techniques. The invention provides vertically aligned $TiO_2$ nanotube arrays adherent on three-dimensionally configured arrays of Ti surfaces; these arrays can induce a strong cell adhesion and significantly enhance the formation kinetics of cells. In one aspect, three-dimensionally placed nano-gaps between aligned $TiO_2$ nanotubes allow a continuous supply of various nutrients to the growing cells. The $TiO_2$ nanotube array can be fabricated on the surface of a three dimensional array of wire or ribbon shaped Ti, which can be retractable from or permanently kept in the 3-D grown cells. In one aspect, a 3-dimensional cell and tissue culture device, with optionally stored biological agents within the nanotube reservoirs, improves growth of healthy liver cells and other cells, and maintains the functionality of the cells. Such cultured cells can be useful for rapid supply of needed cells for R&D or therapeutics, for preparation of partial or full implant organs, for externally controllable drug release and therapeutic treatments, for efficient toxicity testing of drugs and chemicals, and for diagnosis/detection of disease or forensic cells.

SUMMARY

The invention provides three-dimensional arrays comprising: a solid substrate comprising Ti wires, ribbons or rods, or any combination thereof; and, a plurality of vertically aligned, laterally spaced, nanotubes associated with the substrate, wherein each nanotube comprises a nanopore. The outer diameter of each nanotube can be about 10-1000 nm, or about 30-300 nm, or about 60-200 nm.

In one aspect, the nanopore of each nanotube comprises a diameter of about 20% of the outer diameter of the nanotube, or, a diameter of about 50% of the outer diameter of the nanotube. In one aspect, the height of each nanotube is about 40-1000 nm, or, the height of each nanotube is about 100-400 nm. In one aspect, the aspect ratio of each nanotube is less than about 10, or the aspect ratio of each nanotube is less than about 5. In one aspect, the alignment angle of the vertically aligned nanotubes is about 0-45 degrees off the vertical direction. In one aspect, the alignment angle of the vertically aligned nanotubes is about 0-30 degrees off the vertical direction. In one aspect, adjacent, vertically aligned nanotubes are laterally spaced from about 2-100 nm, or adjacent, vertically aligned nanotubes are laterally spaced from about 5-30 nm.

In one aspect, the nanotubes comprise a biocompatible surface, e.g., a compound comprising Ti, Ti oxide ($TiO_2$), ceramic, noble metals, and/or polymer materials or a combination thereof. In one aspect, the compound comprises $TiO_2$.

The invention provides three-dimensional array compositions and methods for three-dimensionally culturing cells, e.g., bone cells, liver cells, kidney cells, blood vessel cells, skin cells, periodontal cells, stem cells, and other human or animal organ cells; wherein the organ can comprise bone cells, liver cells, kidney cells, blood vessel cells, skin cells, periodontal cells, stem cells, and other human or animal organ cells.

In one aspect, the three-dimensional array compositions of the invention further comprise a means for retracting the nanotubes from the three-dimensionally cultured cells such that only the cells/organs are left. In one aspect, the three-dimensionally cultured cells or organs are permanently or semi-permanently associated with the nanotubes of the array.

The invention provides compositions and methods for accelerating the growth of cells, the method comprising contacting the cells with an array of the invention (e.g., a three-dimensional array) in the presence of a nutrient fluid suitable for sustaining growth of the cells. In one aspect, the cell growth is accelerated by about 100%, 200%, or by about 300%. In one aspect, the nutrient fluid is supplied under the growing cells through the spacing between the parallel nanotubes.

The invention provides compositions (e.g., implants) comprising three-dimensional arrays comprising: a solid substrate comprising Ti wires, ribbons or rods, or any combination thereof; and, a plurality of vertically aligned, laterally spaced, nanotubes associated with the substrate, wherein each nanotube comprises a nanopore, and wherein the array comprises dental cells suitable for implantation and regeneration of dental tissue in a subject.

The invention provides compositions (e.g., implants) comprising three-dimensional arrays comprising: a solid substrate comprising Ti wires, ribbons or rods, or any combination thereof; and, a plurality of vertically aligned, laterally spaced, nanotubes associated with the substrate, wherein each nanotube comprises a nanopore and wherein the array comprises orthopaedic cells suitable for implantation and regeneration of bone and/or joint tissue in a subject.

The invention provides compositions (e.g., implants) comprising three-dimensional arrays comprising: a solid substrate comprising Ti wires, ribbons or rods, or any combination thereof; and, a plurality of vertically aligned, laterally spaced, nanotubes associated with the substrate, wherein each nanotube comprises a nanopore, and wherein the array comprises one or more biologically active agents or chemicals comprising therapeutic drugs, growth factors, proteins, collagens, stem cells, enzymes, hormones, nucleic acids (e.g., vectors, siRNAs, RNAs, DNAs, genes) antibiotics, antibodies, radioisotopes and/or magnetic nanoparticles.

The invention provides compositions (e.g., implants) comprising three-dimensional arrays comprising: a solid substrate comprising Ti wires, ribbons or rods, or any combination thereof; and, a plurality of vertically aligned, laterally spaced, nanotubes associated with the substrate, wherein each nanotube comprises a nanopore, and wherein the array comprises a colloidal composition comprising magnetic nanoparticles interspersed with a biological agent selected from the group consisting of therapeutic drugs, cancer drugs, growth factors, proteins, collagens, stem cells, enzymes, hormones, nucleic acids (e.g., vectors, siRNAs, RNAs, DNAs, genes), antibiotics, and antibodies.

The invention provides methods for selectively releasing a biological agent in a subject, the method comprising implanting an array of the inventions in a subject and contacting the array with ultrasonic or magnetic agitation of the colloidal composition, wherein the biological agent is released from the array. In one aspect, the magnetic nanoparticle comprises iron-oxide particles of magnetite ($Fe_3O_4$) or maghemite ($\gamma$-Fe2O3) or a combination thereof. The nanoparticles can be about 5-50 nm in average diameter. The magnetic agitation can comprise external stimulation of the magnetic nanoparticles by alternating current (AC) magnetic field. The biological agent can be released from the array by mechanical agitation/movement of the magnetic particles or by heating of the composition resulting from the AC magnetic field.

The invention provides methods for treating a cell proliferation disorder, the method comprising: implanting a three dimensional array of the invention in to a subject, wherein the array is implanted at or near the site of a cell proliferation disorder; and, contacting the array with magnetic agitation, wherein the agitation accelerates biological agent release and provides magnetic hyperthermia treatment at the site of implantation.

The invention provides systems for growing and harvesting selected cells, the system comprising: a three dimensional array of the invention operably associated with a device for removing the cells or tissue from the array; and a computer operably associated with a), wherein the computer comprises instructions for automatically contacting the cells with a suitable growth media and for harvesting the mature cells. In one aspect, cells are bone cells, kidney cells, blood vessel cells, skin cells, liver cells, liver parenchymal cells, endothelial cells, adipocytes, fibroblastic cells, Kupffer cells, kidney cells, blood vessel cells, periodontal cells, odontoblasts, dentinoblasts, cementoblasts, enameloblasts, odontogenic ectomesenchymal tissue, osteoblasts, osteoclasts, fibroblasts, and other cells and tissues involved in odontogenesis or bone formation, stem cells or a combination thereof. The cells also can be embryonic or adult stem cells. In one aspect, the cells are removed by trypsinization. In one aspect, the cells are harvested using mechanical means such as suction and centrifugal process, or optionally in combination with trypsinization.

The invention provides methods for diagnosing or detecting a condition, disease or an exposure to a toxic agent comprising implanting a biochip comprising an array (e.g., a three dimensional cell-comprising array) of the invention in a subject. The invention provides methods detecting biological or chemical warfare agents (e.g., anthrax), including gases, bacteria, spores and the like, the method comprising providing an X-Y matrix subdivided array of nanotube comprising a plurality of nanotubes, each nanotube comprising a specific type of cell for further analysis.

The invention provides biometric or biomimetic arrays comprising liver cells (e.g., liver parenchymal cells) for performing drug/chemical toxicity testing, the array comprising an array of the invention and liver cells (e.g., liver parenchymal cells) for evaluation of new drugs, cosmetics, dyes, preservatives and/or natural products for testing of safety and toxicity issues. In one aspect, the array is contacted with a test material comprising chemicals, polymers or injection fluids. In one aspect, the "biomimetic" is an "artificially arranged system of living cells", or, in addition to conventional material fabrication approaches comprising mimicking the natural biological process (e.g., the devices and methods of the invention can either be an "artificially arranged system of living cells" or mimic a natural system or process, e.g., a tissue or organ system, or a mixture thereof).

The invention provides methods for manufacturing the arrays of the invention, as described herein.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

Figure 25:
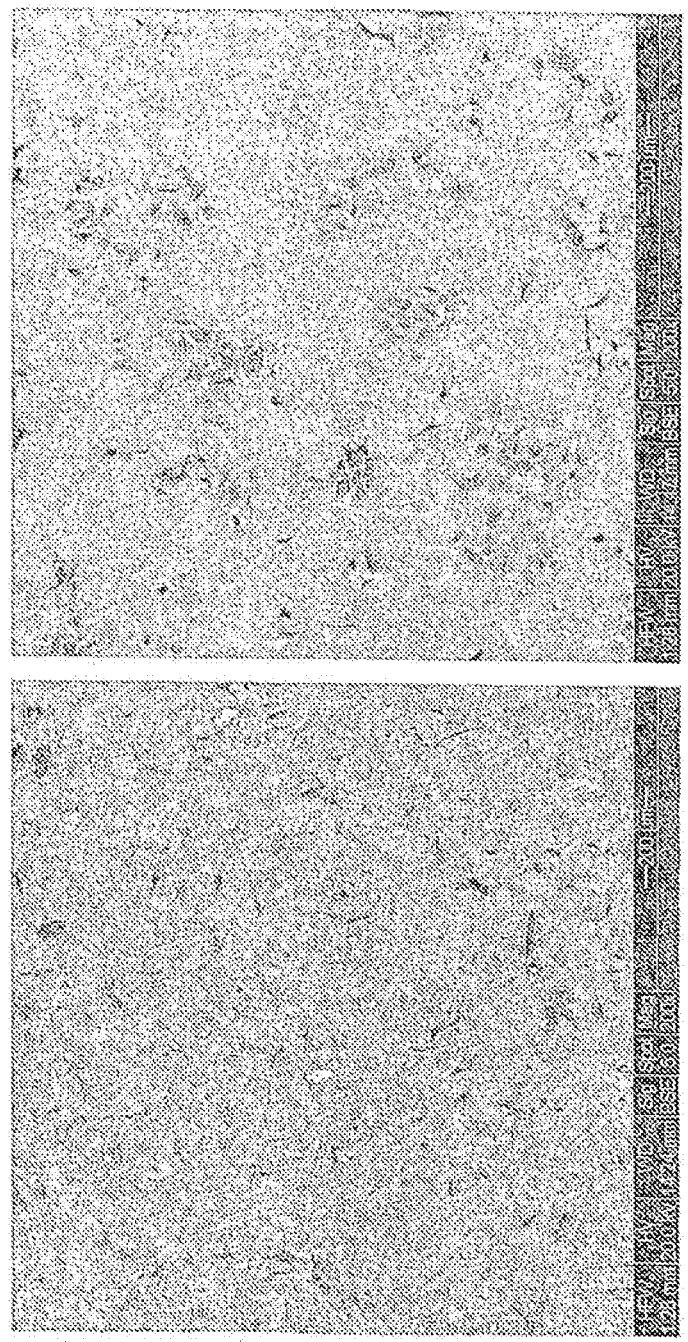

FIG. 25: FIG. 25(a)-(b) show comparative backscattered electron SEM images of liver cell growth on FIG. 25(a) sand blasted, roughened Ti; FIG. 25(b) exemplary $TiO_2$ nanotube array surface of the invention.

FIG. 26: FIG. 26(a)-(b) schematically illustrate cell growth on exemplary $TiO_2$ nanotubes of the invention in different positions; FIG. 26(a), vertically positioned; FIG. 26(b), horizontally upright positioned; FIG. 26(c), horizontally inverted positioned.

FIG. 27: FIG. 27(a)-(b) schematically illustrate accelerated growth of 3-dimensional, tube-shaped cells such as blood vessel cells, as in FIG. 27(a), or enzyme/hormone secretion tubes, cultured using an exemplary retractable Ti wire array substrate of the invention, as in FIG. 27(b), with each wire having a $TiO_2$ nanotube arrayed surface (a pull out titanium wire array substrate with each wire having titanium oxide surface).

Figure 28:
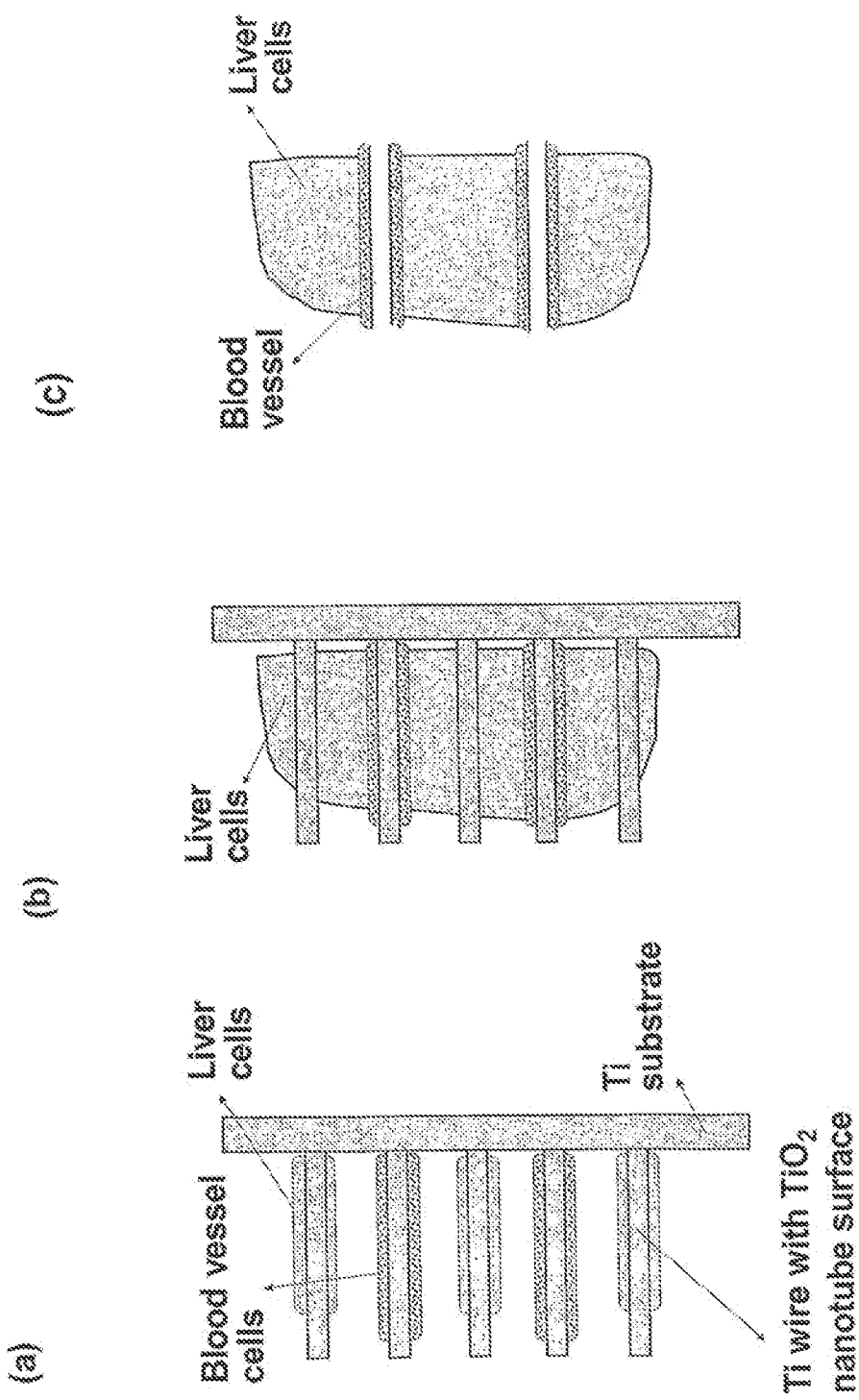

FIG. 28: FIG. 28(a)-(c) schematically illustrate the exemplary 3-dimensional cell growth process of culturing at least two types of cells together on a Ti wire array of the invention, comprising $TiO_2$ nanotube surface according to the invention; FIG. 28(a) illustrates the growth of non parenchymal stromal cells (e.g., blood vessel cells) on Ti; FIG. 28(b) illustrates the growth of parenchymal cells (e.g., liver cells); FIG. 28(b) illustrates the step of removing the Ti wire array by it pulling out from the growing cells.

Figure 29:
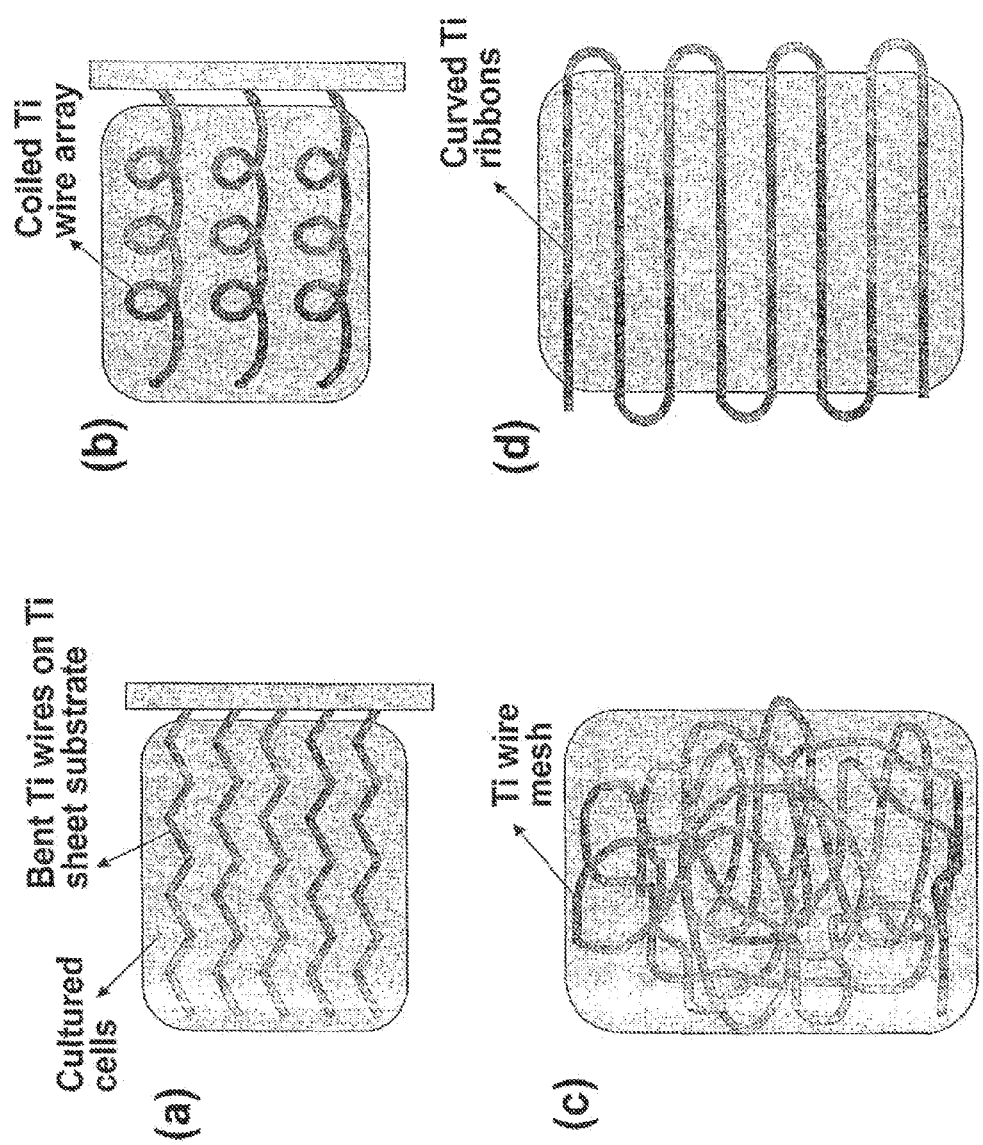

FIG. 29: FIG. 29(a)-(d) schematically illustrate accelerated culture of 3-D cells with permanently retained Ti wires, e.g., bent wires on Ti sheet substrate, as illustrated in FIG. 29(a); coiled Ti wire array, as illustrated in FIG. 29(b); networks or sponges having $TiO_2$ nanotube arrayed surfaces, e.g., Ti wire mesh, as illustrated in FIG. 29(c); and, ribbons, e.g., curved Ti ribbons, as illustrated in FIG. 29(d).

It is to be understood that the drawings are for purposes of illustrating the concepts of the invention and are not to scale. Like reference symbols in the various drawings indicate like elements.

DETAILED DESCRIPTION

The invention provides nano-scaled materials that can exhibit extraordinary physical, mechanical and biological properties, which cannot be achieved by micro-scaled or bulk counterparts.

In one aspect, a $TiO_2$ phase can be prepared by various techniques such as sol-gel method, electrophoretic deposition and anodization. See, e.g., Lakshmi, et al., Chemistry of Materials, Vol. 9, page 2544-2550 (1997), Miao, et al., Nano Letters, Vol. 2, No. 7, page 717-720 (2002); Gong, et al., Journal of Materials Research, Vol 16, No 12, page 3331-3334 (2001). In one aspect, a $TiO_2$ phase can be prepared by various techniques such as sol-gel method (see, e.g., U.S. Pat. No. 7,014,961); photolithographic patterning of a photoresist layer by pattern-wise exposure to short-wavelength ultraviolet light through a pattern-bearing photomass, as described in U.S. Pat. No. 6,593,034; electrophoretic deposition and anodization. See, e.g., Lakshmi, et al. (1997) Chemistry of Materials, 9:2544-2550; Miao, et al. (2002) Nano Letters 2:717-720; Gong, et al. (2001) J. Materials Res. 16:3331-3334; Macak (2005) Chem. Int. Ed., 44:7463-7465.

In one aspect, bioactive materials, such as hydroxyapatite and calcium phosphate, are coated on Ti surface; this can make the Ti surface more bioactive. See, e.g., Shirkhanzadeh et al, Journal of Materials Science Letters, Vol. 10, page (1991), de Groot et al., Journal of Biomedical Materials Research, Vol. 21, page 1375-1381 (1987), and Cotell et al., Journal of Applied Biomaterials, Vol. 8, page 87-92 (1992). In one aspect, the interface is bonded with an integrated structure of the invention comprising a locked-in configuration with a much increased adhesion area; e.g., a discrete, less continuous layer to minimize interface stress and delamination. In one aspect, accelerated hydroxyapatite and bone growth is accomplished on a mechanically adherent $TiO_2$ nanotube surface on Ti substrate, as described by, e.g., Oh (2005) Biomaterials 26:4938-4943.

The invention provides implants comprising three-dimensionally configured cells, and methods and devices for producing these three-dimensionally cultured cells. The invention provides nanotubule structures useful as a substrate for efficient liver cell culture devices; and in one aspect, the liver cells are grown quickly in vitro without a major loss of their capability for complex functions.

The $TiO_2$ nanotubule structures of the invention can comprise three dimensional surfaces for cell culture devices in vitro as well as in vivo, and bio-artificial liver support devices. This invention provides 2-D and 3-dimensional cell culture devices comprising $TiO_2$ nanotubule structures; which in one aspect enable accelerated growth of cells, e.g., bone cells, kidney cells, blood vessel cells, skin cells, liver cells, liver parenchymal cells, endothelial cells, adipocytes, fibroblastic cells, Kupffer cells, kidney cells, blood vessel cells, periodontal cells, odontoblasts, dentinoblasts, cementoblasts, enameloblasts, odontogenic ectomesenchymal tissue, osteoblasts, osteoclasts, fibroblasts, and other cells and tissues involved in odontogenesis or bone formation, stem cells or a combination thereof; including organized mixed cell groups, including functional organ cell groups, such as mixed and organized liver or kidney cells; as well as other structural cells such as blood vessel cells, enzyme secretion vessels, periodontal, bone, teeth, or other hard tissue cells. These cultured cells can be useful for a variety of applications including i) organ-related therapeutic medical treatment including liver or kidney disease treatment, ii) orthopaedic, dental or periodontal processes, iii) supply of cells for various research or therapeutic purposes, and iv) disease diagnostic or toxicity testing of new drugs or chemicals.

Referring to the drawings, FIG. 1 schematically illustrates exemplary devices comprising self-organized $TiO_2$ nanotube arrays grown on titanium metal or alloy substrate to accelerate cell proliferation according to the invention. In alternative aspects, the $TiO_2$ nanotubes or any other biocompatible nanotubes desirable for the exemplary devices have typical desired dimension of about 10-1000 nm in diameter, or about 30-300 nm, or about 60-200 nm in diameter. In alternative aspects, the desired heights of the tubules are determined in part by the desired aspect ratio as relatively short height with an aspect ratio of less than about 10, or in one aspect less than 5 is preferred for ease of storing and eventual dispensing of drugs or biological agents intentionally placed within the tubule cavity, which can maintain the function of the cells being cultured such as liver cells, thus help the proliferation of the cells. In alternative aspects, desired height is about 40-1000 nm, or about 100-400 nm.

In alternative aspects, the vertical alignment with open top pore is crucial for bio implant and related applications being described in this disclosure, as the open top of the nanowire allows the penetration of the cells into the nanopore cavity for good adhesion as illustrated in FIG. 1, and also allows easy supply of the biological agents stored in the nanopores. In alternative aspects, the desired angle of vertical alignment is within than 5, 10, 20, 30 or 40 degrees off the perpendicular axis.

In alternative aspects, the base material for the 2D or 3D cell growth structure can be pure Ti or can be an alloy based on Ti such as Ti—V—Al alloys or other solid solution hardened or precipitation hardened alloys with increased mechanical strength and durability onto which an oxide nanotubes are formed. In alternative aspects, similar metals such as Zr, Hf, Ce and their oxide nanotubes are also used. Microstructural analysis of the exemplary cell-growth promoting nanostructure was carried out using by scanning electron microscopy (SEM) and transmission electron microscopy (TEM), as depicted in FIGS. 2 and 3. These exemplary structures comprise vertically aligned, biocompatible $TiO_2$ with a typical dimension of the hollow nanotubes in FIGS. 2 and 3 being approximately 100 nm outer diameter and approximately 70 nm inner diameter with approximately 15 nm in wall thickness, and approximately 250 nm in height.

The exemplary $TiO_2$ nanotubule array structure shown in FIGS. 2-3 was fabricated by anodization technique using a Ti sheet (0.25 mm thick, 99.5% purity) which is electrochemically processed in a 0.5% HF solution at 20 V for 30 min at room temperature. A platinum electrode (thickness: 0.1 mm, purity: 99.99%) was used as the cathode. To crystallize the as-deposited, amorphous-structured $TiO_2$ nanotubes into the desired anatase phase, the specimens were heat-treated at 500° C. for 2 hrs. In alternative aspects, it is preferred that the amorphous $TiO_2$ nanotubes is crystallized to anatase phase by heat treatment, because an amorphous $TiO_2$ phase tends to be more susceptible to breakage by external stresses as compared to a crystalline phase.

In alternative aspects, an important factor for healthy cell growth is a continuous supply of nutrients including proteins, mineral ions, fluid, etc. to the cell through the flow of body fluid. The gap (spacing) between adjacent exemplary $TiO_2$ nanotubules in FIGS. 2 and 3 serves such a function of allowing the body fluid to continuously pass through and supply nutrients to the bottom side of the growing cells. In alternative aspects, the desired gap between the nanotubules is in the range of about 2-100 nm, or about 5-30 nm. In some aspects, too small a gap reduces the effectiveness of nutrient body fluid flow while too large a gap can pose a danger of reduced mechanical stability in the event of vertical or lateral stress or pressure. A transmission electron microscope (TEM) photograph shown for an exemplary inventive $TiO_2$ nanotube array structure, FIG. 3(c), gives an average of approximately 15 nm spacing between the nanotubes.

Accelerated Cell Growth on $TiO_2$ Nanotube Array

In order to estimate the effect of having an extremely fine nanostructure such as the vertically aligned $TiO_2$ nanotubes on cell growth behavior, an osteoblast cell growth on $TiO_2$ nanotubes was carried out as an example. The results indicate that the introduction of nanostructure significantly improves bioactivity of implant and enhances osteoblast adhesion and growth. In alternative aspects, an adhesion of anchorage-dependent cells such as osteoblasts is a crucial prerequisite to subsequent cell functions such as synthesis of extracellular matrix proteins, and formation of mineral deposits.

All the experimental specimens (0.5×0.5 cm$^2$) used for cell adhesion assays were sterilized by autoclaving. A pure Ti sheet polished by emery paper (#600 grit size) and chemically cleaned was used as a control group sample. For cell adhesion studies, MC3T3-E1 osteoblast cells (rat cells of the type CRL-2593, sub-clone 4, ATCC, Rockville, Md.) were used. Each 1 mL of cells was mixed with 10 mL of alpha minimum essential medium ($\alpha$-MEM) in the presence of 10% fetal bovine serum (FBS) and 1% penicillin-streptomycin. The cell suspension was plated in a cell culture dish and incubated under 37° C., 5% $CO_2$ environment. When the concentration of the MC3T3-E1 osteoblastic cells reached approximately $3 \times 10^5$ cells/mL, they were seeded onto the experimental substrate of interest (Ti $O_2$ or Ti) which were then placed on a 12-well polystyrene plate, and stored in a $CO_2$ incubator for 2, 12, 24 or 48 hrs to observe cell morphology and count viable attached cells as a function of incubation time. The concentration of the cells seeded onto the specimen substrate was approximately $5 \times 10^4$ cells/mL.

After the selected incubation period, the samples were washed with 0.1 M phosphate buffer solution (PBS) and distilled water, respectively, and fixed with 2.5% glutaraldehyde in 0.1 M PBS for 1 hr. After fixing, they were rinsed three times with 0.1 M PBS for 10 min. For microscopic examination of cell structures and morphologies, the samples were dehydrated in a graded series of alcohol (50%, 75%, 90% and 100%) for 10 min and subsequently dried by supercritical point $CO_2$. The dehydrated samples were sputter-coated with approximately 2 nm thick gold for SEM examination. The morphology of $TiO_2$ nanotubes as well as that of the adhered cells were observed using SEM and TEM. In the quantitative assay, the adhered cells on sample surface were counted from back-scattered SEM images.

In alternative aspects, the invention provides vertically aligned $TiO_2$ nanotube coatings comprising one or more of the following structures, which can provide structural advantages for reduced interfacial failure:

i) a vertically aligned $TiO_2$ nanotube coating fabricated to be thin, typically less than 1000 nm, preferably less than 400 nm;

ii) a coating having a strong chemical bonding on the Ti substrate as the $TiO_2$ nanotube coating was prepared via chemical process, and since a common element of Ti is shared by the substrate and the coating.

iii) a $TiO_2$ nanotube structure of FIGS. 2 and 3 is made to be not continuous but is discrete, with a gap between adjacent nanotubes of approximately 15 nm. The desired lateral gap dimension is in the range of about 2-100 nm, or about 5-30 nm. Such a lateral sub-division of a nanotube array structure can be important for minimizing the interfacial stresses between two dissimilar materials joined together, with the two materials involved often having substantially different crystal structure, lattice parameter, and coefficient of thermal expansion.

It has experimentally been confirmed that the vertically aligned $TiO_2$ nanotubes of the invention are strongly adherent to the Ti metal base, as it was very difficult to remove the nanotubes from the Ti surface by attempting to delaminate or scrape off or by bending of the Ti substrate. Such a strongly bonded and stable bone-promoting coating is important, especially in consideration of possible interference by fibroblast cells during bone growth near the Ti implants.

The invention also accommodates the fact that fibroblast cells are prone to attach on smooth surface layers, in contrast to the osteoblastic cells which can attach well on rough surface (see, e.g., Salata (2004) J. Nanobiotechnology 2:3 (2004), and provides such smooth surface layers interspersed with vertically aligned $TiO_2$ nanotubes of the invention. In one aspect, in making a cell-comprising device of the invention, an opportunity and time is given for the fibrous tissues to form at the boundary interface between the implant and the growing bone. These tissues can keep osteoblasts from adhering onto the surface of a Ti implant; however, they can also cause an undesirable loosening of the Ti implant. Thus, in another aspect, a rapid and strong adhesion of osteoblasts on implant surfaces is provided for to effect successful bone growth.

In addition to the advantages in mechanical properties, the gaps present between adjacent $TiO_2$ nanotubes of the devices of the invention also may be useful as a pathway for continuous supply of the body fluid with ions, nutrients, proteins, etc. This may contribute positively to the health of the growing cells. In some aspects, in the absence of such pathways the proliferating cells may completely cover the bioactive implant material surface and the bottom surface of the growing osteoblast cells would then have very limited access to body fluid.

Presented in FIG. 7 are SEM micrographs showing the growth and adhesion of the osteoblast cells (after 2 hrs) on vertically nanoporous $TiO_2$ nanotubes. The micrographs clearly indicate that the filopodia of propagating osteoblast cells actually go into the vertical nanopores of the $TiO_2$ nanotubes. The observed rapid adherence and spread of osteoblastic cells cultured on $TiO_2$ nanotubes could be caused by three reasons. First, vertically aligned $TiO_2$ nanotubes exhibit enormously larger surface areas than the flat Ti surface. Second, the pronounced vertical topology contributes to the locked-in cell configuration. Thirdly, the pathway in-between $TiO_2$ nanotube arrays can allow the passage of body fluid and act as the supply/storage route of nutrient, which is an essential biological element for cell growth.

FIG. 8 represents the comparative back-scattered SEM micrographs of the cells cultured on (a) pure Ti, (b) amorphous $TiO_2$ nanotubes, and (c) anatase $TiO_2$ nanotubes after 48 hrs of incubation. It is evident that the MC3T3-E1 osteoblast cell's adhesion and growth is significantly accelerated on $TiO_2$ nanotubes, and more so on anatase $TiO_2$ nanotubes as compared to the amorphous $TiO_2$ nanotubes. The plot of the number of adhered cells as a function of culture period, FIG. 9, clearly confirms this trend, with the speed of cell adhesion and growth on anatase $TiO_2$ nanotubes being significantly higher after 48 hr culture, by as much as approximately 400% as compared to the Ti surface. It is noted that at the early stage, e.g., after 2 hr incubation, there was no significant statistical difference in the data among the three surfaces investigated However, the number of attached cells on the $TiO_2$ nanotubes dramatically increases as the culture time is extended to 12, 24 and 48 hrs.

The accelerated cell growth on vertical $TiO_2$ nanotube array is not restricted to the osteoblast cells. A similar behavior is seen with other cells, for example, it has been found that liver cell growth is substantially accelerated on $TiO_2$ nanotube array. This is shown in FIG. 25 as comparative back scattered electron SEM images of the liver cells (rat hepatocyte #AML-12) cultured for 48 hrs on FIG. 25(*a*) prior art, sand blasted and roughened Ti using #60 grit sand blasting medium, (b) inventive $TiO_2$ nanotube array surface. As is evident from FIG. 25(*b*), the liver cells adhere and grow much faster on the vertically aligned and laterally separated $TiO_2$ nanotubes than on the prior-art sand blast roughened Ti of FIG. 25(*a*). In fact, not much of the liver cell growth was seen on the sand-blasted Ti, as mostly the dark-colored surface roughness defects covers the SEM image of the sample surface.

Three-Dimensional Cell Growth

The invention provides compositions (e.g., devices, such as artificial organ systems) for use as organ or hard tissue replacements. In one aspect, these compositions comprise 2D and/or three-dimensional (3-D) growth of cells. In one aspect, these compositions comprise only 3-D cell structures, with a substantial volume rather than a thin, two-dimensional (2-D) surface coverage of cells. In this aspect, a 3-D cell culture technique comprise use of the biocompatible Ti oxide nanotube surface of the invention in a 3-D configuration.

In one aspect, devices of the invention can incorporate cultured cells growing in a two-dimensional configuration covering the surface of a cell culture substrate. The invention also provides devices facilitating cells growing in a three-dimensional configuration, as in the actual living body; or a combination of 2-D and 3-D configurations.

Three-dimensional cell culturing of some aspects of the invention provide for a faster route for growth and supply of increased number of cells, not only for liver cell related applications, but for producing a number of other cells in a healthy and accelerated manner. Devices and methods of the invention can supply, e.g., for implantation, various types of cells, including bone cells, liver cells, kidney cells, blood vessel cells, skin cells, periodontal cells, stem cells, and other human or animal organ cells. Devices and methods of the invention can be used for drug toxicity testing using toxin-sensitive liver cells, fast detection and diagnosis of diseased cells and/or possible detection of biological warfare agents, including cells exposed to those agents, e.g., including epidemic diseases, anthrax or SARS; and in one aspect, the devices and methods of the invention can utilize only a very small or trace quantity of cells, e.g., by in one aspect accelerating cell growth speed, for example, via the three-dimensional cell culture devices of the invention.

In one aspect, the invention provides mixed hepatocyte co-culture systems with non-liver derived cells. In one aspect, this provides microbiological environments similar to those in vivo by optimizing cell-cell interactions.

The invention provides a culture method and culture device that will allow artificial in vitro (or in vivo) growth of healthy, fully functional and long-lasting liver cells that can be transplanted to the patients in need of liver cells. In one aspect, the invention provides a culture method and culture device that can meet the demands for supply of the cells for toxicity testing of enormous numbers of new or experimental drugs, chemicals, and therapeutics being developed in the pharmaceutical and chemical industry. With the unique toxin-filtering capability of liver cells, any toxicity of a new drug can be manifested first by the reaction of the liver cells. In one aspect, the invention provides a culture method and culture device comprising an array of liver cells that can be utilized as a fast testing/screening vehicle to simultaneously evaluate the potential toxicity of many new drugs and compounds.

Referring to the drawings, FIG. 23 schematically illustrates an exemplary approach: the growth base is made of subdivided and three-dimensionally positioned Ti wires, ribbons, or rods, as illustrated in FIG. 23(a), which is in this particular case made to be retractable so that the final cultured 3-D cells or organs do not contain the Ti metal any more as might be desired for some applications, although Ti and $TiO_2$ are well known to be biocompatible.

The base material can be pure Ti or can be an alloy based on Ti such as Ti—V—Al alloys or other solid solution hardened or precipitation hardened alloys with increased mechanical strength and durability. While examples of accelerated cell and bone growth compositions and methods of the invention can comprise use of the substrate material comprising Ti and/or its alloys, the compositions (devices) of the invention can also comprise other elements having Ti by at least 20%, 30%, 40%, or 50% or more weight %. Compositions (devices) of the invention can also comprise related metals such as Zr, Hf, Nb, Ta, Mo, W, and their alloys. Compositions (devices) of the invention can also comprise other metals and alloys, such as stainless steel, Au, Ag, Pt and their alloys; e.g., for such 3-D cell growth; and in one aspect, these alternative materials can be used as long as a coating of Ti and Ti oxide, Zr, Hf, Nb, Ta, Mo, W and/or their oxides, and/or their alloys, with a thickness of at least 1, 2, 3, 4, or 5 or more nm, and the coating coverage of at least 20%, 30%, 40%, 50%, 60%, 70%, 80% or more of the total surfaces is used.

To obtain relatively large surface area for cell growth, the desired titanium metal wire (or rod) diameter or ribbon thickness in FIG. 23(a) is in the range of about 10 μm-50,000 μm, or between about 25-2,500 p.m. In one aspect, the desired volume fraction of the metal for the given targeted cell volume at the end of the planned cell culture period is at least 10% in volume, or at least 30% in volume. In one aspect, each of the wire or ribbon surfaces is anodized, and can be heat treated to produce aligned; in one aspect, to produce an anatase-structured $TiO_2$ nanotube array covering the surface. In one aspect, a preferred dimension of the $TiO_2$ nanotubes comprises a diameter of between about 10-1000 nm, or between about 30-300 nm, or between about 60-200 nm in diameter. In one aspect, a desired height being in the range of about 40-1000 nm, or between about 100-400 nm. In one aspect, a desired angle is preferably vertical with an allowance of 5, 10, 15, 20, 25, 30 or 35 degrees variation off the perpendicular axis. In one aspect, the desired gap dimension between adjacent nanotubes is in the range of about 2-100 nm, or about 5-30 nm.

In one aspect, for three dimensional cell cultures comprising a merging of cells grown from adjacent wires or ribbons, a desirable spacing between the parallel neighboring branches of wires and ribbons can be at most 10 times the thickness of an average monolayer cell thickness, or alternatively, at most 5 times the thickness of an average monolayer cell. In one aspect, in the case of bone growth, it is the mineral that grows—not a living cell, so the desired spacing between the neighboring branches can be much larger, with a desired spacing being at most 100 times the thickness of osteoblast cell, or alternatively, at most 50 times.

In one aspect, the shape of these $TiO_2$ nanotube coated Ti wires or ribbons is desirably straight so that the metal arrays can be pulled out after desired volume of the cells are cultured, as illustrated in FIGS. 23(b) and (c). The cultured growth will continue after the metal wire or ribbon array template structure is pulled out, and any minor surface damage or the thin empty gap created by the vacated template will be repaired/filled, as illustrated in the exemplary FIG. 23(d). Such a three-dimensionally cultured cell volume in an accelerated and nutrient-supplied manner can be useful for a variety of applications including creation of a partial or full artificial organs of e.g., liver, kidney, bone, periodontal tissue, blood vessel cells, skin cells, stem cells, and other human or animal organ cells etc.

The 3-D cultured cells can be in any orientation, as illustrated in FIG. 26, e.g., horizontal, vertical or upside down depending on specific needs, e.g., the in vivo culture environment, for example, in the case of organ implants in human, animal, or xenotransplantation of human organs which are temporarily cultured in animals prior to human implantation.

Growth of Tube-Shaped Cells/Organs

An alternative embodiment of the invention is schematically illustrated in FIG. 27. Here, an accelerated culture of 3-dimensional, tube-shaped cells (such as blood vessel cells or enzyme/hormone secretion tubes, intestine tubes) is described. On the Ti wire or rods having $TiO_2$ nanotube array surface, the cells are cultured into the tube configuration, after which the rods are pulled out to leave a ready made tubular cells. Such a tube-shaped cells can be used for repairing a damaged blood vessels, enzyme/hormone secretion tubes and intestine tubes.

Co-Culturing

Yet another embodiment of the invention is the 3-dimensional cell growth process of culturing at least two types of cells together as illustrated in FIG. 28. The 3-dimensional cell growth devices of the invention, as the artificial human or animal organs of the invention, can contain more than one type of cells. The invention provides for co-culturing a mixed collection of cells (e.g., bone, liver cells), for example, all the various cell types found in a particular tissue or organ system, or alternatively, enough cell types to sustain an artificial tissue or organ system to produce a desired effect, e.g., an artificial liver, growth of a tooth, functional pancreas, and the like. Co-culturing a mixed collection of cells can be beneficial in obtaining a higher quality cells.

In one aspect, cells are co-cultured using Ti wire or rods having $TiO_2$ nanotube array surface, at least two different types of cells can be co-cultured. For example, in the case of liver cell cultures or artificial livers of the invention, parenchymal liver cells (hepatocytes) are cultured together with at least one of the following cells: fibroblast cells, blood vessel cells, Kupffer cells, epithelial cells, endothelial cells, skin cells (keratinocytes), hematopoietic cells, bone marrow cells, stem cells, etc. Similarly, a culture of other organ cells using the inventive approach can be carried out using an appropriate combination of cells.

In FIG. 28, an exemplary combination of parenchymal liver cells (hepatocytes) and blood vessel cells is described. After both types of cells are grown in an appropriate configuration, the Ti wires/rods array structure can be pulled out if desired.

Permanent or Semi-Permanent 3-D Cell/Organ Implants

In one aspect of making the 3-dimensional cell growth devices of the invention, e.g., the artificial human or animal organs of the invention, $TiO_2$ nanotube-coated Ti wire/rod array structures can be removed. Alternatively, these array structures can be left in to be a component of inorganic-organic composite structure.

In one aspect, for three dimensional cell cultures comprising a merging of cells grown from adjacent wires or ribbons, a desirable spacing between the parallel neighboring branches of wires and ribbons can be at most 10 times the thickness of an average monolayer cell thickness, or alternatively, at most 5 times the thickness of an average monolayer cell. In one aspect, in the case of bone growth, it is the mineral that grows—not a living cell, so the desired spacing between the neighboring branches can be much larger, with a desired spacing being at most 100 times the thickness of osteoblast cell, or alternatively, at most 50 times.

Schematically illustrated in FIG. 29 is the configuration of the accelerated culture of 3-D cells with permanently retained Ti wires, ribbons, networks or sponges having $TiO_2$ nanotube arrayed surfaces. In one aspect, since both $TiO_2$ and Ti are known to be biocompatible, the metal structure does not necessarily have to be pulled out. For such a permanently retained metal structure, a locally bent or curved Ti wire/ribbon configuration is preferred so as to provide a mechanical locking, more stable structure, as illustrated by FIG. 29(a)-(d).

Nanopore-Reserviored Template for Multifunctional 3-D Cell/Organ Growth

In one aspect of making the 3-dimensional cell growth devices of the invention, e.g., the artificial human or animal organs of the invention, a 3-D configured array of Ti wires, rods and ribbons is used. In one aspect, 3-D configured array of Ti wires, rods and ribbons may be beneficial because the vertical pores of the $TiO_2$ nanotubes on the surface of Ti can be utilized as a reservoir of various biologically active agents to provide multi-functional capabilities, e.g., as illustrated schematically in FIG. 13. For example, the nanopores and/or nanotubes of the structures of the invention can be filled, or "loaded" with therapeutic drugs, growth factors, proteins, collagens, enzymes, hormones, nucleic acids (e.g., RNA, DNA, vectors, siRNA, genes), antibiotics, antibodies, magnetic nanoparticles, radioisotopes and so forth. The filling of the $TiO_2$ nanotubes pores (and also in-between the nanotubes) can be effected by a number of different methods, for example, using ultrasonic agitation of the $TiO_2$ nanotube coated Ti in a solution containing one or more of the biologically active agents. The nanosize pores of $TiO_2$ nanotubes, as compared to microsized pores, can have an advantage of being able to keep the stored biological agents much longer and allow slower release over a longer period of time. However, the 3-dimensional cell growth devices of the invention can also comprise a mix of nanosized pores and micro-sized pores.

In one aspect, 2-D or 3-D organ (e.g., liver, kidney, spinal cord, pancreas), orthopedic (e.g., artificial joints), dental or periodontal cell implants comprising the $TiO_2$ nanotube coated Ti structure have the advantage of a continuous supply of biological agents, small molecules or other chemicals desired to be used in the cell growth, differentiation or maintenance process. For example, bone morphogenic protein (BMP) type or collagen type growth factor, or infection-preventing antibiotics (such as penicillin, streptomycin, vancomycin), or nucleic acids such as vectors, can be slowly released from the $TiO_2$ nanotube. An efficient and healthier cell or bone growth can be designed.

Similarly as in the case of 3-D bone growth, the invention provides for 3-D culturing of other cells or cell systems, such as liver or kidney cells/organs, spinal cord systems, pancreas, and the like, by using the slowly releasing biological agents, small molecules or other chemicals from the $TiO_2$ nanotube reservoir. Drugs such as anti-cancer drugs can be incorporated in the nanotube pores, e.g., when the cultured 3-D cells/organ is to be implanted into a body of a patient, e.g., whose cancerous organs have been partially or fully removed.

In addition to the in vitro type cell culture, the 3-D base structure of $TiO_2$ nanotube coated Ti (which can be pre-filled with one or more types of drugs and biological agents, small molecules or other chemicals) can also be left permanently or semi-permanently as an in vivo implanted 3-D cells/organ as a source of slow drug release within an individual, e.g., a test or production animal, or a human body, because both Ti and $TiO_2$ are known to be biocompatible.

Externally Controllable Drug Release in 3-D Growing Cells/Organs

Figure 12:
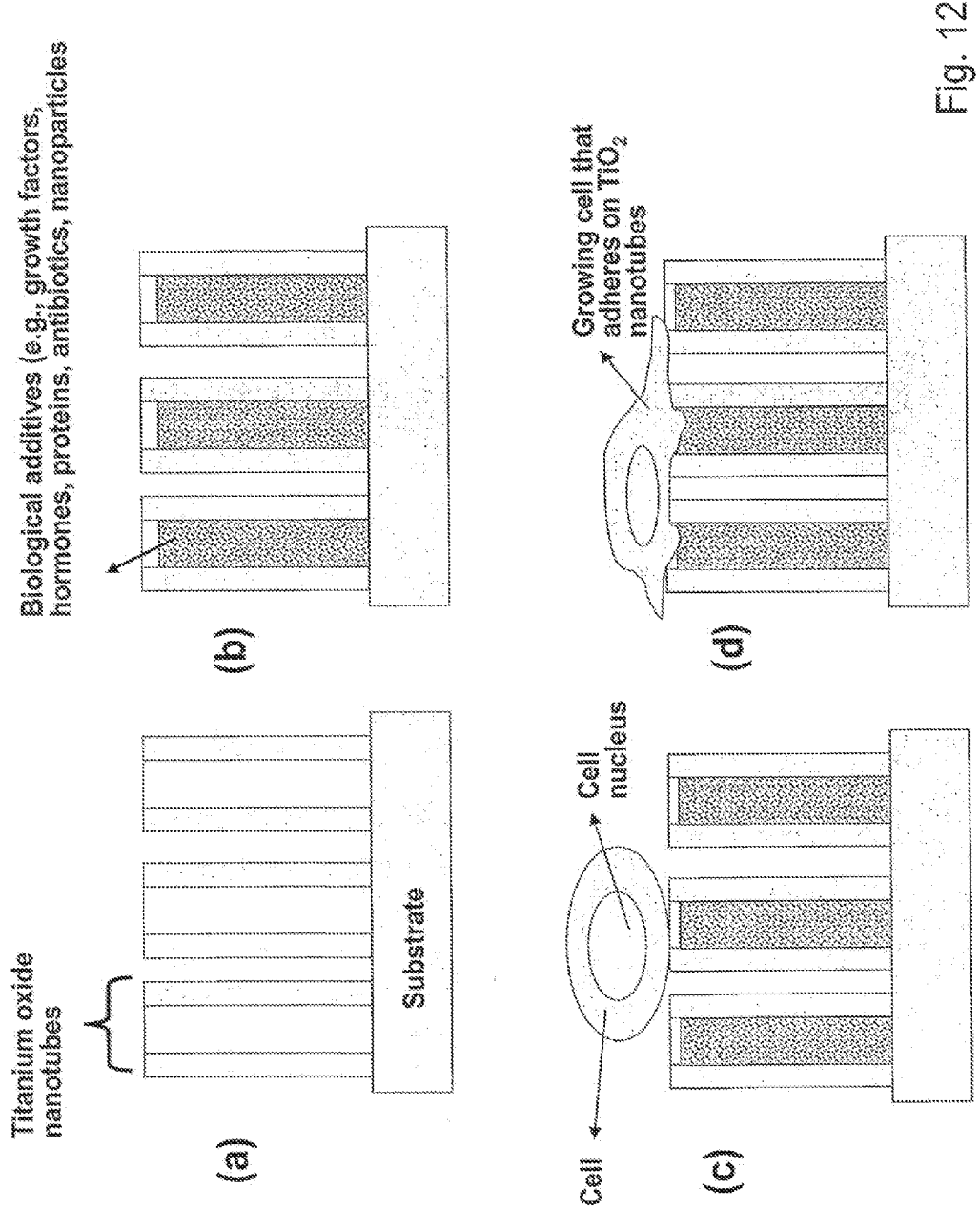
FIG. 12.

The invention provides multi-functional implants comprising remote-controllable media, e.g., magnetic nanoparticles. An agent to be delivered, e.g., a biological agent, such as a cancer drug, or other reagent, drug, isotope and the like, can be placed, together with magnetic nanoparticles, in the nanopores of the $TiO_2$ nanotubes, e.g., as illustrated in FIG. 12.

The controllable media, e.g., magnetic nanoparticle, can be stimulated/activated to release the substance (e.g., drug, etc.) contained therein, for example, by ultrasonic or magnetic agitation of a colloidal liquid containing a mixture of the substance (e.g., drug solution) and the controllable media, e.g., particles. Exemplary magnetic nanoparticles for such use include biocompatible iron-oxide particles of magnetite ($Fe_3O_4$) or maghemite ($\gamma$-$Fe_2O_3$) in the particle size regime of about 2 to 100 nm, or 5 to 50 nm, in average diameter. External stimulation of the magnetic nanoparticles by orientation-changing magnetic field or alternating current (AC) magnetic field can help release the agent to be delivered, e.g., a biological agent, such as a cancer drug, by mechanical agitation/movement of the magnetic particles or by heating of the agent-particle (e.g., drug-particle) mixture due to the AC magnetic field.

In one aspect, magnetic-nanoparticle-comprising $TiO_2$ nanotube structures of the invention are useful for treatment of cancer via a combination of externally controllable drug release and magnetic hyperthermia treatment, for example, as an implant in bone cancer area or other cancer regions in general. The methods and compositions of the invention can incorporate magnetic hyperthermia treatments of cancer, e.g., using high frequency alternating current (AC) magnetic fields, e.g., as described by Jordan (1999) J. Magnetism and Magnetic Materials 194:185-196. The magnetic particles can be confined within the nanopores, thus minimizing any complications that may arise from the nanoparticles in human body, yet induce local temperature rise for the magnetic hyperthermia treatment of cancer.

3-D Cell Proliferation—Maintenance, and Cell Supply Devices

Cell growth devices of the invention, e.g., the $TiO_2$ nanotubes of the invention, can accelerate 2-D or 3-D cell growth. The increased number of cells generated by such a device in a 3-D configuration can be useful for accelerated supply of various types of cells, such as bone cells, liver cells, kidney cells, blood vessel cells, skin cells, periodontal cells, stem cells, and other human or animal organ cells, and other human or animal cells for various R&D, screening or therapeutic uses. Cell growth devices of the invention include artificial organ systems, and systems for growing or regenerating tissues, e.g., growing teeth or regenerating liver or nerve tissue. Thus, cell growth devices of the invention also incorporate biological agents such as biomolecular growth factors, cytokines, collagens, antibiotics, antibodies, drug molecules, small molecules, inorganic nanoparticles, etc. within nanopores, nanotubes or nanoreservoirs for maintenance of these cells.

In one aspect, cells are cultured in or on a device of the invention in a biocompatible environment with needed nutrient media. In one aspect, cells so proliferated on vertically aligned $TiO_2$ nanotube arrays of the invention are then harvested and supplied for other uses. One method of harvesting the grown 3-D cells off the $TiO_2$ nanotube substrates is to use a linearly retractable, Ti base structure as illustrated in FIG. 23. Another method is to use a process known as "trypsinization", discussed above. A combination of the template retracting and trypsinization can also be utilized; for example, the 3-D cultured cells on an array vertically arranged Ti wires, rods or ribbons (having $TiO_2$ nanotube covered surfaces) can be physically removed (e.g., by low-power vacuum suction) along the vertical direction after appropriate trypsinization treatment. The retrieved cells are then washed and stored.

In addition to the utility for supply of cells, the 3-D cultured cells can be prepared using subdivided-Ti based culturing devices of the invention which comprise $TiO_2$ nanotubes or nanopores. Harvested cultured cells, or the devices themselves, can be in vivo implanted as cells, tissues or organs. For example, a patient can be supplied with cultured cells, and/or implanted with a three-dimensional functional cell system, e.g., functional liver, kidney, or blood vessel cells or organs, e.g., as illustrated in FIG. 11(a). The invention also provides three-dimensionally cultured bones or tissues can be utilized as dental, periodontal or orthopaedic body implants as illustrated in FIG. 11(b).

Analytical Diagnostic Biochip

In one aspect, the rapid growth of cells is facilitated by using a large surface area on a device of the invention. The invention's 3-D culturing compositions and methods can be useful for carrying out fast diagnosis and detection of certain types of cells, and certain cell states, e.g., as in the detection of the presence of a disease or other agent, e.g., a poison or toxin, such as a biological or chemical warfare agent, e.g., *bacillus*, such as an anthrax spore.

In one aspect, an X-Y matrix subdivided array of $TiO_2$ nanotube array structure can be produced as illustrated in FIG. 17. The devices of the invention facilitate rapid diagnosis of diseases (especially epidemic diseases) or presence of certain agents or chemicals, e.g., a poison or toxin, such as a biological or chemical warfare agent, e.g., an anthrax spore, bacteria or viruses). The devices of the invention can be used in the rapid identifying of cells to produce forensic evidence; particularly where rapid detection is essential even when the available quantity of the cells is relatively small. Each of the exemplary detection elements in FIG. 24 contains a multiplicity of $TiO_2$ nanotubes on which various types of cells are placed and allowed to rapidly proliferate. As a sufficient number of cells are grown in a 3-D configuration in a shorter period of time, this enables an easier and faster detection.

For analysis of cell types, various exemplary techniques, illustrated in FIG. 18, can be used, including (a) optical detection of morphology and size (using a microscope, fluorescent microscope, or CCD camera sensing of fluorescent or quantum dot tagged cells), (b) chemical or biological detection (e.g., based on signature reactions), (c) magnetic sensor detection (e.g., by using magnetically targeted antibody and its conjugation with certain types of antigens).

Liver Cell Array Device for Drug/Chemical Toxicity Testing

Another application of the bio-chip apparatus of the invention is illustrated in FIG. 17; this exemplary device can be utilized as a base structure to culture cells, e.g., liver cells, for testing of new drugs, as illustrated in FIG. 24. The device can comprise parenchymal cells (hepatocytes), and/or other cells from a liver environment, such as endothelial cells, adipocytes, fibroblastic cells and Kupffer cells.

The three-dimensionally structured, $TiO_2$-nanotube-coated array of Ti wires or ribbons enables a rapid and healthy culture of liver cells in a desirable three-dimensional configuration. In one aspect, the apparatus can be utilized for testing drug toxicity or chemical toxicity (e.g., natural products, perfumes, cosmetics, dyes and the like). For toxicity testing, the three-dimensionally structured $TiO_2$-nanotubes can create a cell culture comprising an array of three-dimensionally configured liver cells, e.g., a mixed cell culture comprising an array of three-dimensionally configured liver cells including any combination of parenchymal cells (hepatocytes), endothelial cells, adipocytes, fibroblastic cells, Kupffer cells.

The invention provides bio-chips comprising an array of healthy, three-dimensionally cultured liver cells, e.g., 10×10, 100×100 or 1000×1000 cell sensing elements to allow simultaneous evaluation of many agents (e.g., poisons, drugs) for much accelerated screening and, e.g., development of biologically acceptable drugs, cosmetics and the like. Any chemical, polymer, injection fluid or composite that may be useful for in vivo applications can be rapidly tested for toxicity using a device of the invention, e.g., the exemplary devices illustrated in FIG. 17 and FIG. 24.

For analysis of the response of liver cells, various exemplary detection/analysis mechanisms such as illustrated in FIG. 18 can be utilized, for example, (a) optical or microscopic sensing, (b) chemical or biological detection, and (c) magnetic sensor detection.

It is understood that the above-described embodiments are illustrative of only a few of the many possible specific embodiments which can represent applications of the invention. Numerous and varied other arrangements can be made by those skilled in the art without departing from the spirit and scope of the invention. For example, a thin coating of biomolecules or chemical molecules can optionally be applied on the surface of $TiO_2$ nanotubes to further enhance the attachment of cells.

For example, the invention provides varied arrangements of laterally gapped nanotube arrays of the invention, and the materials involved, e.g., the nanotubes and the substrate that the nanotubes are adhered to, are not necessarily Ti oxide nanotubes on Ti-based metals, but may comprise any material, e.g., a biocompatible material. Devices of the invention can be fabricated using other biocompatible materials or non-biocompatible materials, e.g., coated with biocompatible and/or bioactive surface layers, such as Ti, or they can be coated with inert biocompatible surface layers, such as a metal, ceramic or polymer layer. In one aspect, a thin coating of biomolecules or chemical molecules can be applied on the surface of $TiO_2$ nanotubes to further enhance the attachment of cells.

In one aspect, nanotube arrays (e.g., for incorporating biological agents in a nanopore or nanotube reservoir, and to enhance cell adhesion) with desirable gaps between adjacent nanotubes (e.g., to allow continuous supply of body fluid and nutrients for healthy cell growth) can be fabricated by using modern high-resolution lithography such as electron beam lithography, laser beam lithography, ion-beam lithography, or by using self-assembly techniques and associated processing approaches (see discussion, above).

The examples set forth above are provided to give those of ordinary skill in the art with a complete disclosure and description of how to make and use the preferred embodiments of the compositions, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

IV. ARTICLES COMPRISING DUAL STRUCTURED AND DIMENSION-CONTROLLED BIOMATERIALS NANOSTRUCTURE FOR ACCELERATED CELL AND BONE GROWTH, AND METHODS FOR MAKING SUCH STRUCTURES

The invention provides lock-in nanostructures comprising a plurality of nanopores or nanotubes, wherein the nanopore or nanotube entrance has a smaller diameter or size than the rest (the interior) of the nanopore or nanotube. The invention provides dual structured biomaterial comprising micro or macro pores and nanopores. The invention provides biomaterials having a surface comprising a plurality of enlarged diameter nanopores and/or nanotubes.

SUMMARY

This invention provides novel, biocompatible nanostructured biomaterials, devices comprising such biomaterials, and fabrication methods thereof. The novel biomaterials can enable accelerated cell growth and can be useful for a variety of uses including orthopaedic, dental, cell/organ implants, therapeutics, disease diagnostic, drug toxicity testing, and cell supply applications. The invention provides lock-in nanostructures comprising a plurality of nanopores or nanotubes, wherein the nanopore or nanotube entrance has a smaller diameter or size than the rest (the interior) of the nanopore or nanotube. The invention provides dual structured biomaterial comprising micro or macro pores and nanopores. The invention provides biomaterials having a surface comprising a plurality of enlarged diameter nanopores and/or nanotubes.

The invention provides lock-in nanostructures comprising a plurality of nanopores or nanotubes, wherein the nanopore or nanotube entrance has a smaller diameter or size than the rest (the interior) of the nanopore or nanotube. The invention provides dual structured biomaterial comprising micro or macro pores and nanopores. The invention provides biomaterials having a surface comprising a plurality of enlarged diameter nanopores and/or nanotubes.

The invention also discloses a variety of novel surface configurations of implant or substrate materials in such a way that not only nanoscale interfacial adhesions occur, but microscale and macroscale lock-in structure is also provided to guard against slippage of the implant on tensile stress or breakage of the bond on shear stress. In one aspect, substrate materials comprise novel surface configurations having Ti and Ti oxide; and in alternative aspects, also have alloys comprising Ti or Ti oxide by at least 5%, 6%, 7%, 8%, 9%, 10%, 11%, 12%, 13%, 14%, 15%, 20%, 25%, 30%, 35%, 40%, 45%, 50%, 60%, 70% or 75% weight %. In another aspect, other related materials such as Zr, Hf, Nb, Ta, Mo, W, and their oxides, or alloys of these metals and oxides by at least 5%, 6%, 7%, 8%, 9%, 10%, 11%, 12%, 13%, 14%, 15%, 20%, 25%, 30%, 35%, 40%, 45%, 50%, 60%, 70% or 75% weight % is used. Other materials such as Si, Si oxide, carbon, diamond, noble metals (such as Au, Ag, Pt and their alloys), polymer or plastic materials, or composite metals, ceramics or polymers can also be utilized, e.g., to produce and use similar desired surface configurations for bio implant and cell growth applications. In one aspect, these additional materials (e.g., Si, Si oxide, carbon, diamond, noble metals, etc.) are used; where in one aspect, these material are used as long as a coating of Ti and Ti oxide, Zr, Hf, Nb, Ta, Mo, W and their oxides, as well as their alloys, are present with a thickness of at least 1, 2, 3, 4, 5, 6, 7, 8, 9, or 10 nm or more, and the coating coverage of at least 15%, 20%, 25%, 30%, 35%, 40%, 45%, 50%, 60%, 70% or 80% or more of the total surfaces is provided.

The invention describes dimension-controlled biocompatible nanostructures with accelerated cell growth characteristics as well as enhanced bone growth together with improved adhesion and mechanical properties. In one aspect, biomaterials of the invention provide i) a desirable lock-in pore structure with the pore entrance smaller than the remainder of the pore dimension for mechanically stable attachment of grown bones or cells, ii) a dual structure comprising macro or micro cavities, and iii) sufficiently large nanopores and/or nanotubes by pre-patterning and guided chemical or electrochemical reactions for efficient storage of biological agents and biomolecules for enhanced bio-reactions. In one aspect, these dimension-controlled nanopore and/or nanotube structures either comprise (or consist of) or are covered (completely or partially) with a biocompatible material, such as $TiO_2$, or equivalent.

In one aspect, the dimension-controlled nanopore and/or nanotube structures of the invention are useful for rapid production of healthy cells including liver cells, bone cells, kidney cells, blood vessel cells, skin cells, periodontal cells, odontoblasts, dentinoblasts, cementoblasts, enameloblasts, odontogenic ectomesenchymal tissue, osteoblasts, osteoclasts, fibroblasts, and other cells and tissues involved in odontogenesis or bone formation and/or stem cells, to name just a few examples. The structures according to the invention can be useful for reliable and faster orthopaedic (orthopedic) or dental bone repair, for preparation of partial or full implant organs, for externally controllable drug release and therapeutic treatments, for efficient toxicity testing of drugs and chemicals, and for diagnosis/detection of disease or forensic cells.

All publications, patents, patent applications, GenBank sequences and ATCC deposits, cited herein are hereby expressly incorporated by reference for all purposes.

BRIEF DESCRIPTION OF THE DRAWINGS

The advantages, nature and additional features of the invention will appear more fully upon consideration of the illustrative embodiments described in the accompanying drawings.

Figure 30:
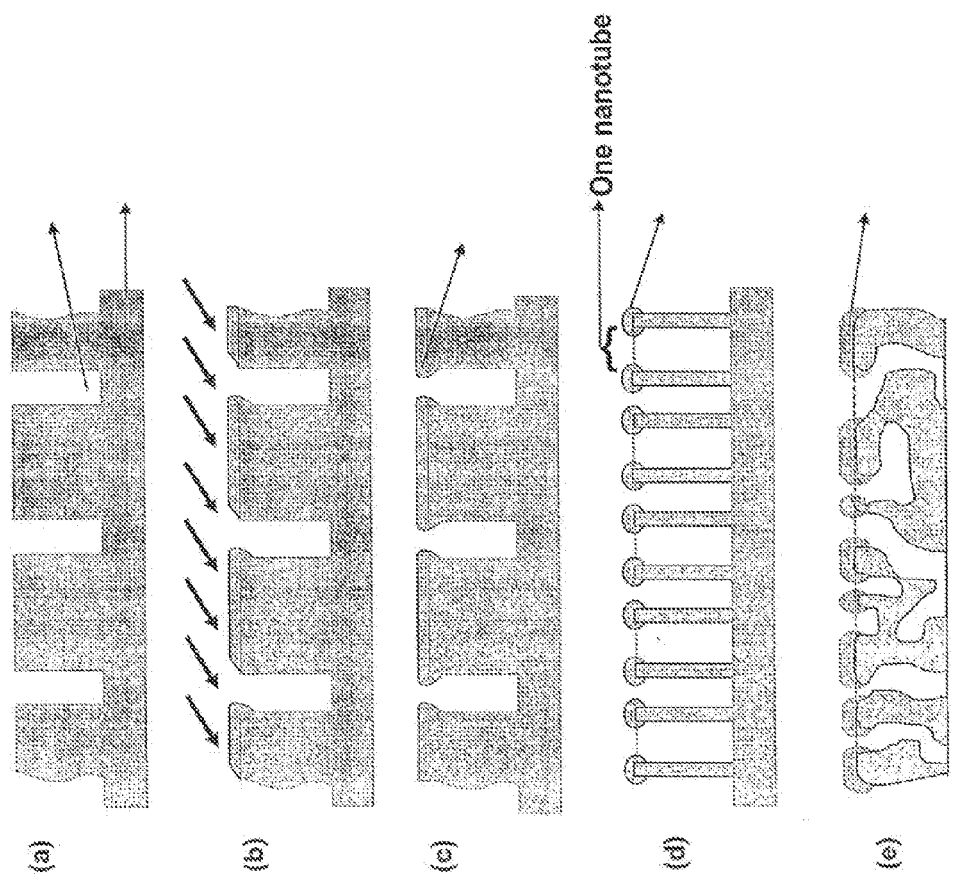

FIG. 30: FIG. 30(a)-(e) schematically illustrate exemplary configurations of a dimensionally controlled, lock-in structure with the size or diameter of the entrance of the pores made smaller by oblique incident deposition of biocompatible materials such as Ti or $TiO_2$; FIG. 30(a) illustrates an exemplary nano- or micro-pore array comprising implant material (e.g., Ti, $TiO_2$, Zr, $ZrO_2$, etc., Si, $SiO_2$, polymers, metals ceramics, composites); FIG. 30(b) illustrates an exemplary nano- or micro-pore array comprising oblique deposition of Ti, $TiO_2$, Zr, $ZrO_2$, etc.; FIG. 30(c) illustrates an exemplary nano- or micro-pore array comprising additional diameter-reducing deposit (e.g., of Ti, $TiO_2$, Zr, $ZrO_2$, etc.) on pore entrance by substrate rotation; FIG. 30(d) illustrates an exemplary nano- or micro-pore array comprising a diameter-reducing deposit (e.g., of Ti, $TiO_2$, Zr, $ZrO_2$, etc.) on the nanotube and gap entrance; FIG. 30(e) illustrates an exemplary nano- or micro-pore array comprising diameter-reducing deposit (e.g., of Ti, $TiO_2$, Zr, $ZrO_2$, etc.) on entrance to random pores.

Figure 31:
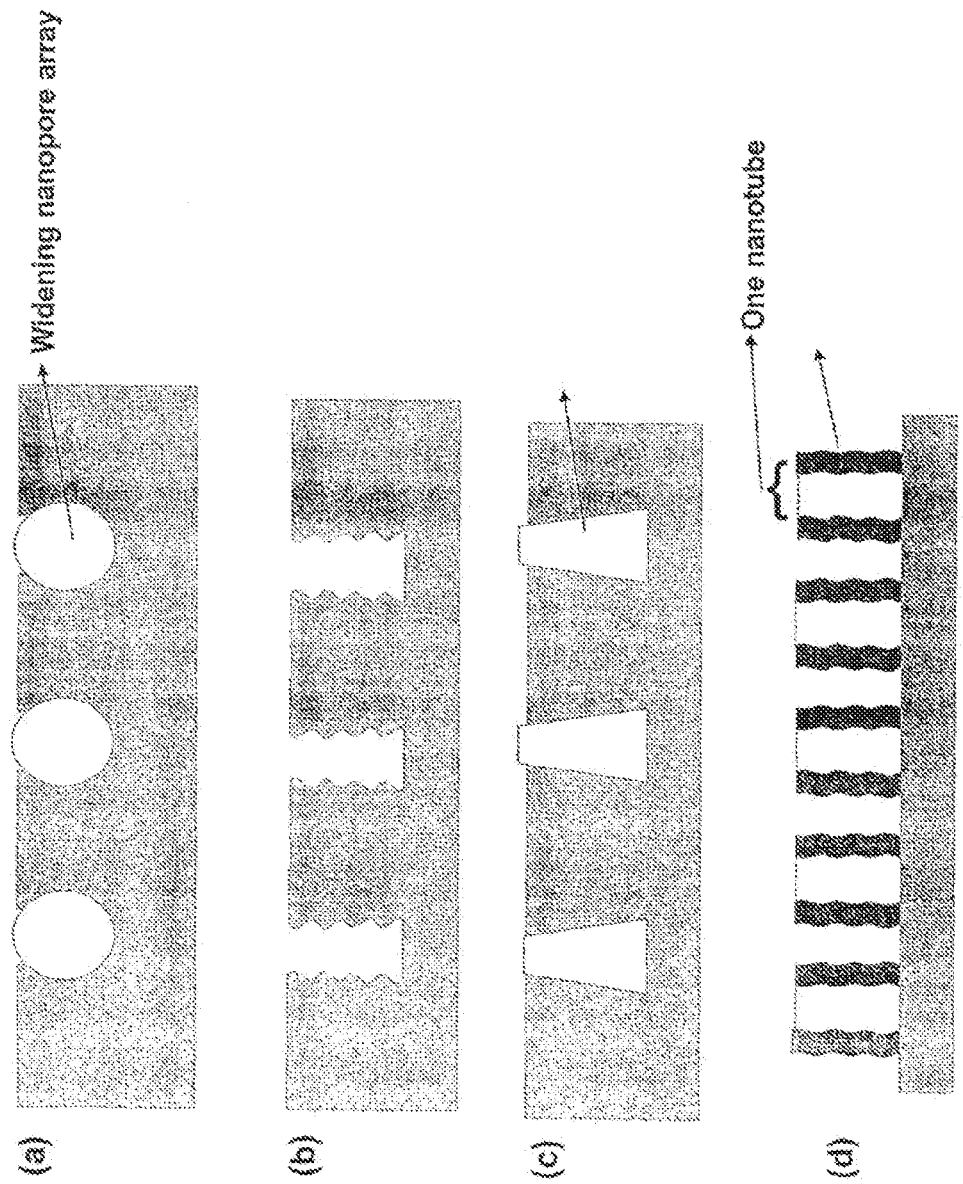

FIG. 31: FIG. 31(a)-(d) schematically illustrate alternative types of lock-in nanostructures of the invention, e.g., for enhanced mechanical stability of cells or grown hard structures, e.g., grown bones or teeth: FIG. 31(a) illustrates random-diametered re-entrant oval or circular nanopores (e.g., with an exemplary implant or bio-substrate of Ti, $TiO_2$, Zr, $ZrO_2$, Zr, Hf, Nb, Ta, Mo, W and/or their oxides, and/or alloys of these metals or oxides); FIG. 31(b) illustrates rectangular cavity with corrugating walls (an exemplary implant comprising corrugated nanopore array); FIG. 31(c) illustrates re-entrant triangular cross-sectioned pores (illustrating an exemplary implant comprising a pore with a gradient diameter having an expanding dimension from the pore entrance); FIG. 31(d) illustrates exemplary nanotubes with corrugating walls (an exemplary implant comprising nanotube with corrugated walls).

Figure 32:
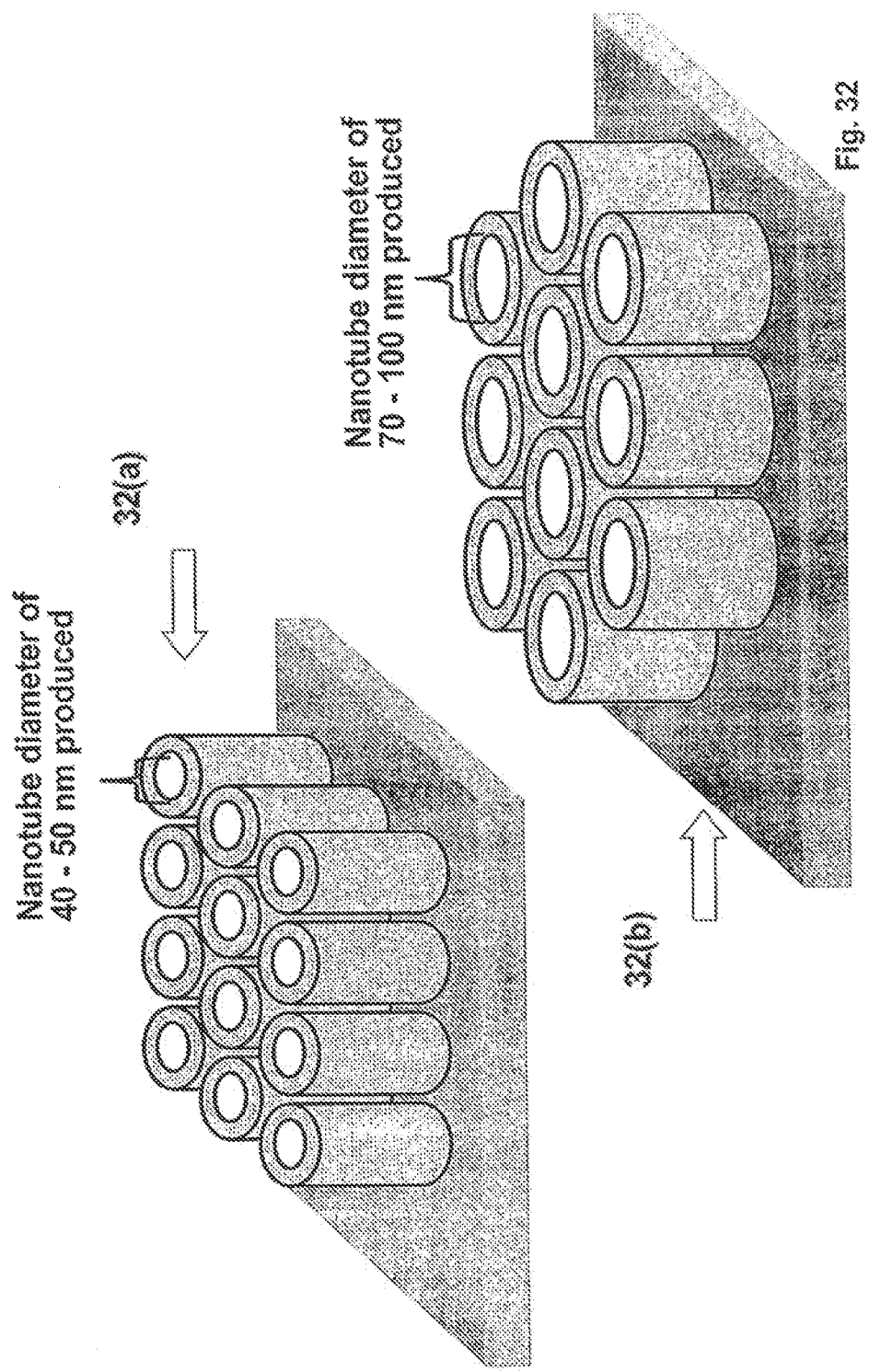

FIG. 32: FIG. 32(a)-(b) schematically illustrate titanium nanotubes of the invention formed by electrolytic anodization, showing the limited range of nanotube diameter control available by voltage control, and the dependence of $TiO_2$ nanotube diameter on anodization voltage applied; FIG. 32(a) illustrates an exemplary anodization processing at 15 V for 30 min in 0.5% HF at room temperature; FIG. 32(b) illustrates an exemplary anodization comprising processing at 20 V for 30 min in 0.5% HF at room temperature.

Figure 33:
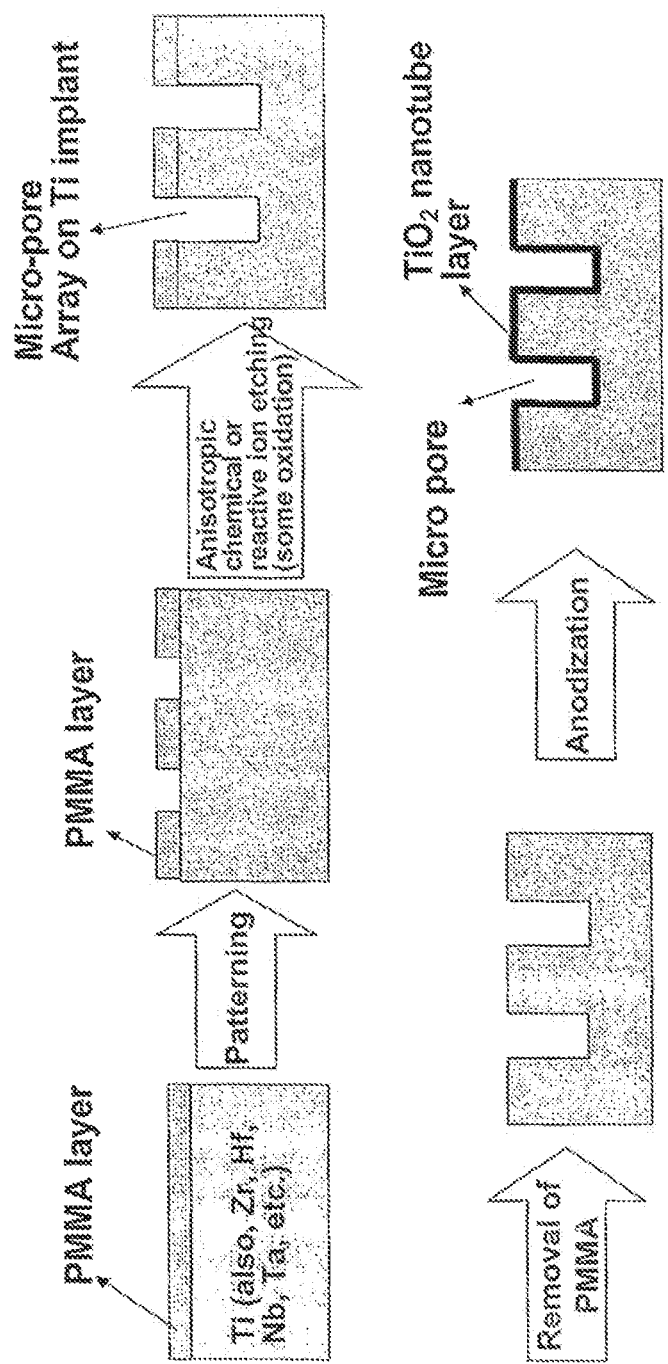
Figure 34:
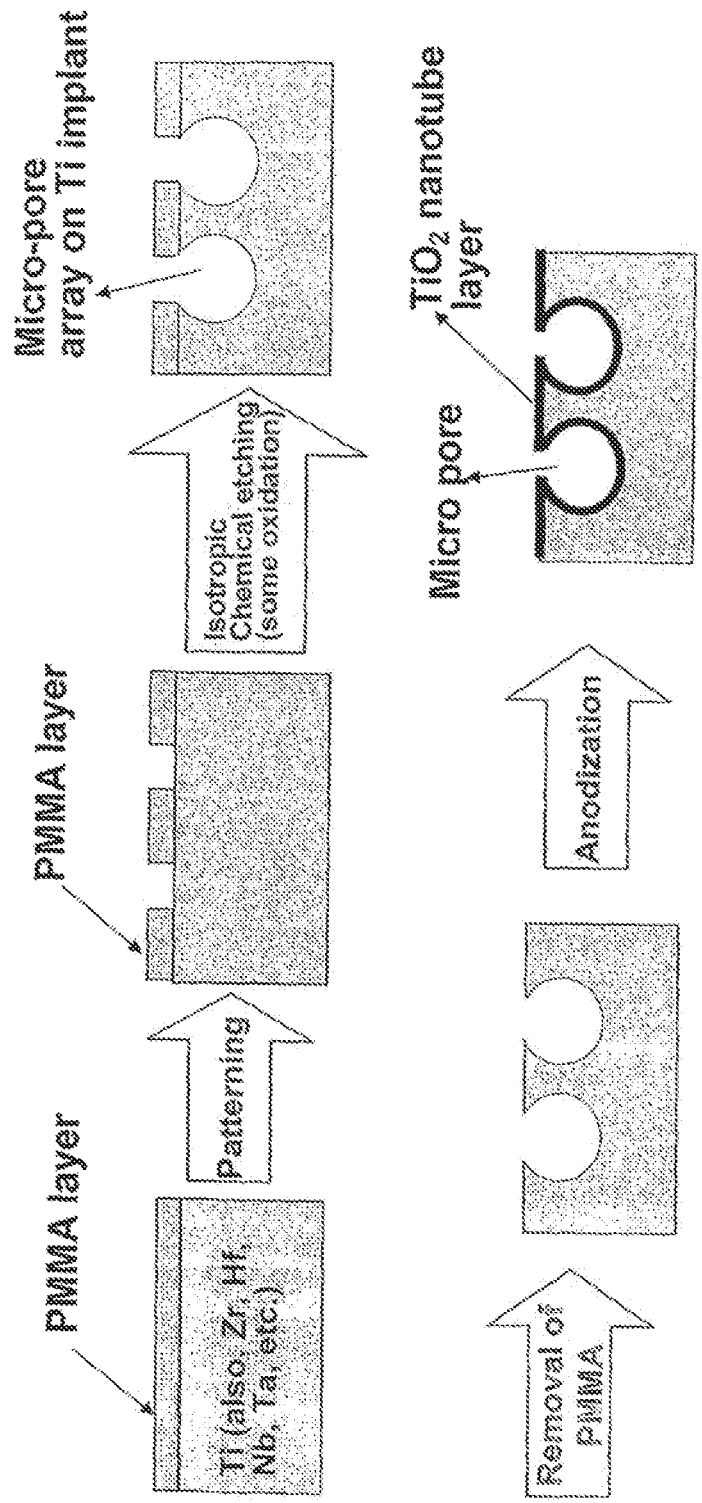

FIG. 33 and FIG. 34 schematically illustrate an exemplary micro-nano-dual pore structure of the invention (a micro-nano-dual pore structure of anisotropically ion etched microcavities and anodization-induced surface $TiO_2$ nano tubes) comprising: FIG. 33, anisotropically ion etched microcavities and anodization-induced surface $TiO_2$ nanotubes; and FIG. 34, isotropically etched microcavities and anodization-induced surface $TiO_2$ nanotubes.

Figure 35:
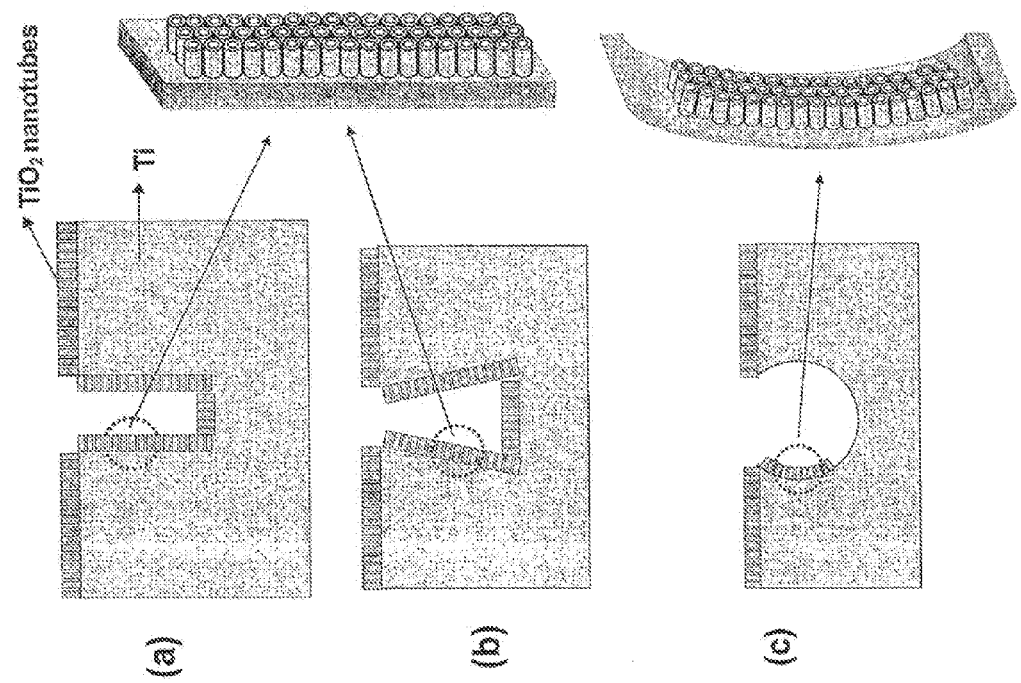

FIG. 35: FIG. 35(a)-(c) schematically illustrate higher magnification illustrations of FIG. 33 and FIG. 34 structures showing the details of the titanium oxide nanotubes formed on the top and pore surfaces; FIG. 35(a), an exemplary box-shaped pore; FIG. 35(b), an exemplary narrow-orificed shaped pore; FIG. 35(c), an exemplary round-shaped pore.

Figure 36:
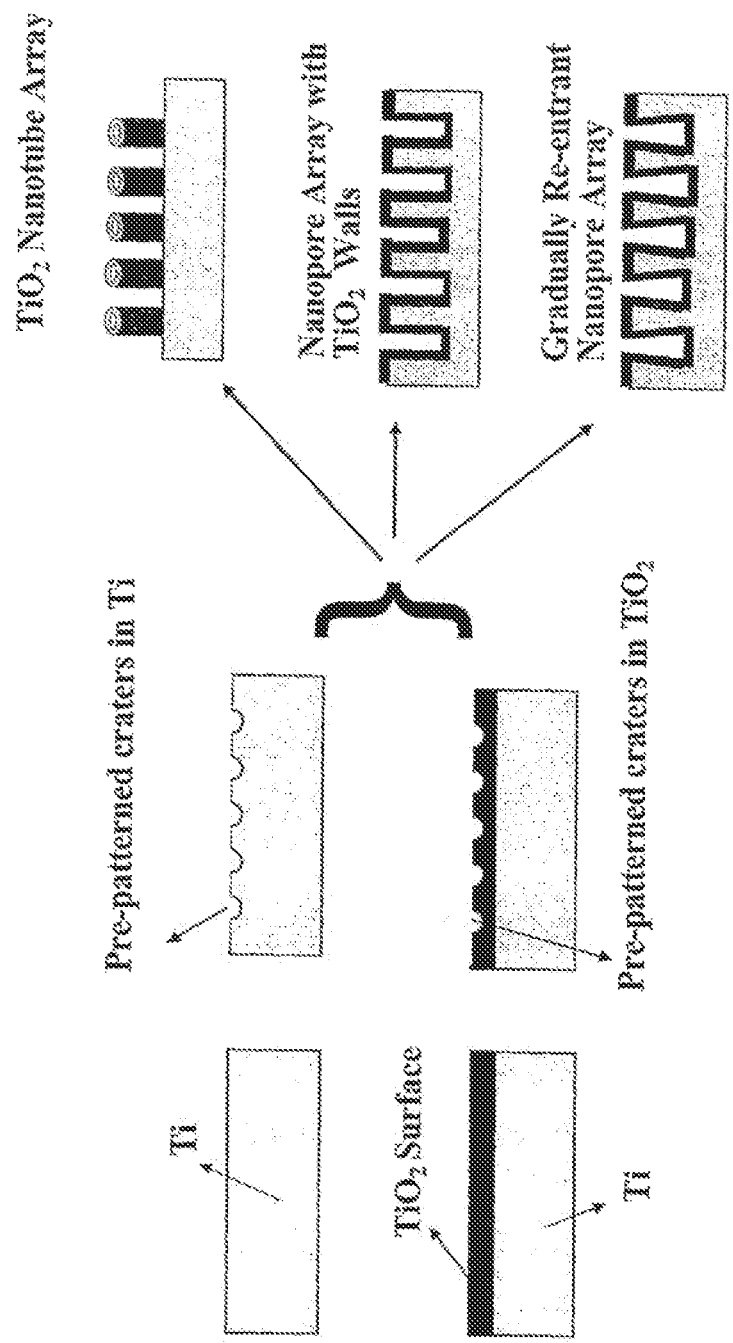

FIG. 36 schematically illustrates an exemplary procedure and structure for guided synthesis of enlarged-diameter nanotubes and nanopores of $TiO_2$ using pre-patterning of craters on Ti or $TiO_2$ surface (an exemplary guided synthesis protocol for fabrication of larger diameter nanotubes and nanopores with e.g., greater than 200 nm, 300 nm, 400 nm, or more in diameter); including illustration of pre-patterned craters in Ti make, e.g., by e-beam litho, photolitho, nano imprint litho, etc., and chemical etch or anodizing.

Figure 37:
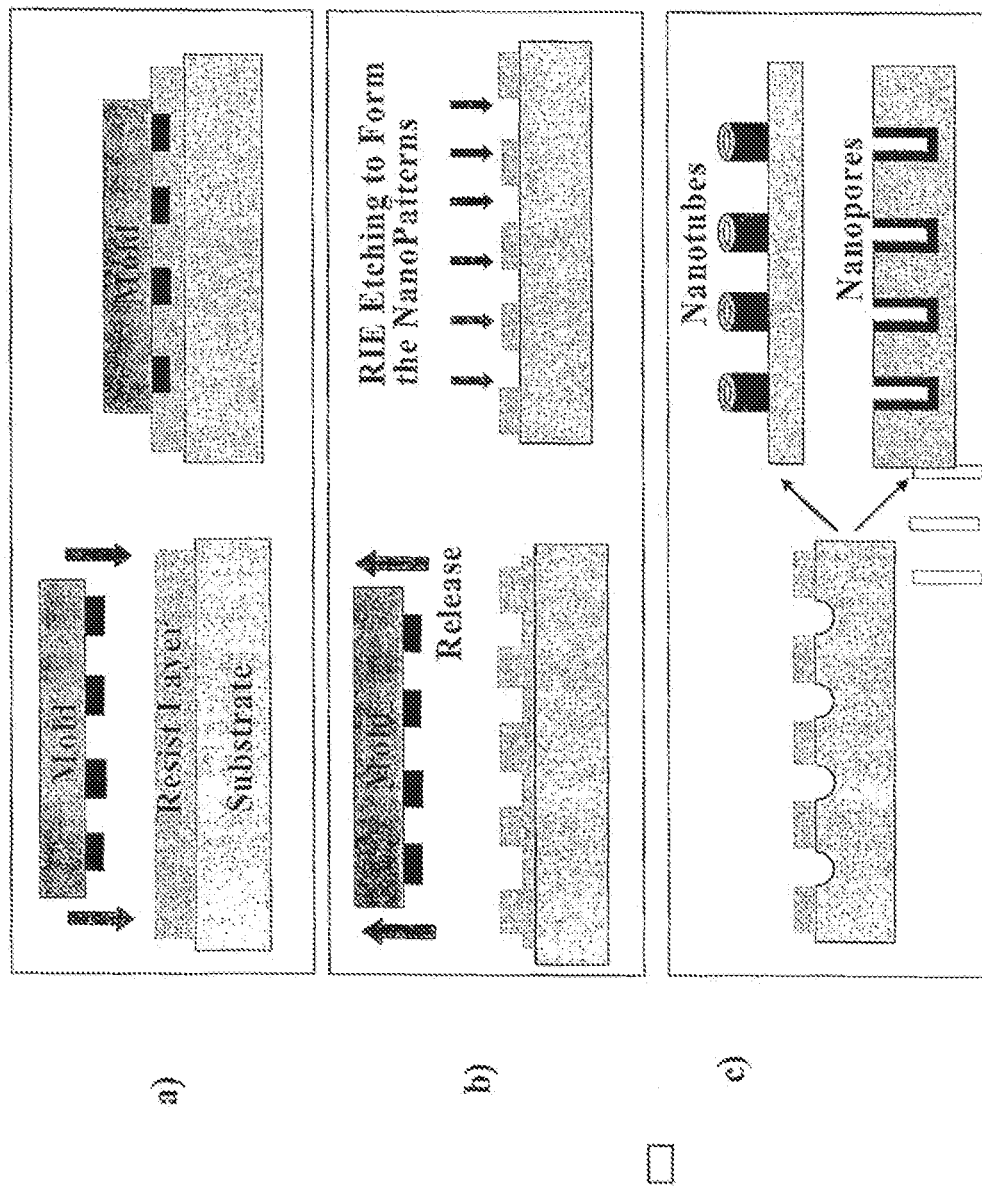

FIG. 37: FIG. 37(a)-(c) schematically illustrate an exemplary nano-imprinting lithography process comprising use of nano imprinting to pre-pattern craters on Ti or $TiO_2$ surface for guided synthesis of larger diameter $TiO_2$ nanotubes and nanopores; FIG. 37(a) illustrates an exemplary imprinting process; FIG. 37(b) illustrates an exemplary pattern formation process; FIG. 37(c) illustrates an exemplary pre-pattern etch and anodization process.

Figure 38:
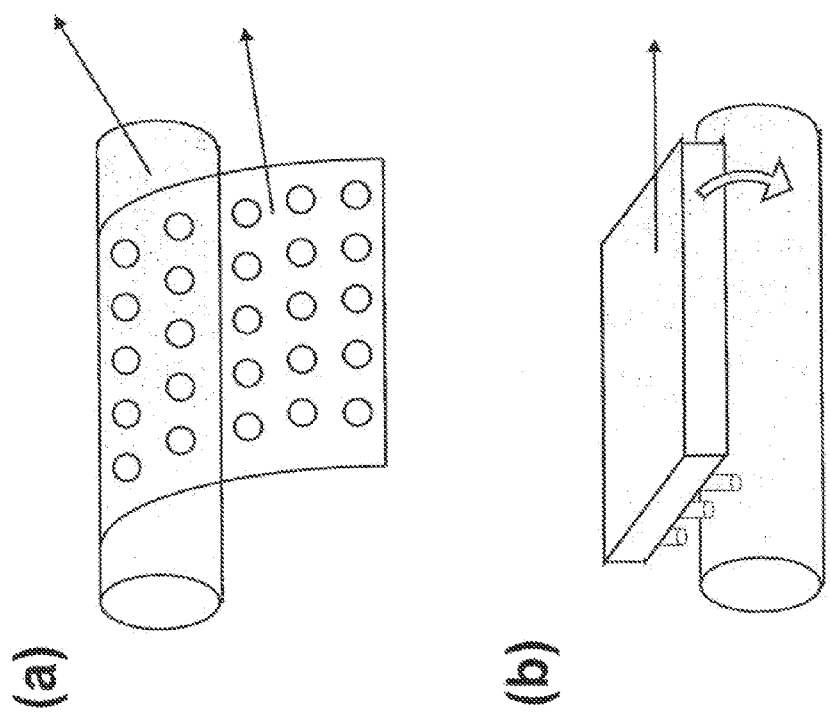

FIG. 38: FIG. 38(a)-(b) schematically illustrate exemplary processes of guided etch nano patterning on non-flat surfaces using: FIG. 38(a), on, e.g., a cylinder or random shape substrate and/or implant, using a conformable or stretchable elastomeric mask sheet (using conformable and/or stretchable mask sheets for guided patterning on non-flat surfaces); FIG. 38(b) elastomeric roll stamping (elastomeric nano-implant stamp for roll stamping of surface patterns for local etching and guided patterning on cylindrical/round substrate or implant).

Figure 39:
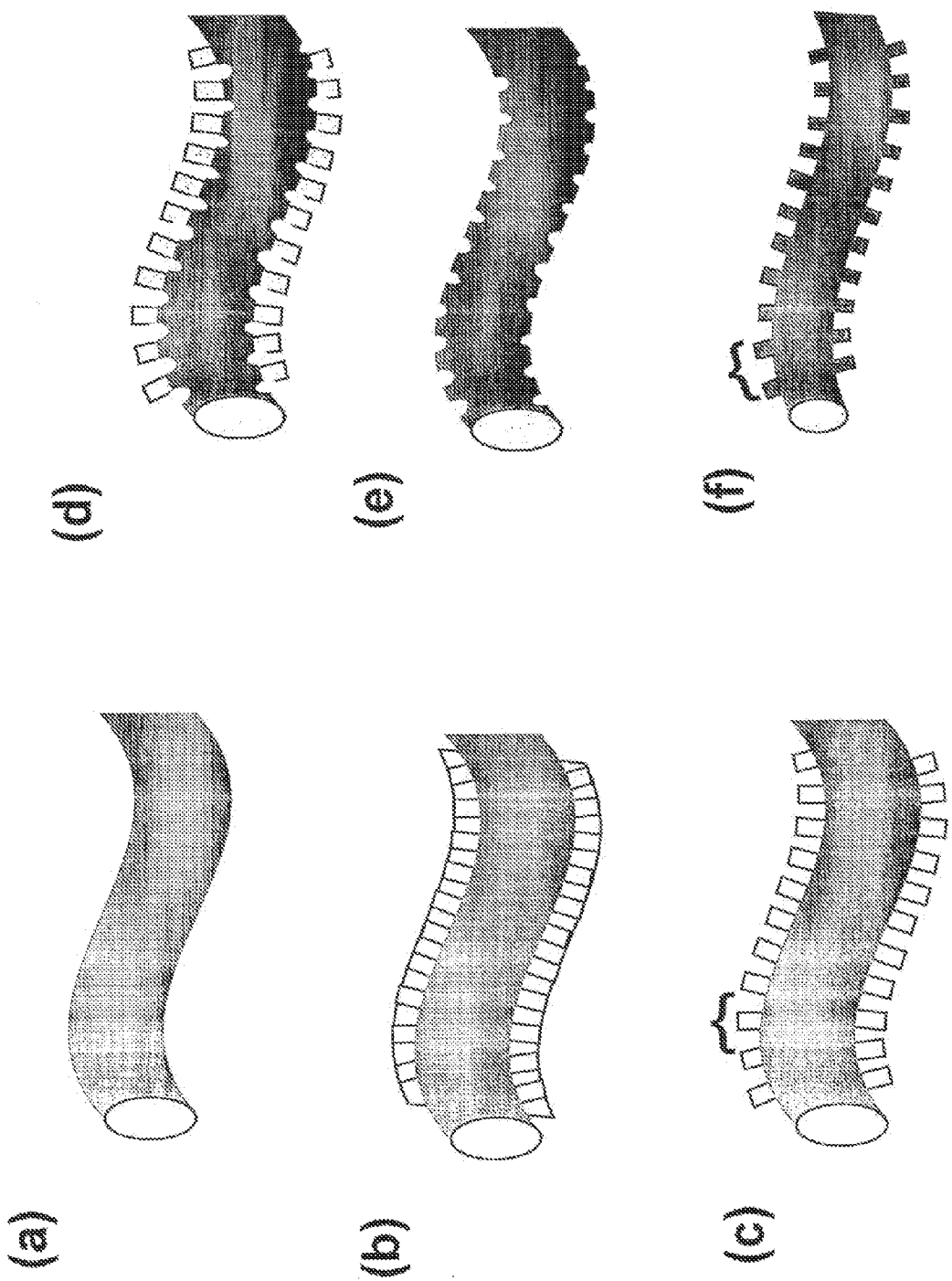

FIG. 39: FIG. 39(a)-(f) schematically illustrate exemplary uniform nanopore or nanotube arrays of the invention on non-flat surface by guided etching using a vertically two-phase decomposed coating: FIG. 39(a), illustrates a starting cylinder or random shape substrate/implant (e.g., Ti wire) material; FIG. 39(b), illustrates the step of coating of textured material (e.g., co-sputtered layer, decomposable diblock copolymer, spinodally decomposing alloy, etc.) on the starting cylinder or random shape substrate/implant; FIG. 39(c), illustrates the resultant nanopored coating after preferential etching away of one phase; FIG. 39(d), illustrates the step of etching through the pore for formation of guiding craters; FIG. 39(e), illustrates the step of removing the coating; FIG.

39(*f*), illustrates the optional step of additional etching or anodization to produce deeper nanopores or nanotubes on the implant surface.

Figure 40:
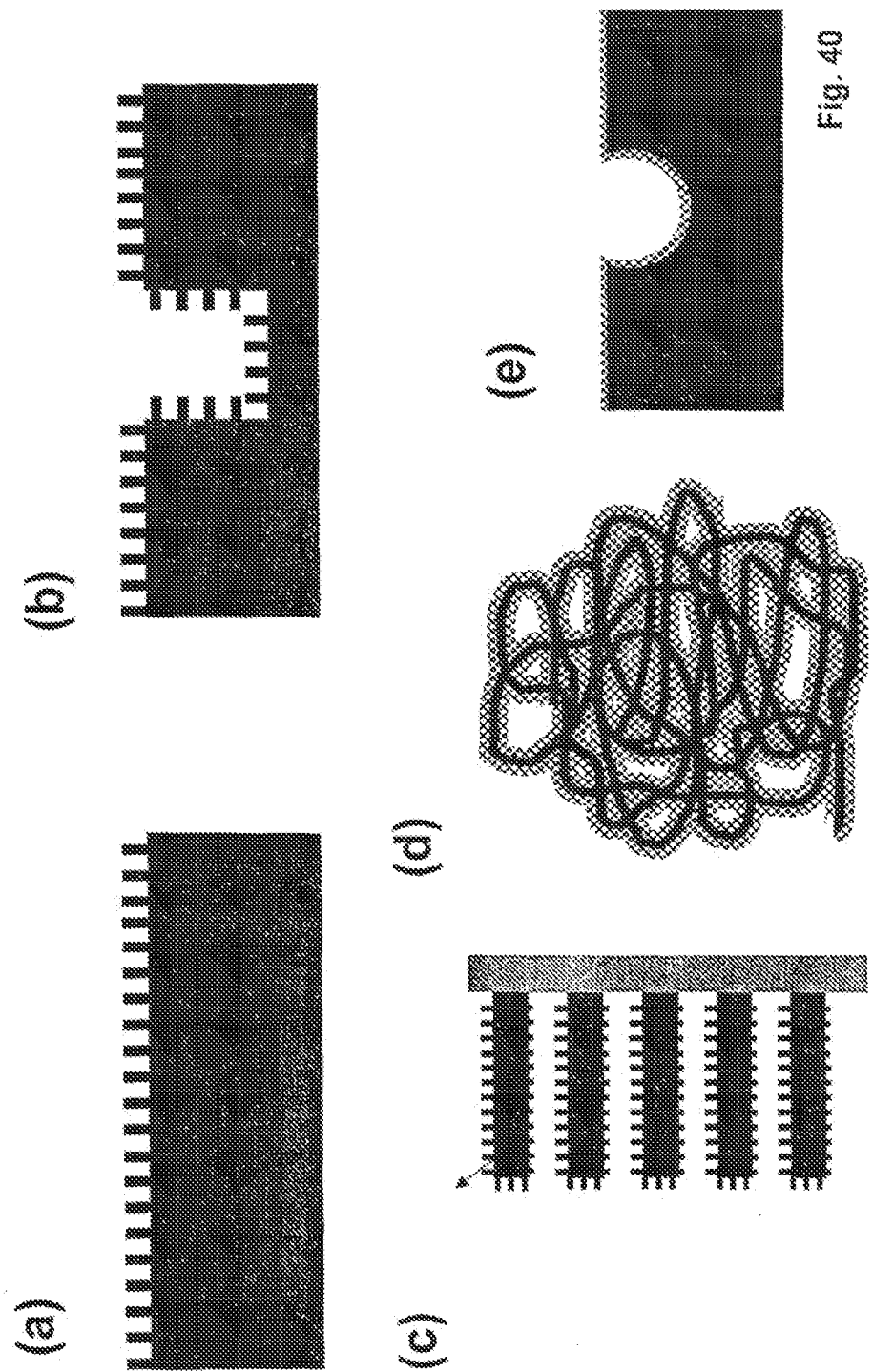

FIG. 40: FIG. 40(*a*)-(*e*) schematically illustrate exemplary size-controlled, uniform nanopore or nanotube array on various surfaces by guided etching using a vertically two-phase decomposed coating of periodically or spinodally decomposing alloy, which optionally can comprise biological agents or functional nanoparticles stored in the pores on various shaped nano-structure surfaces, such as magnetic particles, metals or SPR (surface plasmon resonance) particles, quantum dots, fluorescence particles, bio-conjugated particles, for (accelerated) cell/bone growth, protein harvest, delivery of drugs, genes, chemicals, therapeutics, etc: FIG. 40(*a*), illustrates an exemplary nanopore or nanotube array on a flat surface; FIG. 40(*b*), illustrates an exemplary array as a coarse-patterned surface; FIG. 40(*c*), illustrates an exemplary array as a parallel Ti sheet or wire array; FIG. 40(*d*), illustrates an exemplary array as a wire mesh, bundle or foam (e.g., made of Ti); FIG. 40(*e*), illustrates an exemplary array as a re-entrant cavity surface (e.g., Ti or Ti-coated Si).

Figure 41:
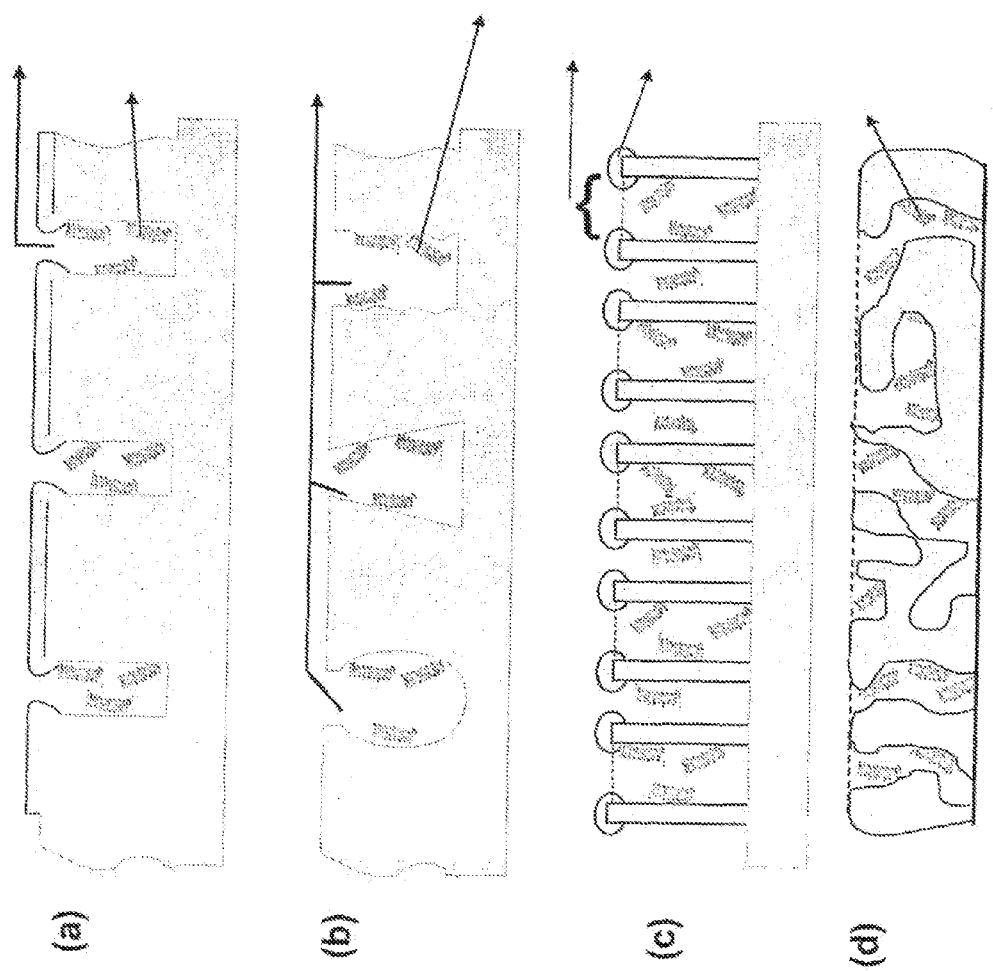

FIG. 41: FIG. 41(*a*)-(*d*) schematically illustrate exemplary bone or cell locking nanopore and/or nanotube array with biological agents inserted for accelerated bone or cell growth, protein or hormone harvest, drug delivery, and therapeutics: FIG. 41(*a*), illustrates an exemplary nano pore array with reduced entrance dimension (Ti, $TiO_2$, etc) and a trapped biological agent (e.g., collagen, growth factor, magnetic particles, DNAs, antibiotics, therapeutic drugs, etc.); FIG. 41(*b*) illustrates an exemplary nanopore array comprising various bone-locking or cell-locking shapes of nanopores for convenient storage of biological agents, e.g., collagen, etc.; FIG. 41(*c*) illustrates an exemplary nanopore array comprising nanotube (e.g., $TiO_2$ or coated with $TiO_2$) having diameter-reducing deposits on the nanotube and/or gap entrances; FIG. 41(*d*) illustrates collagen, etc. inside bone-locking or cell-locking random shapes of exemplary nanopores.

Figure 42:
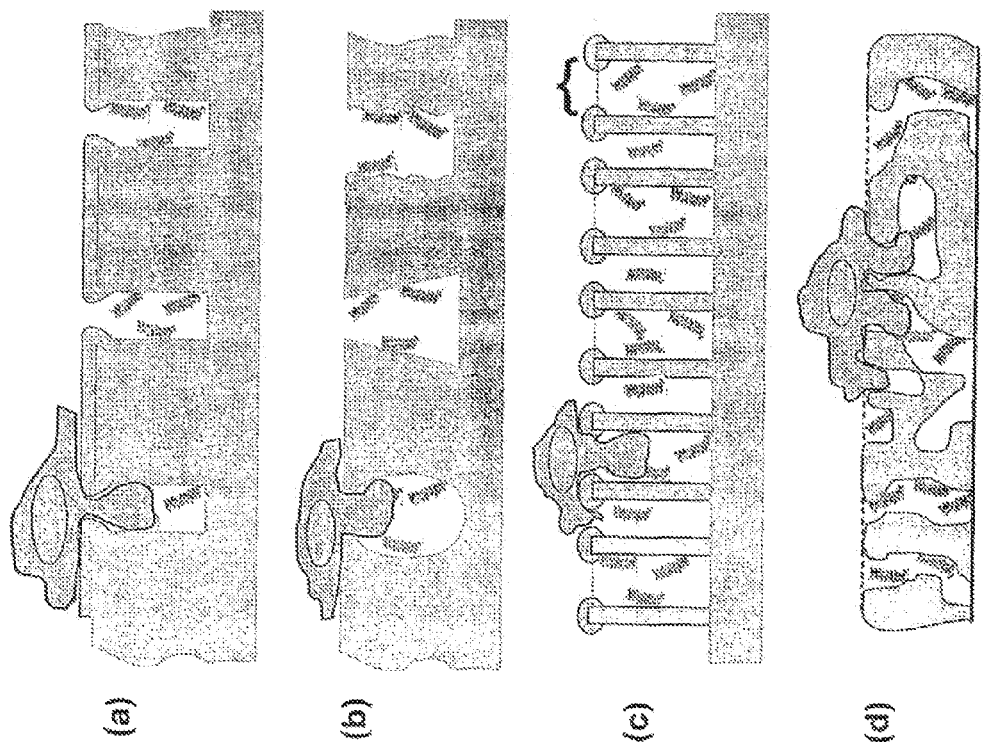

FIG. 42: FIG. 42(*a*)-(*d*) schematically illustrate exemplary arrays comprising cells or bone growing and locked-in on a re-entrant shaped nano-structure surface: FIG. 42(*a*), schematically illustrates an exemplary nanopore array with reduced entrance dimension, optionally containing biological agents, and cells (or bone) growing and locked in on the re-entrant shaped nano-structure surface; FIG. 42(*b*), schematically illustrates an exemplary nanopore array comprising various bone-locking or cell-locking shapes of nanopores (with optional biological agents); FIG. 42(*c*), schematically illustrates an exemplary nanotube (e.g., $TiO_2$ or coated with $TiO_2$) comprising a diameter-reducing deposit on nanotube and gap entrance; FIG. 42(*d*), schematically illustrates bone-locking or cell-locking random shapes of exemplary nanopores (with optional biological agents).

Figure 43:
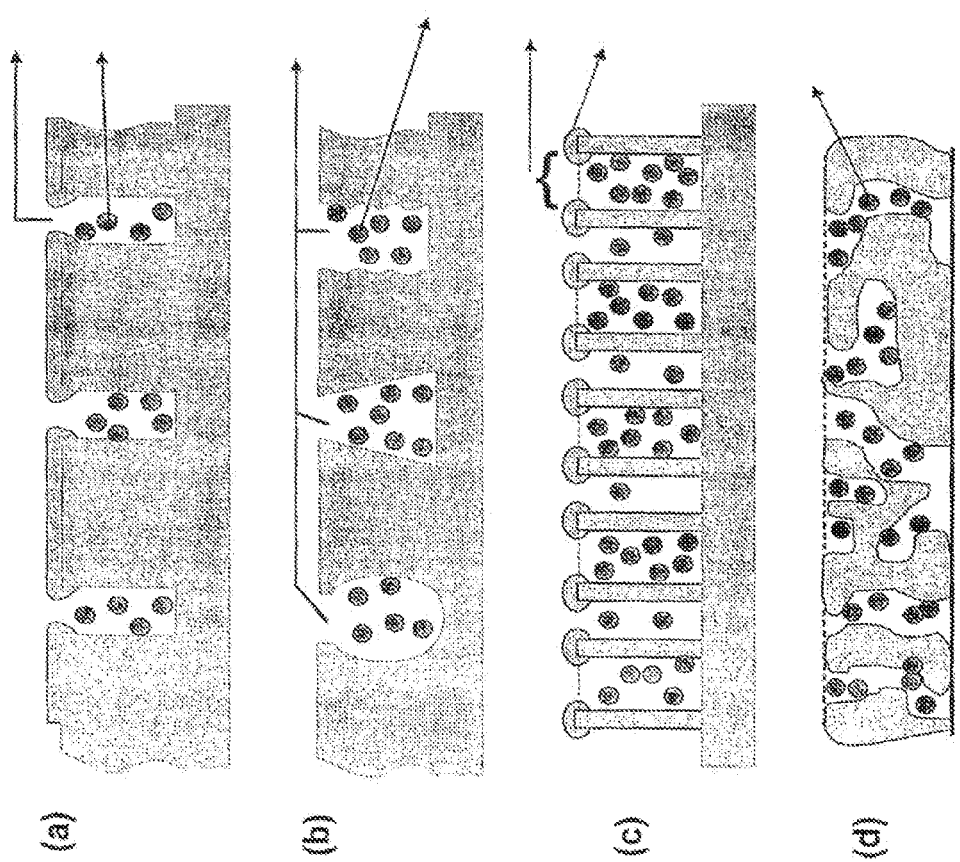

FIG. 43: FIG. 43(*a*)-(*d*) schematically illustrate exemplary nanopore or nanotube array with functional nanoparticles stored in the pore on various shaped nano-structured surfaces for accelerated cell or bone growth, protein harvest, drug delivery, and therapeutics: FIG. 43(*a*), schematically illustrates an exemplary nanopore array with reduced entrance dimension (Ti, $TiO_2$, etc), comprising trapped functional nanoparticles (magnetic particles, novel metal or SPR particles, quantum dots, fluorescence particles, bio-conjugated particles for delivery of drugs, genes, chemicals, etc.); FIG. 43(*b*), schematically illustrates exemplary bone-locking or cell-locking shapes of nanopores of the invention for convenient storage of biological agents, magnetic particles, etc.; FIG. 43(*c*) schematically illustrates an exemplary nanotube (e.g., $TiO_2$ or coated with $TiO_2$) comprising a diameter-reducing deposit on nanotube and gap entrance; FIG. 43(*d*), schematically illustrates exemplary pores comprising inserted nano- or micro-particles (e.g., magnetic particles, quantum dots, fluorescence particles, bio-conjugated particles for delivery of drugs, genes, chemicals, etc.) inside bone-locking or cell-locking random shapes of nanopores.

Figure 44:
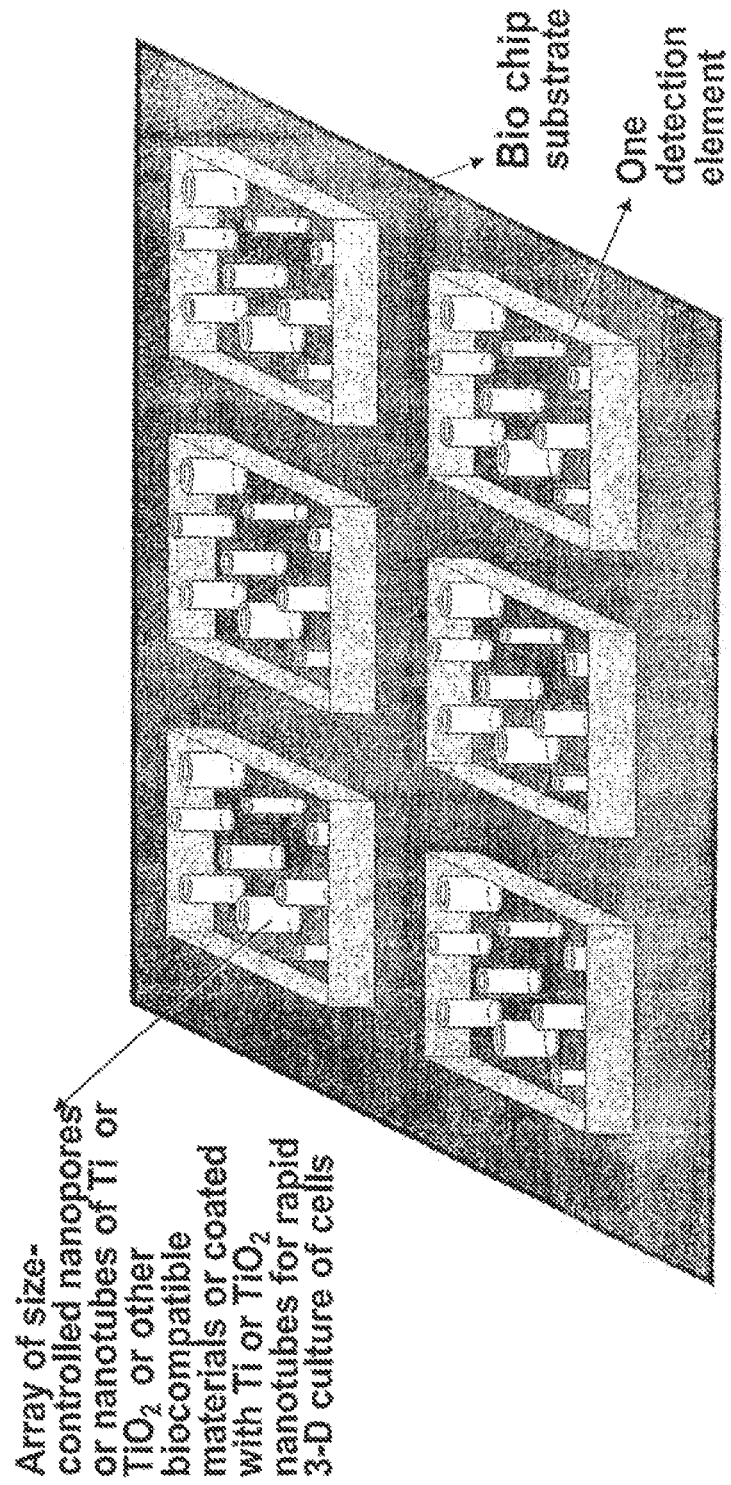

FIG. 44 schematically illustrates an exemplary cell growth device comprising the dimension-controlled biomaterials as an array on a biochip (for use, e.g., as an array for drug toxicity testing), and an array of size-controlled (and varied sized) nanopores and/or nanotubes.

Figure 45:
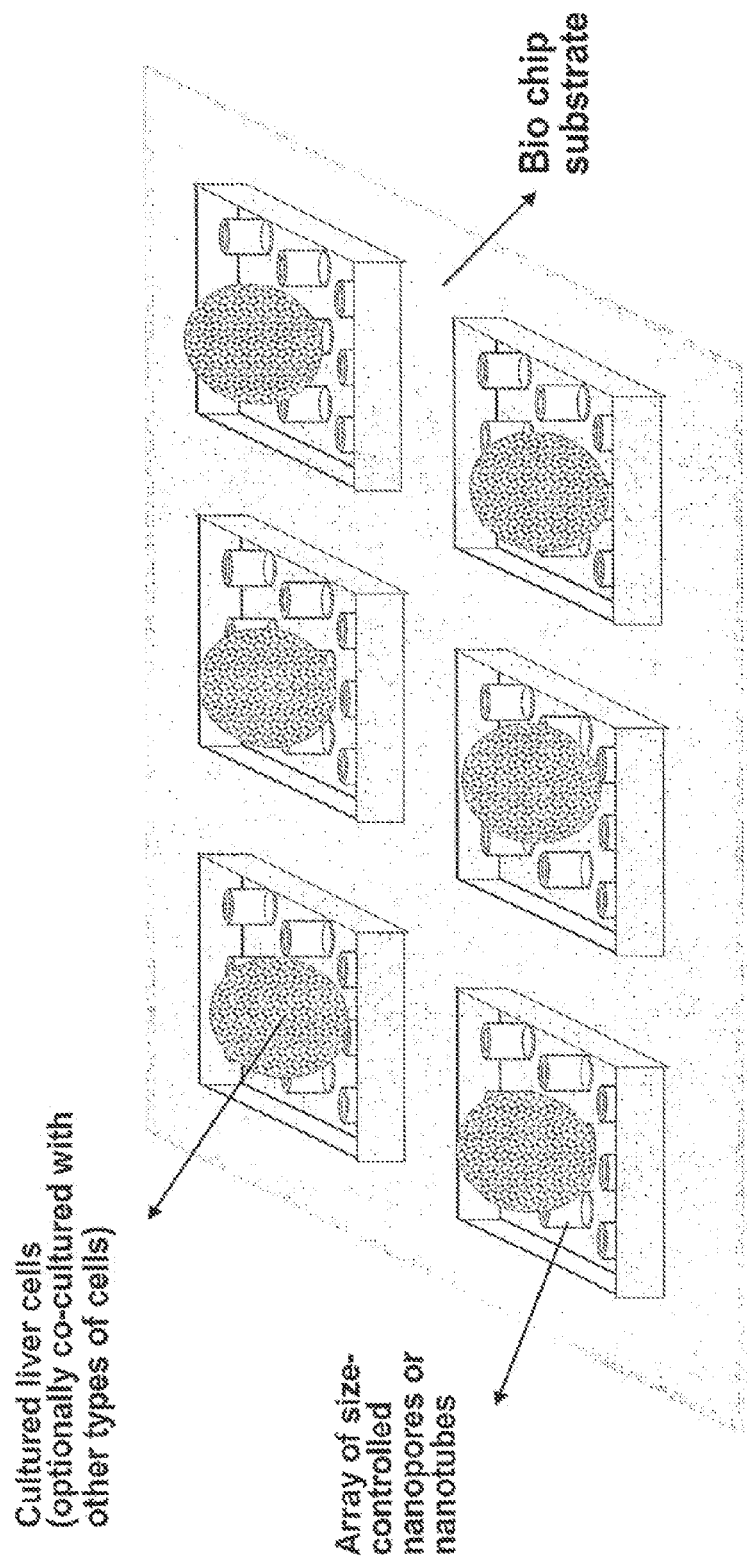

FIG. 45 schematically illustrates an exemplary biochip device, e.g., for toxicity testing of drugs or chemicals, with the device comprising an array of cultured cells, e.g., liver cells, grown on dimension-controlled biomaterials, wherein in one aspect the array comprises cultured liver cells optionally co-cultured with other types of cells.

It is to be understood that the drawings are for purposes of illustrating the concepts of the invention and are not to scale.

DETAILED DESCRIPTION

The invention provides nano-scaled materials that, in some aspects, can exhibit extraordinary physical, mechanical and biological properties which cannot be achieved by micro-scaled or bulk counterparts. The invention provides compositions comprising Ti and Ti alloys, which are corrosion resistant, light, yet sufficiently strong for load-bearing, and are machinable. The invention provides compositions comprising biocompatible metals which osseo-integrate, either as direct chemical or physical bonding with adjacent bone surfaces without forming a fibrous tissue interface layer.

The invention provides compositions that allow enhanced cell and bone growth due to their nanotubule or nanopore design and the Ti or $TiO_2$ in the nanopore or nanotube configurations. The invention also provides compositions comprising nanostructures made of Ti or $TiO_2$, or equivalent structures, made of other materials but coated with a biocompatible Ti or $TiO_2$ film. These structures of the invention allow enhanced cell adhesion and accelerated growth, for example, by at least about 10%, 20%, 25%, 50%, 75%, 100%, 125%, 150%, 175%, 200%, 250%, 300%, 400% or 500% or more faster.

The invention also provides compositions comprising: lock-in nanostructures which have re-entrant characteristics of a nanopore or nanotube entrance, and also having a smaller diameter (or size in general) than the rest of the nanopore or nanotube dimensions on the device; in one aspect this allows the cells or bones grown in or on the device to be mechanically more firmly attached to the device. In one aspect, to achieve substantial benefit of the lock-in structure, at least 10%, 20%, 25%, 50%, 70%, 75%, 80%, 90% or 100% of the pores have a lock-in nanostructure. In one aspect, the re-entrant characteristics of the nanopore or nanotube entrance comprises having an average entrance diameter (or average pore size if they are not circular) by at least 10% to 50% smaller, including at least 15%, 20%, 25%, 30%, 35%, 40%, 45%, 50%, 70%, 75%, 80%, 90% or 100% smaller than the rest of the nanopore or nanotube dimension so that the cells or bones grown are mechanically more firmly attached.

The invention also provides compositions comprising: ii) dual structured biomaterials comprising a micro or macro pores in combination with surfaces covered with finer $TiO_2$ nanotubes. In one aspect, the dual-sized structures allow micro- or macro-scale growth of bones, essentially completely filling the large pores to guard against the slippage or mechanical failure of grown bones against tensile or shear stresses, while enabling accelerated osteoblast cell growth on the nanotube-covered surface of the implants.

In one aspect, the dual structure comprises micro or macro pores, e.g., in a re-entrant configuration, and having an average diameter (or equivalent diameter if the pores are not circular) in the range of between about 0.5-1,000 µm, or between about 1-100 µm, together with a nanostructure consisting of nanopores or nanotubes having an average pore diameter in the range of between about 30-600 nm. In one aspect, the relative ratio of the micro/macro pores versus (vs) nanopores in the dual structure is such that the micro/macro pores occupy at least 10%, 15%, 20%, 25%, 30%, 35%, 40%, 45%, 50%, 70%, 75%, 80%, 90% or more area fraction of the implant or bio-substrate surface; and, in one aspect, at least 20% but less than 50% to maximize the accelerated cell culture or bone growth via the nanopore or nanotubule portion of the surface.

The invention also provides compositions comprising: iii) enlarged diameter nanopores and nanotubes suitable for efficient storage of biological agents, fabricated by guided chemical or electrochemical etching. In one aspect, such an enhanced diameter allows easier incorporation of biological or chemical agents such as growth factors, collagens, various proteins/biomolecules, nucleic acids (e.g., vectors, DNA, RNA, siRNA, genes), antibiotics, hormones, drugs such as cancer drugs or diabetes drugs, radioisotopes, functional particles like magnetic, metallic, ceramic, polymer particles for hyperthermia or magnetic hyperthermia treatment of tumors, with the particles optionally conjugated with other molecules for drug delivery, accelerated cell/bone growth, therapeutic treatments, etc. In one aspect, the desirable, enlarged nanopore and nanotube diameter (or equivalent diameter if the pores are not circular) comprises at least about 150, 200, 250, 300, 350, 400, 450, 500, 550, 600, 650, 700, 750, 800 or 850 or more nm.

In some aspect, biomaterial structures of the invention enable accelerated growth of cells, e.g., functional organ cells, such as liver or kidney cells as well as other structural cells such as blood vessel cells, enzyme secretion vessels, periodontal cells, odontoblasts, dentinoblasts, cementoblasts, enameloblasts, odontogenic ecto-mesenchymal tissue, osteoblasts, osteoclasts, fibroblasts, and other cells and tissues involved in odontogenesis or bone formation, or other hard tissues, and/or stem cells. The availability of such cultured cells can be useful for a variety of applications including i) organ-related therapeutic medical treatment including liver or kidney disease treatment, ii) orthopaedic, dental or periodontal processes, iii) supply of cells for various research or therapeutic purposes, and iv) disease diagnostic or toxicity testing of new drugs or chemicals.

Nanotube or nanopore structures of the invention can substantially improve cell adhesion and growth kinetics. In one aspect, adhesion of anchorage-dependent cells such as osteoblasts is a crucial prerequisite to subsequent cell functions such as synthesis of extracellular matrix proteins, and formation of mineral deposits. In one aspect, many types of cells beside the osteoblast cells remain healthy and grow fast if they are well-adhered onto a substrate surface, while the cells not adhering to the surface tends to stop growing.

The invention provides vertically or parallel-aligned nanostructure arrays, which can have structural advantages for reduced interfacial failure.

The nanostructure arrays of the invention can comprise vertically or parallel-aligned nanopore or nanotube arrays fabricated to be thin, e.g., less than 2000 nm, or less than 400 nm. The nanostructure arrays of the invention can comprise the same material as a base substrate material to ensure for strong bonding and mechanical stability of the nanotube or nanopore array, for example, $TiO_2$-covered nanopores or nanotubes; which in one aspect, have a common element Ti shared with the implant substrate material titanium to provide a strong chemical bonding.

Referring to the drawings, FIG. 30 schematically illustrates exemplary configurations of a dimensionally controlled, lock-in structure with the size or diameter of the entrance of the pores made smaller by oblique incident deposition of biocompatible materials such as Ti or $TiO_2$. In one aspect, an oblique incident evaporation or sputtering technique is utilized to deposit a material preferentially near the entrance of the nanopores or nanotubes. In one aspect, materials to be deposited as a thin film comprise Ti or $TiO_2$.

Alloys containing Ti with at least about 10%, 15%, 20%, 25%, 30%, 35%, 40%, 45% or 50% or more weight % Ti can also be utilized. The use of other related materials such as Zr, Hf, Nb, Ta, Mo, W, and their oxides, or alloys of these metals and oxides by at least about 10%, 15%, 20%, 25%, 30%, 35%, 40%, 45% or 50% or more weight % is not prohibited. Other materials such as Si, Si oxide, carbon, diamond, noble metals (such as Au, Ag, Pt and their alloys), polymer or plastic materials, or composite metals, ceramics or polymers can also be utilized to produce and use similar surface configurations, e.g., for bio implant and cell growth applications; and in one aspect comprising a coating of Ti and Ti oxide, Zr, Hf, Nb, Ta, Mo, W and their oxides, as well as their alloys, wherein a thickness of at least 1, 2, 3, 4, 5, 6, 7, 8, 9 or 10 or more nm and the coating coverage of at least 10%, 15%, 20%, 25%, 30%, 35%, 40%, 45%, 50%, 60%, 70% or 80% more of the total surfaces is provided.

The shadowing effect of the obliquely deposited material, FIG. 30(b), results in the lock-in structure with the rotation of the sample resulting in a more uniform, symmetrical pore entrance narrowing, FIG. 30(c). The diameter-reducing deposit can also be made on $TiO_2$ nanotubes, FIG. 30(d), or on the randomly pored structure prepared for example, by thin film deposition or etching of a duplex mixed structure. The sputtering for the nanopore entrance narrowing can be carried out by DC, pulse DC or RF sputtering methods. Smooth continuous film, rough topology film, or highly porous structure can be obtained. See, e.g., Thornton, J. Vac. Sci. Technol. A4(6), 3059 (1986); Meng et al "Investigations of titanium oxide films deposited by dc active magnetron sputtering in different sputtering pressures", Thin Solid Films 226, 22 (1993), by K. Robbie et al "Fabrication of thin films with highly porous microstructure", J. Vacuum Science & Technology, 13(3), 1032 (1995), and J. Rodriguez et al, "Reactively sputter deposited titanium oxide coatings with parallel Penniform microstructure", Adv. Mater. 12(5), 341 (2000).

Shown in FIG. 31 are various alternative types of lock-in pore structure for enhanced mechanical stability of grown bones. By virtue of the re-entrant nature of the pores, bones grown (and cells cultured) are mechanically better locked, and a tensile stress would not cause the bones or cells partially or fully in the pores would not slip out easily. FIG. 31(a) shows exemplary re-entrant oval or circular pores, which can be fabricated by patterned coverage, e.g., by lithographically patterned PMMA (polymethylmecarthrylate) or other patternable polymer, followed by isotropic chemical etching of Ti with acids. FIG. 31(b) represents rectangular cavities with corrugating walls, which is fabricated by alternating isotropic vs anisotropic chemical etching or reactive ion etching. Such isotropic vs anisotropic etching techniques are well known in silicon and MEMS (micro-electro-mechanical systems) fabrication. As an example embodiment, a Ti implant can be isotropic vs anisotropic alternatively etched to obtain a structure of FIG. 31(b), which can be oxidized (chemically or by oxygen atmosphere treatment) to exhibit $TiO_2$ surface. As another example embodiment, a Si wafer can be isotropic vs anisotropic alternatively etched, to obtain a structure of FIG. 31(b), and the surface can be coated by biocompatible Ti or $TiO_2$ by sputtering or evaporation. FIG. 31(c) shows re-entrant triangular cross-sectioned pores, which can be fabricated, for example, by anisotropic etching using gradually altered electric field in the case of electrochemical etching, or gradually increasing concentration of etchant during the process of pore formation. Shown in FIG. 31(d) are nanotubes such as $TiO_2$ with corrugating walls which can be fabricated by using alternating larger and smaller electric field during anodization of Ti and its alloys, for example, by alternating between 15 and 20 volts of potential during anodization in hydrofluidic acid or ammonium fluoride etchant or by alternating the pH value during the anodization electrochemical etching.

Substrate materials for the exemplary FIG. 31 structures can be Ti or Ti oxide as well as alloys containing Ti or Ti oxide by at least 50% weight %. Other related materials such as Zr, Hf, Nb, Ta, Mo, W, and their oxides, or alloys of these metals and oxides by at least 50% weight % can also be used. Other materials such as Si, Si oxide, carbon, diamond, noble metals (such as Au, Ag, Pt and their alloys), polymer or plastic materials, or composite metals, ceramics or polymers can also be utilized to produce and use similar desired surface configurations, e.g., for bio implant and cell growth applications; which in one aspect, these materials can be used as long as a coating of Ti and Ti oxide, Zr, Hf, Nb, Ta, Mo, W and their oxides, as well as their alloys, wherein a thickness of at least 1, 2, 3, 4, 5, 6, 7, 8, 9 or 10 or more nm and the coating coverage of at least 10%, 15%, 20%, 25%, 30%, 35%, 40%, 45%, 50%, 60%, 70% or 80% more of the total surfaces is provided.

FIG. 32 illustrates titanium nanotubes formed by electrolytic anodization, showing the anodization voltage dependence of $TiO_2$ nanotube diameter. It is seen that anodization of Ti is generally difficult to provide a large diameter pores or nanotubes with a limited range of fabricated $TiO_2$ nanotube diameter to less than approximately 100-150 nm (inside diameter). In some aspects, this dimension of approximately 100-150 nm is often not large enough to incorporate biological agents and biomolecules, and is also not large enough for a substantial portion of cells (typically many micrometers in size) to go into the pore and form a locked-in structure, although a portion of the filopodia branches can get into the pore and improve cell adhesion and cell growth kinetics.

In some aspects, to obtain a larger pore or nanotube diameter (or a larger average pore entrance dimension), a patterned and guided pore formation, e.g., various lithographical means, is desirable as illustrated in FIG. 33 and FIG. 34. A proper combination of isotropic and anisotropic etching process can be incorporated to form such structures. In some aspects, the process can create a "micro-nano dual pore structure" of e.g., in the desired range of about 0.5-1,000 µm in average diameter, or about 1-100 µm diameter range, using the guided patterning, the pore surface of which is again covered by e.g., very fine approximately 100 nm diameter regime $TiO_2$ nanotubes through additional processing of anodization.

The dual structure, illustrated in FIG. 35(a)-(c) as higher magnification illustrations of the exemplary FIG. 33 and FIG. 34 structures show the details of the titanium oxide nanotubes formed on the top and pore surfaces.

In some aspects, such a dual structure is desirable for three purposes of: i) allowing an increased portion of cells into the pores, or for propagating cells micrometers in size to go into the pores, resulting in enhanced adhesion and accelerated cell growth, ii) enhanced mechanical stability of grown bone lock-in against tensile or shear stress, and/or, iii) easier insertion/storage of biological agents and biomolecules.

The biological agents that can be stored/trapped in exemplary nanostructures include growth factors, collagens, various proteins/biomolecules, genes, DNAs, antibiotics, drugs such as cancer drugs or diabetes drugs, functional particles like magnetic, metallic, ceramic, polymer particles for hyperthermia or magnetic hyperthermia treatment of tumors, with the particles optionally conjugated with other molecules for drug delivery, accelerated cell/bone growth, therapeutic treatments, etc. Cell growth inhibiting drugs can also be inserted in nanopores or nanotubes of the invention, for example, on the surface of stents to minimize restenosis or on the surface of other implants (e.g., drug delivery modules) to prevent/minimize scar tissue formation.

In some aspects, making the dual structured nanopore structure of the exemplary FIGS. 33 to 35, comprises a guided synthesis of "enlarged-diameter nanotubes and nanopores" with essentially vertically aligned configuration of between about 30, 35, 40 or 45 degrees to about 90 degrees angle relative to the surface. Aligned nanopores or nanotubes with a diameter (or equivalent size) of greater than approximately 150 nm or more is difficult to fabricate with currently known methods. In some aspects, such desired "enlarged-diameter nanotubes and nanopores" can be fabricated by pre-patterning with an array of small craters, e.g., on the order of the diameter of the intended final pore/nanotube diameter first formed on the implant or bio-substrate surface, e.g., by lithography and other approaches as described herein.

The lithographic patterning of craters can be carried out by photolithography (including UV, deep UV and extreme UV lithography, laser interference lithography, etc.), e-beam or ion beam lithography, nano imprint lithography, and various other known techniques (see also discussion, above). In some aspects, once the pre-patterned craters are formed with a desirable size, location and periodicity, the implant or bio-substrate can be subjected to the chemical, electrochemical or ion etching to form desired larger-diameter aligned pores or nanotubes.

Exemplary structures of the enlarged-diameter nanotubes and nanopores are schematically illustrated in FIG. 36. The desired range of average diameter for the enlarged and guided nanopores and nanotubes is at least approximately 150 nm, or about at least 200, 250, 300, 350, 400, 450 or 500 or more nm. In some aspects, for the sake of desired large surface area for accelerated cell and bio reactions, the desired diameter of the enlarged nanopores and nanotubes is kept below 0.5, 1, 2, 3, 4, 5, 6, 7, 8, 9, or 10 µm; unless, in one aspect, a dual micro-nano structure of the invention is introduced to make all exposed surfaces of the enlarged pores or nanotubes covered with yet finer $TiO_2$ nano nanotubes.

Described in FIGS. 36 to 40 are various exemplary techniques for obtaining enlarged-diameter nanotube and nanopore structures. Shown in FIG. 36 is an exemplary lithographic patterning approach for crater array fabrication, while FIG. 37 schematically illustrates an exemplary process of using nano imprinting to pre-pattern craters on Ti or $TiO_2$ surface for guided synthesis of larger diameter $TiO_2$ nanotubes and nanopores. Such nano imprint lithography technique is convenient for mass production of a large number of implants or bio substrates as simple stamping operation can accomplish the pre-patterning of craters without resorting to complicated and often costly photolithography or e-beam lithography patterning of each part. In some aspects, another major advantage is the ability to use elastomeric stamp with compliance, which allows reliable stamping on large-area, nominally-flat surfaces of Ti or other biocompatible substrates and implants in which the flatness is not always guaranteed to ensure reliable stamping over a large sample area.

In some aspects, the bio implant parts are more often than not in a non-flat surface geometry. Therefore it is desirable to have a convenient and effective means of fabricating the pre-patterned craters for guided introduction of enlarged-diameter nanopores or nanotubes, e.g., on the surface of Ti implants. FIG. 38 illustrates exemplary processes of guided etch nano patterning of identical patterns on non-flat surfaces using (a) conformable or stretchable elastomeric mask sheet, (b) elastomeric roll stamping.

In some aspects, a technique of forming such a desired uniform nanopore or nanotube array on non-flat surface comprises introducing guided etching using a vertically two-phase decomposable coating as illustrated in FIG. 39. Here, a non-flat substrate or implant (e.g., bent Ti wire) is coated with a material which is then decomposed into a vertically aligned two-phase structure (e.g., decomposable diblock copolymer layer heated to decompose into two phases, a spinodal alloy coating heated to decompose into two phases, etc.) as illustrated in FIG. 39(a)-(b). The two phase structure is then differentially etched, e.g., by chemical etching or ion etching to exhibit a nanopored structure as illustrated in FIG. 39(c). The base non-flat substrate or implant material is etched through the nanopores in the coating layer to create an array of craters (FIG. 39(d)). The coating layer material is then etched away (FIG. 39(e)) and the substrate is subjected to anodization or chemical etch to introduce deeper nanopores or nanotubes on the implant surface (FIG. 39(f)).

In some aspects, diblock copolymers are made up of two chemically different polymer chains or blocks while they are joined by a covalent bond. Because of this connectivity constraint yet chemical incompatibility with each other, the diblock copolymers tend to phase separate and self assemble into an ordered (often with a hexagonal geometry), nanoscale, mixed-phase composites. Depending on the chemistry and decomposition conditions, they can form an ordered array with one of the polymer components taking a nanocylinder shape embedded in the other polymer component. Examples of diblock copolymers include a mixture of polystyrene-polybutadiene and that of polystyrene-polyisoprene. The diblock copolymers are diluted with a solvent such as toluene, and can be dip coated, brush coated or spray coated on a substrate. When the heat is applied and drying proceeds and the copolymer concentration and temperature reaches a critical point, the phase decomposition of the diblock copolymer into an ordered structure takes place. The desired temperature rise to nucleate and grow the ordered decomposed diblock copolymer structure is typically in the range of between about 50° C. to 350° C., or between about 100° C. to 250° C.

In some aspects, the spinodal alloys can be spontaneously decomposed into a uniform two phase structure by heating to a high temperature within the spinodal range. Fe—Cr—Co, Al—Ni—Co—Fe, Cu—Ni—Fe, Cu—Ni—Co, and Al—Si alloys are well known examples of spinodal alloys. Due to the difference in chemical etchability between the two decomposed phases, a nanoporous structure of FIG. 39(c) can be obtained.

FIG. 40 illustrates an exemplary size-controlled, uniform nanopore or nanotube array on various surfaces by guided etching using a vertically two-phase decomposed coating of periodically decomposing diblock copolymer or spinodally decomposing alloy of FIG. 39. The size-controlled, uniform nanopore or nanotube array can be formed on various exemplary surfaces by guided etching, i.e., on a flat surface (FIG. 40(a)), on a coarse-patterned surface (FIG. 40(b)), on parallel Ti sheet or wire array (FIG. 40(c)) which can be useful for three-dimensional cell or organ structure, on wire mesh, wire bundle or scaffold type highly porous metal foam (e.g., made of Ti or its alloy) (FIG. 40(d)), and on re-entrant cavity surface (e.g., pre-shaped Ti or Ti-coated Si) (FIG. 40(e)).

In some aspects, the 3-D cultured cells are prepared using parallel Ti sheet, wire array or foam arrays with nanopore or nanotube array surface structure, e.g., see the exemplary structures in FIGS. 40(c) and (d); these can be useful for a variety of applications including in vivo implanting of cells or organs. A patient can be supplied with in vitro cultured and in vivo implanted, three-dimensional functional cells such as liver, kidney, or blood vessel cells or organs. Three-dimensionally cultured bones or tissues can also be utilized as dental, periodontal or orthopaedic body implants.

In some aspects, to obtain relatively large surface area for cell growth, the desired thickness of the titanium metal ribbon, or the desired diameter of the metal wire or foam in FIG. 40(c) or (d) is in the range of about 10 μm-50,000 μm, or about 25 to 2,500 μm. In some aspects, the desired volume fraction of the metal for the given targeted cell volume at the end of the planned cell culture period is at least 10% in volume, or at least 30% in volume. In some aspects, each of the ribbon surfaces is made to contain an aligned nanopore or nanotube array; in some aspects, with a diameter being in the range of about 10-1000 nm, or about 30-300 nm, or about 60 to 200 nm in diameter; in some aspects, the desired height being in the range of about 40 to 2000 nm, or about 100-400 nm; in some aspects, the desired angle is vertical with an allowance of about 10, 20, 30, 40 or 50 degrees variation off the perpendicular axis.

In some aspects, the shape of these nanostructure-surface ribbons is straight so that the metal arrays can be optionally pulled out after desired volume of the cells are cultured. In some aspects, the cultured growth will continue after the metal wire or ribbon array template structure is pulled out, and any minor surface damage or the thin empty gap created by the vacated template will be repaired/filled by growing cells. In some aspects, such a three-dimensionally cultured cell volume in an accelerated manner can be useful for a variety of applications including creation of a partial or full artificial organs of e.g., liver, kidney, bone, periodontal tissue, blood vessel cells, skin cells, stem cells, and other human or animal organ cells etc. In some aspects, the 3-D cultured cells, according to the invention, can be in any orientation, i.e., horizontal, vertical or upside down depending on specific needs especially in the in vivo culture environment, for example, in the case of organ implants in human, animal, or xenotransplantation of human organs which are temporarily cultured in animals prior to human implantation.

In some aspects, biological agents or functional nanoparticles can additionally be stored in the surface nanopores or nanotubes on these various shaped substrates or implants. The functional nanoparticles include magnetic particles, novel metal or SPR (surface plasmon resonance) based photoluminescent particles, quantum dots, fluorescence particles, bio-conjugated particles, which are added for the purpose of accelerated cell/bone growth, protein harvest (as a result of accelerated cell growth, proliferation, and secretion), delivery of drugs, genes, chemicals, therapeutics, etc.

Referring to the drawings, FIG. 41 schematically illustrates an exemplary bone- or cell-locking nanopore/nanotube array with biological agents inserted for accelerated bone or cell growth, protein harvest, drug delivery, and therapeutics.

As described earlier in relation to FIG. 30, dimensionally controlled, lock-in structures with the size or diameter of the entrance of the pores made smaller than the rest of the pore dimension below by oblique incident deposition of biocompatible materials such as Ti or $TiO_2$. An oblique incident evaporation or sputtering technique is utilized to deposit a material preferentially near the entrance of the nanopores or nanotubes.

In some aspects, the biological agents that can be stored/trapped in nanostructures of the invention comprise growth factors, collagens, various proteins/biomolecules, genes, DNAs, antibiotics, hormones, drugs such as cancer drugs or diabetes drugs, functional particles like magnetic, metallic, ceramic, polymer particles for hyperthermia or magnetic hyperthermia treatment of tumors, with the particles optionally conjugated with other molecules for drug delivery, accelerated cell/bone growth, therapeutic treatments, etc.

Cell growth inhibiting drugs can also be inserted in the nanopores or nanotubes of the invention, for example, on the surface of stents to minimize restenosis or on the surface of other implants (e.g., drug delivery modules) to prevent/minimize scar tissue formation. The entrance-diameter-reducing deposit can be made on a variety of porous structures such as on rectangular cross-section shape pores, on re-entrant shape pores, on $TiO_2$ nanotubes, or on the randomly pored structures prepared for example, by thin film deposition or etching of a duplex mixed structure. FIG. 12 schematically illustrates cells or bone growing and locked in on these entrance-diameter-reduced or re-entrant shaped nanostructure surface.

In some aspects, instead of biomolecules, functional nanoparticles such as magnetic particles, novel metal or SPR (surface plasmon resonance) photoluminescent particles, quantum dots, fluorescence particles, bio-conjugated particles for delivery of drugs, genes, chemicals, etc. can be stored in the pores on various shaped nanostructure surface as illustrated in FIG. 43, for accelerated cell or bone growth, protein harvest, drug delivery, and therapeutics such as hyperthermia or magnetic hyperthermia treatment of tumors.

FIG. 11 schematically illustrates various potential in vivo or ex vivo applications of exemplary dimension-controlled biomaterials capable of accelerated cell/bone growth or functional drug delivery and therapeutics. In some aspects, nanopore or nanotube structures described in relation to FIGS. 30 to 43 can be utilized for these biomedical device applications. Examples shown include orthopaedic and dental implants, cell or organ implants, drug delivery devices such as controlled release of insulin by magnetic actuation, artificial liver devices, drug-protected stents (e.g., to prevent/minimize restenosis) or other tubules inserted into blood vessels and in various other body parts, and therapeutic devices such as magnetic field induced local heating for cancer treatment. In some aspects, cell growth inhibiting drugs can be inserted in the exemplary nanopores or nanotubes of implants such as drug delivery modules to prevent/minimize scar tissue formation.

Illustrated in FIG. 15 is an exemplary magnetically actuated, on-off controllable or programmable, remote drug release device comprising exemplary biomaterials of the invention. Remote magnetic field such as approximately 100 KHz AC magnetic field can be utilized to activate the drug release by preferential heating of the magnetic nanoparticles stored in the nanopores of implants, thus allowing temperature-gradient-induced drug movement from the nanopores into the human body. Suitable magnetic nanoparticles for such use include biocompatible iron-oxide particles of magnetite ($Fe_3O_4$) or maghemite ($\gamma$-$Fe_2O_3$) in the particle size regime of about 5 to 50 nm in average diameter.

In some aspects, a mechanical agitation and induced movement of the magnetic particles themselves in the pores containing the stored drugs can be utilized as an alternative mechanism of drug release. In this case, a rather lower frequency AC magnetic field actuation with a gradient magnetic field is preferred in order to allow movement of magnetic particles against the viscosity of the fluid in the nanopores. In some aspects, a desired frequency range is approximately 1-10,000 Hz, or between about 10-1,000 Hz.

In these exemplary approaches, the drugs are released any time of the day only when desired, and can be turned off completely when it is no longer needed, so the side effects of drugs are minimized. In some aspects, similar magnetic particle and external field combination can also be utilized for cancer treatment, for example, through an implant devices containing the nanoporous structure (e.g., entrance-diameter-reduced nanopores or nanotubes) placed in the vicinity of cancerous regions, for example, in the liver containing inoperable distribution of recurring/growing cancer cells. In some aspects, repeated hyperthermia treatments, e.g., over many months, are used, e.g., by on-off type continual activation of external magnetic field can gradually kill the cancer cells near the cancerous regions.

FIG. 16 illustrates an exemplary method of harvesting cells cultured in an accelerated way using dimension-controlled biomaterials. In some aspects, the nanopore or nanotube structures comprising $TiO_2$ or related materials accelerate growth of certain types of cells. In some aspects, the increased number of cells generated by such a device can be useful for accelerated supply of cells, especially rare cells such as stem cells for various R&D or therapeutic uses. As illustrated in FIG. 16(a), the cells are cultured in an exemplary biocompatible environment with needed nutrient media. The cells so proliferated on the nanopore or nanotube arrays are then harvested and supplied for other uses.

One method of harvesting the grown cells off the biomaterial substrate is to use a process known as "trypsinization". Once cells are grown completely on whole surface of cell culture flask, the media fluid is removed by suction. After rinsing of the cells twice with PBS (phosphate buffer solution), trypsin is added to detach the cell from the surface. In general, approximately 2-3 ml of trypsin is used for detaching cells grown on 10 $cm^2$ cell culture dish. After a few minutes, most of the cells are detached from the surface, as illustrated in FIG. 16(b). After adding approximately 10 ml of new medium, this fluid containing the detached stem cells is poured into a centrifuge tube. After centrifugation at appropriate rotation speed and time, all of the cells are separated. The medium is removed by suction, and approximately 1 ml of new media is added for storage of the harvested cells or for additional culture. To estimate the number of proliferated cells, trypan blue assay are employed in conjunction with hematocytometry. The cells can also be in situ proliferated on the implant surfaces as the $TiO_2$ as well as Ti substrate are biocompatible.

In some aspects, the dimension controlled Ti oxide nanopore or nanotube structure is also useful for carrying out fast diagnosis and detection of certain types of cells such as diseased cells, or cells exposed to biological or chemical warfare agents. In some aspects, an X-Y matrix subdivided array of dimension-controlled nanopore or nanotube array structures are produced as illustrated in FIG. 44. Various exemplary nanopore or nanotube structures described in relation to FIGS. 30 to 43, can be utilized for accelerated cell detection/diagnosis.

In some aspects, the dimension controlled Ti oxide nanopore or nanotube structures are used in the diagnosis of diseases (especially epidemic diseases) or detection of toxins, bacteria or viruses, e.g., where a rapid detection is essential even when the available quantity of the cells is relatively small. Each of the detection elements in FIG. 44 which contains a multiplicity of the dimension controlled nanopores or nanotubes on which various types of cells to be analyzed are placed and allowed to rapidly proliferate to a sufficient number for easy detection.

For analysis of cell types, various exemplary techniques, illustrated in FIG. 18 can be used, including (a) optical detection of morphology and size (using a microscope, fluorescent microscope, or CCD camera sensing of fluorescent or quantum dot tagged cells), (b) chemical or biological detection (e.g., based on signature reactions), (c) magnetic sensor detection (e.g., by using magnetically targeted antibody and its conjugation with certain types of antigens).

Another exemplary application of the bio-chip apparatus of the invention is illustrated in FIG. 44; this aspect utilizes the bio-chip apparatus a base structure to culture liver cells for testing of new drugs, as illustrated in FIG. 45, showing an exemplary bio-chip device for toxicity testing of drugs or chemicals, with the device comprising an array of cultured liver cells grown rapidly and healthy manner on the dimension-controlled biomaterials. As in the cell detection/diagnosis applications, various the bio-chip apparatus nanopore or nanotube structures, e.g., as described in FIGS. 30 to 43, can be utilized for the liver cell culture and toxicity test applications. A variation of the embodiments include having a parallel wire, rod or plate shape base structure in a vertically (or near vertically) arranged configuration (with each rod or plate base containing parallel, yet laterally spaced apart nanopore or nanotube array) in order to make the 3-D culture more effective.

In some aspects, the three-dimensionally structured, nanopore or nanotube arrays of the invention enable a rapid and healthy culture of cells, e.g., liver, kidney or other cells, in a desirable three-dimensional configuration. In some aspects, the apparatus is utilized for testing drug toxicity or chemical toxicity. The invention provides bio-chips comprising arrays of healthy, three-dimensionally cultured liver cells, e.g., 10×10, 100×100 or 1000×1000 cells as sensing elements to allow simultaneous evaluation of many drugs for much accelerated screening and development of biologically acceptable drugs. Likewise, many chemicals, polymers, injection fluids, and composites that may be useful for in vivo applications can be rapidly tested for toxicity using the exemplary device of FIG. 19. The accelerated, healthy liver cell growth device of FIG. 19 can also be utilized as the basis of artificial liver devices for patients waiting for transplant or as a temporary aid to liver function after transplant. Other functional organs applications such as artificial kidney can also be considered.

It is understood that the above-described embodiments are illustrative of only a few of the many possible specific embodiments which can represent applications of the invention. Numerous and varied other arrangements can be made by those skilled in the art without departing from the spirit and scope of the invention. For example, the materials involved do not have to be Ti oxide nanotubes on Ti-based metals, as the nanotubes and the substrate that the nanotubes are adhered to can be other biocompatible materials or non-biocompatible materials coated with biocompatible and bioactive surface layer such as Ti, or coated with biocompatible but bio-inert surface layer such as novel metal or polymer layer. Also, a thin coating of biomolecules or chemical molecules can optionally be applied on the surface of $TiO_2$ nanopores or nanotubes to further enhance the attachment of cells.

V. BIOMATERIALS WITH SIZE-RANDOMIZED SURFACE NANOPORES, FABRICATION METHOD THEREOF, AND DEVICES AND ARTICLES OF MANUFACTURE COMPRISING SUCH MATERIALS

The invention provides products of manufacture comprising a size-randomized and shape-randomized nanopore- or nanotube-comprising surfaces. In one aspect, these compositions are made by a method comprising providing a composition comprising a Ti or Ti oxide surface; depositing a semi-wettable coating on the Ti or Ti oxide surface by employing lithographic patterning or by a thin film deposition technique, wherein the coating decomposes into nano- or micro-islands of local etch masks; and chemical etching or electrochemical anodization of the etch-masked surface, thereby generating a size-randomized and shape-randomized nanopore- or nanotube-comprising surface.

In some aspects, because the same type of cells having substantially varying cell size and shape from one cell to another, e.g., liver cells, grow better when co-cultured with other types of cells, such as endothelial or fibroblast cells which have significantly different cell sizes, the invention provides devices and methods comprising use of mixed cell cultures, e.g., liver cells, pancreas cells and the like, with endothelial cells, fibroblast cells, fat cells, blood vessel cells stem cells and the like. Aspects of the invention comprising size-randomized nanopores and nanotubes allow efficient culture and co-culturing of cells, for example, for artificial in vitro or in vivo growth of healthy, fully functional and long-lasting liver cells.

SUMMARY

The invention provides novel, biocompatible nanostructured biomaterials, devices comprising such biomaterials, and fabrication methods thereof. The novel biomaterials can enable accelerated cell growth and can be useful for a variety of uses including orthopaedic, dental, cell/organ implants, therapeutics, disease diagnostic, drug toxicity testing, and cell supply applications. The invention provides products of manufacture comprising a size-randomized and shape-randomized nanopore- or nanotube-comprising surfaces. In one aspect, these compositions are made by a method comprising providing a composition comprising a Ti or Ti oxide surface; depositing a semi-wettable coating on the Ti or Ti oxide surface by employing lithographic patterning or by a thin film deposition technique, wherein the coating decomposes into nano- or micro-islands of local etch masks; and chemical etching or electrochemical anodization of the etch-masked surface, thereby generating a size-randomized and shape-randomized nanopore- or nanotube-comprising surface.

In some aspects, preferred substrate materials with exemplary surface configurations comprise Ti and Ti oxide, and/or alloys containing Ti or Ti oxide by at least about 10%, 15%, 20%, 25%, 30%, 35%, 40%, 45% or 50% or more weight %. However, the use of other related materials such as Zr, Hf, Nb, Ta, Mo, W, and their oxides, or alloys of these metals and oxides by at least about 10%, 15%, 20%, 25%, 30%, 35%, 40%, 45% or 50% or more weight % can be used. Other materials such as Si, Si oxide, carbon, diamond, noble metals (such as Au, Ag, Pt and their alloys), polymer or plastic materials, or composite metals, ceramics or polymers can also be utilized to produce and use similar desired surface configurations, e.g., for bio implant and cell growth applications; where in one aspect, these materials are used as long as a coating of Ti and Ti oxide, Zr, Hf, Nb, Ta, Mo, W and their oxides, as well as their alloys, with a thickness of at least 1, 2, 3, 4, 5, 6, 7, 8, 9 or 10 or more nm and the coating coverage of at least 10%, 15%, 20%, 25%, 30%, 35%, 40%, 45%, 50%, 60%, 70% or 80% more of the total surfaces is provided.

The invention provides size-randomized biocompatible nanostructures with accelerated cell growth characteristics as well as enhanced bone growth together with improved adhesion and mechanical properties. The exemplary biomaterials have a range of nanopore or nanotube diameters which allow more efficient co-culture of various cells, in particular, for efficient culture of healthy liver cells and organs as a mixed co-culture of hepatocyte cells together with non-hepatocyte cells. Such size-randomized structures with biocompatible surface are fabricated, according to the invention, by utilizing semi-wettable coating that decomposes into nano or micro islands of local etch masks, by employing lithographic patterning, or by thin film deposition technique, followed by chemical etching or electrochemical anodization of Ti or related materials in various configurations for planar and three-dimensional cell or bone culture. Such biocompatible nanostructures can be useful for reliable and faster orthopaedic or dental bone repair, for preparation of partial or full implant organs or artificial ex-vivo devices such as artificial liver devices, for externally controllable drug release and therapeutic treatments, for efficient toxicity testing of drugs and chemicals, and for diagnosis/detection of disease or forensic cells.

The invention provides products of manufacture comprising a size-randomized and shape-randomized nanopore- or nanotube-comprising surface made by a method comprising the following steps: (a) providing a composition comprising a Ti or Ti oxide surface; (b) depositing a semi-wettable coating on the Ti or Ti oxide surface by employing lithographic patterning or by a thin film deposition technique, wherein the coating decomposes into nano- or micro-islands of local etch masks; and (c) chemical etching or electrochemical anodization of the etch-masked surface, thereby generating a size-randomized and shape-randomized nanopore- or nanotube-comprising surface.

In one aspect, wherein the composition comprising a Ti or Ti oxide surface comprises a Ti- or Ti oxide-comprising plate, sheet, wire, mesh or foam. In one aspect, the distribution of the nanopore or nanotube sizes is such that at least one third of the pores or tubes have their average diameter equal to or less than 30%, 40%, 50%, 60% or 70% of the overall average pore diameter, while another one third of the pores have their average diameter at least 100%, 125% or 150%, the overall average pore diameter. In one aspect, the at least one third of the pores or tubes have their average diameter equal to or less than 10%, 20%, 30%, 40%, 50% or 60% of the overall average pore diameter. In one aspect, the at least one quarter of the pores or tubes, or 10%, 20%, 30%, 40%, 50% or 60% of the pores or tubes, have their average diameter equal to or less than 10%, 20%, 30%, 40%, 50% or 60% of the overall average pore diameter. In one aspect, the one third of the pores have their average diameter at least 115%, 125%, 150%, 175%, 200% or more of the overall average pore diameter.

In one aspect, the nanopore or nanotube entrance has a smaller diameter or size than the rest (the interior) of the nanopore or nanotube. In one aspect, the nanopore or nanotube entrance has an average entrance diameter or average pore size by at least 10% to 50% smaller, or at least 15%, 20%, 25%, 30%, 35%, 40% or 45%, smaller than the rest (the interior) of the nanopore or nanotube dimension.

In one aspect, the nanopore or nanotube have an average diameter, or equivalent diameter if the pores are not circular, in the range of between about 0.5 to 1,000 µm, or between about 1 to 100 µm, and optionally the entrances of the micro or macro pores have a smaller diameter or size than the rest (the interior) of the micro or macro pores; and, a surface area covered with $TiO_2$ nanotubes having an average pore diameter in the range of between about 30-600 nm, wherein optionally the relative ratio of the micro/macro pores of (a) and the nanopores of (b) in the dual structure is such that the micro/macro pores occupy at least 10% area fraction of the dual structured biomaterial, or optionally at least 20% but less than 50%.

In one aspect, the product of manufacture further comprises a plurality of cells, wherein the cells comprise liver cells, liver parenchymal cells, endothelial cells, adipocytes, fibroblastic cells, Kupffer cells, kidney cells, blood vessel cells, skin cells, periodontal cells, odontoblasts, dentinoblasts, cementoblasts, enameloblasts, odontogenic ectomesenchymal tissue, osteoblasts, osteoclasts, fibroblasts, and other cells and tissues involved in odontogenesis or bone formation, stem cells or a combination thereof.

The invention provides products of manufacture comprising any of the compositions of the invention described herein comprising Ti and Ti oxide; alloys comprising Ti or Ti oxide by at least 50% weight %; Zr; Hf; Nb; Ta; Mo; W; oxides of Zr, Hf, Nb, Ta, Mo or W; or alloys of Zr, Hf, Nb, Ta, Mo or W comprising at least 50% weight % of Zr, Hf, Nb, Ta, Mo or W; or Si, Si oxide, carbon, diamond, noble metals, Au, Ag, Pt, or Au, Ag or Pt alloys, polymer or plastic materials, or composite metals, ceramics or polymers with a coating of biocompatible Ti and Ti oxide, Zr, Hf, Nb, Ta, Mo, W and their oxides or alloys of Zr, Hf, Nb, Ta, Mo, W; and optionally with a thickness of at least about 1, 2, 3, 4 or 5 or more nm; and optionally the coating coverage of at least about 20%, 30%, 40%, 50%, 60%, 70%, 80% or more of the total surfaces.

In one aspect, the product of manufacture further comprises a biological agent, small molecule, or other composition, e.g., a growth factor, a collagen, a nucleic acid, an antibiotic, a hormone, a drug, a magnetic particle, a metallic particle, a radioisotope, a ceramic particle, a polymer particle, a drug delivery particle, a lipid, a liposome, a carbohydrate, a nucleic acid or a combination thereof.

In one aspect, the size-randomized and shape-randomized nanopores or nanotubes form a vertically or parallel-aligned nanostructure array, or a combination thereof (see discussion, above).

The invention provides implants comprising a product of manufacture of the invention, including any of the nanostructures (e.g., nanotubes, nanopore-comprising structures) described herein.

The invention provides bioreactor comprising a product of manufacture of the invention, including any of the nanostructures (e.g., nanotubes, nanopore-comprising structures) described herein.

The invention provides artificial organs comprising a product of manufacture of any of claims 1 to 12.

The invention provides disease or toxin detection devices comprising a product of manufacture of the invention, including any of the nanostructures (e.g., nanotubes, nanopore-comprising structures) described herein. In one aspect, the disease or toxin detected is SARS, influenza (e.g., the so-called "bird flu") or anthrax.

The invention provides orthopaedic or dental prostheses comprising a product of manufacture of the invention, including any of the nanostructures (e.g., nanotubes, nanopore-comprising structures) described herein.

The invention provides methods of making a product of manufacture comprising a size-randomized and shape-randomized nanopore- or nanotube-comprising surface, the method comprising the following steps: (a) providing a composition comprising a Ti or Ti oxide surface; (b) depositing a semi-wettable coating on the Ti or Ti oxide surface by employing lithographic patterning or by a thin film deposition technique, wherein the coating decomposes into nano- or micro-islands of local etch masks; and (c) chemical etching or electrochemical anodization of the etch-masked surface, thereby generating a size-randomized and shape-randomized nanopore- or nanotube-comprising surface.

All publications, patents, patent applications, GenBank sequences and ATCC deposits, cited herein are hereby expressly incorporated by reference for all purposes.

BRIEF DESCRIPTION OF THE DRAWINGS

Figure 46:
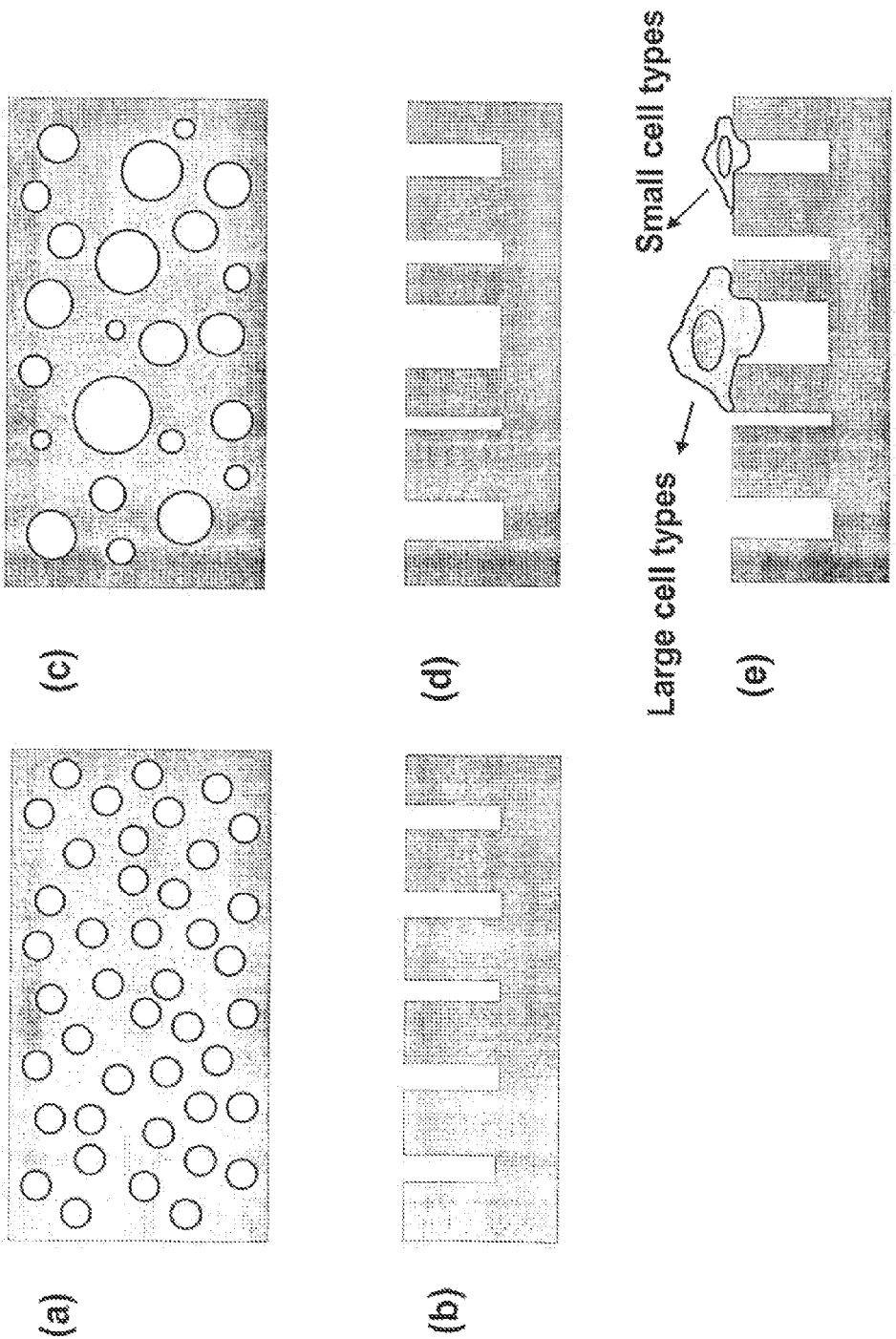

The advantages, nature and additional features of the invention will appear more fully upon consideration of the illustrative embodiments described in the accompanying drawings. In the drawings:

FIG. 46: FIG. 46(c)-(e) schematically illustrate exemplary structures of the invention comprising configurations of exemplary size-randomized nanopore structures of biocompatible materials (e.g., for accelerated cell/bone growth, e.g., multi-cell-type co-culture, protein harvest, drug delivery, therapeutics, etc.), comprising Ti or $TiO_2$, with the size or diameter of the entrance of the pores having a varied distribution of dimensions, as illustrated in FIG. 1(c)-(e), as compared to the uniform sized nanopores FIGS. 46(a) and 46(b); FIG. 46(a), top view of an exemplary equal-diameter nanopore array; FIG. 46(b), side view of exemplary equal-diameter pores; FIG. 46(c), top view of random-sized exemplary nanopores; FIG. 46(d), side view of exemplary random-sized pores; FIG. 46(b), nanopore structure with large and small cells.

FIG. 47: FIG. 47(a)-(f) schematically illustrate exemplary structures of the invention comprising size-randomized pore formation on flat surface, e.g., illustrate an exemplary process for making a randomized pore formation on, e.g., a Ti wire, mesh, or sheet surface using semi-wettable or island-forming coating (e.g., for accelerated cell/bone growth especially multi-cell-type co-culture): FIG. 47(a) illustrates a starting material comprising, e.g., a cylinder or random shape substrate/implant (e.g., Ti wire); FIG. 47(b) illustrates application of a semi-wettable coating, which can be broken up or balled up into islands (e.g., a spray- or dip-coated polymer which balls up on drying, or a sputtered or evaporated metal film which balls up into islands on heating); FIG. 47(c) illustrates formation of balled up islands with random distribution of sizes; FIG. 47(d) illustrates the step of chemical or electrochemical oxidation into $TiO_2$ surface oxide except the island regions; FIG. 47(e) illustrates the step of dissolving away the islands to form random sized craters; FIG. 47(f) illustrates the step of chemical etching or anodization using the craters as the preferred reaction sites for deeper nanopores on the implant surface.

Figure 48:
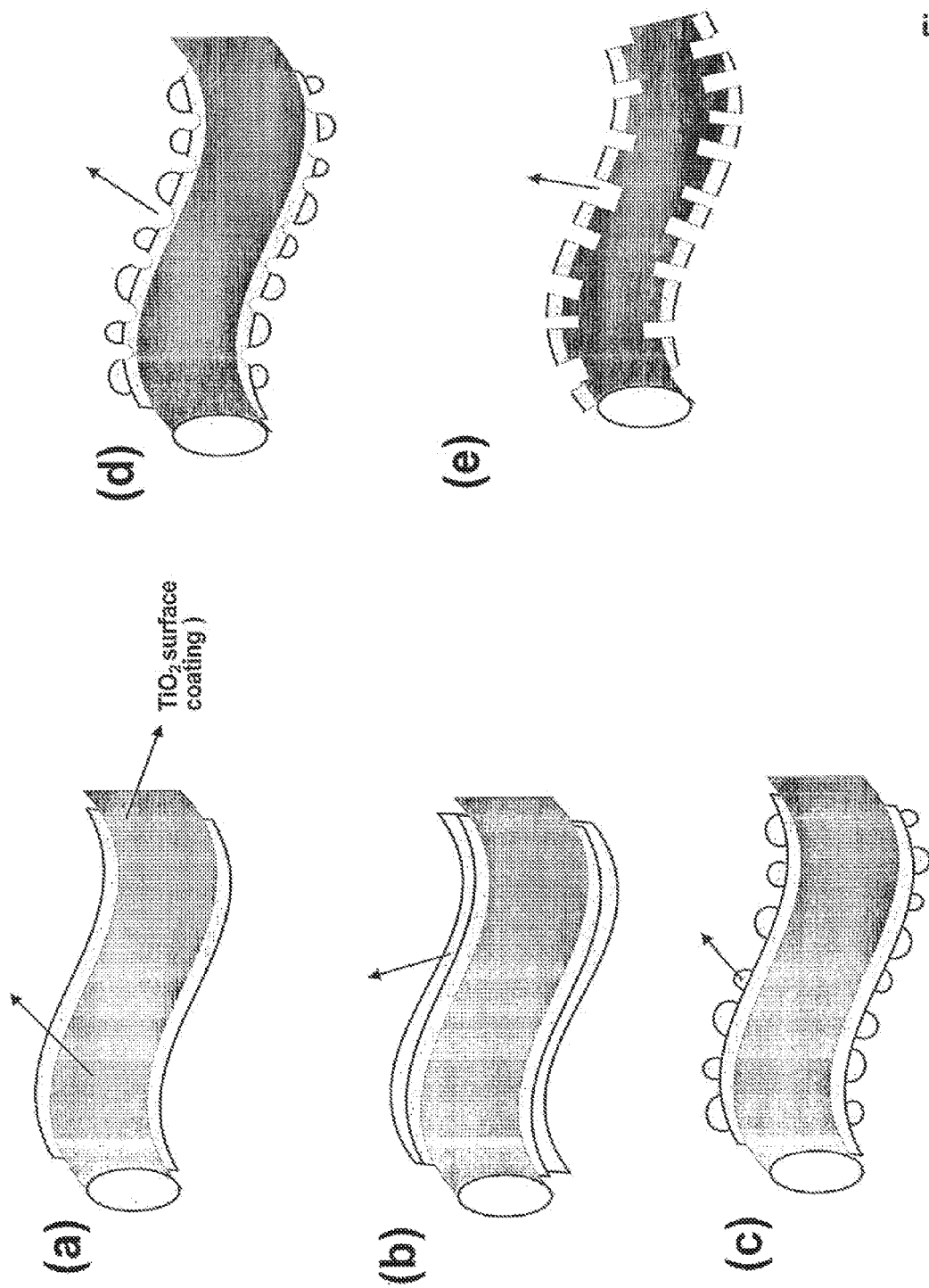

FIG. 48: FIG. 48(a)-(e) schematically illustrate exemplary structures of the invention comprising size-randomized pore formation on flat or non-flat $TiO_2$ covered surface such as a Ti plate, sheet, wire, mesh, or foam by using semi-wettable or island-forming coating as a local mask: 48(a), illustrates a starting material comprising, e.g., a cylinder or random shape substrate/implant pre-oxidized Ti (e.g., Ti wire with $TiO_2$ surface coating); 48(b) illustrates application of a semi-wettable coating which can be broken up or balled up into islands (e.g., a spray- or dip-coated polymer which balls up on drying, or a sputtered or evaporated metal film which balls up into islands on heating); 48(c) illustrates formation of balled up islands with random distribution of sizes; 48(d) illustrates the step of chemical or electrochemical etching of $TiO_2$ surface oxide except the island regions to form craters; 48(e) illustrates the step of chemical etching or anodization using the craters as the preferred reaction sites for deeper nanopores or nanotubes on the implant surface.

FIG. 49: FIG. 49(a)-(d) schematically illustrate an exemplary process, a randomized pore formation on non-flat substrates such as Ti wire, rod, mesh surface using nanoparticle-containing coating, this process being an alternative method of using a polymer or an aqueous solution containing nanoparticles of coating material (polymer, metal or salt) for formation of island masks; FIG. 49(a), illustrates a starting material comprising, e.g., a cylinder or random shape substrate/implant pre-oxidized Ti (e.g., Ti wire with $TiO_2$ surface coating); FIG. 49(b), illustrates application of a coating containing nanoparticles of polymer, metal or salt; FIG. 49(c), illustrates the step of drying or heating to have isolated islands of nanoparticles as mask islands; FIG. 49(d), illustrates the step of chemical etching or anodization through mask islands, or formation of Ti-oxide coating except the mask islands followed by chemical etching or anodization.

Figure 50:
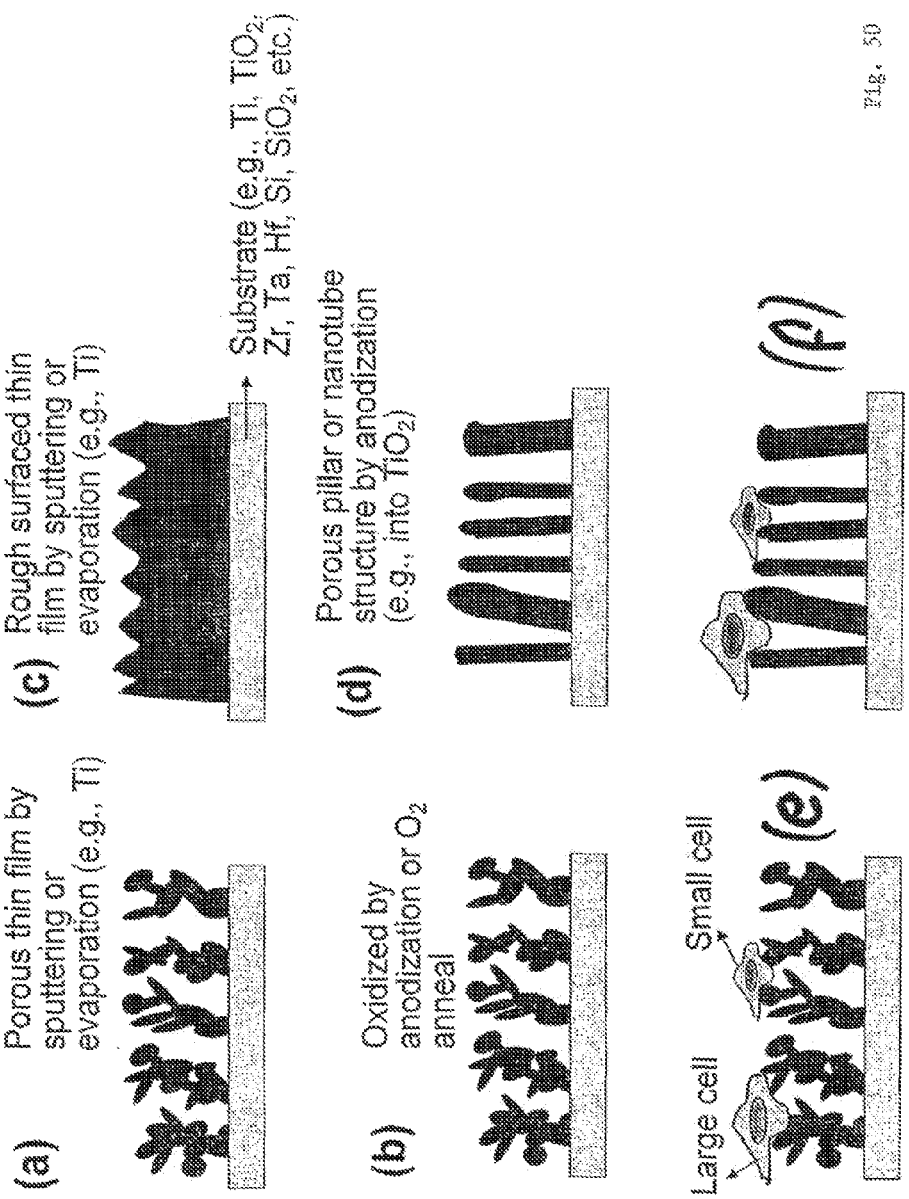

FIG. 50: FIG. 50(a)-(f) schematically illustrate exemplary structures of the invention comprising randomized pore sizes and shapes fabricated by thin film deposition. FIG. 50(a)-(b), (d), illustrate as-deposited porous structure; FIG. 50(c)-(d), (f), illustrate rough surfaced thin film followed by anodization; FIG. 50(a) illustrates an exemplary array surface comprising a porous thin film made by sputtering or evaporation (e.g., Ti); FIG. 50(b) illustrates an exemplary array surface oxidized by anodization or $O_2$ annealing; FIG. 50(c) illustrates an exemplary array surface comprising a rough-surfaced thin film made by sputtering or evaporation (e.g., Ti, $TiO_2$, Zr, Ta, Hf, Si, $SiO_2$); FIG. 50(d) illustrates an exemplary array surface comprising a porous pillar or nanotube structure by anodization (e.g., into $TiO_2$); FIG. 50(e) illustrates the exemplary (a) or (b) with large and small cells; FIG. 50(f) illustrates the exemplary (c) or (d) with large and small cells.

Figure 51:
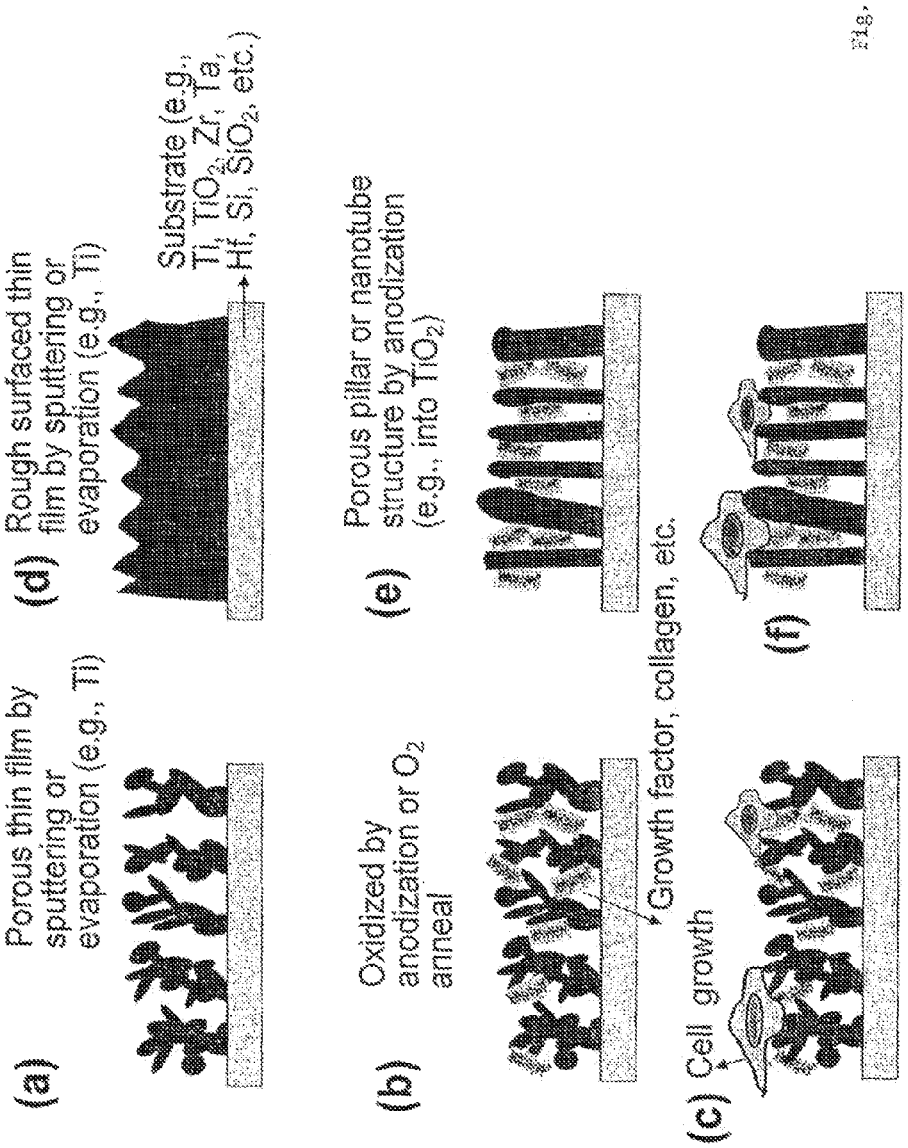

FIG. 51: FIG. 51(a)-(f) schematically illustrate exemplary structures of the invention comprising randomized pore size and shape fabricated by thin film deposition, with a biological agent inserted into the nanopores: FIG. 51(a)-(c), illustrate as-deposited porous structure; FIG. 51(d)-(f) illustrate rough surfaced thin film followed by anodization; FIG. 51(a) illustrates an exemplary array surface comprising a porous thin film made by sputtering or evaporation (e.g., Ti); FIG. 51(b) illustrates an exemplary array surface oxidized by anodization or $O_2$ annealing, with another composition, e.g., a growth factor, a collagen; FIG. 51(c) illustrates the exemplary (a) or (b) with large and small cells; FIG. 51(d) illustrates an exemplary array surface comprising a rough-surfaced thin film made by sputtering or evaporation (e.g., Ti, $TiO_2$, Zr, Ta, Hf, Si, $SiO_2$); FIG. 51(e) illustrates an exemplary array surface comprising a porous pillar or nanotube structure by anodization (e.g., into $TiO_2$), with another composition, e.g., a growth factor, a collagen; FIG. 51(f) illustrates the exemplary (d) or (e) with large and small cells.

FIG. 52: FIG. 52(a)-(c) schematically illustrate exemplary structures of the invention comprising porous $TiO_2$ structure made by evaporation, or sputtering process as illustrated in FIG. 52(a); or as sputtered porous structure; or as illustrated in FIG. 52(b) with a collagen type biological agent inserted into the nanopores; or as illustrated in FIG. 52(c) with functional nanoparticles (such as magnetic or other movable functional particles, including, e.g., drugs, nucleic acids, growth factors, hormones, etc., for local heating, local magnetic field generation, generating electrical impulses, drug delivery, etc) inserted into the nanopores.

FIG. 53: FIG. 53(a)-(d) schematically illustrate exemplary structures of the invention comprising lithographically created random-sized pores or nanotubes according to the invention (for accelerated cell/bone growth, e.g., multi-cell-type co-culture, protein harvest, drug delivery, therapeutics, etc.): FIG. 53(a) illustrates use of lithography through a randomly shaped mask (e.g., by photo-, electron-, ion-, nanoimprint-lithography, or laser speckle interference pattern) to generate random-sized pores or nanotubes; FIG. 53(b) illustrates the resultant etched random-size pore or pillar pattern (with optional coating with $TiO_2$, etc.); FIG. 53(c) illustrates biological agents inserted into the nanopores, with a cultured cell, FIG. 53(d) illustrates functional nanoparticles added into the nanopores, wherein the pores can also contains (or the nanopores can also comprise) a biological agent, e.g., a drug, nucleic acid, a growth factor, hormones, magnetic or other movable functional particles, or bio-conjugated particles, etc., for, e.g., accelerated or delayed biological reaction, for local heating, local magnetic field, electrical impulses, controlled drug delivery, therapeutics, etc.

Figure 54:
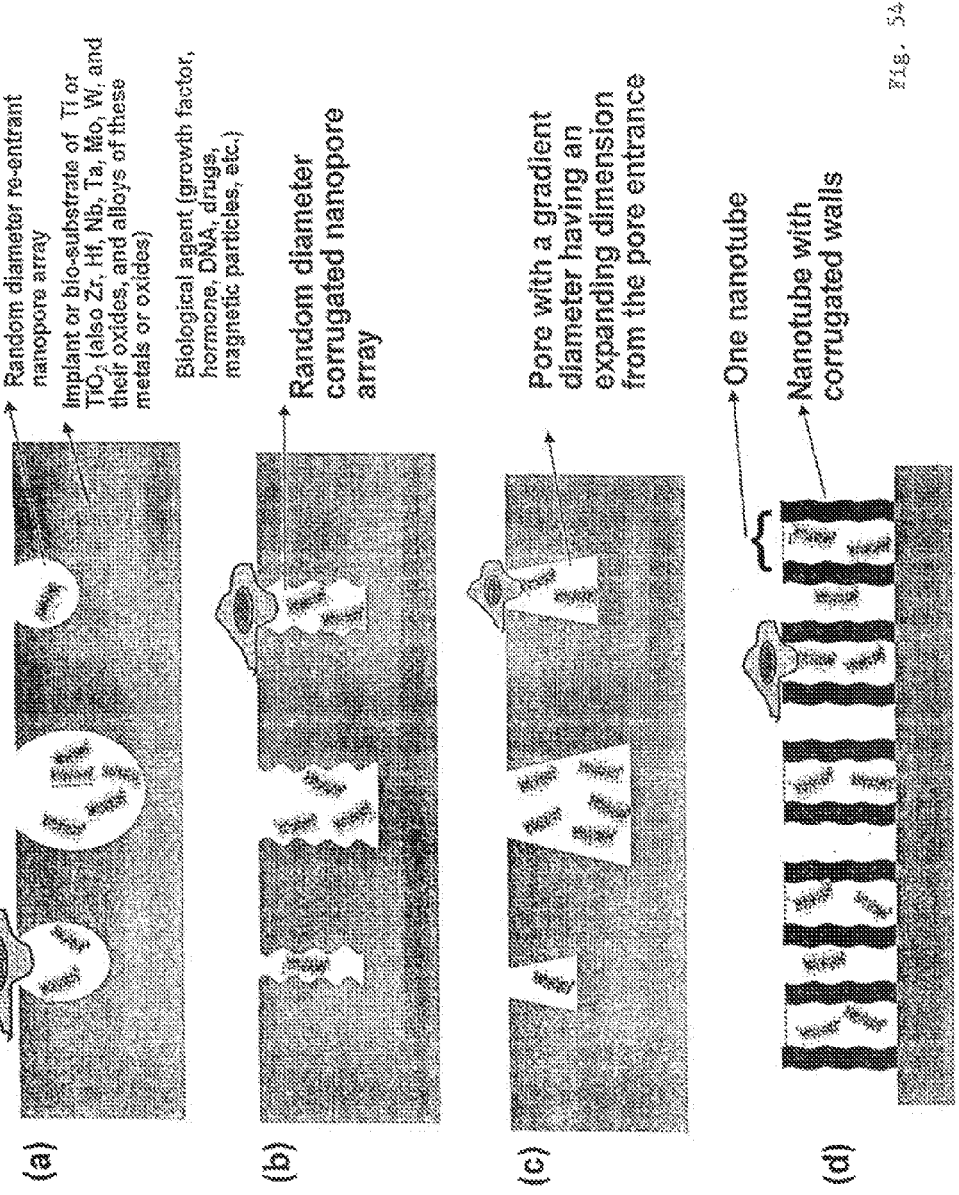

FIG. 54: FIG. 54(a)-(d) schematically illustrate alternative types of lock-in nanostructures of the invention for enhanced mechanical stability of tissues, e.g., grown bones, each nanostructure, e.g., nanopore or nanotube, also comprising a biological agent, e.g., a drug, nucleic acid, a growth factor, hormones, magnetic or other movable functional particles, or bio-conjugated particles, etc., for, e.g., accelerated or delayed biological reaction, for local heating, local magnetic field, electrical impulses, controlled drug delivery, therapeutics, etc., and a cell adherent to the pore/tubule opening: FIG. 54(a) illustrates random-diametered re-entrant oval or circular nanopores (e.g., with an exemplary implant or bio-substrate of Ti, $TiO_2$, Zr, $ZrO_2$, Zr, Hf, Nb, Ta, Mo, W and/or their oxides, and/or alloys of these metals or oxides); FIG. 54(b) rectangular cavity with corrugating walls (an exemplary implant comprising corrugated nanopore array); FIG. 54(c) re-entrant triangular cross-sectioned pores (illustrating an exemplary implant comprising a pore with a gradient diameter having an expanding dimension from the pore entrance); FIG. 54(d) nanotubes with corrugating walls (an exemplary implant comprising nanotube with corrugated walls).

Figure 55:
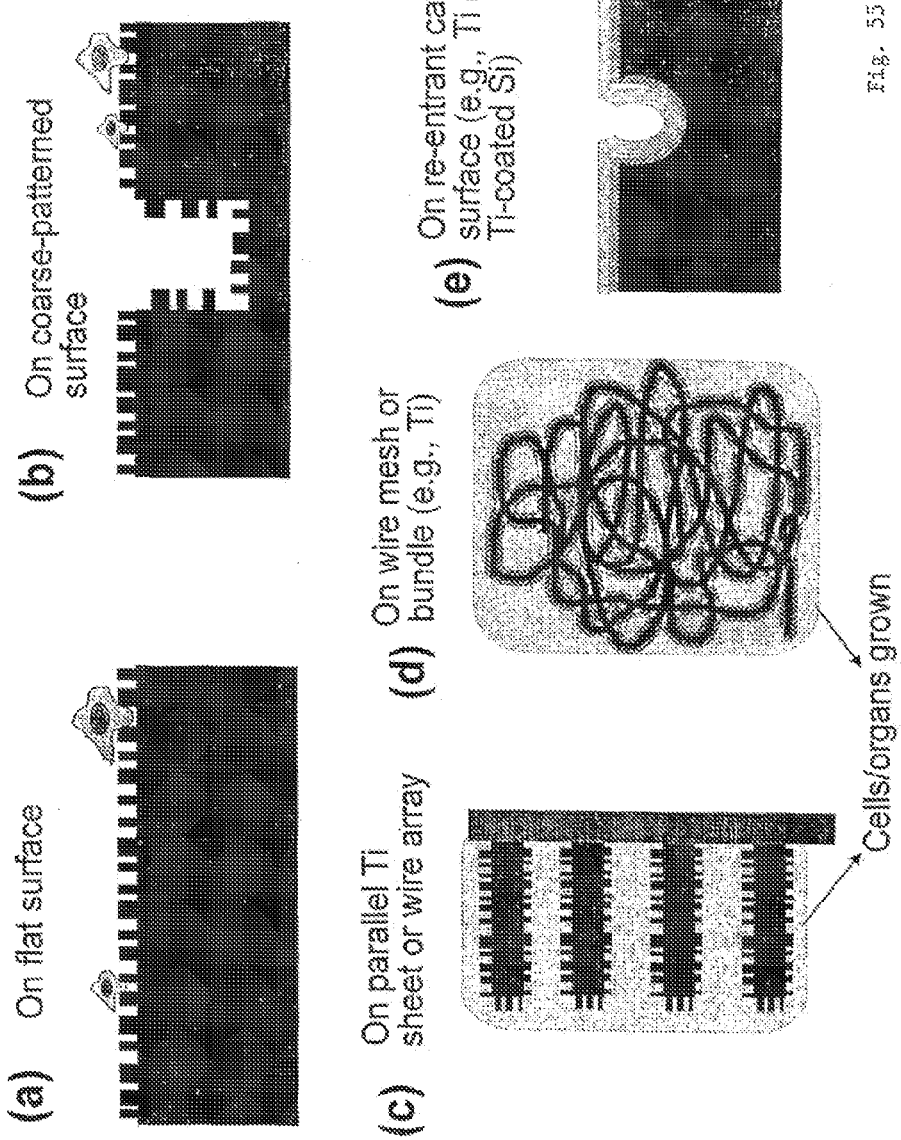

FIG. 55: FIG. 55(a)-(e) schematically illustrate the growth/maintenance of different size/shape cells grown on exemplary size-randomized nanopore or nanotube arrays of the invention comprising various shaped surfaces by guided etching using semi-wettable or island-forming coating, or porous thin film deposition: FIG. 55(a), illustrates an exemplary nanopore or nanotube array on a flat surface, with cells; FIG. 55(b), illustrates an exemplary array as a coarse-patterned surface, with cells; FIG. 55(c), illustrates an exemplary array as a parallel Ti sheet or wire array, with growth/maintenance of cells, tissues and/or organs; FIG. 55(d), illustrates an exemplary array as a wire mesh, bundle or foam (e.g., made of Ti), with growth/maintenance of cells, tissues and/or organs; FIG. 55(e), illustrates an exemplary array as a re-entrant cavity surface (e.g., Ti or Ti-coated Si).

Figure 56:
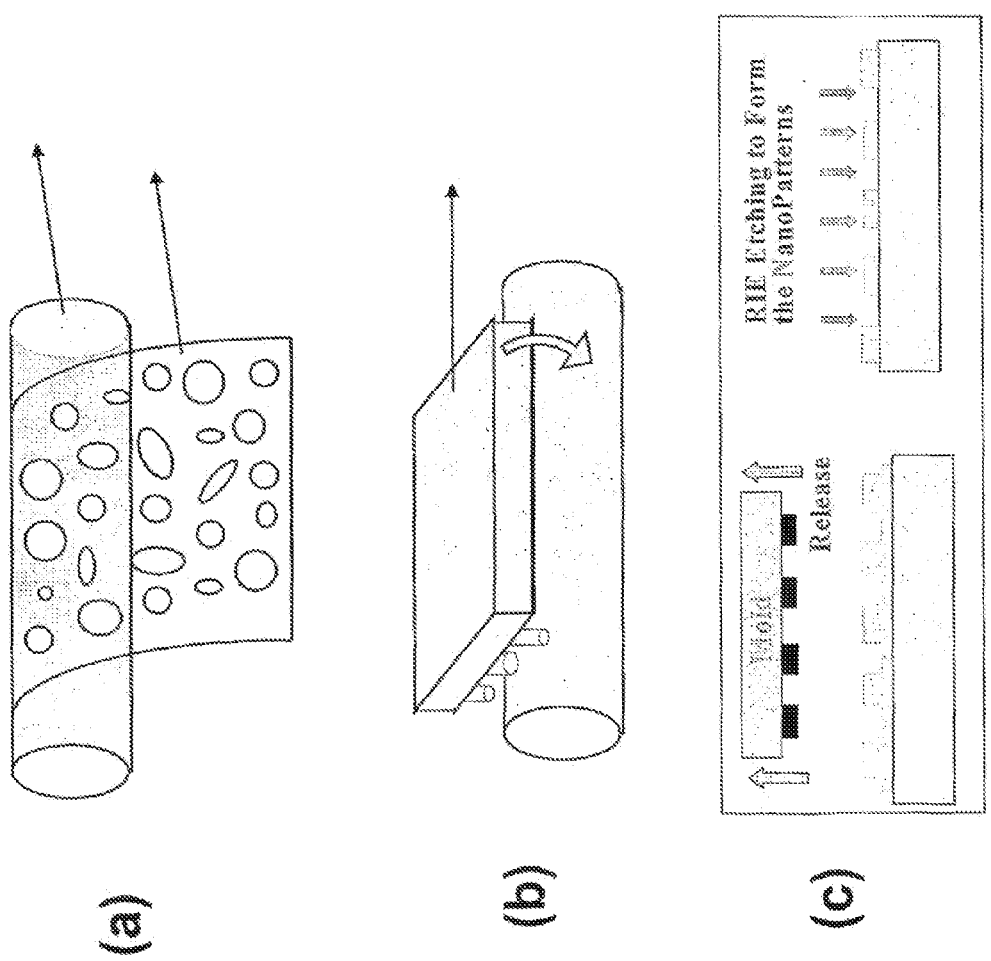

FIG. 56: FIG. 56(a)-(c) schematically illustrate exemplary processes of guided etch nano-patterning of diameter-randomized nanopores or nanotubes: FIG. 56(a), illustrates guided etch nano-patterning on non-flat surfaces using conformable or stretchable elastomeric mask sheet on a cylinder or random shape substrate/implant; FIG. 56(b), illustrates guided etch nano-patterning using elastomeric roll stamping (elastomeric nano-implant stamp for roll stamping of surface patterns for local etching and guided patterning); FIG. 56(c), illustrates guided etch nano-patterning using elastomeric flat stamping on large area surfaces (an exemplary process for patterning on a large-area, flat surface using elastomeric nano stamping; in alternative aspects, a Reactive Ion Etching (RIE) approach or direct stamping of island etch mask (or mirror image mask) are used).

FIG. 57: FIG. 57(a)-(b) schematically illustrate FIG. 57(a) cell proliferation on size-randomized nanopores or nanotubes; and FIG. 57(b) an exemplary method of harvesting the cells cultured using trypsinization and/or centrifugation.

FIG. 58 schematically illustrates an exemplary biochip device comprising size-randomized nanopores or nanotubes, e.g., for toxicity testing of drugs or chemicals, with the device comprising an array of cultured cells, e.g., liver cells grown on dimension-controlled biomaterials, wherein in one aspect the array comprises cultured liver cells optionally co-cultured with other types of cells.

It is to be understood that the drawings are for purposes of illustrating the concepts of the invention and are not to scale.

DETAILED DESCRIPTION

The invention provides nano-scaled materials that exhibit extraordinary physical, mechanical and biological properties, which cannot be achieved by micro-scaled or bulk counterparts. The Ti and Ti alloys used in the compositions of this invention are corrosion resistant, light, yet sufficiently strong for load-bearing, and are machinable. Because Ti and Ti alloys are one of the few biocompatible metals which osseointegrate, the compositions of the invention provide a template for direct chemical or physical bonding with adjacent bone surface without forming a fibrous tissue interface layer; e.g., in the orthopedic and dental implants of the invention; incorporating devices as described, e.g., in Handbook of biomaterial properties, ed. J. Black and G. Hasting, London; Chapman & Hall, 1998; B. D. Ratner et al., Biomaterials Science, San Diego, Calif.: Academic press; 1996.

The invention provides compositions allowing accelerated bone growth, which in some aspects is beneficial for fast recovery of patients with implant operations for repair of joints, broken bones, or dental implants. In addition, accelerated cell growth using structured and configured biomaterials of this invention can be useful for a variety of bio-applications. Biocompatible nanostructures of the invention can be made to serve multi-functional roles to additionally accelerate bone and cell growth, its practical usefulness can be further enhanced.

The invention provides compositions and methods for cell growth on $TiO_2$ nanotubule array structures as described herein; the compositions of the invention can provide enhanced and designed patterns of cell and bone growth obtainable by modifying the Ti or $TiO_2$ in nanopore, nano-reservoir or nanotube configurations. For example, even the same type of cells have substantially varying cell size and shape from one cell to another, and some type of cells, especially the liver cells, seem to grow better when co-cultured with other types of cells, such as endothelial or fibroblast cells which have significantly different cell sizes. The invention provides compositions comprising nanopore, nano-reservoir or nanotube configurations appropriate for the growth, differentiation and maintenance of a varied cell population, e.g., to form a functional tissue or organ, e.g., as in an artificial organ, such as an artificial liver or kidney.

In this invention, improved biomaterials with nanostructures with size-randomized (and also shape-randomized) nanopore or nanotube structure are provided, which are especially suitable for co-culture of hepatocytes with other cells. These biomaterials are made of Ti or $TiO_2$ or equivalent structures, or made of other materials and then coated with a biocompatible Ti or $TiO_2$ film.

In one aspect, the size-randomized nanopore or nanotube structures of the invention have a sufficient distribution of pore entrance diameter (or average diameter if non-circular) to allow enhanced cell adhesion and accelerated growth of, for example by at least about 10%, 20%, 25%, 50%, 60%, 75%, 100%, 125%, 150%, 175%, 200%, 250%, 300%, 400% or 500% faster.

In one aspect, the desired distribution of the nanopore sizes in the nanostructure is such that at least one third of the pores have their average diameter which is equal to or less than 10%, 20%, 25%, 50%, 60%, 70% or 75%, or equal to or less than 50% of the overall average pore diameter, while another one third of the pores have their average diameter which is at least 125%, 150%, 175%, 200%, 250%, 300%, 400% or 500% the overall average pore diameter. As in some aspects, the size-randomized nanopores or nanotubes have larger diameters, these will be more suitable for efficient insertion and storage of biological agents in the nanopores.

The biological agents that can conveniently be stored in the nanopores include growth factors, collagens, various proteins/biomolecules, nucleic acids (e.g., siRNA, DNA, RNA, vectors, genes), antibiotics, hormones, drugs such as cancer drugs or diabetes drugs, functional particles like magnetic, radioisotopes, dyes, metallic, ceramic, polymer particles. The functional particles can be utilized for hyperthermia or magnetic hyperthermia treatment of tumors, with the particles optionally conjugated with other molecules for drug delivery, accelerated cell/bone growth, therapeutic treatments, etc.

Biomaterial structures of the invention can enable accelerated growth of functional organ cells such as liver or kidney cells as well as other structural cells such as blood vessel cells, enzyme secretion vessels, periodontal, bone, teeth, or other hard tissue cells growth. The availability of such cultured cells can be useful for a variety of applications including i) organ-related therapeutic medical treatment including liver or kidney disease treatment, ii) orthopedic, dental or periodontal processes, iii) supply of cells for various research or therapeutic purposes, and iv) disease diagnostic or toxicity testing of new drugs or chemicals.

The nanotube or nanopore structures of the invention can substantially improve cell adhesion and growth kinetics; including adhesion of anchorage-dependent cells such as osteoblasts, which is a crucial prerequisite to subsequent cell functions such as synthesis of extracellular matrix proteins and formation of mineral deposits. In one aspect, nanotube or nanopore structures of the invention comprise vertically or parallel-aligned nanostructure arrays; and they can have structural advantages for reduced interfacial failure. In one aspect, a vertically or parallel-aligned nanopore or nanotube array is fabricated to be thin, e.g., less than 3000 nm, 2000 nm, 1500 nm, 1000 nm, 500 nm, 400 nm, 300 nm, 200 nm, or less than 100 nm. In one aspect, nanopore or nanotube arrays of the invention can be made of the same material as the base substrate material to ensure for strong bonding and mechanical stability of the nanotube array, for example, $TiO_2$-covered nanopores or nanotubes have a common element Ti shared with the implant substrate material titanium, thus providing a strong chemical bonding.

Referring to the drawings, FIG. 46 schematically illustrates exemplary configurations of a size-randomized nanopore structure of biocompatible materials such as Ti or $TiO_2$, with the size and shape of the entrance of the pores having a distribution of dimensions as shown in FIG. 46(*c*)-(*e*), as compared to the uniform sized nanopores FIGS. 46(*a*) and (*b*). Such a distribution in size and shape of the nanopores or nanotubes can help achieving enhanced adhesion and accelerated growth of various size and shape cells simultaneously, as illustrated in FIG. 46(*e*). Such size-randomized nanopore or nanotube biomaterial (FIG. 46(*c*)-(*e*)) can be fabricated, according to the invention, by using various mask-guided chemical etching fabrication or thin film deposition approaches.

In one aspect, the pre-patterned, e.g., random patterned, masks (to generate pre-patterned, e.g., random patterned, pores or nanoreservoirs) are prepared by lithographic patterning of craters, e.g., by photolithography (see, e.g., U.S. Pat. Nos. 6,030,266; 5,759,744; 6,946,390), UV or deep UV and extreme UV lithography (see, e.g., U.S. Pat. No. 7,014,961), laser interference lithography (see, e.g., U.S. Pat. No. 5,726,524), e-beam lithography (see, e.g., U.S. Pat. No. 6,956,333), imprint lithography (see, e.g., U.S. Pat. Nos. 7,027,156; 6,842,229), particle multibeam lithography (see, e.g., U.S. Pat. No. 6,989,546) or ion beam lithography (see, e.g., U.S. Pat. Nos. 6,949,756; 6,414,307; 6,303,932 6,924,493), nano imprint lithography, and various other known techniques, or by coated-layer decomposition approach as will be described later in this specification. The random patterned masks also can be prepared by techniques such as sol-gel method (see, e.g., U.S. Pat. No. 7,014,961); photolithographic patterning of a photoresist layer by pattern-wise exposure to short-wavelength ultraviolet light through a pattern-bearing photomas, as described in U.S. Pat. No. 6,593,034; electrophoretic deposition and anodization. See, e.g., Lakshmi, et al. (1997) Chemistry of Materials, 9:2544-2550; Miao, et al. (2002) Nano Letters 2:717-720; Gong, et al. (2001) J. Materials Res. 16:3331-3334; Macak (2005) Chem. Int. Ed., 44:7463-7465.

Once the pre-patterned (including "random patterned") craters are formed with a desirable size, location and distribution, the implant or bio-substrate can be subjected to the chemical, electrochemical or ion etching to form desired size-randomized nanotube, nanopore or nano-reservoir structures, e.g., with aligned nanopores, nano-reservoirs or nanotubes.

Titanium nanotubes, nano-reservoirs or nanopores of the invention also can be formed by electrolytic anodization, for example using 5% hydrofluoric acid and applying approximately 10 to 20 volts of potential, and allowing several minutes to a few hours depending on the temperature and other electrochemical process parameters. It is known that the resultant $TiO_2$ nanotube diameter is dependent on the anodization voltage. The dimension of approximately 100 to 150 nm is often not large enough to incorporate biological agents and biomolecules, and is also not large enough for a substantial portion of cells (typically many micrometers in size) to go into the pore and form a locked-in structure, although a portion of the filopodia branches can get into the pore and improve cell adhesion and cell growth kinetics; thus, in one aspect, the structures of the invention include pores or tubes larger than 100 to 150 nm. From this point of view, in one aspect, the size-randomized nanopore or nanotube structures of the invention offer an advantage in that a substantial portion of the pores can be made larger than approximately 150 nm, as many of the processes of the invention, including lithographically defined masks, semi-wettable balled-up island masks or nanoparticle masks, mask-island-guided or mask-hole-guided etching or anodization, can generate compositions having all or a portion of their nanostructures (e.g., nanopores, nano-reservoirs or nanotubes) larger than 150 nm.

In alternative aspects, larger-diameter-containing nano-reservoir-, nanotube- or nanopore-comprising structures have diameters greater than approximately 150 nm, 175 nm, 200 nm, 250 nm or 300 nm or more, in at least 10%, 15%, 20%, 25%, 30%, 35%, 40%, 45% or 50% more of the total surface area fraction, or up to at least 90% or more of the total surface area fraction.

Exemplary material that can be processed into desired size-randomized or size-designed nano-reservoir-, nanotube- or nanopore-comprising structures include alloys containing Ti with at least 10%, 15%, 20%, 25%, 30%, 35%, 40%, 45% or 50% more weight %. $TiO_2$ can also be utilized. Other related materials such as Zr, Hf, Nb, Ta, Mo, W, and their oxides, or alloys of these metals and oxides by at least about 10%, 15%, 20%, 25%, 30%, 35%, 40%, 45% or 50% or more weight % can be used. Other materials such as Si, Si oxide, carbon, diamond, noble metals (such as Au, Ag, Pt and their alloys), polymer or plastic materials, or composite metals, ceramics or polymers can also be utilized to produce and use similar desired surface configurations, e.g., for the bio implant and cell growth applications of this invention; where in one aspect, these materials are used as long as a coating of Ti and Ti oxide, Zr, Hf, Nb, Ta, Mo, W and their oxides, as well as their alloys, with a thickness of at least 1, 2, 3, 4, 5, 6, 7, 8, 9 or 10 or more nm and the coating coverage of at least 10%, 15%, 20%, 25%, 30%, 35%, 40%, 45%, 50%, 60%, 70% or 80% more of the total surfaces is provided.

Shown in FIG. 47 is an exemplary method of fabricating size-randomized nanopores or nanotubes on non-flat surface such as Ti wire, mesh, or foam, or on a flat surface such as on a Ti plate or sheet, by using semi-wettable or island-forming coating as a local mask. The coating illustrated in FIG. 47(b) can be either a polymer-based material, metal or alloy based material, or a salt based material. A thin coating of polymer can be deposited by a number of well known techniques such as dip coating, spray coating, brush coating, evaporation, chemical vapor deposition, or spin coating (if the object has flat surfaces). The polymer coated object can be either dried to remove the solvent or water or heated to alter the wetting characteristics in such a way that the continuous coating is broken up into islands, as illustrated in FIG. 47(c). The metal or alloy based material can be deposited by sputtering, electroplating, evaporation, chemical vapor deposition, or plasma spray. For a non-flat object, rotation of the object during physical vapor deposition id desired to make sure that most of the surfaces are covered by the deposited material. The metal coated object is then heated to a relatively high temperature of e.g., 300-900° C. to make the metal ball up into islands to reduce the overall free energy. The metal or alloy coating material should be selected in such a way that the degree of alloying with the base metal is minimal so that extensive wetting does not occur. The salt based material can be either a aqueous solution or solvent solution, optionally mixed with viscosity enhancer such as polyvinyl alcohol, can be applied by dip coating or spray coating, brush painting, and heated to form island masks. The salt based coating material can also be applied by evaporation or sputtering, followed by heating to decompose the salt and form mask islands.

The desired thickness of the coating applied depends on the desired size of the islands (masks) since a thinner coating results in smaller diameter islands. The degree of wettability of the coating material on the object also determines the resultant size of the islands. The desired thickness of the coating is typically in the range of anywhere between about 2-2000 nm, or about 5-200 nm.

FIG. 48 schematically illustrates an alternative exemplary method of size-randomized nanopore or nanotube formation using non-flat or flat, $TiO_2$ covered surface such as a Ti wire, mesh, foam, plate, or sheet, by using semi-wettable or island-forming coating as a local mask. Here a pre-$TiO_2$-covered (oxidized or anodized) Ti material, FIG. 48(a), is utilized as the base material, and processed similarly as in the case of FIG. 47. However, this exemplary chemical or electrochemical etching is carried out through the $TiO_2$ except the island-covered regions to form craters, which is then followed by chemical etching or anodization to form size-randomized nanopores or nanotubes as illustrated in FIG. 48(b)-(d).

Alternatively, a polymer-containing or an aqueous solution containing nano particles of coating material (polymer, metal or salt) can be applied on the object by dip coating or spray coating, and then heated to decompose and form islands of masks as illustrated in FIG. 49(a)-(c). Either chemical etching or anodization through mask islands, or formation of Ti-oxide coating except the mask islands followed by chemical etching or anodization can be utilized to obtain the desired nanopore or nanotube array structure as illustrated in FIG. 49(d).

Instead of Ti and Ti-alloy based wire, mesh, foam, plate or sheet, the use of other related materials such as Zr, Hf, Nb, Ta, Mo, W, and their oxides, or alloys of these metals and oxides by at least 10%, 15%, 20%, 25%, 30%, 35%, 40%, 45%, 50%, 60%, 70% or 80% more weight % is not prohibited for the size-randomized nanopore or nanotube structures in FIGS. 46 to 49. Other materials such as Si, Si oxide, carbon, diamond, noble metals (such as Au, Ag, Pt and their alloys), polymer or plastic materials, or composite metals, ceramics or polymers can also be utilized to produce and use similar desired surface configurations for bio implant and cell growth applications; where in one aspect, these material are used as long as a coating of Ti and Ti oxide, Zr, Hf, Nb, Ta, Mo, W and their oxides, as well as their alloys, with a thickness of at least 1, 2, 3, 4, 5, 6, 7, 8, 9 or 10 or more nm and the coating coverage of at least 10%, 15%, 20%, 25%, 30%, 35%, 40%, 45%, 50%, 60%, 70% or 80% more of the total surfaces is provided.

FIG. 50 represents a randomized pore size and shape fabricated by thin film deposition. A proper selection of sputtering pressure and temperature can introduce porous or rough microstructure in deposited thin films. The self shadowing effect of the obliquely deposited thin film material, e.g., by evaporation can be used to form highly porous or rough films. The sputtering deposition can be carried out by DC, pulse DC, RF sputtering, or ion beam deposition methods. The evaporation can be done by thermal or electron beam evaporation process. Depending on the deposition conditions, a smooth continuous film, rough topology film, or highly porous structure can be obtained, e.g., as described by Thornton (1986) J. Vac. Sci. Technol. A4(6):3059; Meng et al "Investigations of titanium oxide films deposited by dc active magnetron sputtering in different sputtering pressures", Thin Solid Films 226, 22 (1993), by K. Robbie et al "Fabrication of thin films with highly porous microstructure", J. Vacuum Science & Technology, 13(3), 1032 (1995); Rodriguez et al, "Reactively sputter deposited titanium oxide coatings with parallel Penniform microstructure", Adv. Mater. 12(5), 341 (2000).

Exemplary highly porous structures of the invention obtained by thin film deposition are schematically illustrated in FIG. 50. A porous Ti thin film can be deposited and oxidized or a porous $TiO_2$ film can directly be deposited as shown in FIG. 50(a)-(c) as a size-randomized nanoporous biomaterial for enhanced cell adhesion and bone growth. Alternatively, a rough or faceted surface topology can be provided by adjusting thin film deposition process parameters, which is then subjected to anodization to form a vertically porous size-randomized nanopore or nanotube structure as illustrated in FIG. 50(d)-(f). In bio applications, these structures can be modified by inserting/storing biological agents in the size-randomized nanopores as shown in FIG. 51.

The biological agents that can conveniently be stored in these nanopores include growth factors, collagens, various proteins/biomolecules, nucleic acids (e.g., genes, DNAs, RNA, siRNAs, vectors) antibiotics, hormones, drugs such as cancer drugs or diabetes drugs, functional particles like magnetic, metallic, ceramic, polymer particles, radioisotopes, and the like. In one aspect, the functional particles are utilized for hyperthermia or magnetic hyperthermia treatment of tumors, with the particles optionally conjugated with other molecules for drug delivery, accelerated cell/bone growth, therapeutic treatments, etc.

In FIG. 52, the size-randomized porous $TiO_2$ structure is directly formed by reactive sputtering process or by evaporation in the presence of oxidizing atmosphere such as by supplying some partial pressure of oxygen during film deposition. These size-randomized porous $TiO_2$ structures can be altered into improved bio materials by inserting/storing biological agents similarly as in the case of FIG. 51 for enhanced cell adhesion and bone growth.

Referring to FIG. 53, the figure schematically illustrates the lithographically created random-sized pores or nanotubes according to the invention. (a) and (b) As-fabricated, (c) biological agent inserted into the nanopores, (d) functional nanoparticles added into the nanopores.

The size-randomized and pattern-randomized masks can be prepared by lithographic patterning of photoresist or e-beam resist layer such as PMMA (polymethylmecarthrylate) or any other positive or negative patternable polymer, as illustrated in FIG. 46(*c*)-(*e*) and FIGS. 53(*a*) and (*b*). Lithography techniques such as photolithography (including UV, deep UV and extreme UV lithography, laser speckle interference lithography, etc.), e-beam or ion beam lithography, nano imprint lithography, and various other known techniques can also be utilized. The patterned geometry can be circular, oval or any irregular shape.

Cells of various sizes and shapes, especially in the case of co-culturing for liver cell growth, are cultured with enhanced cell adhesion, faster proliferation kinetics, and in healthier conditions due to the size-randomized and shape-randomized nanopore or nanotube structure on the surface of the bio implants or bio substrates of the invention. In one aspect, size-randomized biomaterials also allow relatively easier insertion/storage of biological agents such as growth factors, collagens, various proteins/biomolecules, genes, DNAs, antibiotics, hormones, or drugs, as well as functional particles such as magnetic nanoparticles, photoluminescent particles, and other metallic, ceramic, polymer particles. This is due to the presence of some larger diameter nanopores or nanotubes in the distribution of the random pore sizes in the biomaterials. These characteristics are schematically illustrated in FIG. 53(*b*)-(*d*).

In one aspect, size-randomized nanopore or nanotube structures incorporate re-entrant, gradient or corrugated pore wall configurations, as illustrated schematically in FIG. 31 and FIG. 54. Size-randomized nanopore or nanotube structures with at least 50% of the pores having a re-entrant or lock-in nanostructure can also be utilized, as illustrated in the figure. The re-entrant characteristics of the nanopore or nanotube entrance is arbitrarily defined here as having an average entrance diameter (or average pore size if they are not circular) by at least about 10%, 15%, 20%, 25%, 30%, 35%, 40%, 45%, 50%, 60%, 70% or 80% smaller than the rest of the nanopore or nanotube dimension so that the cells or bones grown are mechanically more firmly attached. FIG. 54 schematically illustrates size-randomized nanopores or nanotubes with re-entrant, gradient or corrugated pore wall configuration, together with biological agents stored in the nanopores.

In one aspect, size-randomized nanopore or nanotube structures of the invention have dual structured biomaterials comprising a micro or macro pores in combination with surfaces covered with randomized and finer-scale $TiO_2$ nanotubes, as illustrated in FIG. 35. In one aspect, the dual-sized structure allows micro- or macro-scale growth of bones essentially completely fill the large pores to guard against the slippage or mechanical failure of grown bones against tensile or shear stresses, while enabling accelerated osteoblast cell growth on the nanotube-covered surface of the implants. In one aspect, dual structures comprise any combination of nano-, micro- or macro-pores, or, dual structures comprise a re-entrant configuration having an average diameter (or equivalent diameter if the pores are not circular) in the range of between about 0.5-1,000 μm, or about 1-100 μm; and, in one aspect, dual structures are constructed as a nanostructure comprising size-randomized nanopores or nanotubes having an average pore diameter in the range of between about 30-600 nm. In one aspect, the relative ratio of the micro/macro pores vs nanopores in the dual structure is such that the micro/macro pores occupy at least 10%, 11%, 12%, 13%, 14%, 15%, 20%, 25%, 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75% or more area fraction of the implant or bio-substrate surface; and in one aspect, between about at least 20% but less than 50% to maximize the accelerated cell culture or bone growth via the nanopore portion of the surface.

FIG. 40 illustrates a size-randomized nanopore or nanotube array on various surfaces of the invention by guided etching using various exemplary techniques, e.g., as described in relation to FIGS. 46 to 54, FIG. 31 and FIG. 35. The size-randomized nanopore or nanotube array can be formed on various exemplary surfaces i.e., on a flat surface (FIG. 40(*a*)), on a coarse-patterned surface (FIG. 40(*b*)), on parallel Ti sheet or wire array (FIG. 40(*c*)) which can be useful for three-dimensional cell or organ structure, on wire mesh, wire bundle or scaffold type highly porous metal foam (e.g., made of Ti or its alloy) (FIG. 40(*d*)), and on re-entrant cavity surface (e.g., pre-shaped Ti or Ti-coated Si) (FIG. 40(*e*)).

The structures illustrated in FIGS. 40(*c*) and (*d*) are particularly desirable for accelerated co-culturing of healthy three dimensional cells and organs such as desired for liver cell growth. These 3-D cultured cells can be prepared using parallel Ti sheet, wire array or mesh and foam arrays or the invention with size-randomized nanopore or nanotube array surface structures. These structures can be useful for a variety of applications, including in vivo implanting of cells or organs. A patient can be supplied with in vitro cultured and in vivo implanted, three-dimensional functional cells such as liver, kidney, or blood vessel cells or organs. Three-dimensionally cultured bones or tissues can also be utilized as dental, periodontal or orthopedic body implants.

To obtain relatively large surface area for cell growth, the desired thickness of the titanium metal ribbon, or the desired diameter of the metal wire or foam in FIGS. 40(*c*) and (*d*) is in the range of about 10 μm-50,000 μm, or about 25-2,500 μm. The desired volume fraction of the metal for the given targeted cell volume at the end of the planned cell culture period is at least about 10%, 11%, 12%, 13%, 14%, 15%, 20%, 25%, 30% or more in volume, or at least about 30%, 40% or 50% in volume.

In one aspect, each of the ribbon surface is made to contain an aligned nanopore or nanotube array with a preferred diameter being in the range of 10-1000 nm, or about 30-300 nm, or about 60-200 nm in diameter; and in one aspect, a desired height being in the range of about 40-2000 nm, or about 100-400 nm; and in one aspect, a desired angle is a vertical with an allowance of about a 10, 20, 25, 30 or 35 degree variation off the perpendicular axis.

In one aspect, the shape of these nanostructure-surface ribbons is desirably straight so that the metal arrays can be optionally pulled out after a desired volume of the cells are cultured. In one aspect, the cultured growth will continue after the metal wire or ribbon array template structure is pulled out, and any minor surface damage or the thin empty gap created by the vacated template will be repaired/filled by growing cells. Such a three-dimensionally cultured cell volume in an accelerated manner can be useful for a variety of applications including creation of partial or full artificial organs of e.g., liver, kidney, bone, periodontal tissue, blood vessel cells, skin cells, stem cells, and other human or animal organ cells etc.

In one aspect, the 3-D cultured cells are in any orientation, i.e., horizontal, vertical or upside down depending on specific needs especially in the in vivo culture environment, for example, in the case of organ implants in human, animal, or xenotransplantation of human organs which are temporarily cultured in animals prior to human implantation. FIG. 55 schematically illustrates the enhanced growth of various sized cells and three-dimensional organs on these size-randomized biomaterials.

In one aspect, various biological agents or functional nanoparticles are additionally be stored in the surface nanopores, nanoreservoirs or nanotubes on these various shaped biosubstrates or bioimplants shown, e.g., in FIG. 40 and FIG. 55. The functional nanoparticles include magnetic particles, novel metal or SPR (surface plasmon resonance) based photoluminescent particles, quantum dots, fluorescence particles, bio-conjugated particles, which are added for the purpose of accelerated cell/bone growth, protein harvest (as a result of accelerated cell growth, proliferation, and secretion), delivery of drugs, genes, chemicals, therapeutics, etc.

FIG. 56 illustrates exemplary processes of guided etch nano patterning of size-randomized nanopores or nanotubes on Ti and related bioimplant or bio-substrates. Random size patterning techniques on non-flat surfaces using conformable or stretchable elastomeric mask sheet (FIG. 56(a)), using elastomeric roll stamping (FIG. 56(b)), and elastomeric flat stamping on large area surfaces (FIG. 56(c)) are described. In one aspect, the invention provide for use of nano imprinting to pre-pattern craters on Ti or $TiO_2$ surface for guided synthesis of size-randomized or shape-randomized $TiO_2$ nanotubes and nanopores. Such nano imprint lithography technique is convenient for mass production of a large number of implants or bio substrates as simple stamping operation can accomplish the pre-patterning of craters without resorting to complicated and often costly photolithography or e-beam lithography patterning of each part. In one aspect, an advantage is the ability to use elastomeric stamp with compliance, which allows reliable stamping on large-area, nominally-flat surfaces of Ti or other biocompatible substrates and implants in which the flatness is not always guaranteed to ensure reliable stamping over a large sample area. As bio implant parts are more often than not in a non-flat surface geometry, the invention provides a convenient and effective means of fabricating the pre-patterned craters for guided introduction of size-randomized nanopores or nanotubes on the surface of random shaped Ti implants. FIG. 56(a) illustrates exemplary processes of guided etch nano patterning of size-randomized patterns on non-flat surfaces using a conformable or stretchable elastomeric mask sheet, while FIG. 56(b) illustrates an exemplary use of elastomeric roll stamping on round rod configured implants. FIG. 56(c) illustrates the exemplary nanoimplant process of size-randomized patterns on flat surfaces of implants or bio-substrates.

FIG. 11 schematically illustrates various exemplary in vivo or ex vivo applications of the exemplary size-randomized pored biomaterials capable of accelerated cell/bone growth or functional drug delivery and therapeutics. Various exemplary nanopore or nanotube structures of the invention, e.g., as described in relation to FIGS. 46 to 54, FIG. 31, FIG. 35, FIG. 40, can be utilized for these biomedical device applications. Examples shown include orthopaedic and dental implants, cell or organ implants, drug delivery devices such as controlled release of insulin by magnetic actuation, artificial liver devices, drug-protected stents (e.g., to prevent/minimize restenosis) or other tubules inserted into blood vessels and in various other body parts, and therapeutic devices such as magnetic field induced local heating for cancer treatment. Cell growth inhibiting drugs can also be inserted in the nanopores or nanotubes of implants (e.g., drug delivery modules) to prevent/minimize scar tissue formation.

Illustrated in FIG. 15 is an exemplary magnetically actuated, on-off controllable or programmable, remote drug release device comprising the exemplary biomaterials. Remote magnetic field such as approximately 100 KHz AC magnetic field can be utilized to activate the drug release by preferential heating of the magnetic nanoparticles stored in the nanopores of the exemplary implants, thus allowing temperature-gradient-induced drug movement from the nanopores into the human body. Suitable magnetic nanoparticles for such use include biocompatible iron-oxide particles of magnetite ($Fe_3O_4$) or maghemite ($\gamma$-$Fe_2O_3$) in the particle size regime of 5-50 nm in average diameter.

In one aspect, a mechanical agitation and induced movement of the magnetic particles themselves in the pores containing the stored drugs can be utilized as an alternative mechanism of drug release. In this case, a rather lower frequency AC magnetic field actuation with a gradient magnetic field is preferred in order to allow movement of magnetic particles against the viscosity of the fluid in the nanopores. Exemplary frequency ranges are approximately 1 to 10,000 Hz, or about 10 to 1,000, or about 10 to 100 Hz.

In these aspects, the drugs are released any time of the day only when desired, and can be turned off completely when it is no longer needed, so the side effects of drugs are minimized. A similar magnetic particle and external field combination can also be utilized for cancer treatment, for example, through an implant devices comprising the exemplary nanoporous structure with size-randomized nanopores or nanotubes placed in the vicinity of cancerous regions, for example, in the liver containing inoperable distribution of recurring/growing cancer cells. A repeated hyperthermia treatments, e.g., over many months, by on-off type continual activation of external magnetic field can gradually kill the cancer cells near the cancerous regions.

FIG. 57 illustrates an exemplary method of harvesting cells cultured in an accelerated way using the exemplary biomaterials containing size-randomized nanopores or nanotubes. The exemplary nanopore or nanotube structures comprising $TiO_2$ or related materials accelerate growth of certain types of cells. The increased number of cells generated by such a device can be useful for accelerated supply of cells, especially rare cells such as stem cells for various R&D or therapeutic uses. As illustrated in FIG. 57(a), the cells are cultured in a biocompatible environment with needed nutrient media. The cells so proliferated on the exemplary nanopore or nanotube arrays are then harvested and supplied for other uses. In addition to the cells themselves, it is sometimes desirable to collect secretions from the cells for various useful R&D or therapeutic applications, for example, increased amount of proteins generated as a byproduct of cell proliferation and functioning.

Cultured cells need to be taken off the culture substrates for other uses. One exemplary method of harvesting the grown cells off the biomaterial substrate is to use a process known as "trypsinization". Once cells are grown completely on whole surface of cell culture flask, the media fluid is removed by suction. After rinsing of the cells twice with PBS (phosphate buffer solution), trypsin is added to detach the cell from the surface. In general, approximately 2-3 ml of trypsin is used for detaching cells grown on 10 cm² cell culture dish. After a few minutes, most of the cells are detached from the surface, as illustrated in FIG. 57(b). After adding approximately 10 ml of new medium, this fluid containing the detached stem cells is poured into a centrifuge tube. After centrifugation at appropriate rotation speed and time, all of the cells are separated. The medium is removed by suction, and approximately 1 ml of new media is added for storage of the harvested cells or for additional culture. To estimate the number of proliferated cells, trypan blue assay are employed in conjunction with hematocytometry. The cells can also be in situ proliferated on the implant surfaces as the $TiO_2$ as well as Ti substrate are biocompatible.

In one aspect, size-randomized Ti-oxide nanopore or nanotube structure is also useful for carrying out fast diagnosis and detection of certain types of cells such as diseased cells, or cells exposed to allergens, irritants, toxins, poisons or infectious agents, e.g., bacteria. An X-Y matrix subdivided array of size-randomized nanopore or nanotube array structure can be produced as illustrated in FIG. 44. Any size-randomized nanopore or nanotube structures of the invention, e.g., as described in relation to FIGS. 46 to 54, FIG. 31, FIG. 35, FIG. 40, can be utilized for accelerated cell detection/diagnosis. For diagnosis of diseases (e.g., epidemic diseases) or, detecting exposure to biological or chemical warfare agents (e.g., bacteria or viruses), the invention provides rapid detection devices, even when the available quantity of the cells is relatively small. Each of the exemplary detection elements in FIG. 44 contains a multiplicity of the size-randomized nanopores or nanotubes on which various types of cells to be analyzed are placed and allowed to rapidly proliferate to a sufficient number for easy detection.

For analysis of cell types, various exemplary techniques, illustrated in FIG. 18 can be used, including 18(a) optical detection of morphology and size (using a microscope, fluorescent microscope, or CCD camera sensing of fluorescent or quantum dot tagged cells), 18(b) chemical or biological detection (e.g., based on signature reactions), 18(c) magnetic sensor detection (e.g., by using magnetically targeted antibody and its conjugation with certain types of antigens).

An exemplary application of the invention's bio-chip apparatus, e.g., as illustrated in FIG. 44, utilizes a base structure to culture liver cells for testing of new drugs, as illustrated in FIG. 58, which illustrates an exemplary bio-chip device for toxicity testing of drugs or chemicals, with the device comprising an array of cultured liver cells grown rapidly and healthy manner on the biomaterials containing size-randomized nanopores or nanotubes.

Similarly as in the cell detection/diagnosis applications, various exemplary nanopore or nanotube structures of the invention, e.g., as described in relation to FIGS. 46 to 54, FIG. 31, FIG. 35, FIG. 40, can be utilized for the liver cell culture and toxicity test applications. A variation of the embodiments of FIG. 44 and FIG. 58 include having a parallel wire, rod or plate shape base structure in a vertically (or near vertically) arranged configuration (with each rod or plate base containing parallel, yet laterally spaced apart nanopore or nanotube array) in order to make the 3-D culture more effective for further increased speed of cell proliferation.

As these exemplary three-dimensionally structured, nanopore or nanotube arrays enable a rapid and healthy culture of liver cells in a desirable three-dimensional configuration, the apparatus can be utilized for the important task of testing drug toxicity or chemical toxicity. An exemplary bio-chip comprises an array of healthy, three-dimensionally cultured liver cells, e.g., 10×10, 100×100 or 1000×1000 cells as sensing elements, can thus allow simultaneous evaluation of many drugs for much accelerated screening and development of biologically acceptable drugs. Likewise, many chemicals, polymers, injection fluids, and composites that may be useful for in vivo applications can be rapidly tested for toxicity using the exemplary device of FIG. 58. The accelerated, healthy liver cell growth device of FIG. 58 can also be utilized as the basis of artificial liver devices for patients waiting for transplant or as a temporary aid to liver function after transplant. The invention provides other functional organs applications, such as artificial kidneys.

It is understood that the above-described embodiments are illustrative of only a few of the many possible specific embodiments which can represent applications of the invention. Numerous and varied other arrangements can be made by those skilled in the art without departing from the spirit and scope of the invention. For example, the materials involved do not have to be Ti oxide nanotubes on Ti-based metals, as the nanotubes and the substrate that the nanotubes are adhered to can be other biocompatible materials or non-biocompatible materials coated with biocompatible and bioactive surface layer such as Ti, or coated with biocompatible but bio-inert surface layer such as novel metal or polymer layer. Also, a thin coating of biomolecules or chemical molecules can optionally be applied on the surface of $TiO_2$ nanopores or nanotubes to further enhance the attachment of cells.

Therefore, it should be understood that the invention can be practiced with modification and alteration within the spirit and scope of the appended claims. The description is not intended to be exhaustive or to limit the invention to the precise form disclosed. It should be understood that the invention can be practiced with modification and alteration and that the invention be limited only by the claims and the equivalents thereof.

VI. SUMMARY

The invention provides products of manufacture, e.g., bioassemblies, or devices comprising cells, including mixed cell systems, that can be used as artificial tissues or organs, as chemical testing systems, as production factories for biological agents or for any research or development purpose. For example, the compositions (e.g., devices, products of manufacture) and methods of the invention can be used for detecting a toxin, a poison, an allergen, a biological warfare agent, an infectious disease agent or an irritating agent. In one aspect, the detecting or sensing device comprises providing an X-Y matrix subdivided array of a plurality of nanotubes. The invention provides methods for detecting the effect of a compound on a cell or a tissue or organ comprising contacting a detecting device of the invention with a test material selected from the group consisting of a chemical, a toxin, a poison, a cosmetic, a food, a natural product, an allergen, an irritant, a biological warfare agent, a polymer and an injection fluid.

For example, the invention provides devices, products of manufacture and structures (e.g., bio-assemblies, such as 2-D or 3-D cell-comprising devices as implants or as cell factories or biological agent production sources) comprising titanium dioxide-comprising structures comprising nanotubes or nanopores of approximately equal size, e.g., less that about 100 nm; or comprising macroscopic interlocking structures comprising "openings", reservoirs or pores which themselves may comprise nanotubes or nanopores; or comprising "dual structures", or comprising "interlocking structures" which themselves may comprise nanotubes or nanopores; or comprising biocompatible vertically aligned nanotube array structures, including accelerated cell growth structures; or comprising a lock-in nanostructure comprising a plurality of nanopores or nanotubes, wherein the nanopore or nanotube entrance has a smaller diameter or size than the rest (the interior) of the nanopore or nanotube (e.g., to exhibit a re-entrant configuration); or comprising dual structured biomaterial comprising micro- and/or macro-pores and nanostructures (e.g., nanopores or nanotubes as described herein); or devices and structures comprising random sized pores, e.g., including pores of less than 100 nm; or, devices and structures comprising any combination, or all, of these structures.

For example, a product of manufacture of the invention can further comprise a two or a three-dimensional array of the invention, or a biocompatible vertically aligned nanotube array structure of the invention, or an array of the invention, or a lock-in nanostructure of the invention, or a dual structured biomaterial of the invention, or any combination thereof, e.g., a combination of two or three or more or all of these structures/compositions of the invention.

An implant or artificial organ of the invention can comprise a product of manufacture of the invention, a two or a three-dimensional array of the invention, or a biocompatible vertically aligned nanotube array structure of the invention, or an array of the invention, or a lock-in nanostructure of the invention, or a dual structured biomaterial of the invention, or any combination thereof, e.g., a combination of two or three or more or all of these structures/compositions of the invention.

A bioreactor of the invention can comprise a product of manufacture of the invention, a two or a three-dimensional array of the invention, or a biocompatible vertically aligned nanotube array structure of the invention, or an array of the invention, or a lock-in nanostructure of the invention, or a dual structured biomaterial of the invention, or any combination thereof, e.g., a combination of two or three or more or all of these structures/compositions of the invention.

An artificial tissue or organ of the invention can comprise a product of manufacture of the invention, a two or a three-dimensional array of the invention, or a biocompatible vertically aligned nanotube array structure of the invention, or an array of the invention, or a lock-in nanostructure of the invention, or a dual structured biomaterial of the invention, or any combination thereof, e.g., a combination of two or three or more or all of these structures/compositions of the invention.

A disease detection device of the invention can comprise a product of manufacture of the invention, a two or a three-dimensional array of the invention, or a biocompatible vertically aligned nanotube array structure of the invention, or an array of the invention, or a lock-in nanostructure of the invention, or a dual structured biomaterial of the invention, or any combination thereof, e.g., a combination of two or three or more or all of these structures/compositions of the invention; wherein optionally the disease detected is influenza (flu), SARS or anthrax.

An orthopedic or dental prosthesis of the invention can comprise a product of manufacture of the invention, a two or a three-dimensional array of the invention, or a biocompatible vertically aligned nanotube array structure of the invention, or an array of the invention, or a lock-in nanostructure of the invention, or a dual structured biomaterial of the invention, or any combination thereof, e.g., a combination of two or three or more or all of these structures/compositions of the invention.

For example, the invention provides bio-assemblies comprising cultured animal or human cells, tissues and/or bones attached and grown (and in some aspects, rapidly grown) on biocompatible vertically aligned nanotube array structures with laterally separated nanotube arrangements wherein (a) the cultured cells, tissues and bones can be liver cells, kidney cells, nerve cells, myocytes, odontoblasts, dentinoblasts, cementoblasts, enameloblasts, odontogenic ectomesenchymal tissue, osteoblasts, osteoclasts, fibroblasts, and other cells and tissues involved in odontogenesis or bone formation, stem cells, supportive soft tissues such as muscles, skin cells, tendons, fibrous tissues, periodontal tissues, fat, blood vessels and/or hard tissues such as bone and teeth, either as a single cell type culture or as a co-culture of at least two or more types of cells together; (b) the biocompatible vertically aligned nanotube array structure is strongly adhered on a substrate (e.g., a metallic substrate), and in one aspect has an outer diameter of nanotubes in the range of between about 10 to 1000 nm, or 30 to 300 nm, or 60 to 200 nm; and in one aspect, the inside diameter is open with a diameter of at least about 10%, 20%, 30%, 40% or 50% or more of the outer diameter; and in one aspect the desired height of the tubules is in the range of between about 40 to 800 nm, or 100-400 nm; and in one aspect the aspect ratio is less than 10, 9, 8, 7, 6, 5, 4 or 3; and in one aspect the desired range of variation in the vertical alignment angle within between about 0 to 45 degrees, or 0 to 30 degrees off the vertical direction; and in one aspect, lateral spacing between adjacent nanotubes is in the range of between about 2 to 100 nm, or 5 to 30 nm; and, (c) the biocompatible nanotube array is made of a material comprising: i) titanium oxide on Ti support, a titanium alloy oxide on the alloy support which contains at least about 10%, 20%, 30%, 40% or 50% or more weight % Ti; ii) non-titanium oxide nanotubes of Zr, Hf, Nb, Ta, Mo, W, or alloys of these metals, or any mixture of these among themselves or in an alloyed form with Ti; or iii) coated Si, Si oxide, carbon, diamond, noble metals (such as Au, Ag, Pt and their alloys), polymer or plastic materials, or composite metals, ceramics or polymers; and in one aspect, having a laterally separated nanotube configuration; and in one aspect, having a surface coating with Ti oxide, Ti alloy oxide, or an oxide of Zr, Hf, Nb, Ta, Mo, W and their alloys; and in one aspect, comprising a coating thickness of at least 1, 2, 3, 4, 5, 6, 7, 8, 9, or 10 or more nm; and in one aspect the coating coverage of at least 10%, 20%, 30%, 40%, 50%, 60%, 70%, 80% or 90% or more of the total surfaces.

In one aspect, the cells maintained or grown in these devices of the invention, e.g., the rapidly cultured cells, tissues and/or bones, have accelerated growth kinetics by at least 10%, 20%, 30%, 40%, 50%, 60%, 70%, 80%, 90% 100%, 200%, 300% or more, as compared to the plain Ti metal surface without a nanotube or nanopore structure of the invention.

In one aspect, the aligned titanium oxide nanotubes adhered on titanium have a strong adhesion strength of anywhere between about 100 and 1000 psi, e.g., at least 500, 600, 700, 800, 900 or 1000 or more psi.

In one aspect, devices of the invention further comprise nanostructures comprising sodium titanate or titanium oxide fibers, which in one aspect are present at the tip of nanotubes, e.g., with a fiber thickness of at most 10, 20, 30, 40 or 50 or more nm, e.g., for enhanced hydroxyapatite formation in a living body (e.g., as an implant) or in a simulated body fluid.

In one aspect, devices of the invention comprise inside pores, which can be located in the laterally separated nanotubes, and they can comprise biologically active agents, e.g., therapeutic drugs, growth factors, proteins, enzymes, hormones, nucleic acids (e.g., RNA, DNA, genes, vectors), antibiotics or antibodies, or other substances (e.g., small molecules, radioisotopes, and the like). In one aspect, the inside pores of the laterally separated nanotubes comprise magnetic nanoparticles, metal and/or ceramic nanoparticles.

In one aspect, a nutrient fluid, in either in vivo human or animal body environments (e.g., as implants), or as in vitro cell culture environments, is continuously supplied under the growing cells through gap spacing between the laterally separated nanotubes; this can be in addition to the general nutrient fluid supply route, e.g., the space near the top surface of the growing cells.

In one aspect, the device of the invention, e.g., the bioassembly, is a part of an orthopaedic implant, a dental implant, a periodontal implant, an organ (e.g., a liver) implant, a joint implant, a heart implant, and the like. In one aspect, the device of the invention, e.g., the bioassembly, is a part of an artificial organ, e.g., an artificial liver device, an artificial kidney device and the like.

In one aspect, the inside pores of the vertically aligned nanotubes are reservoirs comprising one or more of various biologically active agents, e.g., therapeutic drugs, growth factors, proteins, enzymes, hormones, nucleic acids (e.g., RNA, DNA, genes, vectors), antibiotics or antibodies, or other substances (e.g., small molecules, radioisotopes, and the like), with the biologically active agents or other substances slowly released from the nanotubes at a rate determined by the nanotube diameter and aspect ratio, and the viscosity and wetting characteristics of the solution containing the biological agents or other substances.

In one aspect of the bio-assembly, the inside pores of the vertically aligned nanotubes are reservoirs containing one or more of various functional nanoparticles with a size of less than about 10, 20, 30, 40 or 50 or more nm in average diameter, or in the range of between about 10 to 300 nm, or 30 to 300 nm, or 60 to 200 nm. In one aspect, functional nanoparticles comprise magnetic, metallic, ceramic and/or polymer particles.

In one aspect of the bio-assembly, both the biological agents or other substances (e.g., small molecules, radioisotopes, and the like) and functional nanoparticles are co-present. In one aspect of the bio-assembly, the structure of the nanotube ends is of partially capped configuration to enhance retaining of the biological or functional agents within the nanotubes and reduce the release rate until externally stimulated for accelerated release. The partial capping of the nanotube ends can be by oblique incident deposition of metallic, ceramic, polymer or other materials.

The invention provides controlled slow-release drug and functional agent delivery devices comprising the structure of: (a) a biocompatible vertically aligned nanotube array structure which is strongly adhered on a metallic substrate, and in one aspect, has an outer diameter of nanotubes in the range of between about 10 to 1000 nm, or 30 to 300 nm, or 60 to 200 nm; and in one aspect the inside diameter is open with a diameter of at least about 10%, 20%, 30%, 40%, 50% or more of the outer diameter; and in one aspect the desired height of the tubules is in the range of between about 40 to 800 nm, or 100 to 400 nm; and in one aspect the desired aspect ratio of less than 10, 9, 8, 7, 6, 5, 4, 3 or 2; and in one aspect the desired range of variation in the vertical alignment angle within between about 0 to 45 degrees, or 0 to 30 degrees off the vertical direction; and in one aspect the desired lateral spacing between adjacent nanotubes in the range of between about 2 to 100 nm, or 5 to 30 nm; and/or (b) a biocompatible nanotube array comprising: i) titanium oxide on Ti support, a titanium alloy oxide on the alloy support which contains at least about 10%, 20%, 30%, 40% or 50% or more weight % Ti; ii) non-titanium oxide nanotubes of Zr, Hf, Nb, Ta, Mo, W, or alloys of these metals, or any mixture of these among themselves or in an alloyed form with Ti; or iii) coated Si, Si oxide, carbon, diamond, noble metals (such as Au, Ag, Pt and their alloys), polymer or plastic materials, or composite metals, ceramics or polymers; and in one aspect, having a laterally separated nanotube configuration; and in one aspect, having a surface coating with Ti oxide, Ti alloy oxide, or an oxide of Zr, Hf, Nb, Ta, Mo, W and their alloys; and in one aspect, comprising a coating thickness of at least 1, 2, 3, 4, 5, 6, 7, 8, 9, or 10 or more nm; and in one aspect the coating coverage of at least 10%, 20%, 30%, 40%, 50%, 60%, 70%, 80% or 90% or more of the total surfaces; and in one aspect the inside pores of the vertically aligned nanotubes are (or act as) reservoirs containing therapeutic drugs or other chemicals; and in one aspect the therapeutic drugs or other chemicals/substances are slowly released from the nanotubes at a rate determined by the nanotube diameter and aspect ratio, and the viscosity and wetting characteristics of the chemical/substance-containing (e.g., drug-containing) solution stored within the nanotubes.

In one aspect, the drugs stored in the nanotubes are cancer treatment drugs, diabetes drugs, bone-growth accelerating drugs, tissue-formation-preventing drugs or anti-stenosis drugs.

In one aspect, the inside pores of the vertically aligned nanotubes additionally contain one or more of various functional nanoparticles with a size of less than 10, 20, 30, 40 or 50 or more nm in average diameter, and can comprise magnetic, metallic, ceramic, or polymer particles. In one aspect, the structure of the nanotube ends is of partially capped configuration to enhance retaining the biological or functional agents within the nanotubes. In one aspect, the partial capping of the nanotube ends is by oblique incident deposition of metallic, ceramic or polymer materials.

The invention provides externally controllable drug delivery devices comprising any structure of the invention, e.g., the nanotube or nanopore configurations described herein, and further comprising compositions to control the timing as well as the quantity of the release of drugs or biological agents, e.g., compositions to control the initiation, starting and stopping of the release by, e.g., ultrasonic or magnetic agitation of the colloidal liquid containing the mixture of the drug solution and the nanoparticles.

In one aspect, the nanoparticles are biocompatible magnetic nanoparticles with an average diameter in the range of between about 5 to 50 nm. In one aspect, the magnetic particles are magnetite ($Fe_3O_4$) or maghemite ($\gamma$-$Fe_2O_3$). In one aspect, the onset and quantity of drug release is controlled by external stimulation of the magnetic nanoparticles by alternating current (AC) magnetic field to induce agitation/movement of the magnetic particles or by heating of the drug-particle mixture due to the AC magnetic field. In one aspect, the device is for cancer treatment using a combination of chemotherapy and magnetic hyperthermia.

The invention provides an in vitro or ex vivo cell proliferation device comprising a culture medium and any structure of the invention (e.g., comprising the nanotube or nanopore configurations described herein), wherein the cells are rapidly multiplied and harvested for supply for research, therapeutic, screening, biodefense or implant applications. In one aspect, these cells are "functional cells," such as liver cells, kidney cells, nerve cells, myocytes, adult stem cells, embryonic stem cells, supportive soft tissues such as muscles, tendons, fibrous tissues, periodontal tissues, fat, blood vessels, and hard tissues such as bone and teeth. In one aspect, cultured cells are harvested by trypsinization. In one aspect, the proliferation of the cells is accelerated by the controlled or externally initiated release of biological or functional agents, as described herein.

The invention provides analytical cell diagnostic biochip systems comprising a cell culture medium, the intended cells to be analyzed, the accelerated cell growth substrate, and a cell growth monitoring detection device wherein the cell growth substrate comprises (a) a biocompatible vertically aligned nanotube array structure of the invention, e.g., one which is strongly adhered on a metallic substrate; and in one aspect and in one aspect, has an outer diameter of nanotubes in the range of between about 10 to 1000 nm, or 30 to 300 nm, or 60 to 200 nm; and in one aspect the inside diameter is open with a diameter of at least about 10%, 20%, 30%, 40%, 50% or more of the outer diameter; and in one aspect the desired height of the tubules is in the range of between about 40 to 800 nm, or 100 to 400 nm; and in one aspect the desired aspect ratio of less than 10, 9, 8, 7, 6, 5, 4, 3 or 2; and in one aspect the desired range of variation in the vertical alignment angle within between about 0 to 45 degrees, or 0 to 30 degrees off the vertical direction; and in one aspect the desired lateral spacing between adjacent nanotubes in the range of between about 2 to 100 nm, or 5 to 30 nm; and/or (b) a biocompatible nanotube array comprising: i) titanium oxide on Ti support, a titanium alloy oxide on the alloy support which contains at least about 10%, 20%, 30%, 40% or 50% or more weight % Ti; ii) non-titanium oxide nanotubes of Zr, Hf, Nb, Ta, Mo, W, or alloys of these metals, or any mixture of these among themselves or in an alloyed form with Ti; or iii) coated Si, Si oxide, carbon, diamond, noble metals (such as Au, Ag, Pt and their alloys), polymer or plastic materials, or composite metals, ceramics or polymers; and in one aspect, having a laterally separated nanotube configuration; and in one aspect, having a surface coating with Ti oxide, Ti alloy oxide, or an oxide of Zr, Hf, Nb, Ta, Mo, W and their alloys; and in one aspect, comprising a coating thickness of at least 1, 2, 3, 4, 5, 6, 7, 8, 9, or 10 or more nm; and in one aspect the coating coverage of at least 10%, 20%, 30%, 40%, 50%, 60%, 70%, 80% or 90% or more of the total surfaces; and in one aspect the inside pores of the vertically aligned nanotubes are (or act as) reservoirs containing therapeutic drugs or other chemicals; and in one aspect the therapeutic drugs or other chemicals/substances are slowly released from the nanotubes at a rate determined by the nanotube diameter and aspect ratio, and the viscosity and wetting characteristics of the chemical/substance-containing (e.g., drug-containing) solution stored within the nanotubes. In one aspect, the cells to be analyzed are cultured with an accelerated growth kinetics by at least 100%, 200% or 300% or more as compared to the plain surface substrate of the same composition but without the said nanotube structure. In one aspect, the diagnosis and detection device is an optical detection device, a chemical or biological detection device, or a magnetic sensor device.

The invention provides analytical cell diagnostic biochip systems where the cells to be detected and counted are diseased cells or cells exposed to toxins, poisons, biological agents, e.g., biological warfare agents, e.g., bacteria or viruses, or are forensic test-related cells. In one aspect, the growth and proliferation of cells to be detected and counted are further accelerated by controlled or externally initiated release of biological or functional agents stored in the reservoir of nanotubes. In one aspect, the biochips are arranged in an X-Y matrix configuration comprising a subdivided array of $TiO_2$ nanotube regions for simultaneous fast diagnosis and detection of diseased cells or cells exposed to toxins, poisons, biological agents, e.g., biological warfare agents, e.g., bacteria or viruses, or, are forensic test-related cells.

The invention provides methods of fabricating in vitro or in vivo cell growth devices (e.g., accelerated cell growth devices) and implants, orthopaedic or dental implant structures, and disease or toxin cell detection devices, forensic cell detection, drug toxicity testing devices, artificial liver devices, artificial kidney devices, all having vertically aligned surface nanotube structures, e.g., by using electrochemical anodization of metallic base implant material, e.g., Ti, Zr, Hf, Nb, Ta, Mo, W and/or alloys of these metals, or alloys with other metals having the alloy contents of less than 10%, 20%, 30%, 40% 50% or more weight % total.

The invention provides methods of fabricating in vitro or in vivo cell growth devices (e.g., accelerated cell growth devices) and implants, orthopaedic or dental implant structures, and disease cell detection devices, forensic cell detection, drug toxicity testing devices, artificial liver devices, artificial kidney devices, all having vertically aligned surface nanotube structure by (a) preparing a laterally separated nanotube array structure by lithographic, chemical, electrochemical or reactive ion etch process on ceramics, Si, Si oxide, carbon, diamond, Au, Pt and their alloys, polymer or plastic materials, ceramic or composite metals, (b) adding a metallic or oxide coating by thin film sputter deposition, evaporation, or CVD deposition of Ti, Zr, Hf, Nb, Ta, Mo, W, or alloys of these metals on the surface of the fabricated nanotube structure, and in some aspects (c) with a coating thickness of at least 1, 2, 3, 4, 5, 6, 7, 8, 9, or 10 or more nm and the coating coverage of at least 10%, 20%, 30%, 40%, 50%, 60%, 70%, 80% or 90% of the total surfaces, and in some aspects (d) the deposited metal is converted to oxide by exposure to oxidizing atmosphere at ambient or heated temperature, by chemical process or by electrochemical oxidation process.

The invention provides methods of fabricating in vitro or in vivo cell growth devices (e.g., accelerated cell growth devices) and orthopaedic or dental implant structures of the invention further comprising multi-functional biological agents incorporated into the nanotube reservoirs, e.g., by ultrasonication. In one aspect, the multi-functional biological agents are incorporated into the nanotube reservoirs by heating the nanotube structure in boiling water to remove the trapped air bubble in the nanotubes.

The invention provides devices, e.g., bio-assemblies, comprising three-dimensionally and cultured (e.g., rapidly cultured) animal or human cells, tissues, organs and bones attached and grown on three-dimensionally configured and closely spaced biocompatible metallic ribbons and wires, wherein (a) the surface of the metallic elements have vertically and parallel-aligned laterally-separated nanotube or nanopore array structure, and in one aspect (b) the rapidly cultured cells, tissues and bones have an accelerated growth kinetics by at least 100%, 200%, 300% or more as compared to the plain metal wire or ribbon surface without the said nanotube or nanopore structure, and in one aspect comprising (c) metallic wires and ribbons made of a material comprising Ti, Zr, Hf, Nb, Ta, Mo, W and/or their alloys with each other or containing other alloying elements of less than 10, 20, 30, 40 or 50 or more weight percent total, and in one aspect (d) the nanotube array or the surface of the nanopore array material comprises an oxides material comprising Ti oxide, Zr oxide, Hf oxide, Nb oxide, Ta oxide, Mo oxide, W oxide, and/or mixed oxide alloyed with each other or containing other alloying element oxides of less than 10, 20, 30, 40 or 50 or more weight percent total. In one aspect, the metallic ribbons and wires are parallel and linearly arranged for easy pull out from the assembly. In one aspect, the metallic ribbons and wires are curved, bent or tangled for mechanical lock-in, reinforcement and support of grown cells.

In one aspect, the rapidly cultured cells, tissues and bones comprise liver cells, kidney cells, nerve cells, myocytes, stem cells, supportive soft tissues such as muscles, tendons, fibrous tissues, skin cells, periodontal tissues, fat, blood vessels, and hard tissues such as bone and teeth, either as a single type cell culture or as a co-culture a co-culture of at least two types of cells together.

In one aspect, the metallic ribbons and wires are subdivided and have a preferred dimension of (a) a thickness of in the range of between about 25 to 2500 micrometers, or 50 to 500 micrometers. In one aspect, spacing between the parallel neighboring branches of metallic wires and ribbons in the cell cultured assembly is at most 5, 10, 15, 20 or more times the thickness of an average monolayer cell thickness, or between at most 5 to 10 times the thickness of an average monolayer cell.

In one aspect, the surface of the ribbons and wires contains an aligned nanopore or nanotube array with the preferred diameter being in the range of between about 10-1000 nm, or 50-500 nm, and in one aspect, the desired height being in the range of between about 40-2000 nm, or 100-400 nm, and in one aspect the desired angle is vertical with an allowance of 10, 20 or 30 degree variation off the perpendicular axis, and in one aspect, the desired volume fraction of the metal for the given targeted cell volume at the end of the planned cell culture period is at least 10%, 20%, 30%, 40% or 50% or more.

In alternative aspects, the bio-assembly comprises an orthopedic, dental or periodontal implant, or an artificial organ, or comprises liver cells and the assembly is a liver or kidney implants, or comprises liver cells and the assembly is an artificial liver device, or comprises liver cells and the assembly is a drug toxicity testing device, or is a cell detection device for rapidly identifying disease, forensic or biological warfare agent-exposed cells, or is a device for rapid cell culture, detachment and supply.

In alternative aspects, biocompatible vertically aligned nanotube array structures are strongly adhered on a metallic wire or ribbon substrate, and can have an outer diameter of nanotubes is in the range of between about 10-1000 nm, or an alignment orientation in the range of between about 0-30 degrees off the vertical direction from the wire or ribbon surface, or the desired lateral spacing between adjacent nanotubes can be in the range of between about 2-100 nm.

In one aspect, nanotubes on the surface of metallic wires and ribbons are made by electrochemical anodization process. Nanotubes on the surface of metallic wires and ribbons also can be made by artificial pattern design and lithography.

The invention provides three-dimensionally and rapidly cultured cells, tissues, organs and bones wherein (a) the surface of the said metallic elements have vertically and parallel-aligned laterally-separated nanotube or nanopore array structure, (b) the cells are attached and grown on three-dimensionally configured and closely spaced biocompatible metallic ribbons and wires, (c) the metallic ribbons and wires are parallel and linearly arranged for rapid cell growth, and then pulled out from the cultured three-dimensional cell assembly so that the cell assembly has no metallic or ceramic substrate left, and in one aspect (d) the substrate-free cell assembly is allowed to heal itself to fill up the space left by the retracted metallic wires and ribbons, and in one aspect (e) the rapidly cultured cells, tissues and bones have an accelerated growth kinetics by at least 100%, 200%, 300% or more as compared to the plain metal wire or ribbon surface without the said nanotube or nanopore structure, and in one aspect (f) the metallic wires and ribbons are made of a material comprising Ti, Zr, Hf, Nb, Ta, Mo, W, and/or their alloy with each other and/or comprising other alloying elements of less than 10, 20, 30, 40, 50 or more weight percent total, and in one aspect (g) the nanotube array or the surface of the nanopore array material comprising an oxides material comprising Ti oxide, Zr oxide, Hf oxide, Nb oxide, Ta oxide, Mo oxide, W oxide, and mixed oxide alloyed with each other or comprising other alloying element oxides of less than 10, 20, 30, 40, 50 or more weight percent total.

In one aspect, the in vivo or in vitro nutrient fluid is supplied under the growing cells through the gap spacing between the nanotubes in addition to the overall space including the top of the cells. In one aspect, the vertical pores of the nanotubes or nanotubes serve as a reservoir and contain various biologically active agents such as therapeutic drugs, growth factors, proteins, collagens, stem cells, enzymes, hormones, nucleic acids (e.g., RNA, DNA, genes, vectors), antibiotics, antibodies, magnetic nanoparticles, radioisotopes and other materials for slow or externally actuated release.

The invention provides controlled-release drug and functional agent delivery devices comprising the structure of three-dimensionally configured and closely spaced biocompatible metallic ribbons and wires wherein (a) the surface of the said metallic elements have vertically and parallel-aligned laterally-separated nanotube or nanopore array structure, (b) the said metallic wires and ribbons are made of a material selected from a list of Ti, Zr, Hf, Nb, Ta, Mo, W, and their alloy with each other or containing other alloying elements of less than 10, 20, 30, 40, 50 or more weight percent total, (c) the nanotube array or the surface of the nanopore array material is an oxides material selected from a list of Ti oxide, Zr oxide, Hf oxide, Nb oxide, Ta oxide, Mo oxide, W oxide, and mixed oxide alloyed with each other or containing other alloying element oxides of less than 10, 20, 30, 40, 50 or more weight percent total, and optionally coated with Ti or Ti oxide film of at least 5 nm thickness and the coating coverage of at least 10%, 20%, 30%, 40%, 50%, 60%, 70%, 80% or 90% of the total surfaces; and in one aspect (d) the biocompatible aligned nanotube or nanotube array structure is strongly adhered on a metallic substrate, and has the desired outer diameter of nanotubes is in the range of 10-1000 nm, the desired range of variation in the vertical alignment angle within 0-30 degrees off the vertical direction, and the desired lateral spacing between adjacent nanotubes in the range of 2-100 nm; and in one aspect (e) wherein the inside pores of the said vertically aligned nanotubes are reservoirs containing biologically active agents including at least one of the therapeutic drugs, growth factors, proteins, enzymes, hormones, nucleic acids (e.g., RNA, DNA, genes, vectors), antibiotics, antibodies, magnetic nanoparticles, radioisotopes and other materials, or functionally active particles such as magnetic nanoparticles, novel metal nanoparticles or ceramic nanoparticles; and in one aspect (f) wherein the drug release device is implanted in a living body and therapeutic drugs are slowly released from the nanotubes at a rate determined by the nanotube diameter and aspect ratio, and the viscosity and wetting characteristics of the drug-containing solution stored within the nanotubes.

The invention provides methods of fabricating in vitro or in vivo cell growth devices and implants, orthopedic or dental implant structures, and disease cell detection devices, forensic cell detection, drug toxicity testing devices, artificial liver devices, artificial kidney devices with a structure of the invention by (a) first arranging metal wires or ribbons into a three-dimensional configuration, (b) then converting their surfaces into a vertically aligned nanotube or nanopore structure by using electrochemical anodization of metallic base implant material comprising Ti, Zr, Hf, Nb, Ta, Mo, W, or alloys of these metals among them or alloys with other metals having the alloy contents of less than 50% weight % total.

The invention provides methods of fabricating in vitro or in vivo cell growth devices and implants, orthopedic or dental implant structures, and disease cell detection devices, forensic cell detection, drug toxicity testing devices, artificial liver devices, artificial kidney devices with a structure of the invention, having vertically aligned surface nanotube structure by (a) preparing a laterally separated nanotube array structure by lithographic, chemical, electrochemical or reactive ion etch process on ceramics, Si, Si oxide, carbon, diamond, Au, Pt and their alloys, polymer or plastic materials, ceramic or composite metals, (b) adding a metallic or oxide coating by thin film sputter deposition, evaporation, or CVD deposition of Ti, Zr, Hf, Nb, Ta, Mo, W, or alloys of these metals on the surface of the fabricated nanotube structure, and in one aspect (c) with a coating thickness of at least 1, 2, 3, 4 or 5 nm and the coating coverage of at least 10%, 20%, 30%, 40%, 50%, 60%, 70%, 80% or 90% of the total surfaces, and in one aspect, (d) the deposited metal optionally converted to oxide by exposure to oxidizing atmosphere at ambient or heated temperature, by chemical process or by electrochemical oxidation process.

The invention provides methods of fabricating in vitro or in vivo cell growth devices and implants, and orthopedic or dental implant structures, wherein multi-functional biological agents of the invention are incorporated into the nanotube reservoirs by ultrasonication.

The invention provides methods of fabricating in vitro or in vivo cell growth devices and implants, and orthopedic or dental implant structures of the invention, wherein multi-functional biological agents of the invention are incorporated into the nanotube reservoirs by heating the nanotube structure in boiling water to remove the trapped air bubble in the nanotubes.

The invention provides bio-assemblies comprising rapidly cultured animal or human cells, tissues, organs and bones attached and grown on dual-structured, biocompatible substrates with both micro and nano topological configurations, wherein (a) the micro configurations have an average diameter (or equivalent diameter if the pores are not circular) in the range of between about 0.5-1,000 µm, or 1-100 µm, (b) the surface of the said substrates have nano configurations of vertically and parallel-aligned laterally-separated nanotube or nanopore array structure with the average nanopore or nanotube diameter in the preferred range of e.g., 30-600 nm, (c) the relative ratio of the micro pores vs nano pores in the dual structure is such that the micro/macro pores desirably occupy at least 10%, 20%, 30%, 40%, 50%, 60%, 70%, 80% or 90% area fraction of the implant or bio-substrate surface, or at least 20% but less than 50%, to maximize the accelerated cell culture or bone growth via the nanopore portion of the surface; and in one aspect (d) the rapidly cultured cells, tissues and bones are selected from a list of functional cells such as liver cells, kidney cells, nerve cells, myocytes, stem cells, supportive soft tissues such as muscles, skin cells, tendons, fibrous tissues, periodontal tissues, fat, blood vessels, and hard tissues such as bone and teeth, either as a single cell type culture or as a co-culture of at least two types of cells together; and in one aspect (e) the rapidly cultured cells, tissues and bones have an accelerated growth kinetics by at least 100%, 200%, 300% or more as compared to the same substrate without the said nanotube or nanopore structure; and in one aspect (f) the said substrate is made of a material selected from a list of Ti, Zr, Hf, Nb, Ta, Mo, W, and their alloy with each other or containing other alloying elements of less than 10, 20, 30, 40 or 50 weight percent total; and in one aspect (g) the nanotube array or the surface of the nanopore array material comprises an oxides material comprising Ti oxide, Zr oxide, Hf oxide, Nb oxide, Ta oxide, Mo oxide, W oxide, and/or mixed oxide alloyed with each other or containing other alloying element oxides of less than 50 weight percent total.

In one aspect, the micro- or nano-features have a lock-in structure with a re-entrant configuration with the pore or nanopore entrance having a smaller diameter than the rest of the pore or nanopore dimension so that the cells or bones grown are mechanically more firmly attached, wherein; the re-entrant feature can be either circular, oval, tapered wall, or corrugated shape, the degree of the maximum re-entrance is at least 10%, 20%, 30%, 40%, 50%, 60%, 70%, 80% or 90% of the largest diameter of the pore or nanopore.

The invention provides methods of fabricating a lock-in structure with a re-entrant pore or nanopore configuration in a bio-assembly of the invention; and in one aspect the re-entrant configuration is obtained by oblique incident physical vapor deposition; and in one aspect, the re-entrant configuration is obtained by gradual increase of electrochemical anodization voltage; and in one aspect, the re-entrant configuration is obtained by a use of isotropic etching on a pattern masked substrate.

In one aspect, the nanopores in the bio assembly serve as a reservoir and contain at list one of various chemicals, substances and/or biologically active agents, e.g., therapeutic drugs, growth factors, proteins, collagens, stem cells, enzymes, hormones, nucleic acids, antibiotics, antibodies, magnetic, metallic, ceramic, polymer, or bio imaging nanoparticles.

In alternative aspects, the dual-structured bio-assemblies are orthopedic or dental implants, artificial organs, or comprise liver cells and the assembly is a liver implants, or comprise liver cells and the assembly is an artificial liver device, or comprises liver cells and the assembly is a drug toxicity testing device, or is a cell detection device for rapidly identifying a disease or conditions, e.g., a diseased cell, or a cell exposed to a biological or chemical warfare agent, or a cell useful in forensic purposes, or is a device for rapid cell culture, detachment and supply.

In alternative aspects, the dual-structured bio-assemblies comprise cells and/or bones cultured in a two- and/or three-dimensional configuration.

The dual-structured bio-assemblies can comprise coated Si, Si oxide, carbon, diamond, noble metals (such as Au, Ag, Pt and their alloys), polymer or plastic materials, or composite metals, ceramics or polymers having a laterally separated nanotube configuration and having a preferential surface coating with Ti oxide, Ti alloy oxide, or an oxide of Zr, Hf, Nb, Ta, Mo, W and their alloys, and in one aspect (c) with a coating thickness of at least 1, 2, 3, 4 or 5 nm and the coating coverage of at least 10%, 20%, 30%, 40%, 50%, 60%, 70%, 80% or 90% of the total surfaces, and in one aspect, (d) the deposited metal optionally converted to oxide by exposure to oxidizing atmosphere at ambient or heated temperature, by chemical process or by electrochemical oxidation process.

In one aspect, the invention provides methods for fabricating the dual-structured bio-assemblies by using a combination of either photo lithography and/or electrochemical anodization, or, by using a combination of nano imprint lithography and electrochemical anodization. In one aspect, the nano-imprint lithography utilizes a compliant elastomeric mask sheet or an elastomeric stamp. In one aspect, the dual-structured bioassembly is fabricated using a combination of guided etching using a vertically two-phase decomposed coating and electrochemical anodization. In one aspect, the dual-structured bioassembly is fabricated using a combination of guided etching using a vertically two-phase decomposed coating of periodically or spinodally decomposing alloy and electrochemical anodization.

In one aspect, the bio-assembly comprises rapidly cultured animal or human cells, tissues, organs and bones attached and grown on enlarged-diameter, surface nanotube array on biocompatible substrates wherein (a) the diameter-enlarged surface nanotube array has a vertically and parallel-aligned and laterally-separated nanotube configuration, and has an average nanotube diameter in the preferred range of at least 50, 100, 150, 200, 250, 300 or more nm diameter. In one aspect, the cultured (e.g., rapidly cultured) cells, tissues and bones are selected from a list of functional cells such as liver cells, kidney cells, nerve cells, myocytes, stem cells, supportive soft tissues such as muscles, skin cells, tendons, fibrous tissues, periodontal tissues, fat, blood vessels, and hard tissues such as bone and teeth, either as a single cell type culture or as a co-culture of at least two types of cells together. In one aspect, the cultured (e.g., rapidly cultured) cells, tissues and bones have an accelerated growth kinetics by at least 100%, 200%, 300% or more as compared to the same substrate without the said nanotube or nanopore structure. In one aspect, the substrate is made of a material comprising Ti, Zr, Hf, Nb, Ta, Mo, W, and/or their alloy with each other or containing other alloying elements of less than 10, 20, 30, 40 or 50 weight percent total. In one aspect, the nanotube array or the surface of the nanopore array material comprises an oxides material selected from a list of Ti oxide, Zr oxide, Hf oxide, Nb oxide, Ta oxide, Mo oxide, W oxide, and mixed oxide alloyed with each other or containing other alloying element oxides of less than 10, 20, 30, 40 or 50 weight percent total.

The invention provides bio-assemblies comprising cultured (e.g., rapidly cultured) cells, e.g., cultured animal or human cells, tissues, organs and/or bones, attached and grown on randomized-diameter, surface nanotube array on biocompatible substrates wherein; (a) the said randomized-diameter, surface nanotube array has a vertically and parallel-aligned and laterally-separated nanotube configuration, and has a desired distribution of the nanopore sizes so that at least one third of the pores have their average diameter which is equal to or less than 70%, 60% 50%, or 40%, or equal to or less than about 50% of the overall average pore diameter, while another one third of the pores have their average diameter which is at least 125%, 150% or 200% or more or the overall average pore diameter and optionally the distribution of the nanopore or nanotube sizes is such that at least one quarter to one half of the pores or tubes have their average diameter equal to or less than 20% to 80% of the overall average pore diameter, while another one quarter to one half of the pores have their average diameter at least 100% to 150%, or 100% to 200%, of the overall average pore diameter.

In one aspect of the diameter-enlarged bio assembly of the invention or the diameter-randomized bio assembly of the invention, the nanopores in the biocompatible substrate have a lock-in structure with a re-entrant configuration with the pore or nanopore entrance having a smaller diameter than the rest of the pore or nanopore dimension so that the cells or bones grown are mechanically more firmly attached, wherein (a) the re-entrant feature can be either circular, oval, tapered wall, or corrugated shape, and/or (b) the degree of the maximum re-entrance is at least 5% or 10% or more of the largest diameter of the pore or nanopore.

In one aspect, the invention provides methods for fabricating a diameter-randomized nanopore- or nanotube-comprising device, e.g., a bio-assembly device of the invention, by guided patterning of substrate surface using a roll stamping of elastomeric nano implant stamp to create an etch mask of diameter-randomized pattern, or, by guided patterning of substrate surface using a large-area elastomeric nano stamping in combination with reactive ion etch or chemical etch.

In one aspect, the invention provides methods for fabricating the controlled-release drug and/or functional agent delivery devices of the invention having a diameter-enlarged and/or a diameter-randomized substrate surface, comprising nanostructures wherein (a) the surface of the substrate has vertically and/or parallel-aligned laterally-separated nanotube or nanopore array structure; and in alternative aspects (b) the substrate is made of a material comprising Ti, Zr, Hf, Nb, Ta, Mo, W, and their alloy with each other or containing other alloying elements of less than 10, 20, 30, 40 or 50 weight percent total; and in alternative aspects (c) the nanotube array or the surface of the nanopore array material comprises an oxides material comprising Ti oxide, Zr oxide, Hf oxide, Nb oxide, Ta oxide, Mo oxide, W oxide, and/or mixed oxide alloyed with each other and/or containing other alloying element oxides of less than 10, 20, 30, 40 or 50 weight percent total, and optionally coated with Ti or Ti oxide film of at least 1, 2, 3, 4, 5, 6, 7, 8, 9, or 10 or more nm thickness; and in alternative aspects a coating coverage of at least 10%, 20%, 30%, 40%, 50%, 60%, 70%, 80% or 90% of the total surfaces; and in alternative aspects (d) the biocompatible aligned nanotubes or nanopores array structure is strongly adhered on a metallic substrate; and in alternative aspects has the desired outer diameter of nanotubes is in the range of between about 10-1000 nm, the desired range of variation in the vertical alignment angle within between about 0-30 degrees off the vertical direction, and the desired lateral spacing between adjacent nanotubes in the range of between about 2-100 nm.

In one aspect, the inside pores of the said vertically aligned nanotubes or nanopores are reservoirs comprising any desired substance, e.g., a chemical, an agent (e.g., a radioisotope, dye), a biologically active agent, e.g., therapeutic drugs, growth factors, proteins, enzymes, hormones, nucleic acids, antibiotics, or antibodies, or functionally active particles such as magnetic nanoparticles, novel metal nanoparticles or ceramic nanoparticles. In one aspect, the drug release device is implanted in a living body and therapeutic drugs are slowly released from the nanotubes or nanopores at a rate determined by the nanotube diameter and aspect ratio, and the viscosity and wetting characteristics of the drug-containing solution stored within the nanotubes. In one aspect, the drugs stored in the nanotubes or nanopores comprise cancer treatment drugs, diabetes drugs, bone-growth accelerating drugs, tissue-formation-preventing drugs or anti-stenosis drugs.

In one aspect, for the controlled-release drug and/or functional agent delivery devices of the invention having a diameter-enlarged and/or a diameter-randomized nanotube- or nanopore-comprising substrate surface, the structure of the nanotube or nanopore ends are of partially capped configuration to enhance retaining the desired composition, e.g., small molecule, biological or other functional agents within the nanotube or nanopore. In one aspect, the drug release is externally controllable so that the timing as well as the quantity of the release of drugs or biological agents is initiated and stopped at will by ultrasonic or magnetic agitation of the colloidal liquid containing the mixture of the drug solution and the nanoparticles, as discussed above.

The invention provides analytical cell diagnostic biochip systems comprising a cell culture medium, the intended cells to be analyzed, a cell growth substrate comprising a diameter-enlarged bioassembly of the invention or the diameter-randomized bioassembly of the invention, and cell growth monitoring detection device wherein the diagnosis and detection device, e.g., an optical detection device, a chemical or biological detection device and/or magnetic sensor device. In one aspect, the cells to be detected and counted are diseased cells, cells exposed to biological or chemical warfare agents, toxins, poisons, or forensic-test-related cells. In one aspect, the growth and proliferation of cells to be detected and counted are further accelerated by controlled or externally initiated release of biological or functional agents stored in the reservoir of nanotubes.

It should be understood that the invention can be practiced with modification and alteration within the spirit and scope of the appended claims. The description is not intended to be exhaustive or to limit the invention to the precise form disclosed. It should be understood that the invention can be practiced with modification and alteration and that the invention be limited only by the claims and the equivalents thereof.

What is claimed is:

1. A lock-in nanostructure comprising a plurality of nanotubes, wherein:
    (a) at least a nanotube of the plurality of nanotubes has a locked-in nanotube entrance that is smaller in size than an interior of the nanotube to exhibit a re-entrant configuration;
    (b) the plurality of nanotubes have an outer diameter of between about 10 to 1000 nm;
    (c) a height of at least a nanotube of the plurality of nanotubes has a height of at least about 40 nm;
    (v) a vertical alignment angle of at least a nanotube of the plurality of nanotubes is within from about 0 to 45 degrees off a vertical direction, or about 5, 10, 15, 20, 25, 30 or 35 degrees variation off a perpendicular axis; and
    (vi) a lateral spacing between adjacent nanotubes of the plurality of nanotubes is from about 2 to 100 nm.

2. The lock-in nanostructure of claim 1, wherein the locked-in nanotube entrance has an average entrance diameter that is at least 10% to 50% smaller than the interior of the nanotube.

3. The lock-in nanostructure of claim 1, wherein the plurality of nanotubes comprise a Ti or a $TiO_2$.

4. A dual structured biomaterial comprising:
    (a) a plurality of micro-pores, wherein the plurality of micro-pores has an average or equivalent diameter of between about 0.5-1,000 μm (microns); and
    (b) a surface area at least 10% covered with a plurality of nanotubes, wherein
    (i) the plurality of nanotubes have an outer diameter of between 10 to 1000 nm;
    (ii) the height of at least a nanotube of the plurality of nanotubes has a height of at least about 40 nm;
    (iii) a vertical alignment angle of at least a nanotube of the plurality of nanotubes is within from about 0 to 45 degrees off a vertical direction, or about 5, 10, 15, 20, 25, 30 or 35 degrees variation off a perpendicular axis; and
    (iv) a lateral spacing between adjacent nanotubes of the plurality of nanotubes is from about 2 to 100 nm.

5. The dual structured biomaterial of claim 4, wherein the dual structured biomaterial comprises, or is contained within, an implant any of an artificial organ and a joint.

6. The lock-in nanostructure of claim 1, further comprising a plurality of cells.

7. An implant comprising the lock-in nanostructure of claim 1.

8. A bioreactor comprising the lock-in nanostructure of claim 1.

9. An artificial organ comprising the lock-in nanostructure of claim 1.

10. A disease detection device comprising the lock-in nanostructure of claim 1, wherein optionally the disease detected is influenza (flu), SARS or anthrax.

11. The lock-in nanostructure of 1, wherein the nanotube entrance has an average entrance diameter that is at least about 15%, 20%, 25%, 30%, 35%, 40% or 45%, smaller than the interior of the nanotube.

12. The lock-in nanostructure of 1, wherein the lock-in nanostructure comprises, or is part of, any of an implant, an artificial organ and a joint.

13. The dual structured biomaterial of claim 4, wherein:
    (a) each of the plurality of nanotubes has an average pore diameter of between about 30-600 nm;
    (b) the relative ratio of the plurality of micro-pores and the plurality of nanotubes is such that the plurality of micro-pores occupy at least about a 5%, 10%, 15%, 20%, 25%, 30%, 35%, 40%, 45% or 50% area fraction of the dual structured biomaterial; or,
    (c) the relative ratio of the plurality of micro-pores is such that the plurality of micro-pores occupy at least about a 20% but less than about a 50% area fraction of the dual structured biomaterial.

14. An implant comprising the dual structured biomaterial of claim 4.

15. A bioreactor comprising the dual structured biomaterial of claim 4.

16. An artificial organ comprising the dual structured biomaterial of claim 4.

17. A disease detection device comprising the dual structured biomaterial of claim 4, wherein optionally the disease detected is influenza (flu), SARS or anthrax.

18. The dual structured biomaterial of claim 4, wherein each micro-pore of the plurality of micro-pores has an entrance that is smaller in size than an interior of the micro-pore.

19. The lock-in nanostructure of 6, wherein the plurality of cells comprise any of liver cells, liver parenchymal cells, endothelial cells, adipocytes, fibroblastic cells, Kupffer cells, kidney cells, blood vessel cells, skin cells, periodontal cells, odontoblasts, dentinoblasts, cementoblasts, enameloblasts, odontogenic ectomesenchymal tissue, osteoblasts, osteoclasts, fibroblasts, a cell or a tissue involved in odontogenesis or bone formation, stem cells and a combination thereof.

20. The dual structured biomaterial of claim 4, further comprising a plurality of cells.

21. The lock-in nanostructure of claim 1, wherein the height of a nanotube of the plurality of nanotubes between about 40 to 2000 nm.

22. The dual structured biomaterial of claim 4, wherein the height of a nanotube of the plurality of nanotubes is between about 40 to 2000 nm.

23. A biocompatible vertically aligned nanotube array structure on a biocompatible substrate comprising a plurality of nanotubes in a laterally separated nanotube arrangement wherein:
 (a) a nanotube of the plurality of nanotubes has an outer diameter of between about 10 to 1000 nm;
 (b) the height of a nanotube of the plurality of nanotubes has a height of at least about 40 nm;
 (c) a vertical alignment angle of at least a nanotube of the plurality of nanotubes is within from about 0 to 45 degrees off a vertical direction, or about 5, 10, 15, 20, 25, 30 or 35 degrees variation off a perpendicular axis; and
 (d) a lateral spacing between adjacent nanotubes of the plurality of nanotubes is from about 2 to 100 nm.

24. The biocompatible vertically aligned nanotube array of claim 23, wherein the height of a nanotube of the plurality of nanotubes is between about 40 to 2000 nm.

25. The biocompatible vertically aligned nanotube array structure of claim 23, wherein:
 (a) the plurality of nanotubes comprise a plurality of biocompatible titanium oxide nanotubes;
 (b) a nanotube of the plurality of nanotubes has an outer diameter of at least about 20, 30, 40, 50, 60, 70, 80, 90 or 100 nm;
 (c) a nanotube of the plurality of nanotubes has an outer diameter of between about 10 to 100 nm outer diameter;
 (d) a nanotube of the plurality of nanotubes has an inner diameter of between about 20, 30, 40, 50, 60, 70, 80, 90 or 100 nm;
 (e) a nanotube of the plurality of nanotubes has an inner diameter of between about 10 to about 90 nm;
 (f) a nanotube of the plurality of nanotubes has a wall thickness of at least about 10, 15, 20, 30, 40, 50, 60, 70, 80, 90 or 100 nm;
 (g) t a nanotube of the plurality of nanotubes has a wall thickness of between about 10 to 100 nm;
 (h) a nanotube of the plurality of nanotubes has a height of about 20, 30, 40, 50, 60, 70, 80, 90, 100, 125, 150, 175, 200, 225 or 250 nm;
 (j) a nanotube of the plurality of nanotubes has a height of between about 20 to 300 nm;
 (j) the biocompatible substrate comprises a titanium sheet;
 (k) the biocompatible substrate is at least about 15, 20, 25, 30, 40, 50, 60, 70, 80, 90, 100, 125, 150, 175, 200, 225 or more nm thick;
 (l) at least about 10% of the biocompatible substrate comprises nanotubes; or
 (m) the biocompatible vertically aligned nanotube array structure comprises any combination of (a) to (l).

* * * * *